United States Patent
Kim et al.

(10) Patent No.: US 10,032,985 B2
(45) Date of Patent: Jul. 24, 2018

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); CHEIL INDUSTRIES INC., Gumi-si, Gyeongsangbuk-do (KR)

(72) Inventors: Chang-woo Kim, Gyeongsangbuk-do (KR); O-hyun Kwon, Yongin-si (KR); Sang-dong Kim, Hwaseong-si (KR); Kyu-young Hwang, Ansan-si (KR); Byoung-ki Choi, Hwaseong-si (KR)

(73) Assignees: SAMSUNG ELECTRONICS CO., LTD., Gyeonggi-Do (KR); CHEIL INDUSTRIES INC., Gyeongsangbuk-Do (KR)

( * ) Notice: Subject to any disclaimer, the term of this patent is extended or adjusted under 35 U.S.C. 154(b) by 565 days.

(21) Appl. No.: 14/293,086

(22) Filed: Jun. 2, 2014

(65) Prior Publication Data

US 2015/0090968 A1 Apr. 2, 2015

(30) Foreign Application Priority Data

Oct. 1, 2013 (KR) .................. 10-2013-0117589

(51) Int. Cl.
*H01L 51/00* (2006.01)
*H01L 51/50* (2006.01)
(Continued)

(52) U.S. Cl.
CPC ........ *H01L 51/0052* (2013.01); *C07D 491/04* (2013.01); *C07D 495/14* (2013.01);
(Continued)

(58) Field of Classification Search
None
See application file for complete search history.

(56) References Cited

U.S. PATENT DOCUMENTS 8,372,312 B1 * 2/2013 Wu .................. C07D 495/14
252/500
9,288,869 B2 3/2016 Han et al.
(Continued)

FOREIGN PATENT DOCUMENTS

KR   10-2011-0116618 A   10/2011
KR   2013-0051807 A      5/2013
(Continued)

OTHER PUBLICATIONS

Boberg et al. (Liebigs Ann. Chem. 1983, p. 1588).*
(Continued)

*Primary Examiner* — J. L. Yang
(74) *Attorney, Agent, or Firm* — Cantor Colburn LLP

(57) ABSTRACT

A condensed cyclic compound represented by Formula 1:

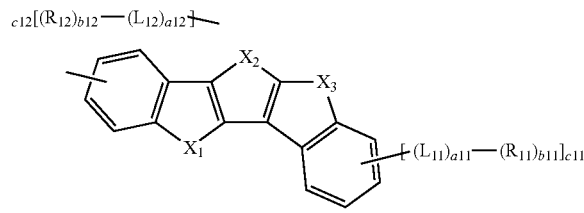

wherein in Formula 1, Groups $X_1$ to $X_3$, $L_{11}$, $L_{12}$, $R_{11}$, and $R_{12}$, and variables a11, a12, b11, b12, c11, and c12 are described in the specification.

24 Claims, 1 Drawing Sheet

(51) Int. Cl.
*C07D 491/04* (2006.01)
*C07D 495/14* (2006.01)
*C07D 519/00* (2006.01)

(52) U.S. Cl.
CPC ........ *C07D 519/00* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/006* (2013.01); *H01L 51/0059* (2013.01); *H01L 51/0081* (2013.01); *H01L 51/0085* (2013.01); *H01L 51/5016* (2013.01)

(56) References Cited

U.S. PATENT DOCUMENTS

| | | | |
|---|---|---|---|
| 2009/0051273 A1* | 2/2009 | Tsuji | ................. H01L 51/5044 |
| | | | 313/504 |
| 2013/0126792 A1 | 5/2013 | Martynova et al. | |

FOREIGN PATENT DOCUMENTS

| | | |
|---|---|---|
| WO | 2012-016630 A1 | 2/2012 |
| WO | 2012073888 A1 | 6/2012 |

OTHER PUBLICATIONS

Balaji et al., "Synthesis and Properties of Symmetric and Unsymmetric Dibenzothienopyrroles", Organic Letters, vol. 11, No. 15, 2009, pp. 3358-3361.

Glinzer et al., "Mass Spectrometry of Sulphur Compounds as Model Substances for Crude Oil Analysis—Bisanellated Thiophenes*", Fresenius Z Anal Chem, vol. 315, 1983, pp. 208-212.

* cited by examiner

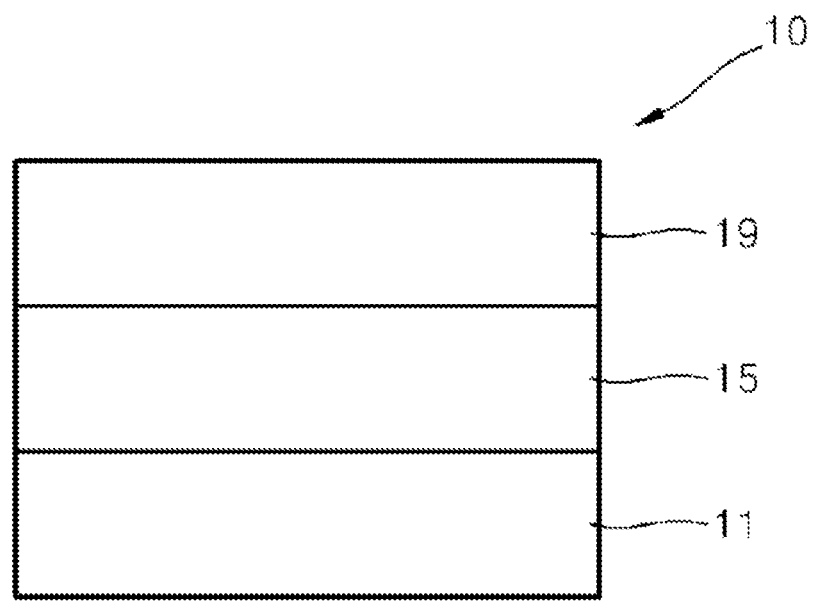

CONDENSED CYCLIC COMPOUND AND ORGANIC LIGHT-EMITTING DEVICE INCLUDING THE SAME

CROSS-REFERENCE TO RELATED APPLICATIONS

This application claims priority to Korean Patent Application No. 10-2013-0117589, filed on Oct. 1, 2013 in the Korean Intellectual Property Office, and all the benefits accruing therefrom under 35 U.S.C. § 119, the content of which is incorporated herein in its entirety by reference.

BACKGROUND

1. Field

One or more embodiments relate to a condensed cyclic compound and an organic light-emitting device including the same.

2. Description of the Related Art

Organic light-emitting devices (OLEDs) are self-emitting devices, which provide advantages such as wide viewing angles, excellent contrast, quick response, high brightness, excellent driving voltage characteristics, and provide full color images.

As an example, an organic light-emitting device includes an anode, a cathode, and an emission layer that is disposed between the anode and the cathode. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, are recombined in the emission layer to produce excitons. These excitons change from an excited state to a ground state, thereby generating light.

Different types of OLEDs have been reported. However, there remains a need in OLEDs having one or more of low driving voltage, high efficiency, high brightness, and long lifespan.

SUMMARY

Provided are a novel condensed cyclic compound and an organic light-emitting device including the same.

Additional aspects will be set forth in part in the description which follows and, in part, will be apparent from the description, or may be learned by practice of the presented embodiments.

An aspect provides a condensed cyclic compound represented by Formula 1 below:

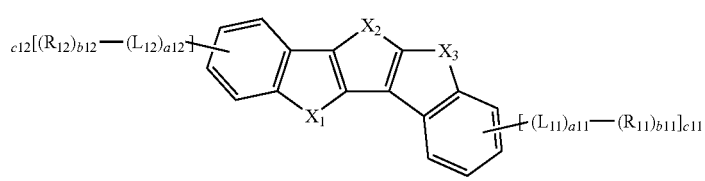

Formula 1 wherein in Formula 1, $X_1$ is $N[(L_1)_{a1}\text{-}(R_1)_{b1}]$, $C[(L_2)_{a2}\text{-}(R_2)_{b2}][(L_3)_{a3}\text{-}(R_3)_{b3}]$, $Si[(L_2)_{a2}\text{-}(R_2)_{b2}][(L_3)_{a3}\text{-}(R_3)_{b3}]$, S, or O;

$X_2$ is $N[(L_4)_{a4}\text{-}(R_4)_{b4}]$, $C[(L_5)_{a5}\text{-}(R_5)_{b5}][(L_6)_{a6}\text{-}(R_6)_{b6}]$, $Si[(L_5)_{a5}\text{-}(R_5)_{b5}][(L_6)_{a6}\text{-}(R_6)_{b6}]$, S, or O;

$X_3$ is $N[(L_7)_{a7}\text{-}(R_7)_{b7}]$, $C[(L_8)_{a8}\text{-}(R_8)_{b8}][(L_9)_{a9}\text{-}(R_9)_{b9}]$, $Si[(L_8)_{a8}\text{-}(R_8)_{b8}][(L_9)_{a9}\text{-}(R_9)_{b9}]$, S, or O;

when $X_2$ is $N[(L_4)_{a4}\text{-}(R_4)_{b4}]$, i) $X_1$ is $C[(L_2)_{a2}\text{-}(R_2)_{b2}][(L_3)_{a3}\text{-}(R_3)_{b3}]$ or $Si[(L_2)_{a2}\text{-}(R_2)_{b2}][(L_3)_{a3}\text{-}(R_3)_{b3}]$, and $X_3$ is $N[(L_7)_{a7}\text{-}(R_7)_{b7}]$, $C[(L_8)_{a8}\text{-}(R_8)_{b8}][(L_9)_{a9}\text{-}(R_9)_{b9}]$, $Si[(L_8)_{a8}\text{-}(R_8)_{b8}][(L_9)_{a9}\text{-}(R_9)_{b9}]$, S, or O, or ii) $X_1$ is $N[(L_1)_{a1}\text{-}(R_1)_{b1}]$, S, or O, and $X_3$ is $C[(L_8)_{a8}\text{-}(R_8)][(L_9)_{a9}\text{-}(R_9)_{b9}]$ or $Si[(L_8)_{a8}\text{-}(R_8)_{b8}][(L_9)_{a9}\text{-}(R_9)_{b9}]$;

provided that a combination of $X_1$ is $C[(L_2)_{a2}\text{-}(R_2)_{b2}][(L_3)_{a3}\text{-}(R_3)_{b3}]$, $X_2$ is S, and $X_3$ is $C[(L_8)_{a8}\text{-}(R_8)_{b8}][(L_9)_{a9}\text{-}(R_9)_{b9}]$ is excluded;

$L_1$ to $L_9$, $L_{11}$, and $L_{12}$ are each independently a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted bivalent non-aromatic condensed polycyclic group, or a substituted or unsubstituted bivalent non-aromatic hetero-condensed polycyclic group, a1 to a9, a11, and a12 are each independently selected from an integer from 0 to 5;

$R_1$, $R_4$, and $R_7$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, or a substituted or unsubstituted monovalent non-aromatic condensed heteropolycyclic group;

$R_2$, $R_3$, $R_5$, $R_6$, $R_8$, $R_9$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), or —B($Q_6$)($Q_7$);

b1 to b9, b11, and b12 are each independently selected from an integer from 1 to 10;

c11 and c12 are each independently 1, 2, 3, or 4;

when c11 is 2 or more, at least two *-($L_{11}$)$_{a11}$-($R_{11}$)$_{b11}$ are identical or different;

when c12 is 2 or more, at least two *-($L_{12}$)$_{a12}$-($R_{12}$)$_{b12}$ are identical or different;

at least one of the substituted $C_3$-$C_{10}$ cycloalkylene group, the substituted $C_3$-$C_{10}$ heterocycloalkylene group, the substituted $C_3$-$C_{10}$ cycloalkenylene group substituted $C_3$-$C_{10}$ heterocycloalkenylene group substituted $C_6$-$C_{60}$ arylene group substituted $C_2$-$C_{60}$ heteroarylene group substituted bivalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, a substituted or unsubstituted $C_7$-$C_{60}$ arylalkyl group, the substituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, the substituted monovalent non-aromatic condensed polycyclic group, and the substituted monovalent non-aromatic condensed heteropolycyclic group may be substituted with a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), or —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); or —N($Q_{31}$)($Q_{32}$), —Si($Q_{33}$)($Q_{34}$)($Q_{35}$), or —B($Q_{36}$)($Q_{37}$); and $Q_1$ to $Q_7$, $Q_{11}$ to $Q_{17}$, $Q_{21}$ to $Q_{27}$, and $Q_{31}$ to $Q_{37}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group; or a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group.

Another aspect provides an organic light-emitting device including:
a first electrode;
a second electrode; and
an organic layer disposed between the first electrode and the second electrode,
wherein the organic layer includes an emission layer and at least one of the condensed cyclic compound represented by Formula 1.

BRIEF DESCRIPTION OF THE DRAWINGS

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, a condensed cyclic compound according to an embodiment is represented by Formula 1 below:

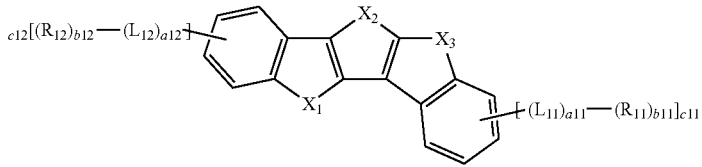

Formula 1

In Formula 1,
$X_1$ is $N[(L_1)_{a1}\text{-}(R_1)_{b1}]$, $C[(L_2)_{a2}\text{-}(R_2)_{b2}][(L_3)_{a3}\text{-}(R_3)_{b3}]$, $Si[(L_2)_{a2}\text{-}(R_2)_{b2}][(L_3)_{a3}\text{-}(R_3)_{b3}]$, S, or O;
$X_2$ is $N[(L_4)_{a4}\text{-}(R_4)_{b4}]$, $C[(L_5)_{a5}\text{-}(R_5)_{b5}][(L_6)_{a6}\text{-}(R_6)_{b6}]$, $Si[(L_5)_{a5}\text{-}(R_5)_{b5}][(L_6)_{a6}\text{-}(R_6)_{b6}]$, S, or O; and
$X_3$ is $N[(L_7)_{a7}\text{-}(R_7)_{b7}]$, $C[(L_8)_{a8}\text{-}(R_8)_{b8}][(L_9)_{a9}\text{-}(R_9)_{b9}]$, $Si[(L_8)_{a8}\text{-}(R_8)_{b8}][(L_9)_{a9}\text{-}(R_9)_{b9}]$, S, or O.

In Formula 1,
when $X_2$ is $N[(L_4)_{a4}\text{-}(R_4)_{b4}]$,
i) $X_1$ is $C[(L_2)_{a2}\text{-}(R_2)_{b2}][(L_3)_{a3}\text{-}(R_3)_{b3}]$ or $Si[(L_2)_{a2}\text{-}(R_2)_{b2}][(L_3)_{a3}\text{-}(R_3)_{b3}]$, and $X_3$ is $N[(L_7)_{a7}\text{-}(R_7)_{b7}]$, $C[(L_8)_{a8}\text{-}(R_8)_{b8}][(L_9)_{a9}\text{-}(R_9)_{b9}]$, $Si[(L_8)_{a8}\text{-}(R_8)_{b8}][(L_9)_{a9}\text{-}(R_9)_{b9}]$, S, or O, or ii) $X_1$ is $N[(L_1)_{a1}\text{-}(R_1)_{b1}]$, S, or O, and $X_3$ is $C[(L_8)_{a8}\text{-}(R_8)_{b8}][(L_9)_{a9}\text{-}(R_9)_{b9}]$ or $Si[(L_8)_{a8}\text{-}(R_8)_{b8}][(L_9)_{a9}\text{-}(R_9)_{b9}]$.

That is, in Formula 1, when $X_2$ is $N[(L_4)_{a4}\text{-}(R_4)_{b4}]$, at least one of $X_1$ and $X_3$ necessarily includes C or Si.

A combination of $X_1$ is $C[(L_2)_{a2}\text{-}(R_2)_{b2}][(L_3)_{a3}\text{-}(R_3)_{b3}]$, $X_2$ is S, and $X_3$ is $C[(L_8)_{a8}\text{-}(R_8)_{b8}][(L_9)_{a9}\text{-}(R_9)_{b9}]$ in Formula 1 is excluded.

Accordingly, the condensed cyclic compound may be represented by one of Formulae 1(1) to 1(115) in which $X_1$, $X_2$, and $X_3$ are defined as below:

| Formula No. | $X_1$ | $X_2$ | $X_3$ |
|---|---|---|---|
| 1(1) | $C[(L_2)_{a2}\text{-}(R_2)_{b2}][(L_3)_{a3}\text{-}(R_3)_{b3}]$ | $N[(L_4)_{a4}\text{-}(R_4)_{b4}]$ | $N[(L_7)_{a7}\text{-}(R_7)_{b7}]$ |
| 1(2) | $C[(L_2)_{a2}\text{-}(R_2)_{b2}][(L_3)_{a3}\text{-}(R_3)_{b3}]$ | $N[(L_4)_{a4}\text{-}(R_4)_{b4}]$ | $C[(L_8)_{a8}\text{-}(R_8)_{b8}][(L_9)_{a9}\text{-}(R_9)_{b9}]$ |
| 1(3) | $C[(L_2)_{a2}\text{-}(R_2)_{b2}][(L_3)_{a3}\text{-}(R_3)_{b3}]$ | $N[(L_4)_{a4}\text{-}(R_4)_{b4}]$ | $Si[(L_8)_{a8}\text{-}(R_8)_{b8}][(L_9)_{a9}\text{-}(R_9)_{b9}]$ |
| 1(4) | $C[(L_2)_{a2}\text{-}(R_2)_{b2}][(L_3)_{a3}\text{-}(R_3)_{b3}]$ | $N[(L_4)_{a4}\text{-}(R_4)_{b4}]$ | S |
| 1(5) | $C[(L_2)_{a2}\text{-}(R_2)_{b2}][(L_3)_{a3}\text{-}(R_3)_{b3}]$ | $N[(L_4)_{a4}\text{-}(R_4)_{b4}]$ | O |
| 1(6) | $Si[(L_2)_{a2}\text{-}(R_2)_{b2}][(L_3)_{a3}\text{-}(R_3)_{b3}]$ | $N[(L_4)_{a4}\text{-}(R_4)_{b4}]$ | $N[(L_7)_{a7}\text{-}(R_7)_{b7}]$ |
| 1(7) | $Si[(L_2)_{a2}\text{-}(R_2)_{b2}][(L_3)_{a3}\text{-}(R_3)_{b3}]$ | $N[(L_4)_{a4}\text{-}(R_4)_{b4}]$ | $C[(L_8)_{a8}\text{-}(R_8)_{b8}][(L_9)_{a9}\text{-}(R_9)_{b9}]$ |
| 1(8) | $Si[(L_2)_{a2}\text{-}(R_2)_{b2}][(L_3)_{a3}\text{-}(R_3)_{b3}]$ | $N[(L_4)_{a4}\text{-}(R_4)_{b4}]$ | $Si[(L_8)_{a8}\text{-}(R_8)_{b8}][(L_9)_{a9}\text{-}(R_9)_{b9}]$ |
| 1(9) | $Si[(L_2)_{a2}\text{-}(R_2)_{b2}][(L_3)_{a3}\text{-}(R_3)_{b3}]$ | $N[(L_4)_{a4}\text{-}(R_4)_{b4}]$ | S |
| 1(10) | $Si[(L_2)_{a2}\text{-}(R_2)_{b2}][(L_3)_{a3}\text{-}(R_3)_{b3}]$ | $N[(L_4)_{a4}\text{-}(R_4)_{b4}]$ | O |
| 1(11) | $N[(L_1)_{a1}\text{-}(R_1)_{b1}]$ | $N[(L_4)_{a4}\text{-}(R_4)_{b4}]$ | $C[(L_8)_{a8}\text{-}(R_8)_{b8}][(L_9)_{a9}\text{-}(R_9)_{b9}]$ |
| 1(12) | $N[(L_1)_{a1}\text{-}(R_1)_{b1}]$ | $N[(L_4)_{a4}\text{-}(R_4)_{b4}]$ | $Si[(L_8)_{a8}\text{-}(R_8)_{b8}][(L_9)_{a9}\text{-}(R_9)_{b9}]$ |
| 1(13) | S | $N[(L_4)_{a4}\text{-}(R_4)_{b4}]$ | $C[(L_8)_{a8}\text{-}(R_8)_{b8}][(L_9)_{a9}\text{-}(R_9)_{b9}]$ |
| 1(14) | S | $N[(L_4)_{a4}\text{-}(R_4)_{b4}]$ | $Si[(L_8)_{a8}\text{-}(R_8)_{b8}][(L_9)_{a9}\text{-}(R_9)_{b9}]$ |
| 1(15) | O | $N[(L_4)_{a4}\text{-}(R_4)_{b4}]$ | $C[(L_8)_{a8}\text{-}(R_8)_{b8}][(L_9)_{a9}\text{-}(R_9)_{b9}]$ |
| 1(16) | O | $N[(L_4)_{a4}\text{-}(R_4)_{b4}]$ | $Si[(L_8)_{a8}\text{-}(R_8)_{b8}][(L_9)_{a9}\text{-}(R_9)_{b9}]$ |
| 1(17) | $N[(L_1)_{a1}\text{-}(R_1)_{b1}]$ | $C[(L_5)_{a5}\text{-}(R_5)_{b5}][(L_6)_{a6}\text{-}(R_6)_{b6}]$ | $N[(L_7)_{a7}\text{-}(R_7)_{b7}]$ |
| 1(18) | $N[(L_1)_{a1}\text{-}(R_1)_{b1}]$ | $C[(L_5)_{a5}\text{-}(R_5)_{b5}][(L_6)_{a6}\text{-}(R_6)_{b6}]$ | $C[(L_8)_{a8}\text{-}(R_8)_{b8}][(L_9)_{a9}\text{-}(R_9)_{b9}]$ |
| 1(19) | $N[(L_1)_{a1}\text{-}(R_1)b_1]$ | $C[(L_5)_{a5}\text{-}(R_5)_{b5}][(L_6)_{a6}\text{-}(R_6)_{b6}]$ | $Si[(L_8)_{a8}\text{-}(R_8)_{b8}][(L_9)_{a9}\text{-}(R_9)_{b9}]$ |
| 1(20) | $N[(L_1)_{a1}\text{-}(R_1)_{b1}]$ | $C[(L_5)_{a5}\text{-}(R_5)_{b5}][(L_6)_{a6}\text{-}(R_6)_{b6}]$ | S |
| 1(21) | $N[(L_1)_{a1}\text{-}(R_1)_{b1}]$ | $C[(L_5)_{a5}\text{-}(R_5)_{b5}][(L_6)_{a6}\text{-}(R_6)_{b6}]$ | O |
| 1(22) | $C[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | $N[(L_7)_{a7}\text{-}(R_7)_{b7}]$ |
| 1(23) | $C[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | $C[(L_8)_{a8}\text{-}(R_8)_{b8}][(L_9)_{a9}\text{-}(R_9)_{b9}]$ |
| 1(24) | $C[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | $Si[(L_8)_{a8}\text{-}(R_8)_{b8}][(L_9)_{a9}\text{-}(R_9)_{b9}]$ |
| 1(25) | $C[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | S |
| 1(26) | $C[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | O |
| 1(27) | $Si[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | $N[(L_7)_{a7}\text{-}(R_7)_{b7}]$ |
| 1(28) | $Si[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | $C[(L_8)_{a8}\text{-}(R_8)_{b8}][(L_9)_{a9}\text{-}(R_9)_{b9}]$ |
| 1(29) | $Si[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | $Si[(L_8)_{a8}\text{-}(R_8)_{b8}][(L_9)_{a9}\text{-}(R_9)_{b9}]$ |
| 1(30) | $Si[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | S |
| 1(31) | $Si[(L_2)_{a2}\text{-}(R_2)_{b2}][(L_3)_{a3}\text{-}(R_3)_{b3}]$ | $C[(L_5)_{a5}\text{-}(R_5)_{b5}][(L_6)_{a6}\text{-}(R_6)_{b6}]$ | O |
| 1(32) | S | $C[(L_5)_{a5}\text{-}(R_5)_{b5}][(L_6)_{a6}\text{-}(R_6)_{b6}]$ | $N[(L_7)_{a7}\text{-}(R_7)_{b7}]$ |
| 1(33) | S | $C[(L_5)_{a5}\text{-}(R_5)_{b5}][(L_6)_{a6}\text{-}(R_6)_{b6}]$ | $C[(L_8)_{a8}\text{-}(R_8)_{b8}][(L_9)_{a9}\text{-}(R_9)_{b9}]$ |
| 1(34) | S | $C[(L_5)_{a5}\text{-}(R_5)_{b5}][(L_6)_{a6}\text{-}(R_6)_{b6}]$ | $Si[(L_8)_{a8}\text{-}(R_8)_{b8}][(L_9)_{a9}\text{-}(R_9)_{b9}]$ |
| 1(35) | S | $C[(L_5)_{a5}\text{-}(R_5)_{b5}][(L_6)_{a6}\text{-}(R_6)_{b6}]$ | S |
| 1(36) | S | $C[(L_5)_{a5}\text{-}(R_5)_{b5}][(L_6)_{a6}\text{-}(R_6)_{b6}]$ | O |
| 1(37) | O | $C[(L_5)_{a5}\text{-}(R_5)_{b5}][(L_6)_{a6}\text{-}(R_6)_{b6}]$ | $N[(L_7)_{a7}\text{-}(R_7)_{b7}]$ |
| 1(38) | O | $C[(L_5)_{a5}\text{-}(R_5)_{b5}][(L_6)_{a6}\text{-}(R_6)_{b6}]$ | $C[(L_8)_{a8}\text{-}(R_8)_{b8}][(L_9)_{a9}\text{-}(R_9)_{b9}]$ |
| 1(39) | O | $C[(L_5)_{a5}\text{-}(R_5)_{b5}][(L_6)_{a6}\text{-}(R_6)_{b6}]$ | $Si[(L_8)_{a8}\text{-}(R_8)_{b8}][(L_9)_{a9}\text{-}(R_9)_{b9}]$ |
| 1(40) | O | $C[(L_5)_{a5}\text{-}(R_5)_{b5}][(L_6)_{a6}\text{-}(R_6)_{b6}]$ | S |
| 1(41) | O | $C[(L_5)_{a5}\text{-}(R_5)_{b5}][(L_6)_{a6}\text{-}(R_6)_{b6}]$ | O |
| 1(42) | $N[(L_1)_{a1}\text{-}(R_1)_{b1}]$ | $Si[(L_5)_{a5}\text{-}(R_5)_{b5}][(L_6)_{a6}\text{-}(R_6)_{b6}]$ | $N[(L_7)_{a7}\text{-}(R_7)_{b7}]$ |
| 1(43) | $N[(L_1)_{a1}\text{-}(R_1)_{b1}]$ | $Si[(L_5)_{a5}\text{-}(R_5)_{b5}][(L_6)_{a6}\text{-}(R_6)_{b6}]$ | $C[(L_8)_{a8}\text{-}(R_8)_{b8}][(L_9)_{a9}\text{-}(R_9)_{b9}]$ |
| 1(44) | $N[(L_1)_{a1}\text{-}(R_1)_{b1}]$ | $Si[(L_5)_{a5}\text{-}(R_5)_{b5}][(L_6)_{a6}\text{-}(R_6)_{b6}]$ | $Si[(L_8)_{a8}\text{-}(R_8)_{b8}][(L_9)_{a9}\text{-}(R_9)_{b9}]$ |
| 1(45) | $N[(L_1)_{a1}\text{-}(R_1)_{b1}]$ | $Si[(L_5)_{a5}\text{-}(R_5)_{b5}][(L_6)_{a6}\text{-}(R_6)_{b6}]$ | S |
| 1(46) | $N[(L_1)_{a1}\text{-}(R_1)_{b1}]$ | $Si[(L_5)_{a5}\text{-}(R_5)_{b5}][(L_6)_{a6}\text{-}(R_6)_{b6}]$ | O |
| 1(47) | $C[(L_2)_{a2}\text{-}(R_2)_{b2}][(L_3)_{a3}\text{-}(R_3)_{b3}]$ | $Si[(L_5)_{a5}\text{-}(R_5)_{b5}][(L_6)_{a6}\text{-}(R_6)_{b6}]$ | $N[(L_7)_{a7}\text{-}(R_7)_{b7}]$ |
| 1(48) | $C[(L_2)_{a2}\text{-}(R_2)_{b2}][(L_3)_{a3}\text{-}(R_3)_{b3}]$ | $Si[(L_5)_{a5}\text{-}(R_5)_{b5}][(L_6)_{a6}\text{-}(R_6)_{b6}]$ | $C[(L_8)_{a8}\text{-}(R_8)_{b8}][(L_9)_{a9}\text{-}(R_9)_{b9}]$ |

-continued

| Formula No. | $X_1$ | $X_2$ | $X_3$ |
|---|---|---|---|
| 1(49) | $C[(L_2)_{a2}-(R_2)_{b2}][(L_3)_{a3}-(R_3)_{b3}]$ | $Si[(L_5)_{a5}-(R_5)_{b5}][(L_6)_{a6}-(R_6)_{b6}]$ | $Si[(L_8)_{a8}-(R_8)_{b8}][(L_9)_{a9}-(R_9)_{b9}]$ |
| 1(50) | $C[(L_2)_{a2}-(R_2)_{b2}][(L_3)_{a3}-(R_3)_{b3}]$ | $Si[(L_5)_{a5}-(R_5)_{b5}][(L_6)_{a6}-(R_6)_{b6}]$ | S |
| 1(51) | $C[(L_2)_{a2}-(R_2)_{b2}][(L_3)_{a3}-(R_3)_{b3}]$ | $Si[(L_5)_{a5}-(R_5)_{b5}][(L_6)_{a6}-(R_6)_{b6}]$ | O |
| 1(52) | $Si[(L_2)_{a2}-(R_2)_{b2}][(L_3)_{a3}-(R_3)_{b3}]$ | $Si[(L_5)_{a5}-(R_5)_{b5}][(L_6)_{a6}-(R_6)_{b6}]$ | $N[(L_7)_{a7}-(R_7)_{b7}]$ |
| 1(53) | $Si[(L_2)_{a2}-(R_2)_{b2}][(L_3)_{a3}-(R_3)_{b3}]$ | $Si[(L_5)_{a5}-(R_5)_{b5}][(L_6)_{a6}-(R_6)_{b6}]$ | $C[(L_8)_{a8}-(R_8)_{b8}][(L_9)_{a9}-(R_9)_{b9}]$ |
| 1(54) | $Si[(L_2)_{a2}-(R_2)_{b2}][(L_3)_{a3}-(R_3)_{b3}]$ | $Si[(L_5)_{a5}-(R_5)_{b5}][(L_6)_{a6}-(R_6)_{b6}]$ | $Si[(L_8)_{a8}-(R_8)_{b8}][(L_9)_{a9}-(R_9)_{b9}]$ |
| 1(55) | $Si[(L_2)_{a2}-(R_2)_{b2}][(L_3)_{a3}-(R_3)_{b3}]$ | $Si[(L_5)_{a5}-(R_5)_{b5}][(L_6)_{a6}-(R_6)_{b6}]$ | S |
| 1(56) | $Si[(L_2)_{a2}-(R_2)_{b2}][(L_3)_{a3}-(R_3)_{b3}]$ | $Si[(L_5)_{a5}-(R_5)_{b5}][(L_6)_{a6}-(R_6)_{b6}]$ | O |
| 1(57) | S | $Si[(L_5)_{a5}-(R_5)_{b5}][(L_6)_{a6}-(R_6)_{b6}]$ | $N[(L_7)_{a7}-(R_7)_{b7}]$ |
| 1(58) | S | $Si[(L_5)_{a5}-(R_5)_{b5}][(L_6)_{a6}-(R_6)_{b6}]$ | $C[(L_8)_{a8}-(R_8)_{b8}][(L_9)_{a9}-(R_9)_{b9}]$ |
| 1(59) | S | $Si[(L_5)_{a5}-(R_5)_{b5}][(L_6)_{a6}-(R_6)_{b6}]$ | $Si[(L_8)_{a8}-(R_8)_{b8}][(L_9)_{a9}-(R_9)_{b9}]$ |
| 1(60) | S | $Si[(L_5)_{a5}-(R_5)_{b5}][(L_6)_{a6}-(R_6)_{b6}]$ | S |
| 1(61) | S | $Si[(L_5)_{a5}-(R_5)_{b5}][(L_6)_{a6}-(R_6)_{b6}]$ | O |
| 1(62) | O | $Si[(L_5)_{a5}-(R_5)_{b5}][(L_6)_{a6}-(R_6)_{b6}]$ | $N[(L_7)_{a7}-(R_7)_{b7}]$ |
| 1(63) | O | $Si[(L_5)_{a5}-(R_5)_{b5}][(L_6)_{a6}-(R_6)_{b6}]$ | $C[(L_8)_{a8}-(R_8)_{b8}][(L_9)_{a9}-(R_9)_{b9}]$ |
| 1(64) | O | $Si[(L_5)_{a5}-(R_5)_{b5}][(L_6)_{a6}-(R_6)_{b6}]$ | $Si[(L_8)_{a8}-(R_8)_{b8}][(L_9)_{a9}-(R_9)_{b9}]$ |
| 1(65) | O | $Si[(L_5)_{a5}-(R_5)_{b5}][(L_6)_{a6}-(R_6)_{b6}]$ | S |
| 1(66) | O | $Si[(L_5)_{a5}-(R_5)_{b5}][(L_6)_{a6}-(R_6)_{b6}]$ | O |
| 1(67) | $N[(L_1)_{a1}-(R_1)_{b1}]$ | S | $N[(L_7)_{a7}-(R_7)_{b7}]$ |
| 1(68) | $N[(L_1)_{a1}-(R_1)_{b1}]$ | S | $C[(L_8)_{a8}-(R_8)_{b8}][(L_9)_{a9}-(R_9)_{b9}]$ |
| 1(69) | $N[(L_1)_{a1}-(R_1)_{b1}]$ | S | $Si[(L_8)_{a8}-(R_8)_{b8}][(L_9)_{a9}-(R_9)_{b9}]$ |
| 1(70) | $N[(L_1)_{a1}-(R_1)_{b1}]$ | S | S |
| 1(71) | $N[(L_1)_{a1}-(R_1)_{b1}]$ | S | O |
| 1(72) | $C[(L_2)_{a2}-(R_2)_{b2}][(L_3)_{a3}-(R_3)_{b3}]$ | S | $N[(L_7)_{a7}-(R_7)_{b7}]$ |
| 1(73) | $C[(L_2)_{a2}-(R_2)_{b2}][(L_3)_{a3}-(R_3)_{b3}]$ | S | $Si[(L_8)_{a8}-(R_8)_{b8}][(L_9)_{a9}-(R_9)_{b9}]$ |
| 1(74) | $C[(L_2)_{a2}-(R_2)_{b2}][(L_3)_{a3}-(R_3)_{b3}]$ | S | S |
| 1(75) | $C[(L_2)_{a2}-(R_2)_{b2}][(L_3)_{a3}-(R_3)_{b3}]$ | S | O |
| 1(76) | $Si[(L_2)_{a2}-(R_2)_{b2}][(L_3)_{a3}-(R_3)_{b3}]$ | S | $N[(L_7)_{a7}-(R_7)_{b7}]$ |
| 1(77) | $Si[(L_2)_{a2}-(R_2)_{b2}][(L_3)_{a3}-(R_3)_{b3}]$ | S | $C[(L_8)_{a8}-(R_8)_{b8}][(L_9)_{a9}-(R_9)_{b9}]$ |
| 1(78) | $Si[(L_2)_{a2}-(R_2)_{b2}][(L_3)_{a3}-(R_3)_{b3}]$ | S | $Si[(L_8)_{a8}-(R_8)_{b8}][(L_9)_{a9}-(R_9)_{b9}]$ |
| 1(79) | $Si[(L_2)_{a2}-(R_2)_{b2}][(L_3)_{a3}-(R_3)_{b3}]$ | S | S |
| 1(80) | $Si[(L_2)_{a2}-(R_2)_{b2}][(L_3)_{a3}-(R_3)_{b3}]$ | S | O |
| 1(81) | S | S | $N[(L_7)_{a7}-(R_7)_{b7}]$ |
| 1(82) | S | S | $C[(L_8)_{a8}-(R_8)_{b8}][(L_9)_{a9}-(R_9)_{b9}]$ |
| 1(83) | S | S | $Si[(L_8)_{a8}-(R_8)_{b8}][(L_9)_{a9}-(R_9)_{b9}]$ |
| 1(84) | S | S | S |
| 1(85) | S | S | O |
| 1(86) | O | S | $N[(L_7)_{a7}-(R_7)_{b7}]$ |
| 1(87) | O | S | $C[(L_8)_{a8}-(R_8)_{b8}][(L_9)_{a9}-(R_9)_{b9}]$ |
| 1(88) | O | S | $Si[(L_8)_{a8}-(R_8)_{b8}][(L_9)_{a9}-(R_9)_{b9}]$ |
| 1(89) | O | S | S |
| 1(90) | O | S | O |
| 1(91) | $N[(L_1)_{a1}-(R_1)_{b1}]$ | O | $N[(L_7)_{a7}-(R_7)_{b7}]$ |
| 1(92) | $N[(L_1)_{a1}-(R_1)_{b1}]$ | O | $C[(L_8)_{a8}-(R_8)_{b8}][(L_9)_{a9}-(R_9)_{b9}]$ |
| 1(93) | $N[(L_1)_{a1}-(R_1)_{b1}]$ | O | $Si[(L_8)_{a8}-(R_8)_{b8}][(L_9)_{a9}-(R_9)_{b9}]$ |
| 1(94) | $N[(L_1)_{a1}-(R_1)_{b1}]$ | O | S |
| 1(95) | $N[(L_1)_{a1}-(R_1)_{b1}]$ | O | O |
| 1(96) | $C[(L_2)_{a2}-(R_2)_{b2}][(L_3)_{a3}-(R_3)_{b3}]$ | O | $N[(L_7)_{a7}-(R_7)_{b7}]$ |
| 1(97) | $C[(L_2)_{a2}-(R_2)_{b2}][(L_3)_{a3}-(R_3)_{b3}]$ | O | $C[(L_8)_{a8}-(R_8)_{b8}][(L_9)_{a9}-(R_9)_{b9}]$ |
| 1(98) | $C[(L_2)_{a2}-(R_2)_{b2}][(L_3)_{a3}-(R_3)_{b3}]$ | O | $Si[(L_8)_{a8}-(R_8)_{b8}][(L_9)_{a9}-(R_9)_{b9}]$ |
| 1(99) | $C[(L_2)_{a2}-(R_2)_{b2}][(L_3)_{a3}-(R_3)_{b3}]$ | O | S |
| 1(100) | $C[(L_2)_{a2}-(R_2)_{b2}][(L_3)_{a3}-(R_3)_{b3}]$ | O | O |
| 1(101) | $Si[(L_2)_{a2}-(R_2)_{b2}][(L_3)_{a3}-(R_3)_{b3}]$ | O | $N[(L_7)_{a7}-(R_7)_{b7}]$ |
| 1(102) | $Si[(L_2)_{a2}-(R_2)_{b2}][(L_3)_{a3}-(R_3)_{b3}]$, | O | $C[(L_8)_{a8}-(R_8)_{b8}][(L_9)_{a9}-(R_9)_{b9}]$ |
| 1(103) | $Si[(L_2)_{a2}-(R_2)_{b2}][(L_3)_{a3}-(R_3)_{b3}]$, | O | $Si[(L_8)_{a8}-(R_8)_{b8}][(L_9)_{a9}-(R_9)_{b9}]$ |
| 1(104) | $Si[(L_2)_{a2}-(R_2)_{b2}][(L_3)_{a3}-(R_3)_{b3}]$, | O | S |
| 1(105) | $Si[(L_2)_{a2}-(R_2)_{b2}][(L_3)_{a3}-(R_3)_{b3}]$, | O | O |
| 1(106) | S | O | $N[(L_7)_{a7}-(R_7)_{b7}]$ |
| 1(107) | S | O | $C[(L_8)_{a8}-(R_8)_{b8}][(L_9)_{a9}-(R_9)_{b9}]$ |
| 1(108) | S | O | $Si[(L_8)_{a8}-(R_8)_{b8}][(L_9)_{a9}-(R_9)_{b9}]$ |
| 1(109) | S | O | S |
| 1(110) | S | O | O |
| 1(111) | O | O | $N[(L_7)_{a7}-(R_7)_{b7}]$ |
| 1(112) | O | O | $C[(L_8)_{a8}-(R_8)_{b8}][(L_9)_{a9}-(R_9)_{b9}]$ |
| 1(113) | O | O | $Si[(L_8)_{a8}-(R_8)_{b8}][(L_9)_{a9}-(R_9)_{b9}]$ |
| 1(114) | O | O | S |
| 1(115) | O | O | O |

According to another embodiment, in Formula 1, $X_2$ may be $C[(L_5)_{a5}-(R_5)_{b5}][(L_6)_{a6}-(R_6)_{b6}]$, $Si[(L_5)_{a5}-(R_5)_{b5}][(L_6)_{a6}-(R_6)_{b6}]$, S, or O (as shown in Formulae 1(17) to 1(115)).

According to another embodiment, in Formula 1, $X_1=X_2=X_3$; or $X_1=X_2$; $X_2 \neq X_3$; or
$X_1 \neq X_2$; $X_2=X_3$; or
$X_1 \neq X_2 \neq X_3$.

For example, in Formula 1,
$X_1=X_2$ and $X_2 \neq X_3$;
$X_1 \neq X_2$ and $X_2=X_3$; or $X_1 \neq X_2 \neq X_3$, but $X_1$, $X_2$, and $X_3$ may not always satisfy these relationships.

According to another embodiment, in Formula 1, $X_1$ may be $N[(L_1)_{a1}$-$(R_1)_{b1}]$;

$X_2$ may be $N[(L_4)_{a4}$-$(R_4)_{b4}]$; or $X_3$ may be $N[(L_7)_{a7}$-$(R_7)_{b7}]$ That is, at least one of $X_1$, $X_2$, and $X_3$ in Formula 1 may include N.

According to another embodiment, in Formula 1, $X_1$ may be $N[(L_1)_{a1}$-$(R_1)_{b1}]$ and $X_3$ may be $N[(L_7)_{a7}$-$(R_7)_{b7}]$ (see Formula 1(91)).

According to another embodiment, the condensed cyclic compound may be represented by Formulae 1(81), 1(70), 1(15), 1(92), or 1(106), but may also be represented by other formulae.

$L_1$ to $L_9$, $L_{11}$, and $L_{12}$ in Formula 1 may be each independently a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted bivalent non-aromatic condensed polycyclic group, or a substituted or unsubstituted divalent non-aromatic heterocondensed polycyclic group.

According to an embodiment, in Formula 1, $L_1$ to $L_9$, $L_{11}$, and $L_{12}$ are each independently phenylene group, pentalenylene group, indenylene group, naphthylene group, azulenylene group, heptalenylene group, indacenylene group, acenaphthylene group, fluorenylene group, spiro-fluorenylene group, benzofluorenylene group, dibenzofluorenylene group, phenalenylene group, phenanthrenylene group, anthracenylene group, fluoranthenylene group, triphenylenylene group, pyrenylene group, chrysenylene group, naphthacenylene group, picenylene group, perylenylene group, pentaphenylene group, hexacenylene group, pentacenylene group, rubicenylene group, coronenylene group, ovalenylene group, pyrrolylene group, thiophenylene group, furanylene group, imidazolylene group, pyrazolylene group, thiazolylene group, isothiazolylene group, oxazolylene group, isooxazolylene group, pyridinylene group, pyrazinylene group, pyrimidinylene group, pyridazinylene group, isoindolylene group, indolylene group, indazolylene group, purinylene group, quinolinylene group, isoquinolinylene group, benzoquinolinylene group, phthalazinylene group, naphthyridinylene group, quinoxalinylene group, quinazolinylene group, cinnolinylene group, carbazolylene group, phenanthridinylene group, acridinylene group, phenanthrolinylene group, phenazinylene group, benzoimidazolylene group, benzofuranylene group, benzothiophenylene group, isobenzothiazolylene group, benzooxazolylene group, isobenzooxazolylene group, triazolylene group, tetrazolylene group, oxadiazolylene group, triazinylene group, dibenzofuranylene group, dibenzothiophenylene group, benzocarbazolylene group, dibenzocarbazolylene, or imidazopyridinylene group or imidazopyrimidinylene group; or phenylene group, pentalenylene group, indenylene group, naphthylene group, azulenylene group, heptalenylene group, indacenylene group, acenaphthylene group, fluorenylene group, spiro-fluorenylene group, benzofluorenylene group, dibenzofluorenylene group, phenalenylene group, phenanthrenylene group, anthracenylene group, fluoranthenylene group, triphenylenylene group, pyrenylene group, chrysenylene group, naphthacenylene group, picenylene group, perylenylene group, pentaphenylene group, hexacenylene group, pentacenylene group, rubicenylene group, coronenylene group, ovalenylene group, pyrrolylene group, thiophenylene group, furanylene group, imidazolylene group, pyrazolylene group, thiazolylene group, isothiazolylene group, oxazolylene group, isooxazolylene group, pyridinylene group, pyrazinylene group, pyrimidinylene group, pyridazinylene group, isoindolylene group, indolylene group, indazolylene group, purinylene group, quinolinylene group, isoquinolinylene group, benzoquinolinylene group, phthalazinylene group, naphthyridinylene group, quinoxalinylene group, quinazolinylene group, cinnolinylene group, carbazolylene group, phenanthridinylene group, acridinylene group, phenanthrolinylene group, phenazinylene group, benzoimidazolylene group, benzofuranylene group, benzothiophenylene group, isobenzothiazolylene group, benzooxazolylene group, isobenzooxazolylene group, triazolylene group, tetrazolylene group, oxadiazolylene group, triazinylene group, dibenzofuranylene group, dibenzothiophenylene group, benzocarbazolylene group, dibenzocarbazolylene, imidazopyridinylene group, or imidazopyrimidinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyridinyl group, and —Si$(Q_{33})(Q_{34})(Q_{35})$. Herein, $Q_{33}$ to $Q_{35}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrysenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group.

According to another embodiment, in Formula 1, $L_1$ to $L_9$, $L_{11}$, and $L_{12}$ are each independently represented by one of Formulae 2-1 to 2-33:
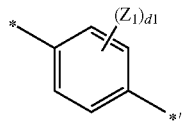
Formula 2-1

Formula 2-2
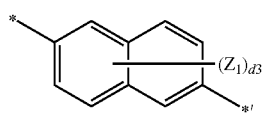
Formula 2-3
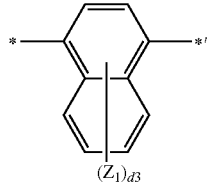
Formula 2-4
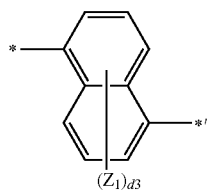
Formula 2-5
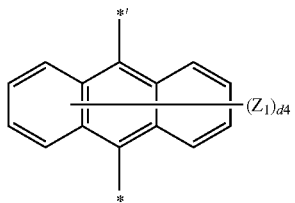
Formula 2-6
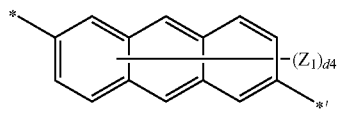
Formula 2-7
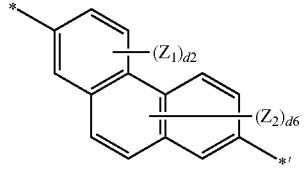
Formula 2-8
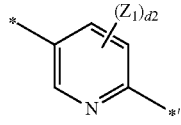
Formula 2-9
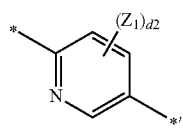
Formula 2-10
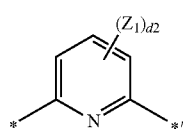
Formula 2-11
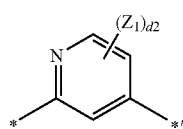
Formula 2-12
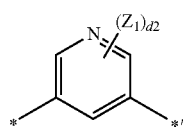
Formula 2-13
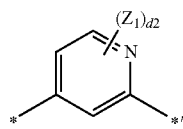
Formula 2-14
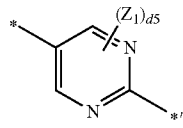
Formula 2-15
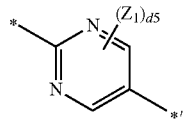
Formula 2-16
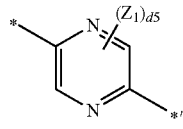
Formula 2-17
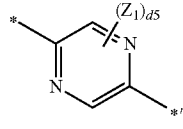
Formula 2-18
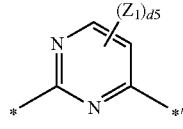
Formula 2-19
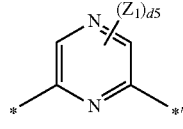
Formula 2-20

-continued

Formula 2-21
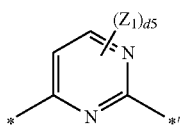

Formula 2-22
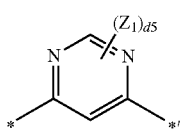

Formula 2-23
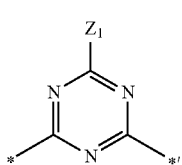

Formula 2-24
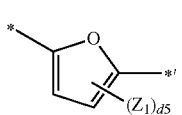

Formula 2-25
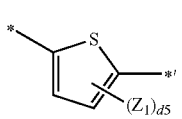

Formula 2-26
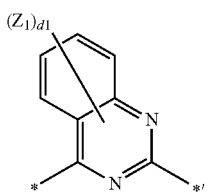

Formula 2-27
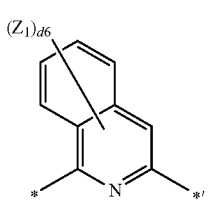

Formula 2-28
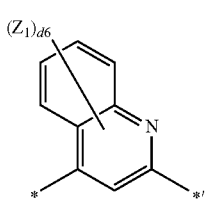

Formula 2-29
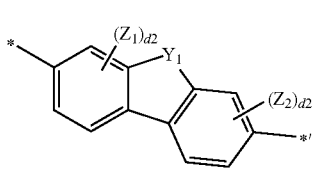

Formula 2-30
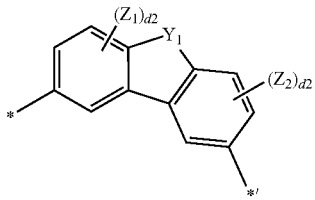

Formula 2-31
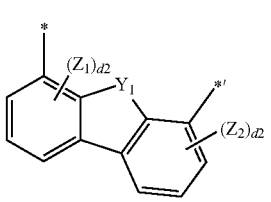

Formula 2-32
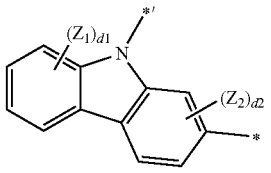

Formula 2-33
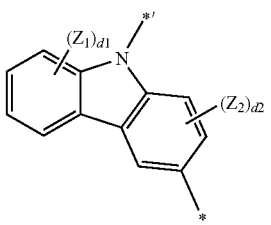

wherein in Formulae 2-1 to 2-33, $Y_1$ may be O, S, S(=O), S(=O)$_2$, C($Z_3$)($Z_4$), N($Z_5$), or Si($Z_6$)($Z_7$);

$Z_1$ to $Z_7$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic condensed heteropolycyclic group, —N($Q_{31}$)($Q_{32}$), —Si($Q_{33}$)($Q_{34}$)($Q_{35}$), or —B($Q_{31}$)($Q_{35}$) ($Q_{31}$ to $Q_{35}$ are understood by referring to the description provided herein);

d1 is an integer of 1 to 4;

d2 is an integer of 1 to 3;

d3 is an integer of 1 to 6;

d4 is an integer of 1 to 8;

d5 is 1 or 2; and d6 is an integer of 1 to 5; and

* and *' may each be a binding site to a neighboring atom.

For example,

* in Formulae 2-1 to 2-32 indicates a binding site to the core of Formula 1 or each of neighboring $L_1$ to $L_9$, $L_{11}$, and $L_{12}$, and

*' in Formulae 2-1 to 2-33 indicates a binding site to each of neighboring $L_1$ to $L_9$, $L_{11}$, and $L_{12}$ or each of $R_1$ to $R_9$, $R_{11}$, and $R_{12}$.

For example, $Z_1$ to $Z_7$ in Formulae 2-1 to 2-33 may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, quinoxalinyl group, or —Si($Q_{33}$)($Q_{34}$)($Q_{35}$), wherein $Q_{33}$ to $Q_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group, but they are not limited thereto.

According to another embodiment, $L_1$ to $L_9$, $L_{11}$, and $L_{12}$ in Formula 1 are each independently represented by one of Formulae 3-1 to 3-59:

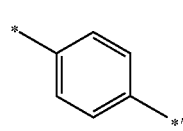

Formula 3-1

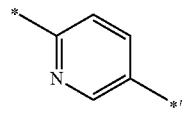

Formula 3-2

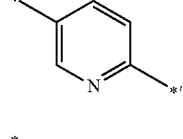

Formula 3-3

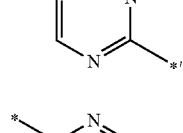

Formula 3-4

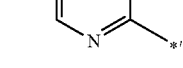

Formula 3-5

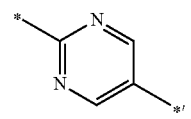

Formula 3-6

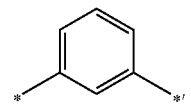

Formula 3-7

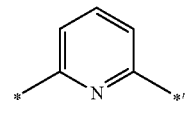

Formula 3-8

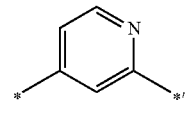

Formula 3-9

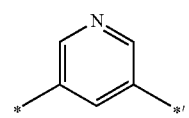

Formula 3-10

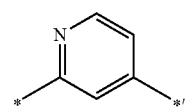

Formula 3-11

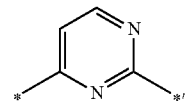

Formula 3-12

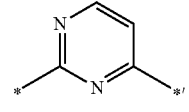

Formula 3-13

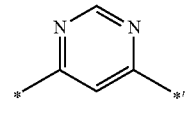

Formula 3-14

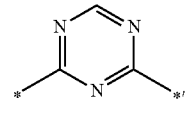

Formula 3-15

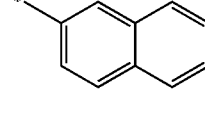

Formula 3-16

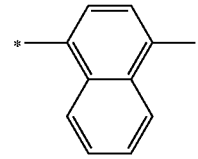

Formula 3-17

Formula 3-11 3-18
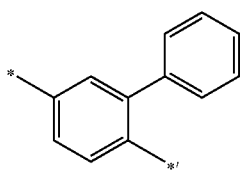
Formula 3-11 3-19
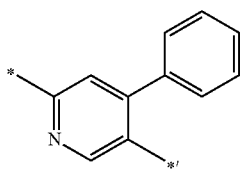
Formula 3-11 3-20
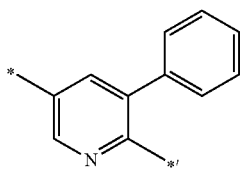
Formula 3-11 3-21
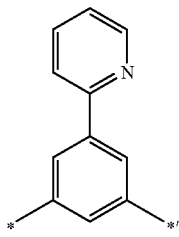
Formula 3-22
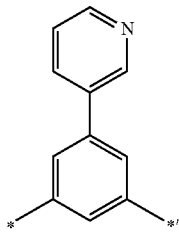
Formula 3-23
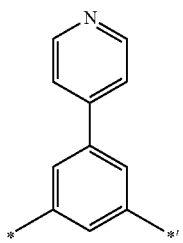
Formula 3-24
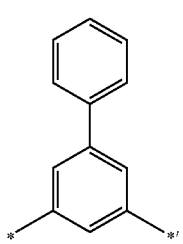
Formula 3-25
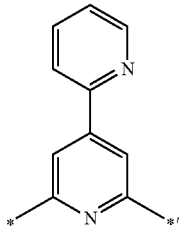
Formula 3-26
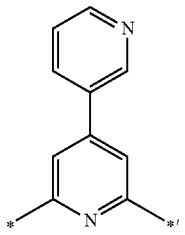
Formula 3-27
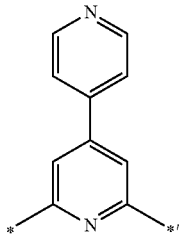
Formula 3-28
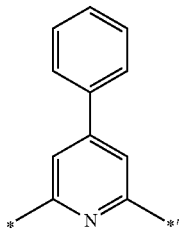
Formula 3-29
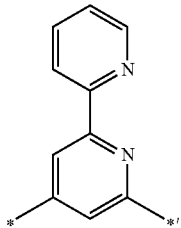
Formula 3-30
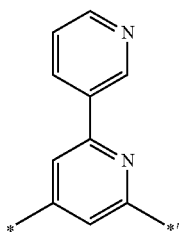

Formula 3-31
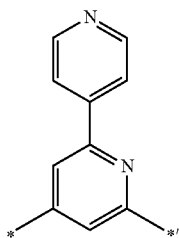
Formula 3-32
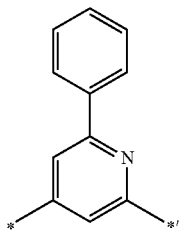
Formula 3-33
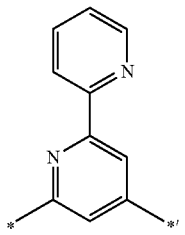
Formula 3-34
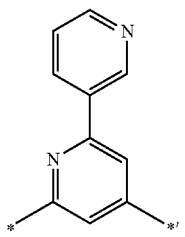
Formula 3-35
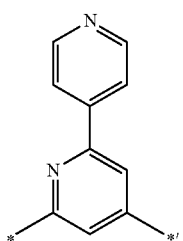
Formula 3-36
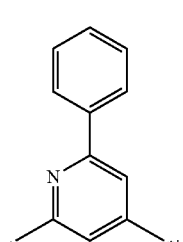
Formula 3-37
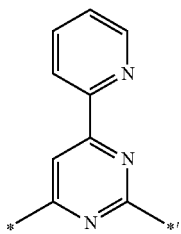
Formula 3-38
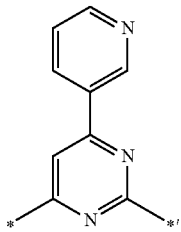
Formula 3-39
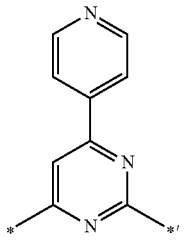
Formula 3-40
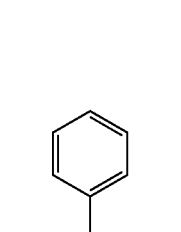
Formula 3-41
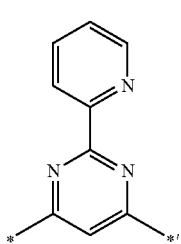
Formula 3-42
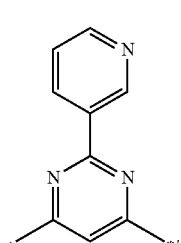

Formula 3-43
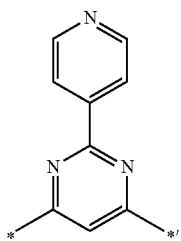
Formula 3-44
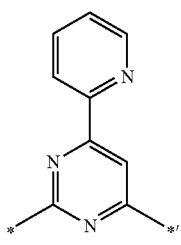
Formula 3-45
Formula 3-46
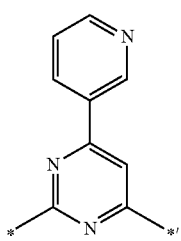
Formula 3-47
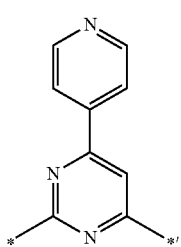
Formula 3-48
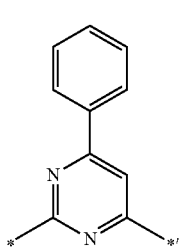
Formula 3-49
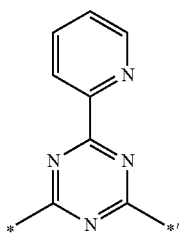
Formula 3-50
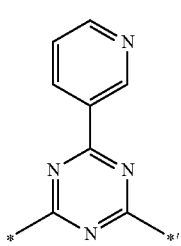
Formula 3-51
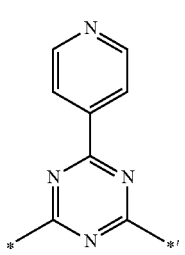
Formula 3-52
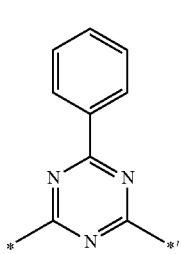
Formula 3-53
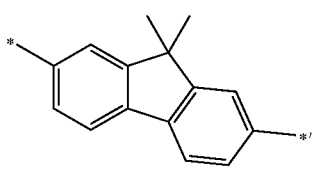
Formula 3-54
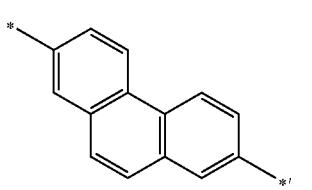

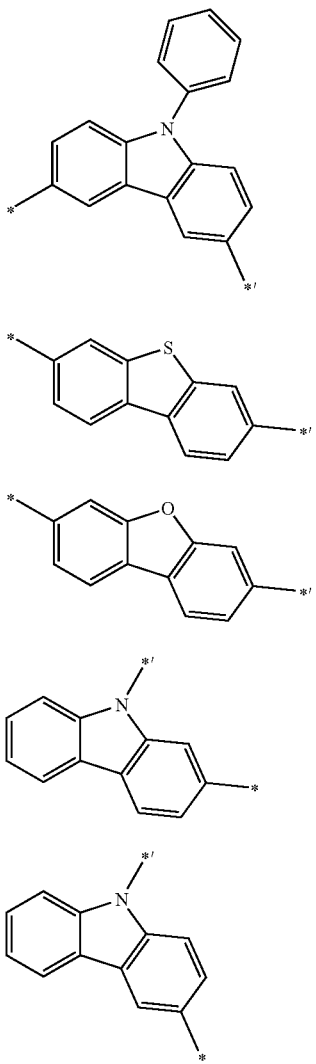

Formula 3-55

Formula 3-56

Formula 3-57

Formula 3-58

Formula 3-59 wherein in Formulae 3-1 to 3-57,

* and *' may each indicate a binding site to a neighboring atom.

a1 in Formula 1 indicates the number of $L_1$, and may be 0, 1, 2, 3, 4 or 5, for example, 0, 1 or 2, or for example, 0 or 1. When a1 is 0, $R_1$ may directly bind to N. When a1 is 2 or more, groups $L_1$ may be identical or different. a4 and a7 may be understood by referring to the description provided in connection with a1 and Formula 1.

a2 in Formula 1 indicates the number of $L_2$, and may be 0, 1, 2, 3, 4 or 5, for example, 0, 1 or 2, or for example, 0 or 1. When a2 is 0, $R_2$ may directly bind to C or Si. When a2 is 2 or more, groups $L_2$ may be identical or different. a3, a5, a6, a8, and a9 may be understood by referring to the description provided in connection with a2 and Formula 1.

a11 in Formula 1 indicates the number of $L_{11}$, and may be 0, 1, 2, 3, 4 or 5, for example, 0, 1 or 2, or for example, 0 or 1. When a11 is 0, $R_{11}$ may directly bind to the core of Formula 1. When a11 is 2 or more, groups $L_{11}$ may be identical or different.

a12 in Formula 1 indicates the number of $L_{12}$, and may be 0, 1, 2, 3, 4 or 5, for example, 0, 1 or 2, or for example, 0 or 1. When a12 is 0, $R_{12}$ may directly bind to the core of Formula 1. When a12 is 2 or more, groups $L_{12}$ may be identical or different.

$R_1$, $R_4$, and $R_7$ in Formula 1 may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, or a substituted or unsubstituted monovalent non-aromatic condensed heteropolycyclic group, and $R_2$, $R_3$, $R_5$, $R_6$, $R_8$, $R_9$, $R_{11}$, and $R_{12}$ in Formula 1 may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), or —B($Q_6$)($Q_7$).

$Q_1$ to $Q_7$, $Q_{11}$ to $Q_{17}$, $Q_{21}$ to $Q_{27}$, and $Q_{31}$ to $Q_{37}$ used herein are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least group one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group.

According to an embodiment, $R_1$, $R_4$, and $R_7$ may be each independently phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluoranthenyl group, triphenylenyl group, pyrenyl group, chrysenyl group, naphthacenyl group, picenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyrimidinyl group, or a group represented by

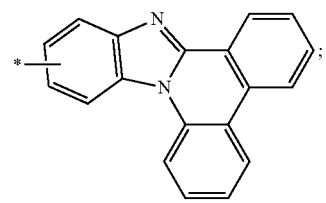

or phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluoranthenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyrimidinyl group, or a group represented by

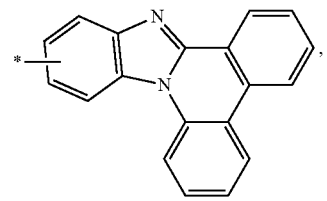

each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si(Q$_{33}$)(Q$_{34}$)(Q$_{35}$), phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, and imidazopyrimidinyl group, wherein Q$_{33}$ to Q$_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group, but they are not limited thereto.

According to another embodiment, R$_2$, R$_3$, R$_5$, R$_6$, R$_8$, R$_9$, R$_{11}$, and R$_{12}$ in Formula 1 may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, or a C$_1$-C$_{20}$ alkoxy group;

a C$_1$-C$_{20}$ alkyl group or a C$_1$-C$_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, phenyl group, naphthyl group, anthracenyl group, pyrenyl group, phenanthrenyl group, pyridinyl group, pyrimidinyl group, triazinyl group, quinolinyl group, isoquinolinyl group, and quinazolinyl group;

phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, picenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyrimidinyl group, or a group represented by

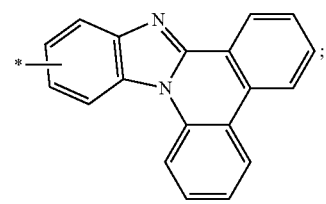

or phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyrimidinyl group, or a group represented by

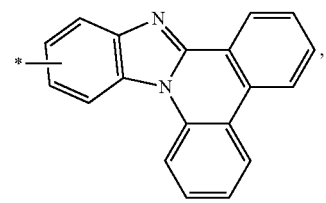

each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, and imidazopyridinyl group, wherein $Q_{33}$ to $Q_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group, but they are not limited thereto.

According to another embodiment, $R_1$, $R_4$, and $R_7$ are each independently selected from Formulae 4-1 to 4-27; and $R_2$, $R_3$, $R_5$, $R_6$, $R_8$, $R_9$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, phenyl group, naphthyl group, anthracenyl group, pyrenyl group, phenanthrenyl group, pyridinyl group, pyrimidinyl group, triazinyl group, quinolinyl group, isoquinolinyl group, and quinazolinyl; or one of Formulae 4-1 to 4-27:

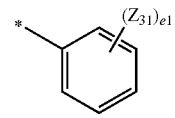

Formula 4-1

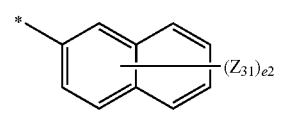

Formula 4-2

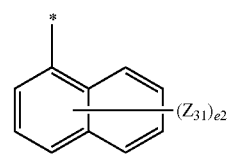

Formula 4-3

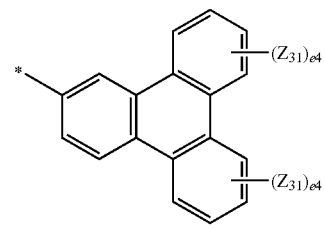

Formula 4-4

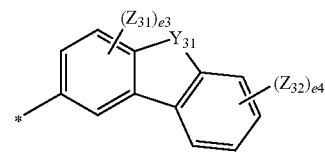

Formula 4-4

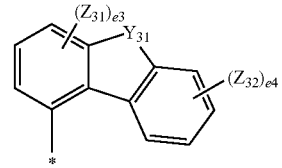

Formula 4-5

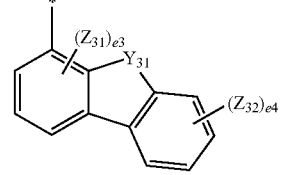

Formula 4-6

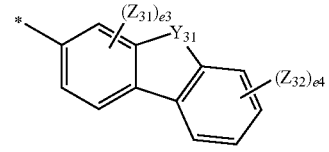

Formula 4-7

Formula 4-8

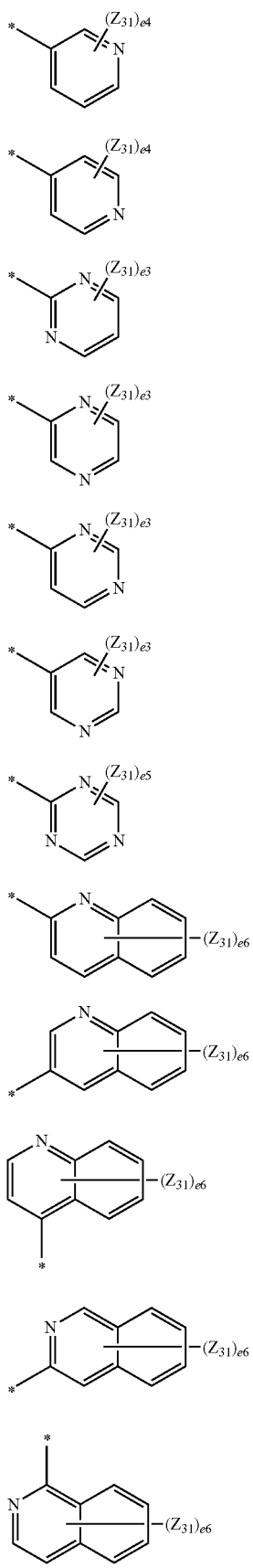

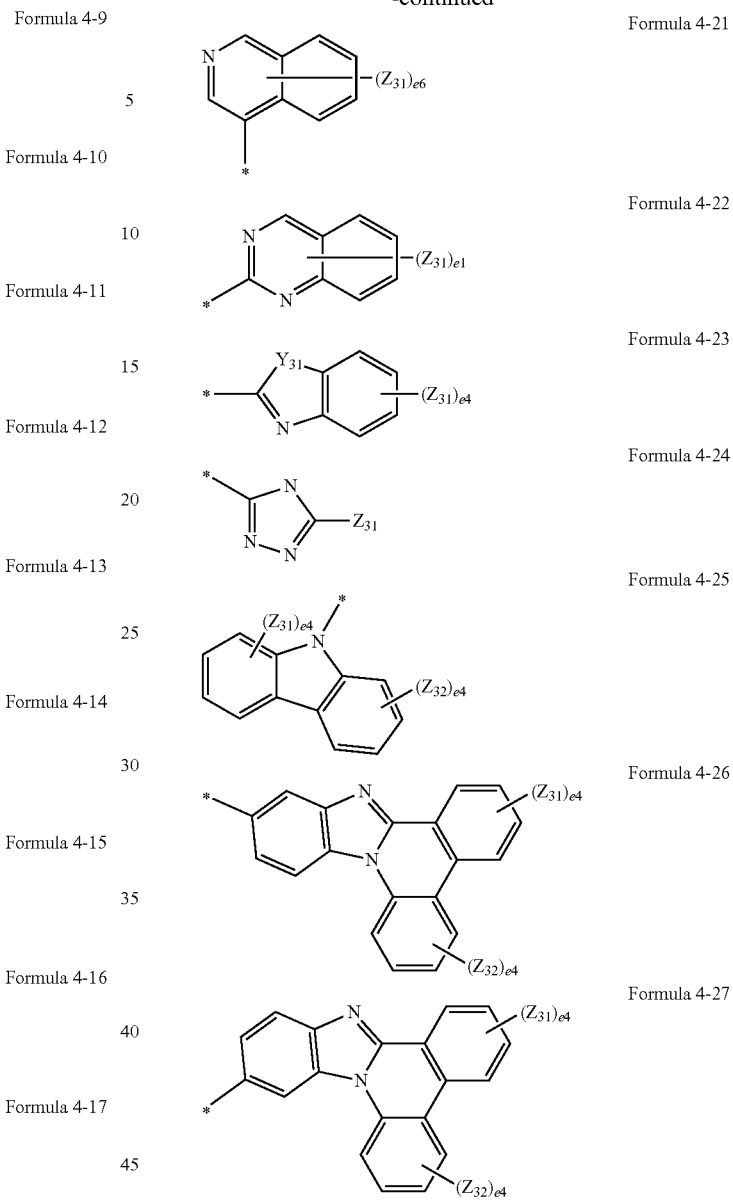

wherein in Formulae 4-1 to 4-27,

Y$_{31}$ may be O, S, C(Z$_{33}$)(Z$_{34}$), N(Z$_{35}$), or Si(Z$_{36}$)(Z$_{37}$);

wherein Z$_{31}$ to Z$_{37}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group, but they are not limited thereto.

e1 may be an integer of 1 to 5;

e2 may be an integer of 1 to 7;

e3 may be an integer of 1 to 3;

e4 may be an integer of 1 to 4;

e5 may be 1 or 2;

e6 may be an integer of 1 to 6; and

* indicates a binding site to a neighboring atom.

For example, e1, e2, e3, e4, e5, and e6 in Formulae 4-1 to 4-27 may be each independently 1 or 2.

According to another embodiment, in Formula 1, $R_1$, $R_4$, and $R_7$ are each independently selected from Formulae 5-1 to 5-51 below;

$R_2$, $R_3$, $R_5$, $R_6$, $R_8$, $R_9$, $R_{11}$, and $R_{12}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, phenyl group, naphthyl group, anthracenyl group, pyrenyl group, phenanthrenyl group, pyridinyl group, pyrimidinyl group, triazinyl group, quinolinyl group, isoquinolinyl group, and quinazolinyl; or one of Formulae 5-1 to 5-51:

Formula 5-1

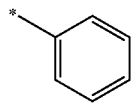

Formula 5-2

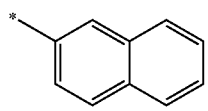

Formula 5-3

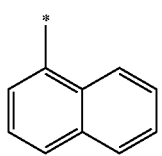

Formula 5-4

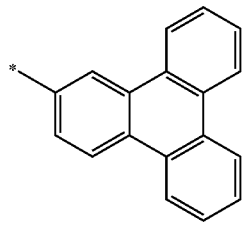

Formula 5-5

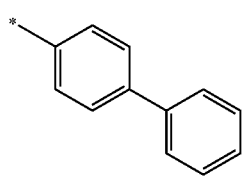

Formula 5-6

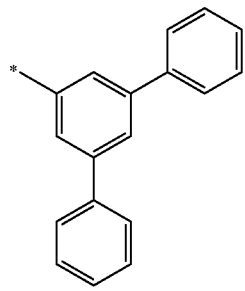

Formula 5-7

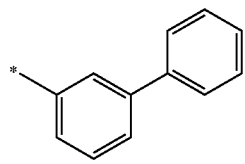

Formula 5-8

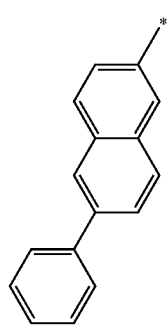

Formula 5-9

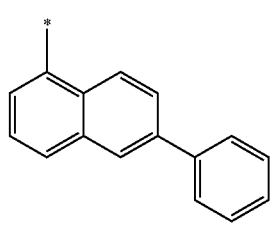

Formula 5-10

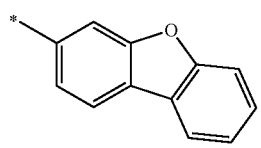

Formula 5-11

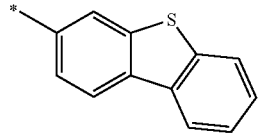

Formula 5-12

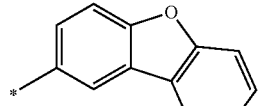

Formula 5-13

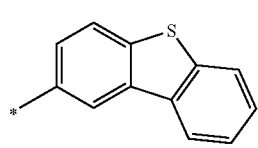

-continued
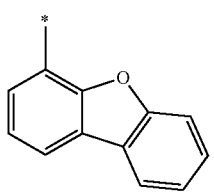
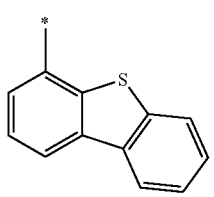
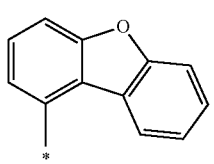
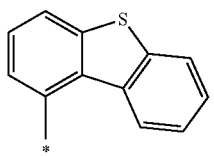
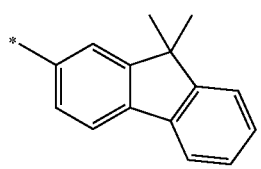
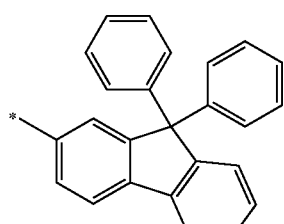
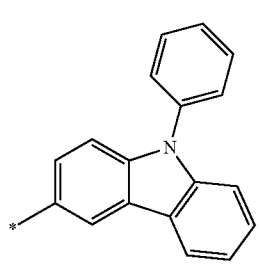
-continued
Formula 5-14
Formula 5-15
Formula 5-16
Formula 5-17
Formula 5-18
Formula 5-19
Formula 5-20
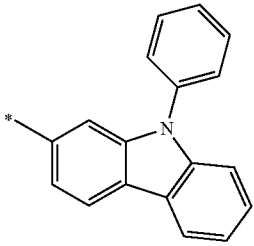
Formula 5-21
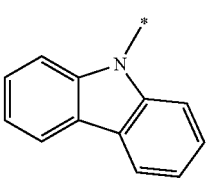
Formula 5-22
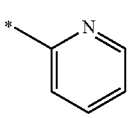
Formula 5-23
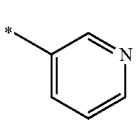
Formula 5-24
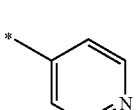
Formula 5-25
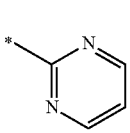
Formula 5-26
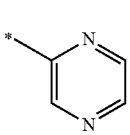
Formula 5-27
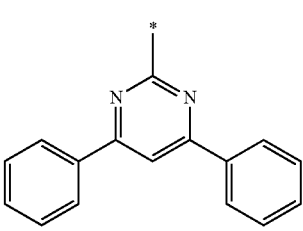
Formula 5-28
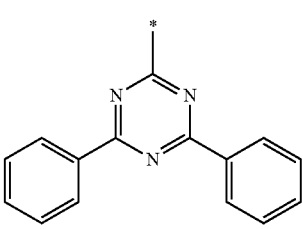
Formula 5-29

-continued
Formula 5-30
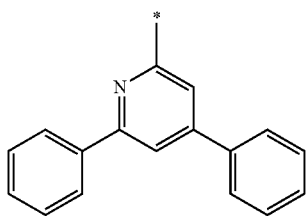
Formula 5-31
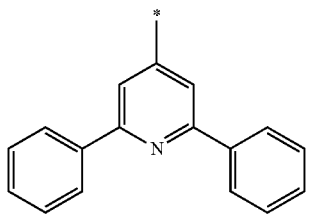
Formula 5-32
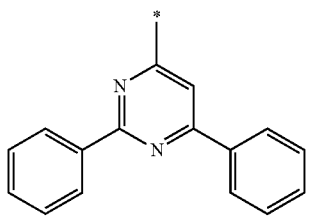
Formula 5-33
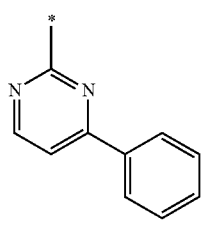
Formula 5-34
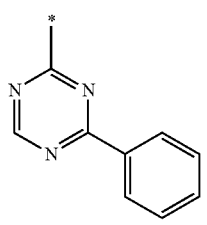
Formula 5-35
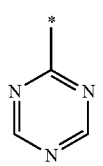
Formula 5-36
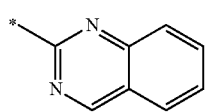
-continued
Formula 5-37
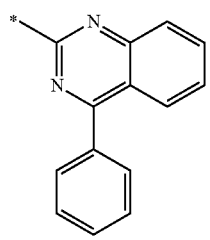
Formula 5-38
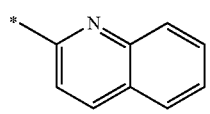
Formula 5-39
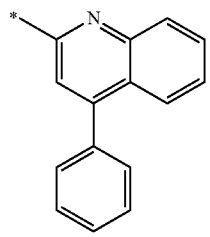
Formula 5-40
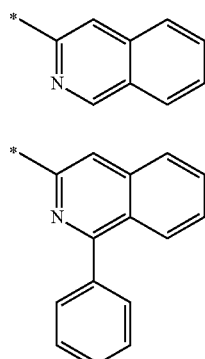
Formula 5-41
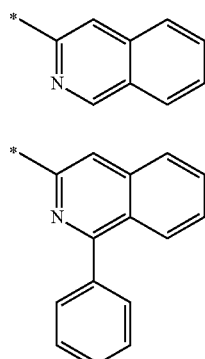
Formula 5-42
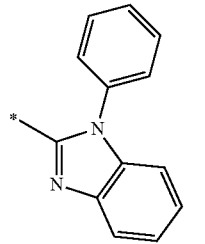
Formula 5-43
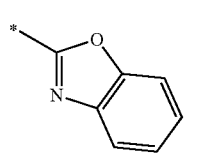
Formula 5-44
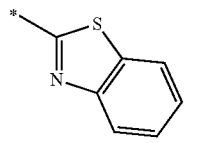

Formula 5-45

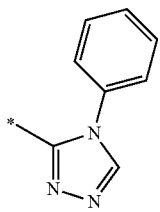

Formula 5-46

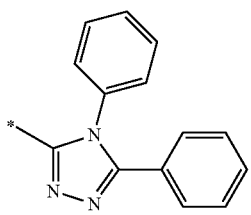

Formula 5-47

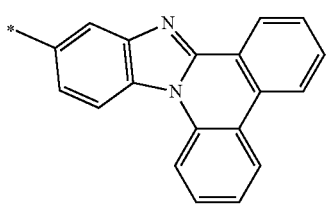

Formula 5-48

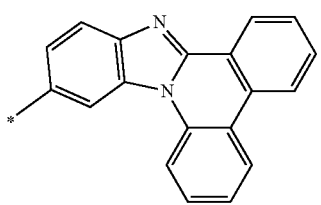

Formula 5-49

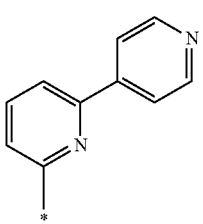

Formula 5-50

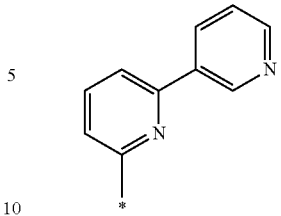

Formula 5-51 b1 in Formula 1 indicates the number of $R_1$, and may be an integer of 1 to 10, for example, an integer of 1 to 3. b1 may be 1 or 2, or 1. When b1 is 2 or more, groups $R_1$ may be identical or different. b2 to b9 may be understood by referring to the description provided in connection with b1 and Formula 1.

b11 in Formula 1 indicates the number of $R_{11}$, and may be an integer of 1 to 10, for example, an integer of 1 to 3. b11 may be 1 or 2, or 1. When b11 is 2 or more, groups $R_{11}$ may be identical or different.

b12 in Formula 1 indicates the number of $R_{12}$, and may be an integer of 1 to 10, for example, an integer of 1 to 3. b12 may be 1 or 2, or 1. When b12 is 2 or more, groups $R_{12}$ may be identical or different.

c11 in Formula 1 indicates the number of moieties represented by $*-(L_{11})_{a11}-(R_{21})_{b11}$) and may be selected from an integer of 1 to 4. c11 may be 1 or 2. When c11 is 2 or more, at least two $*-(L_{11})_{a11}-(R_{11})_{b11}$ may be identical or different.

c12 in Formula 1 indicates the number of moieties represented by $*-(L_{12})_{a12}-(R_{12})_{b12}$) and may be selected from an integer of 1 to 4. c12 may be 1 or 2. When c12 is 2 or more, at least two $*-(L_{12})_{a12}-(R_{12})_{b12}$ are identical or different.

According to an embodiment, c11 and c12 in Formula 1 may both be 1.

In Formula 1, $*-(L_{11})_{a11}-(R_{11})_{b11}$ binds to at least one of $1^{st}$, $2^{nd}$, $3^{rd}$, and $4^{th}$ carbon of ring A (as shown in Formula 1' below), and $*-(L_{12})_{a12}-(R_{12})_{b12}$ binds to at least one of $1^{st}$, $2^{nd}$, $3^{rd}$, and $4^{th}$ carbon of ring B.

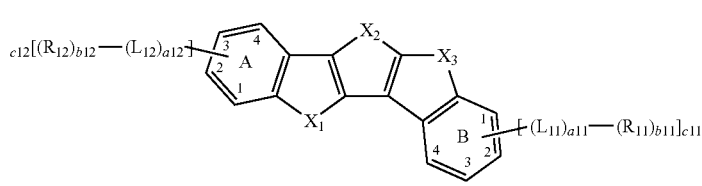

According to an embodiment, in Formula 1, $*-(L_{11})_{a11}-(R_{11})_{b11}$ binds to at least one of $2^{nd}$ and $3^{rd}$ carbon of ring A, and $*-(L_{12})_{a12}-(R_{12})_{b12}$ binds to at least one of $2^{nd}$ and $3^{rd}$ carbon of ring B.

For example, the condensed cyclic compound may be represented by Formula 1A below:

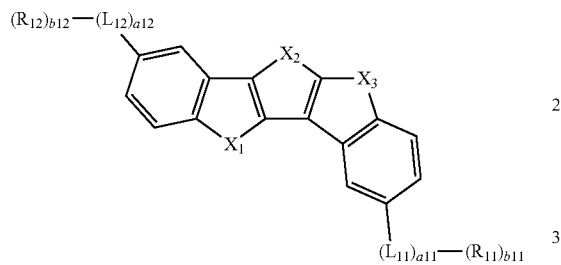

Formula 1A

Substituents of Formula 1A are already described above.

According to another embodiment, the condensed cyclic compound may be represented by Formulae 1-1A, 1-2A, 1-3A, or 1A':

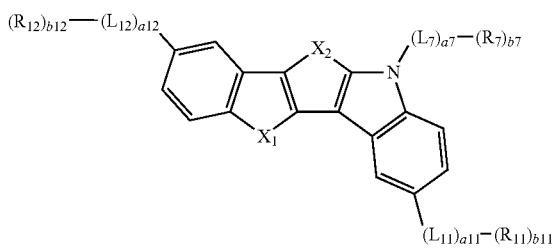

Formula 1-1A

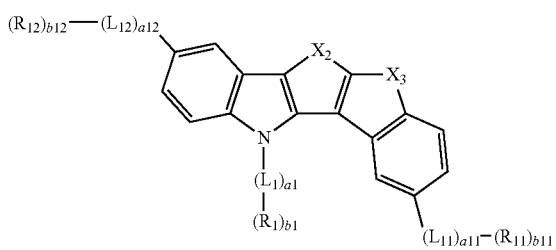

Formula 1-2A

-continued

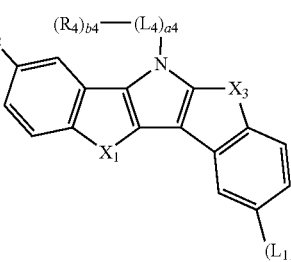

Formula 1-3A

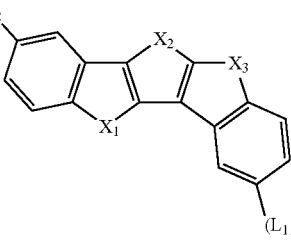

Formula 1A'

Substituents of Formulae 1A', 1-1A, 1-2A, and 1-3A may be understood by referring to corresponding explanation provided herein, except that in Formulae 1-1A, 1-2A, 1-3A, and 1A', $X_1$ is selected from $C[(L_2)_{a2}-(R_2)_{b2}][(L_3)_{a3}-(R_3)_{b3}]$, $Si[(L_2)_{a2}-(R_2)_{b2}][(L_3)_{a3}-(R_3)_{b3}]$, S, and O, $X_2$ is selected from $C[(L_5)_{a5}-(R_5)_{b5}][(L_6)_{a6}-(R_6)_{b6}]$, $Si[(L_5)_{a5}-(R_5)_{b5}][(L_6)_{a6}-(R_6)_{b6}]$, S, and O; and $X_3$ is selected from $C[(L_8)_{a8}-(R_8)_{b8}][(L_9)_{a9}-(R_9)_{b9}]$, $Si[(L_8)_{a8}-(R_8)_{b8}][(L_9)_{a9}-(R_9)_{b9}]$, S, and O (that is, in Formula 1A', $X_1$ is not $N[(L_1)_{a1}-(R_1)_{b1}]$ and $X_2$ is not $N[(L_4)_{a4}-(R_4)_{b4}]$ and $X_3$ is not $N[(L_7)_{a7}-(R_7)_{b7}]$. A compound represented by Formula 1A', wherein $X_1$ is $C[(L_2)_{a2}-(R_2)_{b2}][(L_3)_{a3}-(R_3)_{b3}]$, $X_2$ is S, and $X_3$ is $C[(L_8)_{a8}-(R_8)_{b8}][(L_9)_{a9}-(R_9)_{b9}]$ is excluded.

For example, at least one of $R_7$, $R_{11}$, and $R_{12}$ in Formula 1-1A, at least one of $R_1$, $R_{11}$, and $R_{12}$ in Formula 1-2A, at least one of $R_4$, $R_{11}$, and $R_{12}$ in the Formula 1-3A, and at least one of $R_{11}$ and $R_{12}$ in Formula 1A' may be each independently a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group; or a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group.

For example, at least one of $R_7$, $R_{11}$, and $R_{12}$ in Formula 1-1A, at least one of $R_1$, $R_{11}$, and $R_{12}$ in Formula 1-2A, at least one of $R_4$, $R_{11}$, and $R_{12}$ in Formula 1-3A, and at least one of $R_{11}$ and $R_{12}$ in Formula 1A' are each independently a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a group represented by

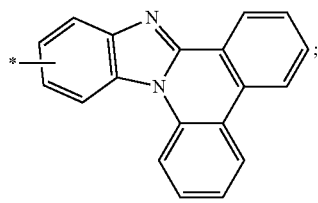

or
a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a group represented by

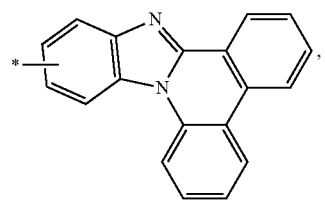

each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a naphthyl group.

According to another embodiment, at least one of $R_7$, $R_{11}$, and $R_{12}$ in Formula 1-1A, at least one of $R_1$, $R_{11}$, and $R_{12}$ in Formula 1-2A, at least one of $R_4$, $R_{11}$, and $R_{12}$ in Formula 1-3A, and at least one of $R_{11}$ and $R_{12}$ in Formula 1A' may be each independently represented by one of Formulae 4-4 to 4-27 (wherein $Y_{31}$ in Formulae 4-4 to 4-7 may be O, S, or $N(Z_{35})$), but may instead be represented by other formulae.

For example, the condensed cyclic compound may be represented by Formulae 1-1A, 1-2A, 1-3A, or 1A', and
$L_1$, $L_4$, $L_7$, $L_{11}$, and $L_{12}$ in Formulae 1-1A, 1-2A, 1-3A, and 1A' are each independently represented by one of Formulae 2-1 to 2-33;
a1, a4, a7, a11, and a12 may be each independently 0, 1, or 2;
$R_1$, $R_4$, $R_7$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a group represented by one of Formula 4-1 to 4-27; and
b1, b4, b7, b11, and b12 may be 1.

Herein, at least one of $R_7$, $R_{11}$, and $R_{12}$ in Formula 1-1A, at least one of $R_1$, $R_{11}$, and $R_{12}$ in Formula 1-2A, at least one of $R_4$, $R_{11}$, and $R_{12}$ in Formula 1-3A, and at least one of $R_{11}$ and $R_{12}$ in Formula 1A' may be each independently represented by Formulae 4-4 to 4-27 (wherein $Y_{31}$ in Formulae 4-4 to 4-7 may be O, S, or $N(Z_{35})$), but may instead be represented by other formulae.

As another example, the condensed cyclic compound may be represented by Formulae 1-1A, 1-2A, 1-3A, or 1A', and
$L_1$, $L_4$, $L_7$, $L_{11}$, and $L_{12}$ in Formulae 1-1A, 1-2A, 1-3A, and 1A' are each independently represented by one of Formulae 3-1 to 3-59;
a1, a4, a7, a11, and a12 may be each independently 0 or 1;
$R_1$, $R_4$, $R_7$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a group represented by one of Formula 5-1 to 5-51; and b1, b4, b7, b11, and b12 may be 1.

thereof, a phosphoric acid or a salt thereof, a $C_1$-$C_{20}$ alkyl group, or a group represented by one of Formulae 4-1 to 4-27;

b1, b4, b7 to b9, b11, b12, c11, and c12 may be 1:

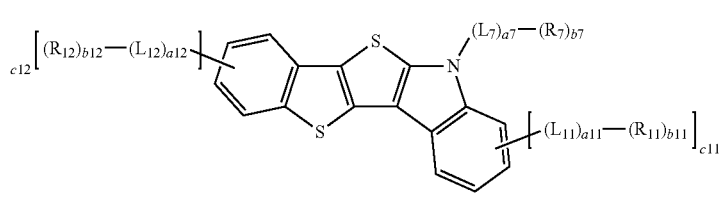

Formula 1(81)

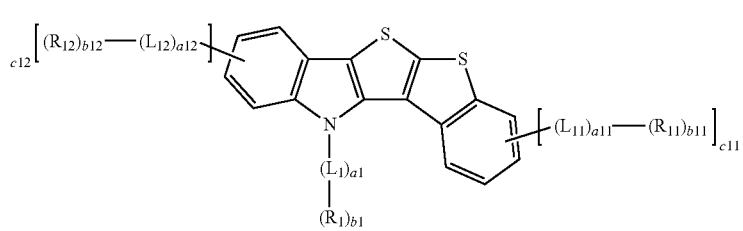

Formula 1(70)

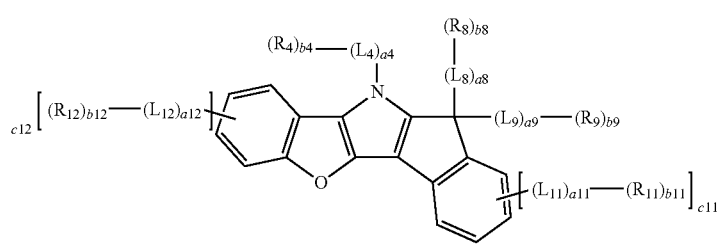

Formula 1(15)

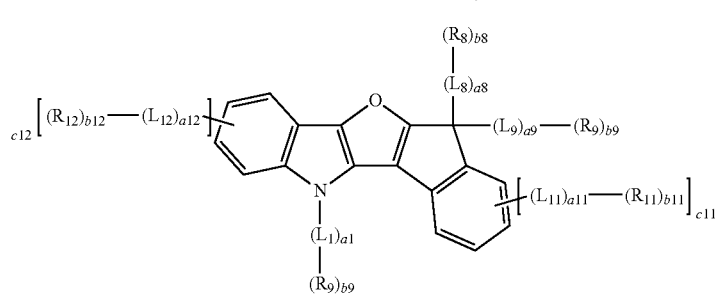

Formula 1(92)

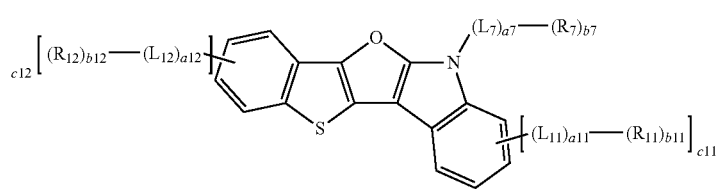

Formula 1(106)

According to another embodiment, the condensed cyclic compound may be represented by Formulae 1(81), 1(70), 1(15), 1(92), or 1(106), and $L_1$, $L_4$, $L_7$ to $L_9$, $L_{11}$, and $L_{12}$ in Formulae 1(81), 1(70), 1(15), 1(92), and 1(106) may be each independently represented by one of Formulae 2-1 to 2-33;

a1, a4, a7 to a9, a11, and a12 may be each independently 0, 1, or 2;

$R_1$, $R_4$, $R_7$ to $R_9$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt According to another embodiment, the condensed cyclic compound may be represented by Formula 1(81), 1(70), 1(15), 1(92), or 1(106), and $L_1$, $L_4$, $L_7$ to $L_9$, $L_{11}$, and $L_{12}$ in Formulae 1(81), 1(70), 1(15), 1(92), and 1(106) may be each independently represented by one of Formulae 3-1 to 3-59;

a1, a4, a7 to a9, a11, and a12 may be each independently 0 or 1;

$R_1$, $R_4$, $R_7$ to $R_9$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a group represented by one of Formulae 5-1 to 5-51;
b1, b4, b7 to b9, b11, b12, c11, and c12 may be 1, but are not limited thereto.
The condensed cyclic compound may be one of Compounds 1 to 208 below, but is not limited thereto:
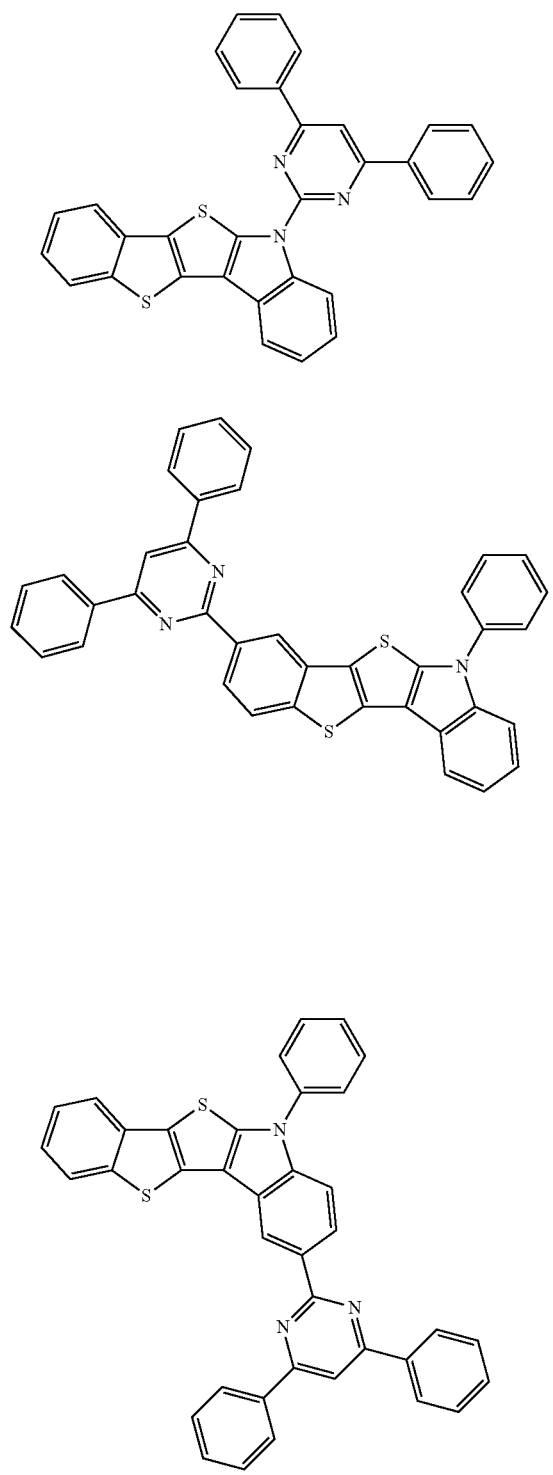
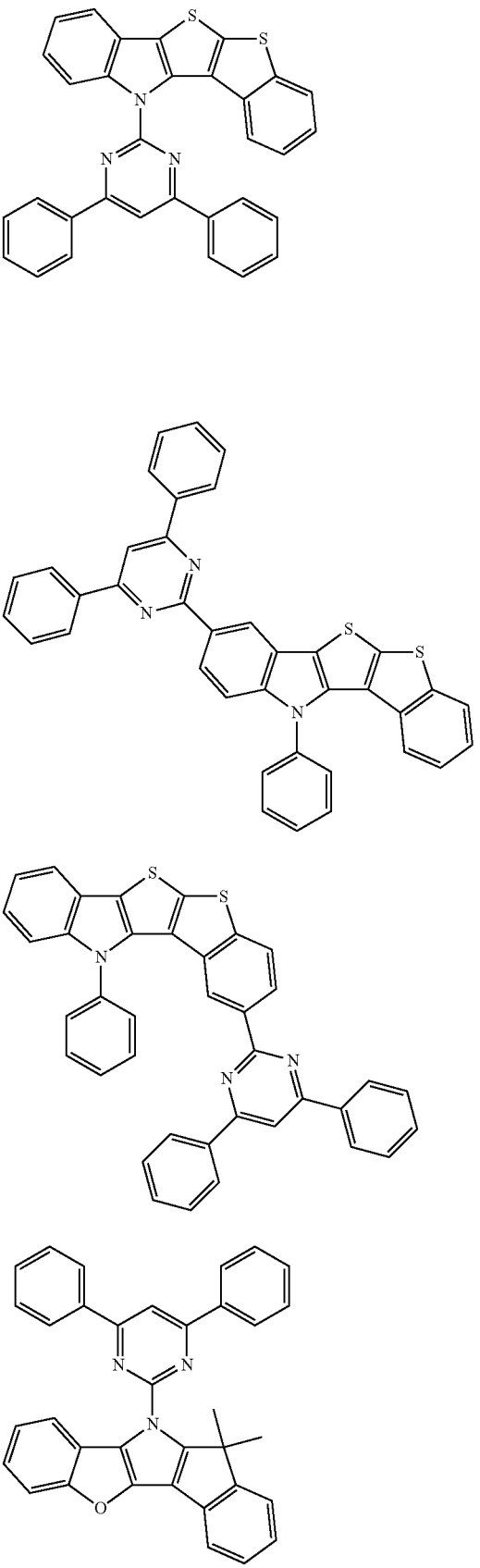

8
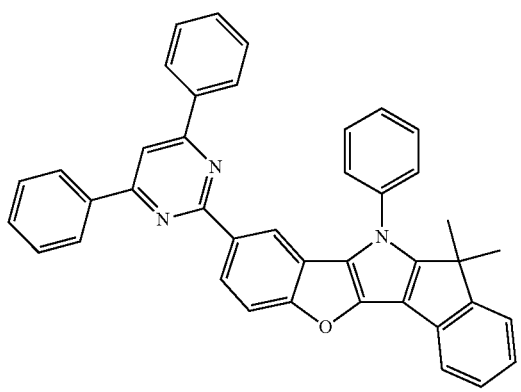
9
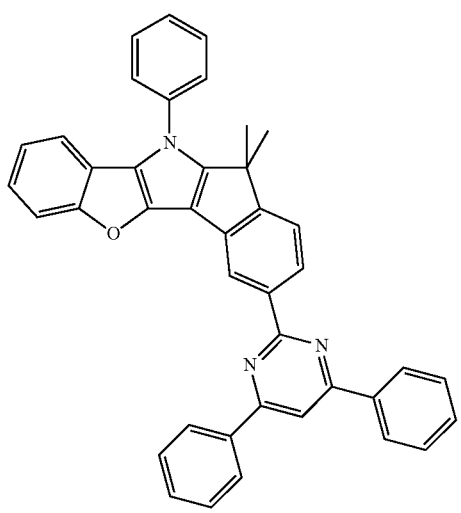
10
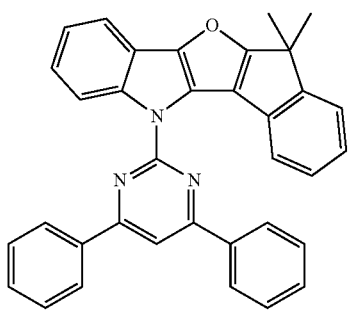
11
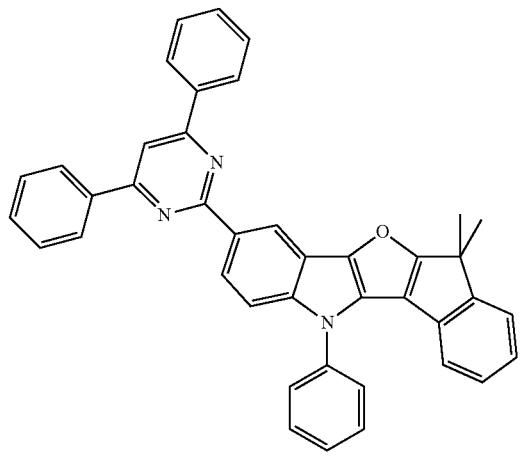
12
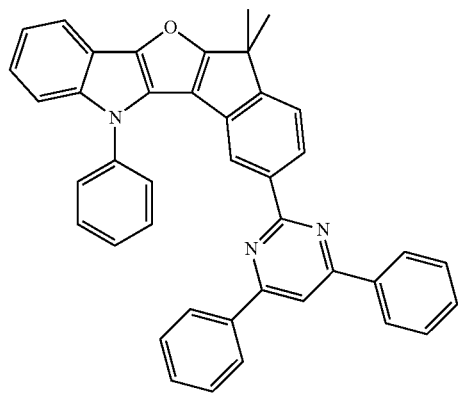
13
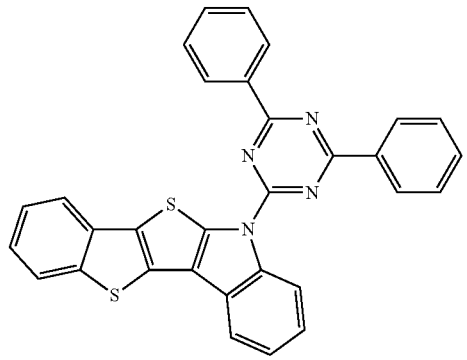
14
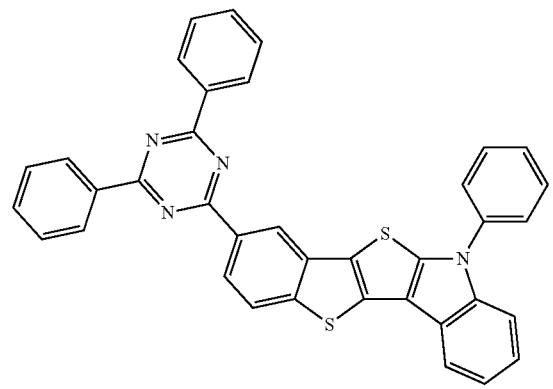

15
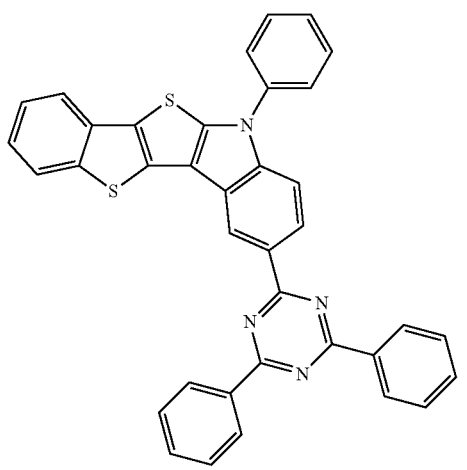
16
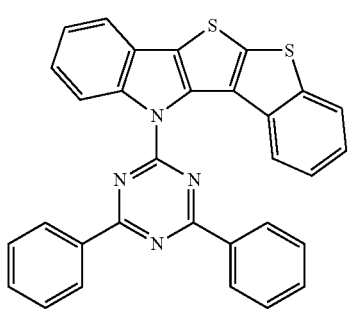
17
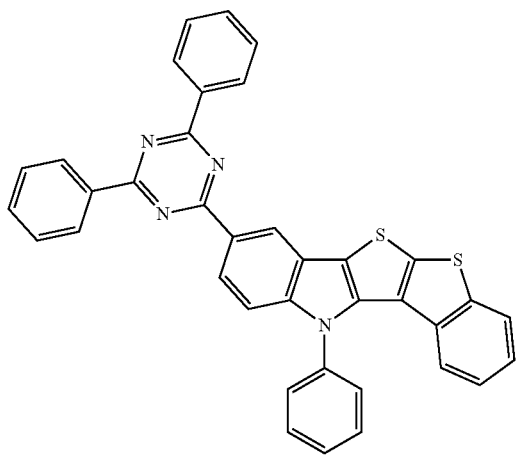
18
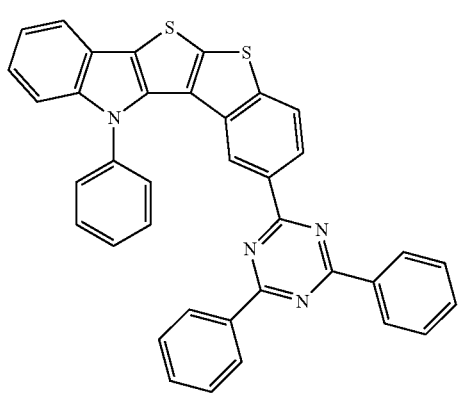
19
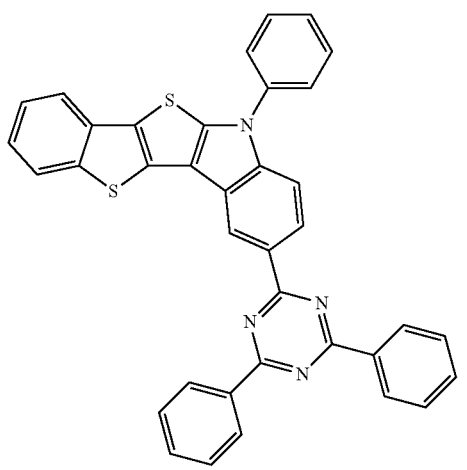
20
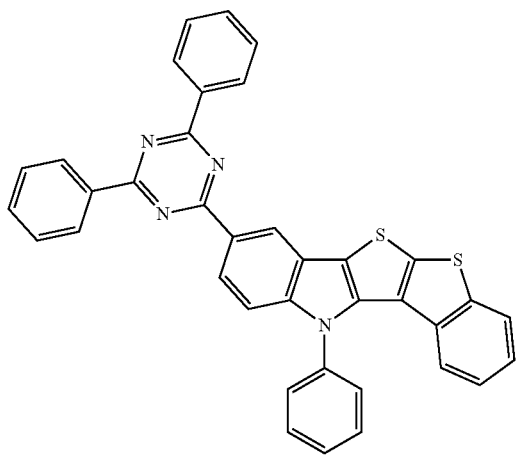
21
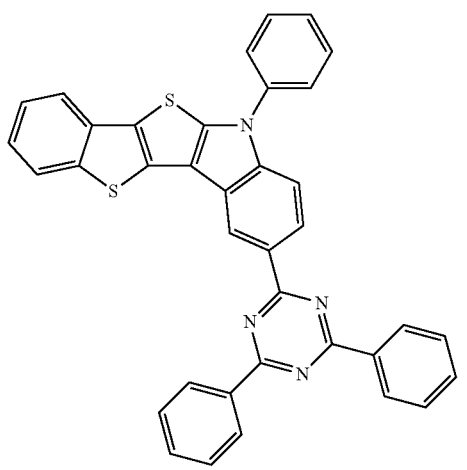
22
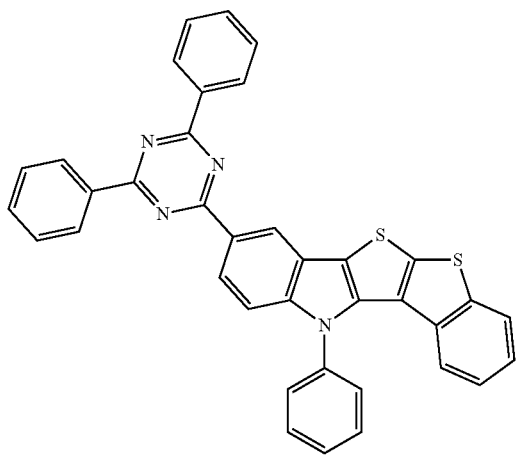

23
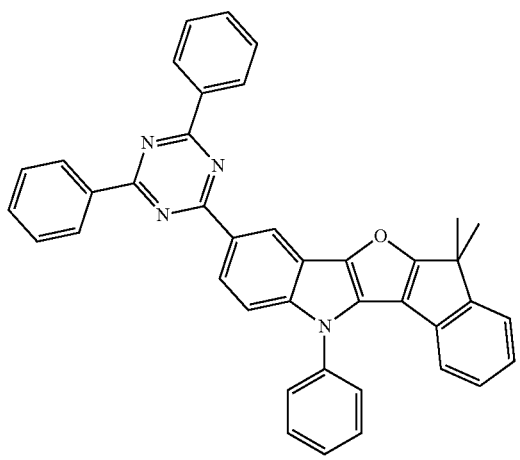
24
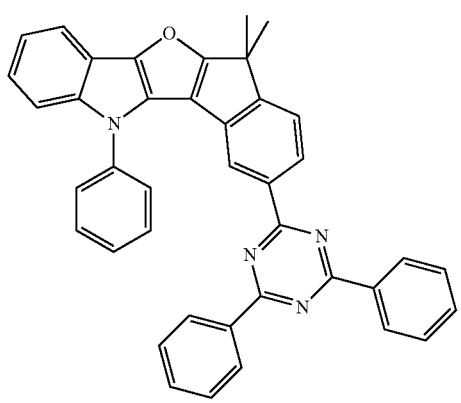
25
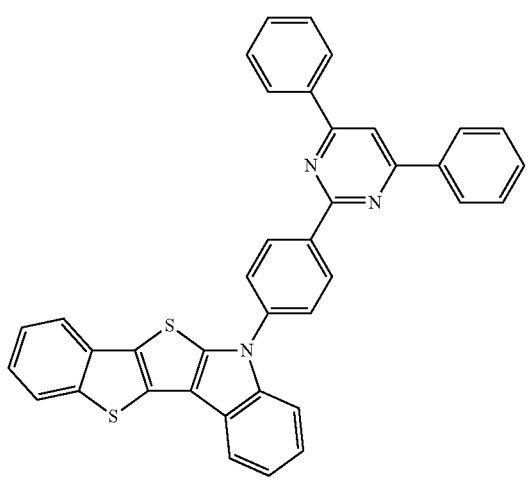
26
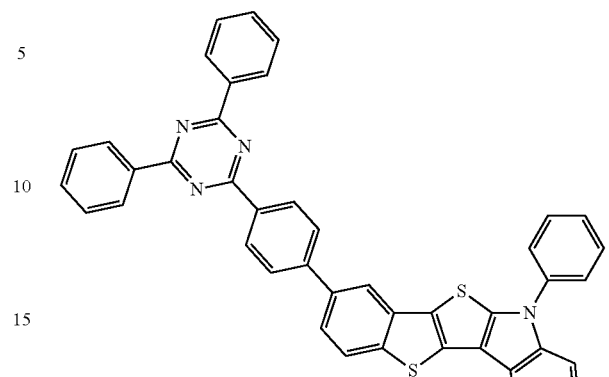
27
28
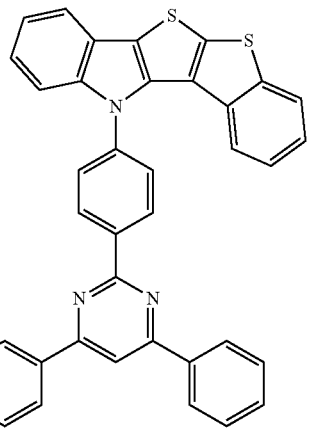

29
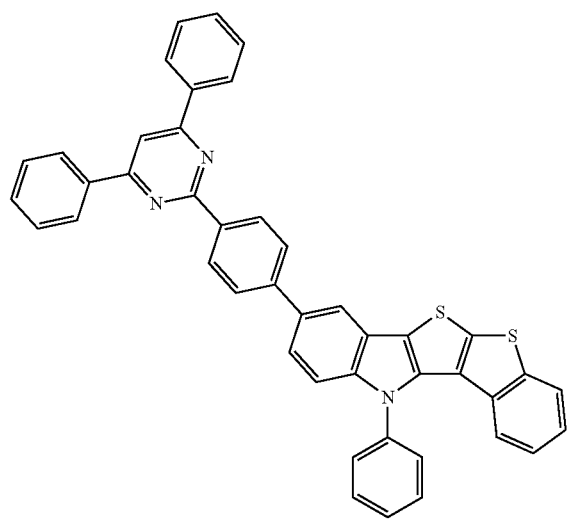
30
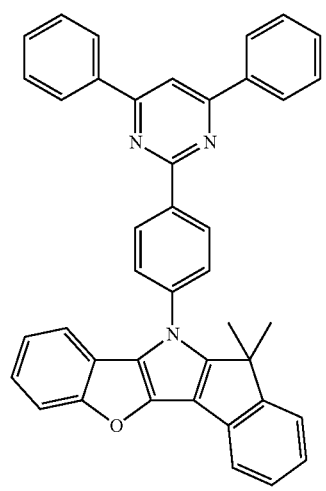
31
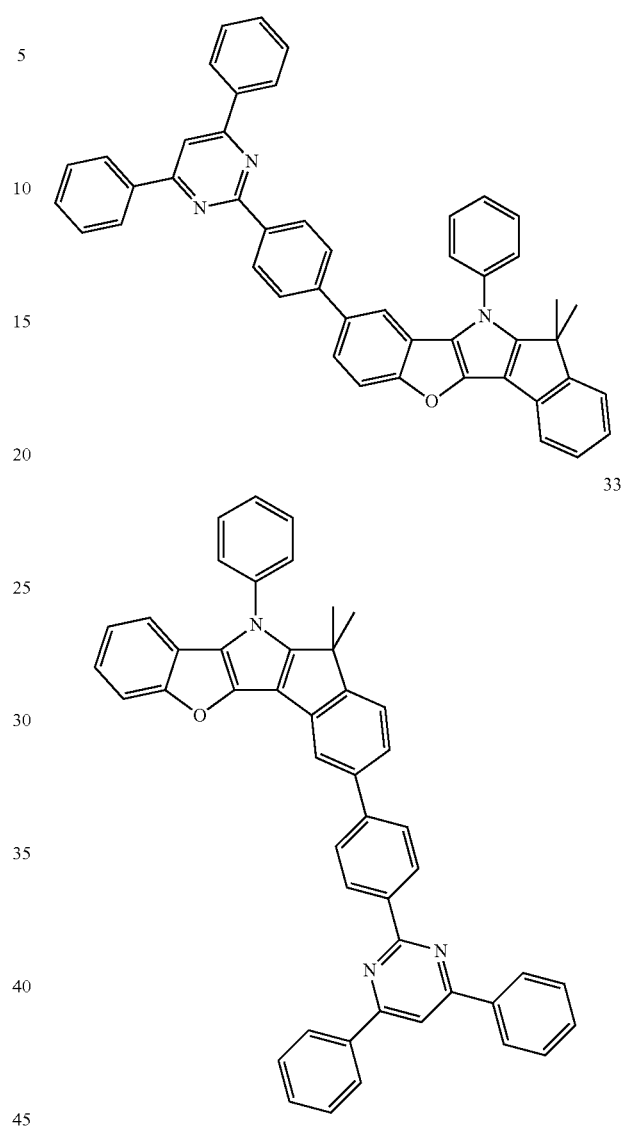
32
33
34
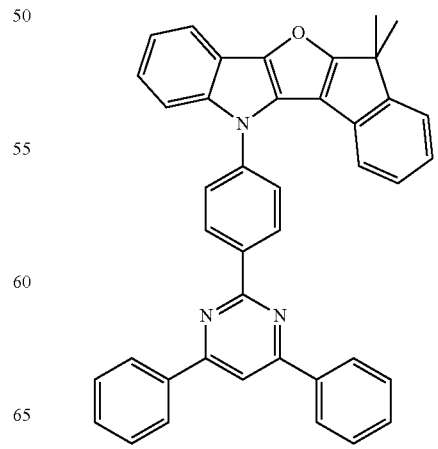

35
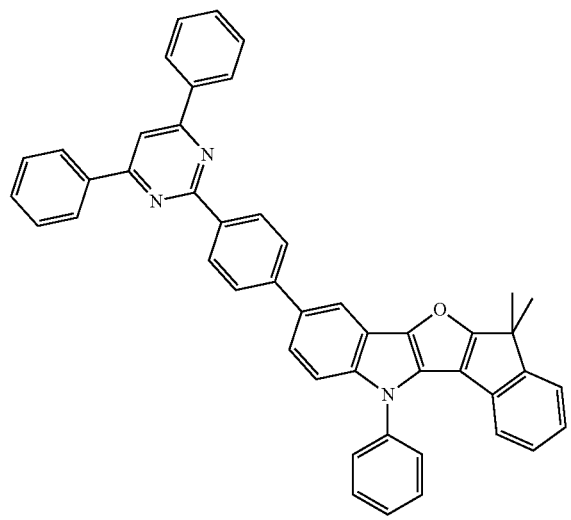
36
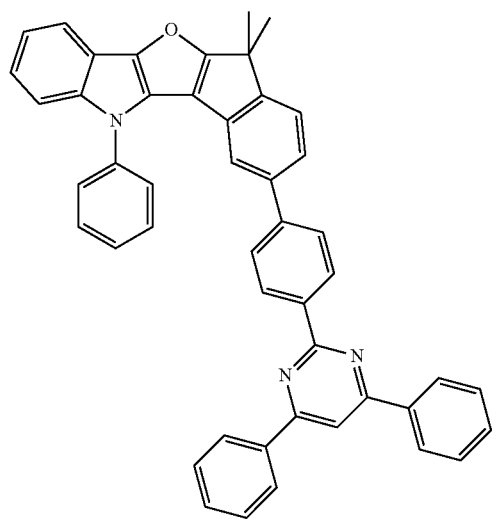
37
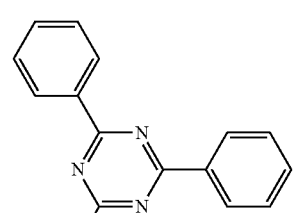
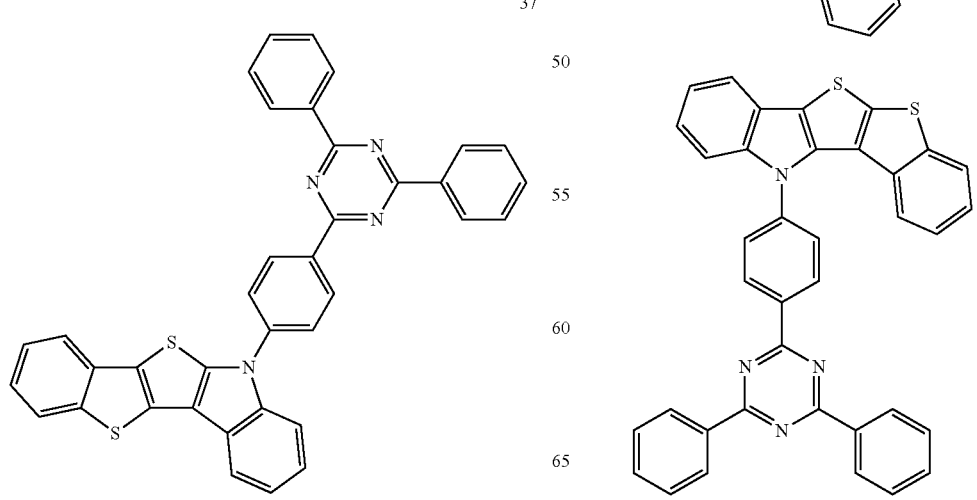
38
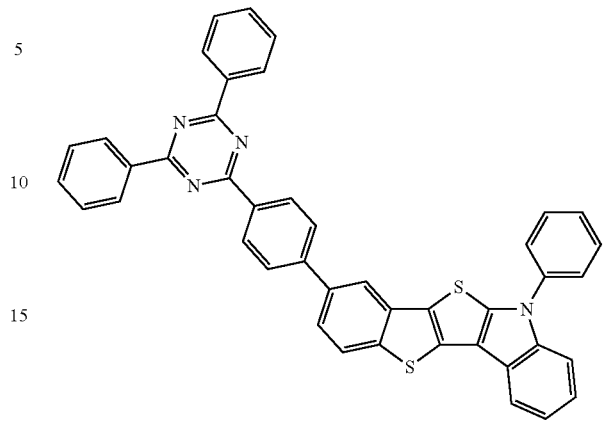
39
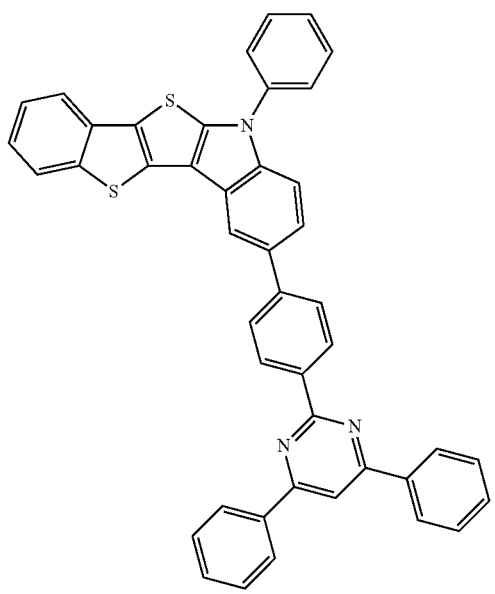
40

41
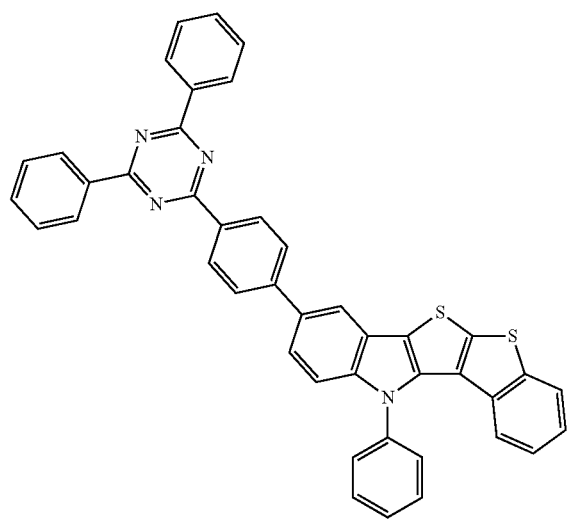
42
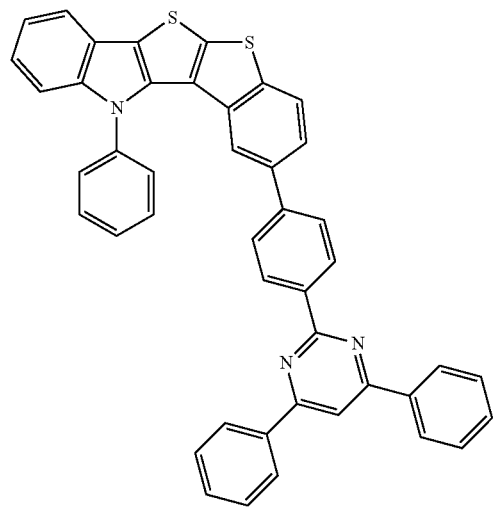
43
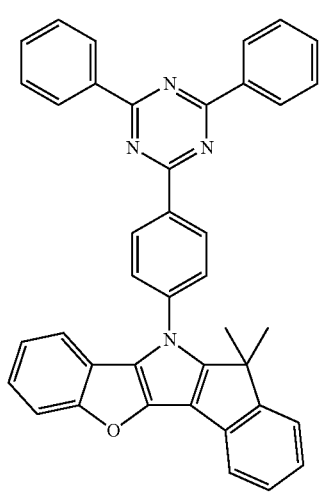
44
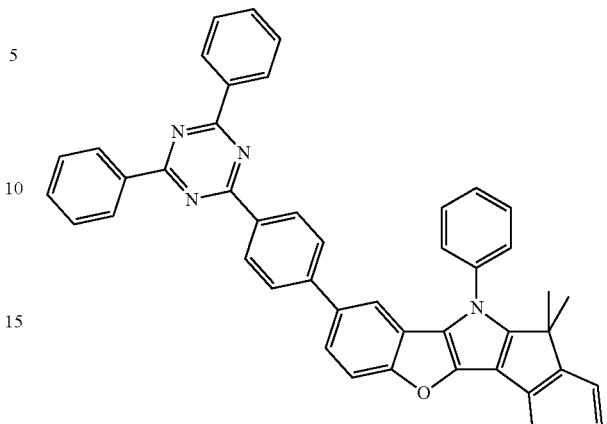
45
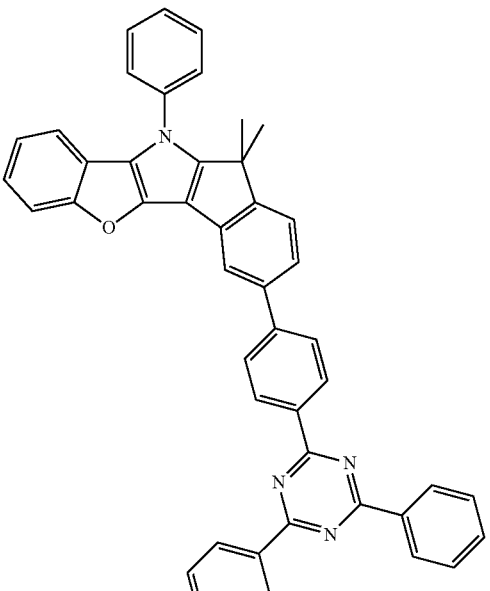
46

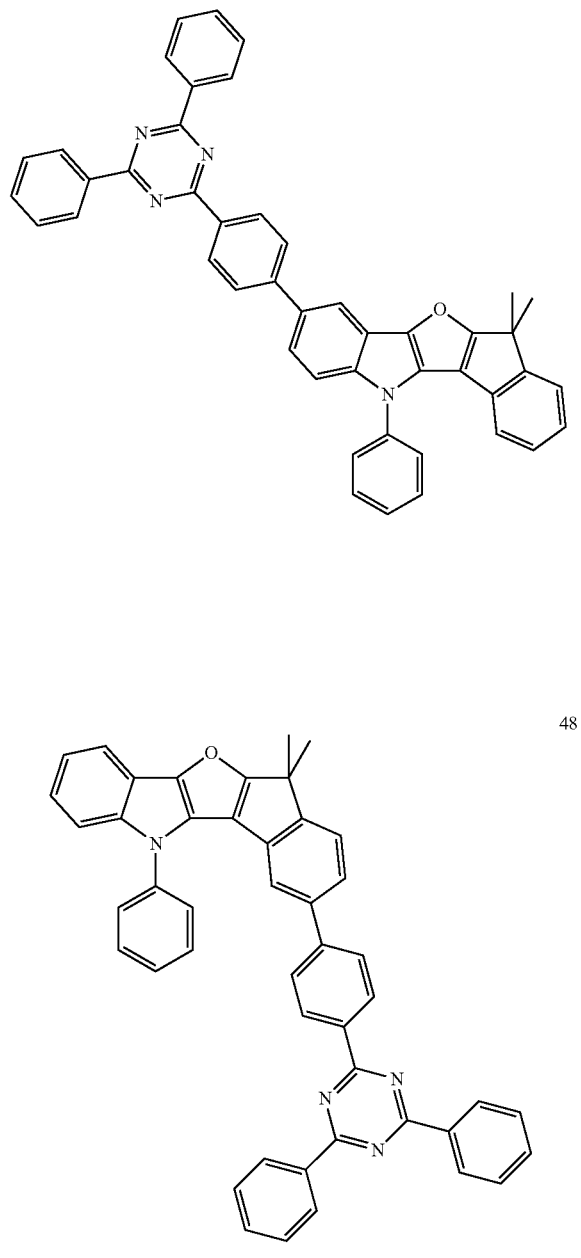
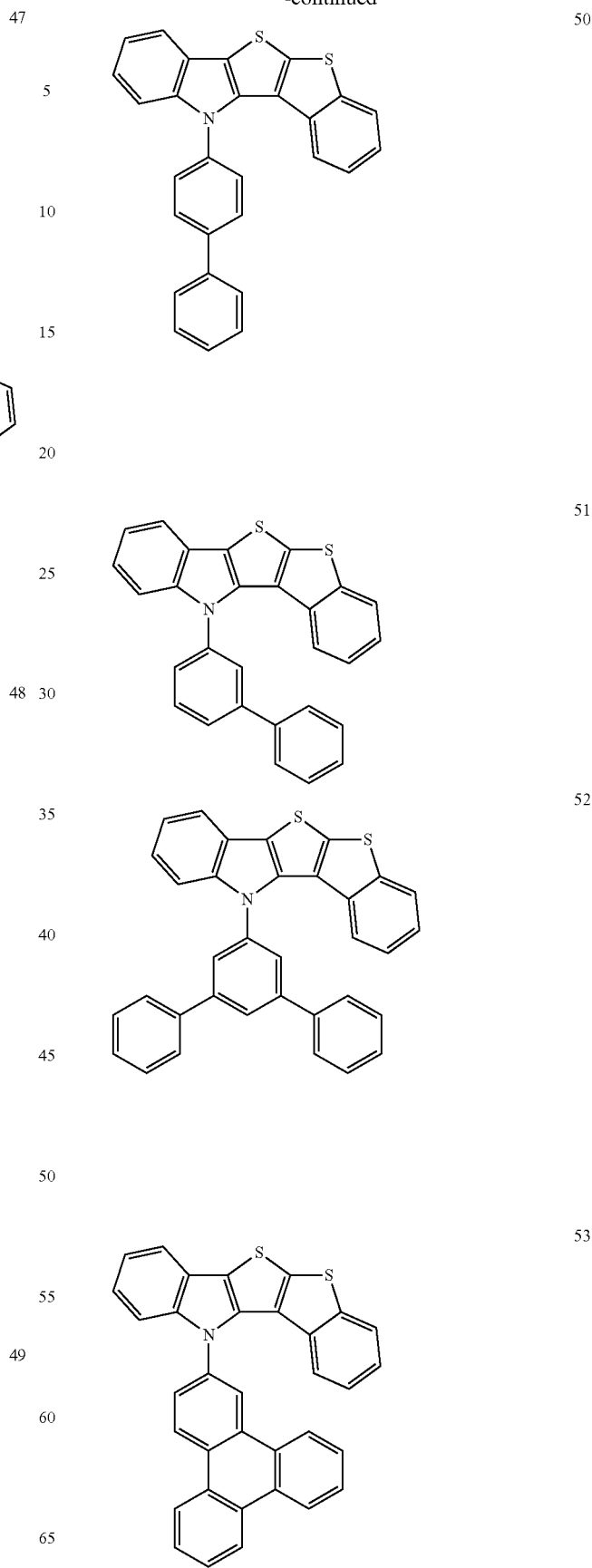

54
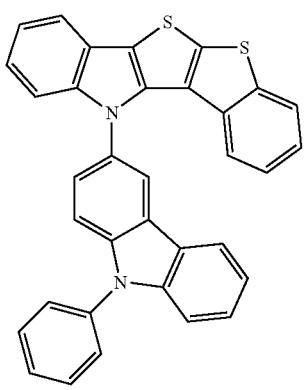
55
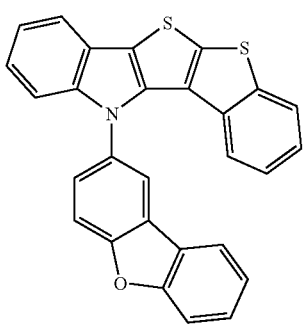
56
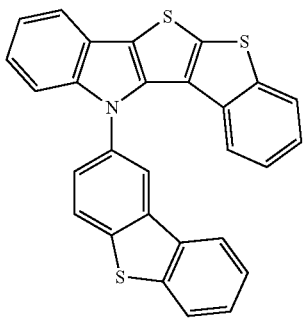
57
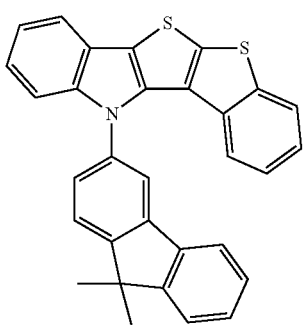
58
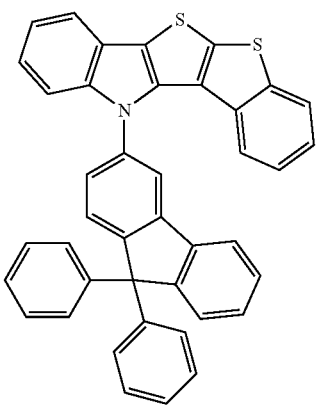
59
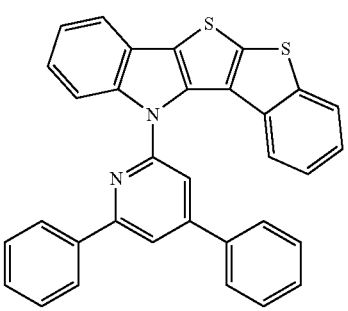
60
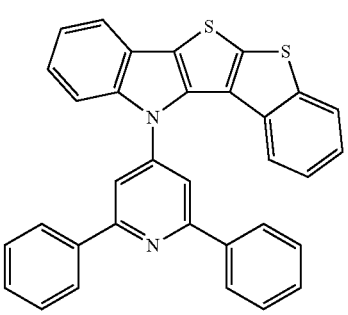
61
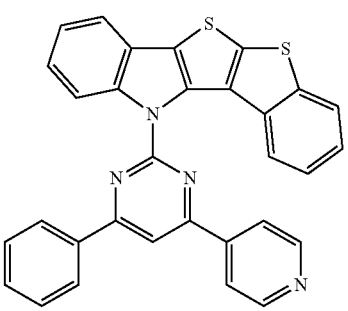
62
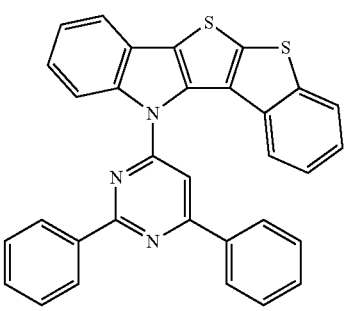

63
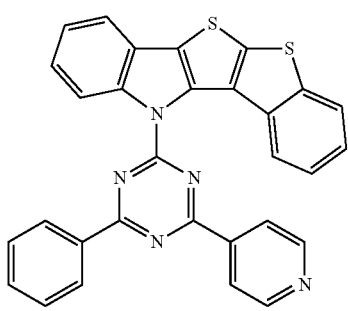
64
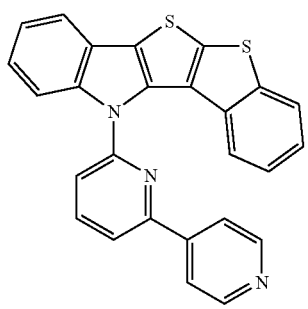
65
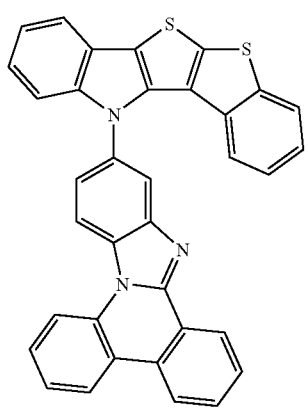
66
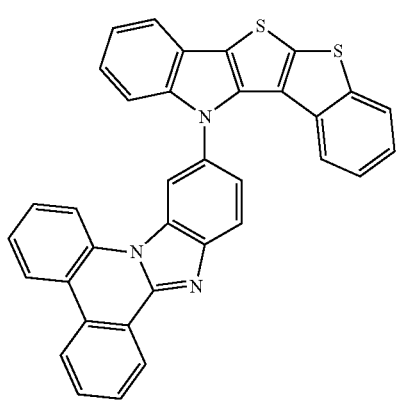
67
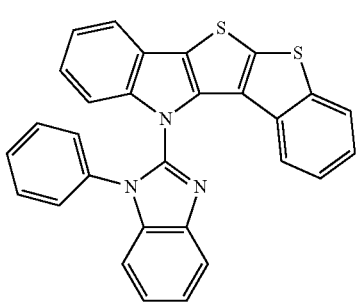
68
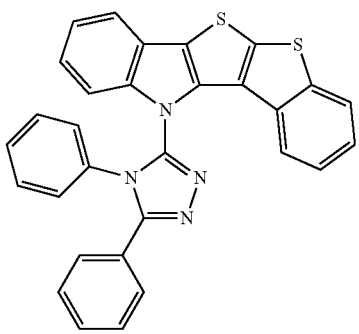
69
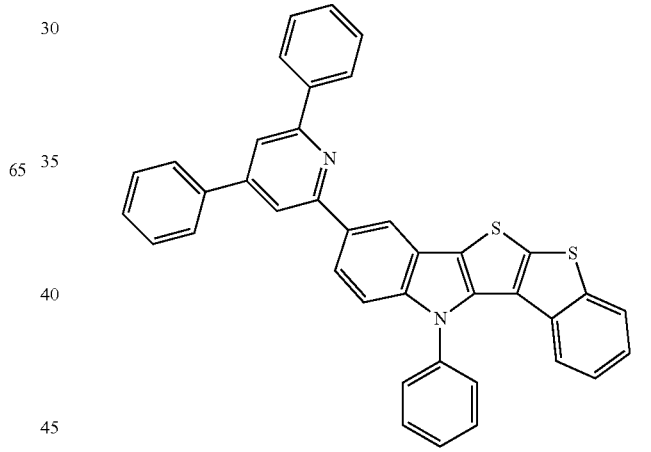
70
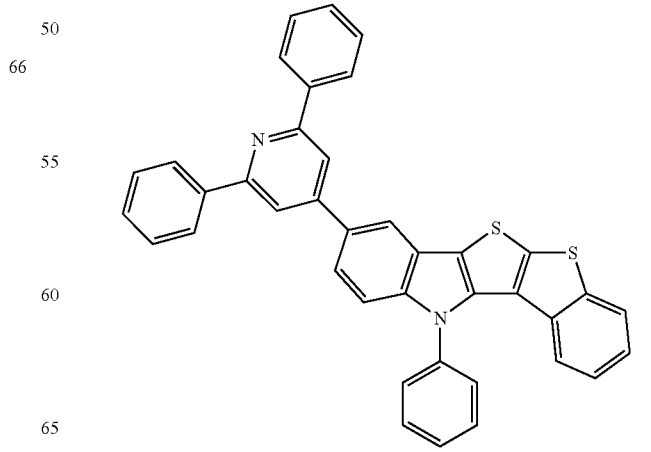

71
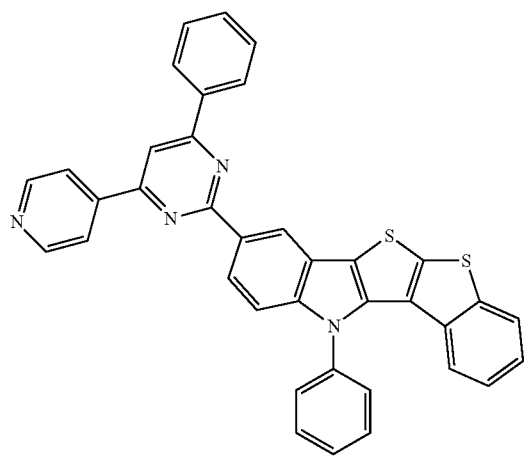
72
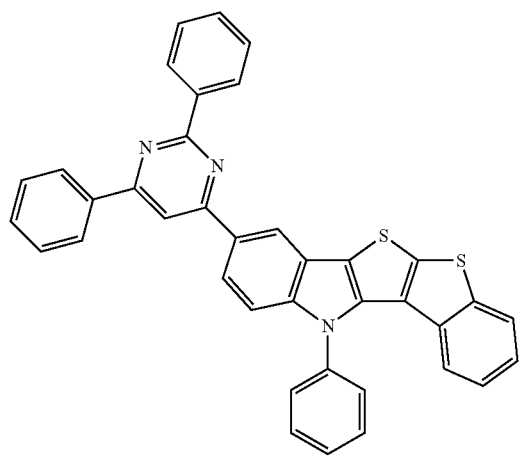
73
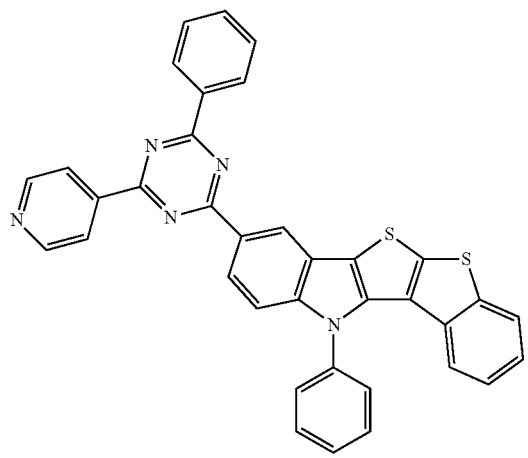
74
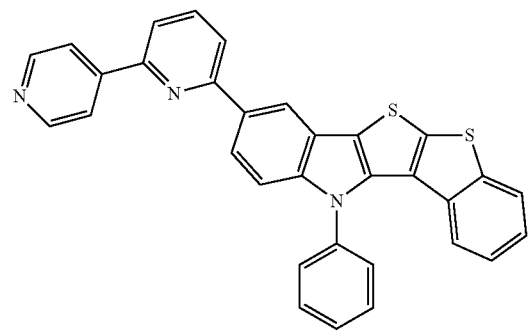
75
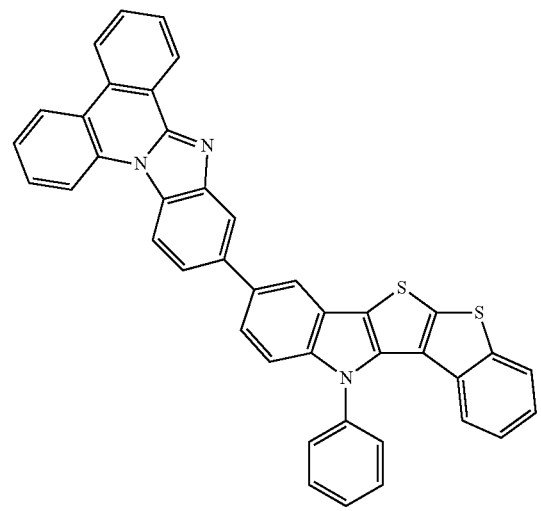
76
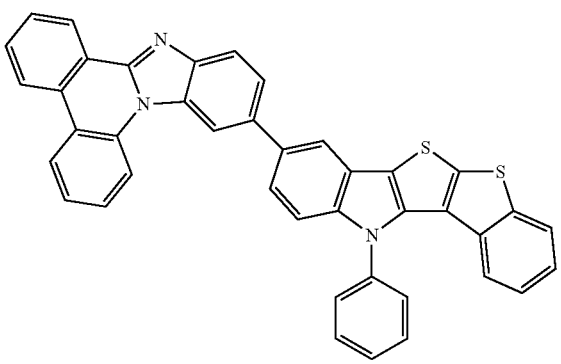
77
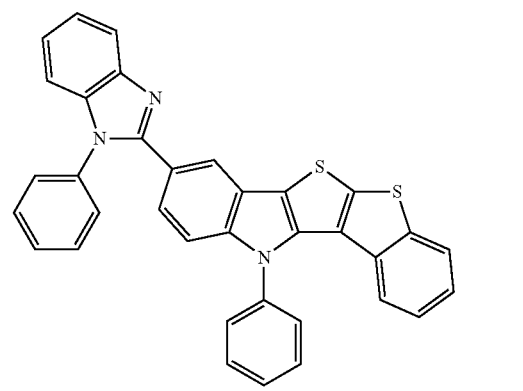

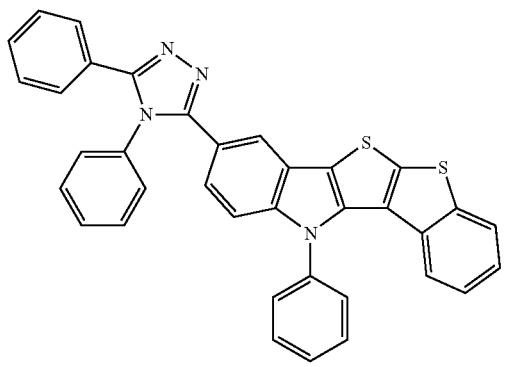
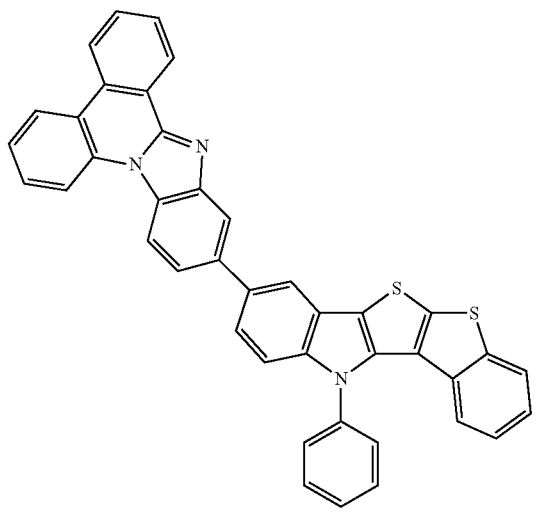
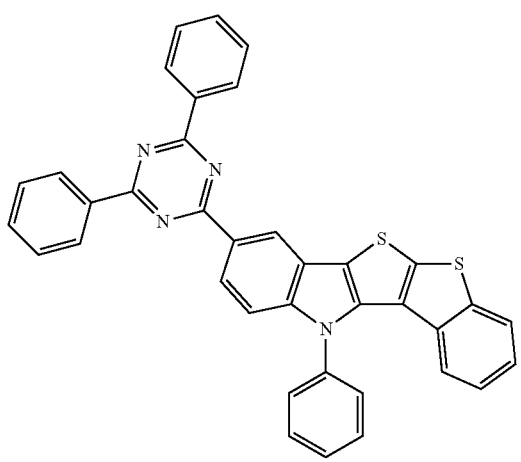
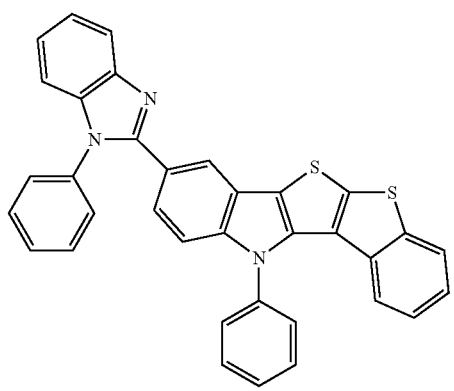

-continued
78
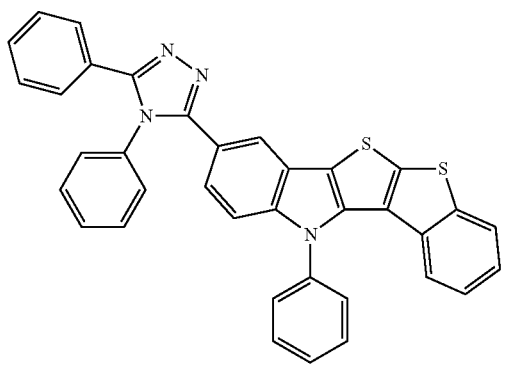
79
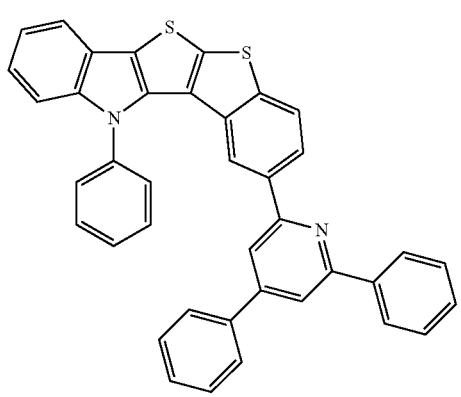
80
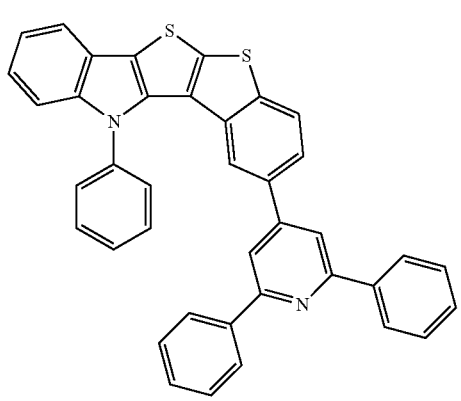
81
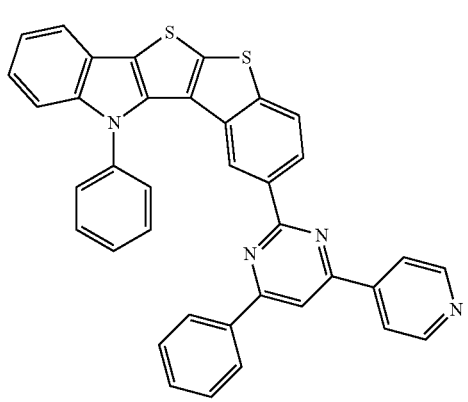
-continued
82
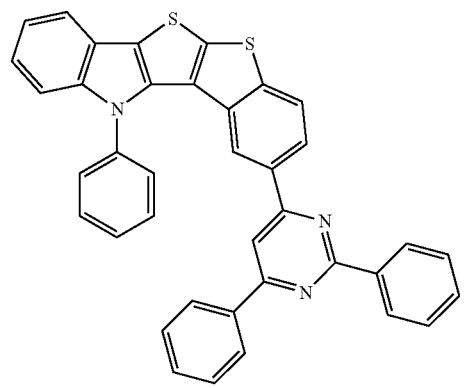
83
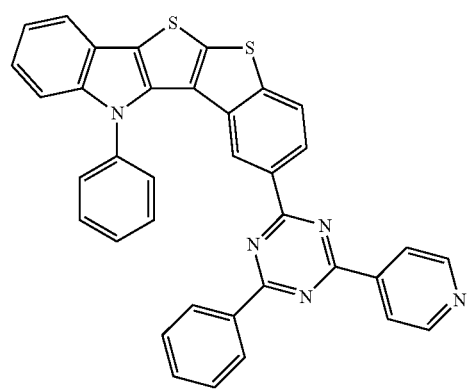
84
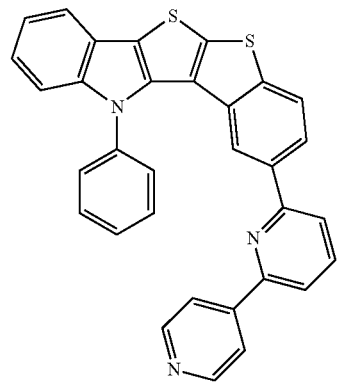
85
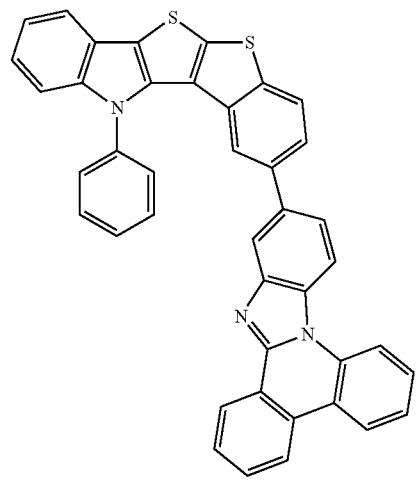

75
-continued
86
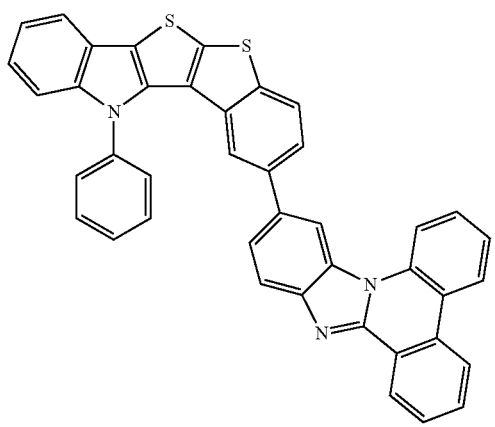
87
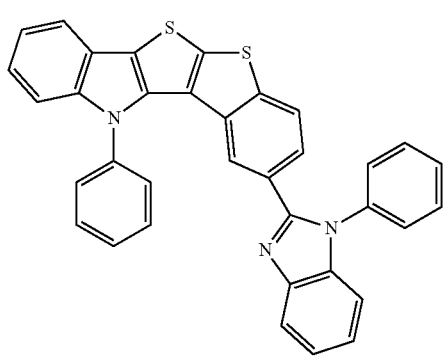
88
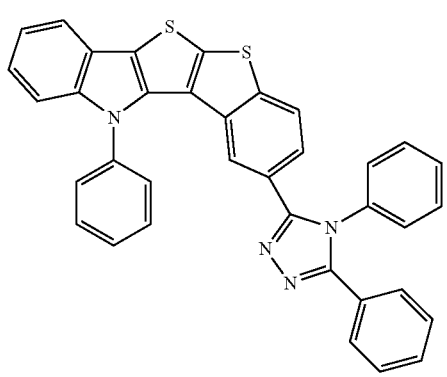
89
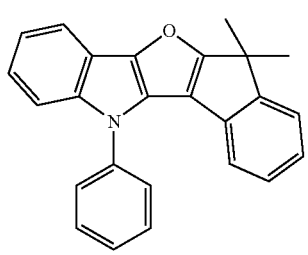
76
-continued
90
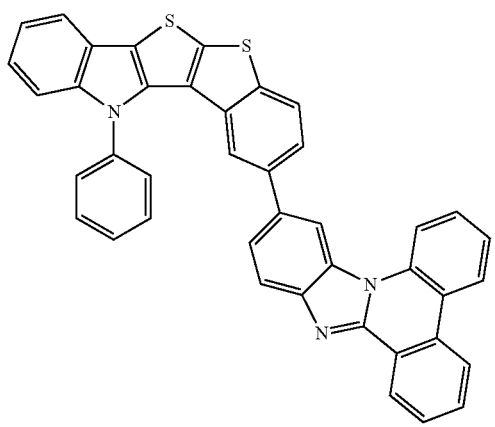
91
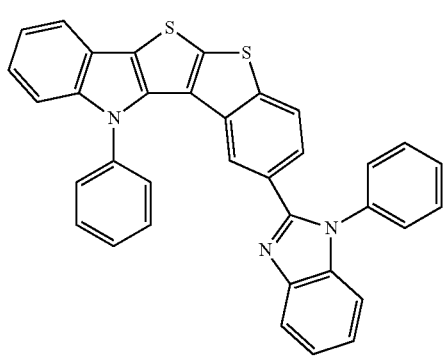
92
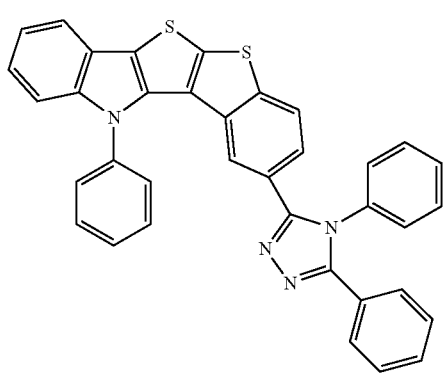
93
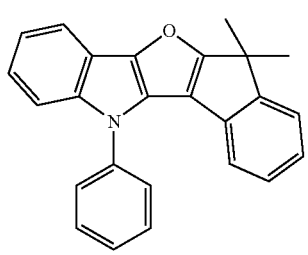

94
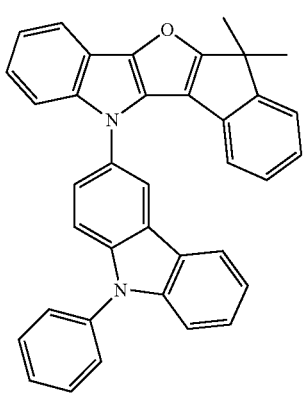
95
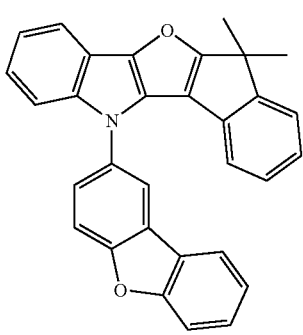
96
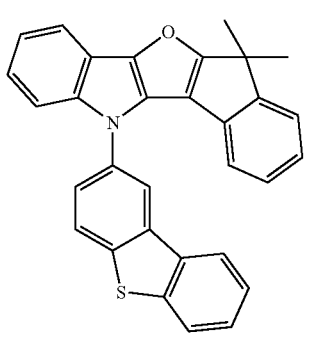
97
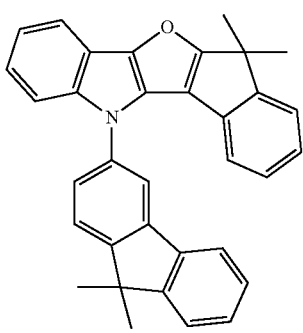
98
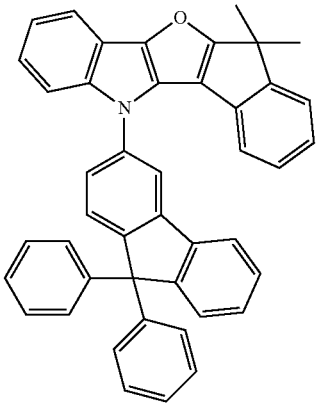
99
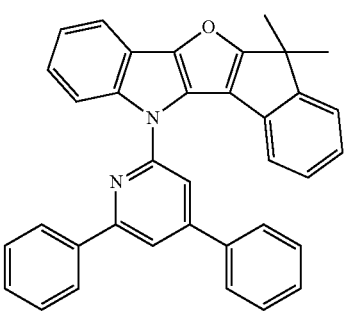
100
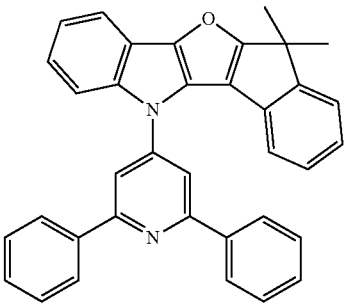
101
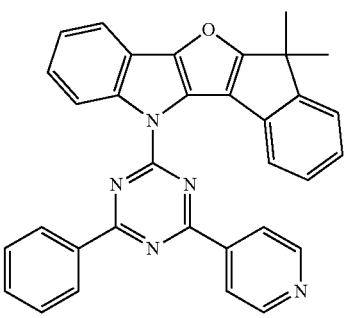

-continued
102
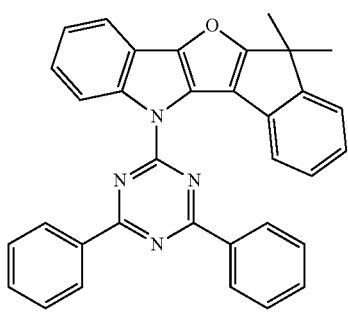
103
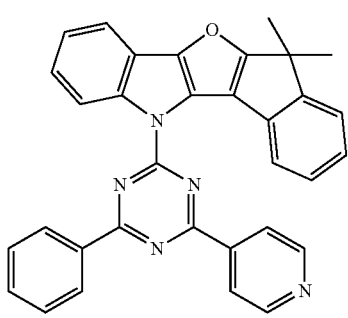
104
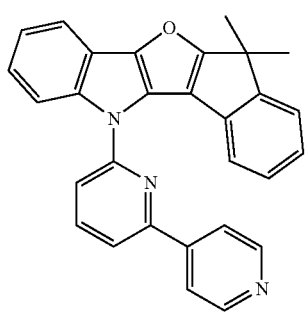
105
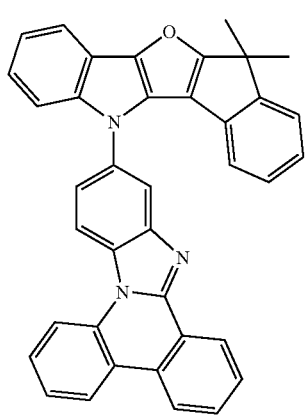
-continued
106
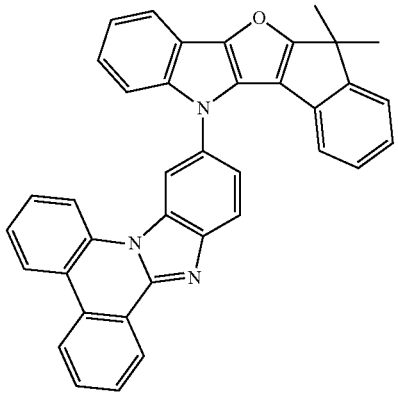
107
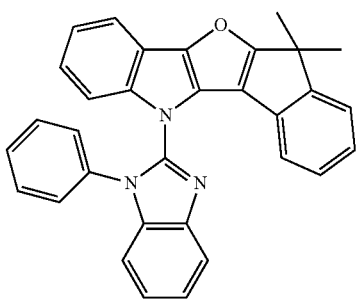
108
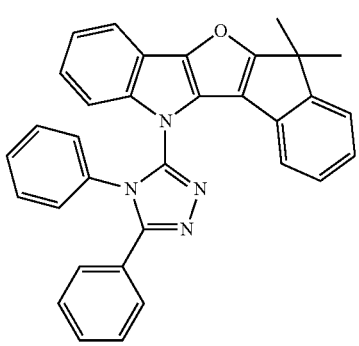
109
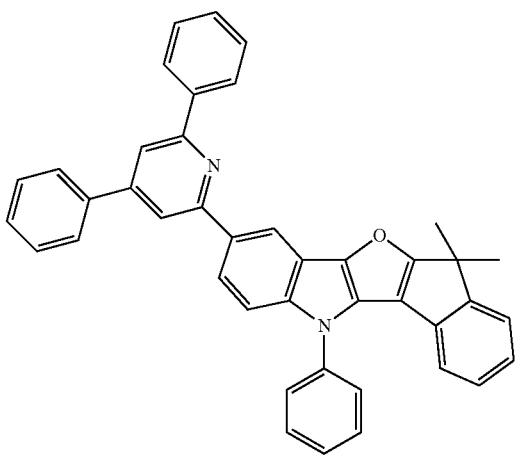

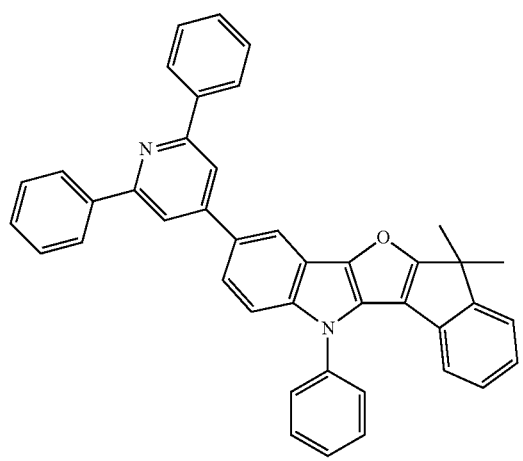

116
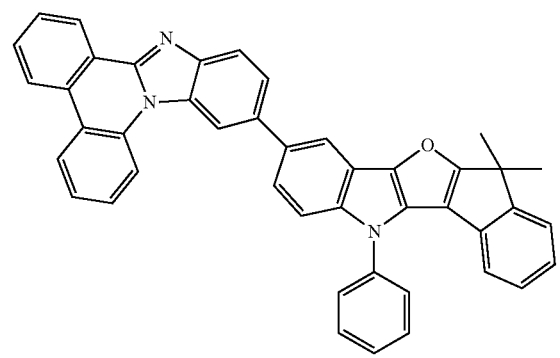
117
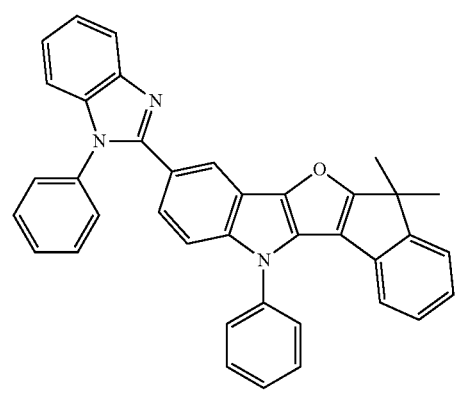
118
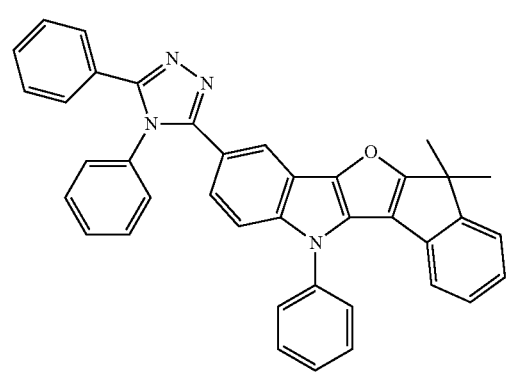
119
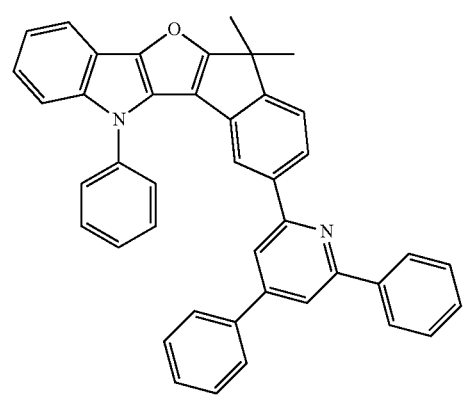
120
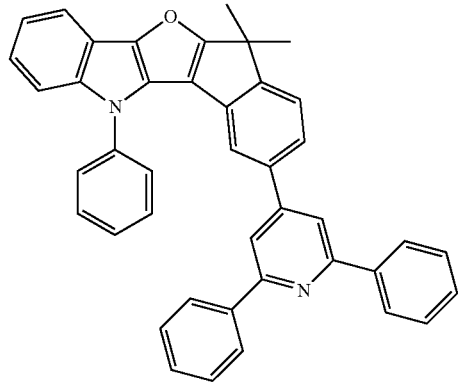
121
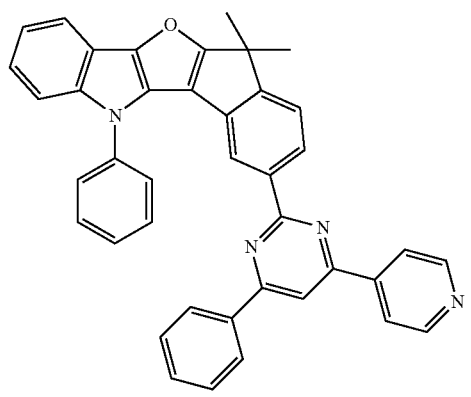
122
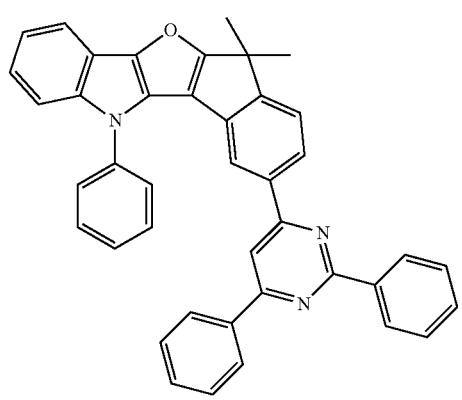
123
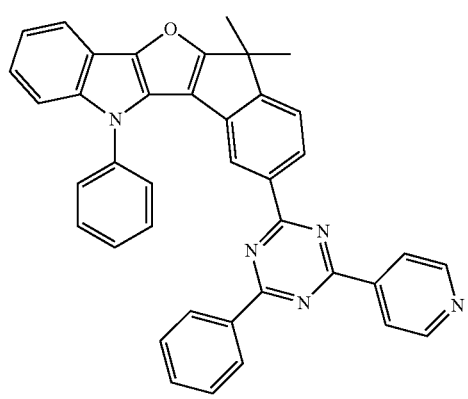

124
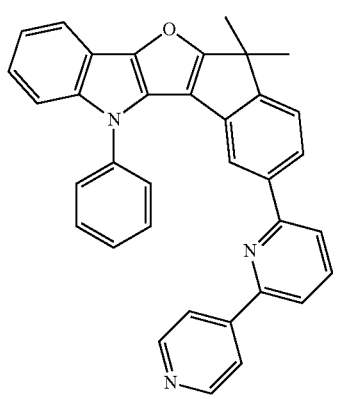
125
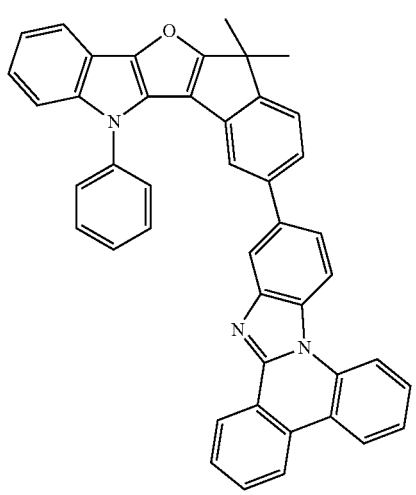
126
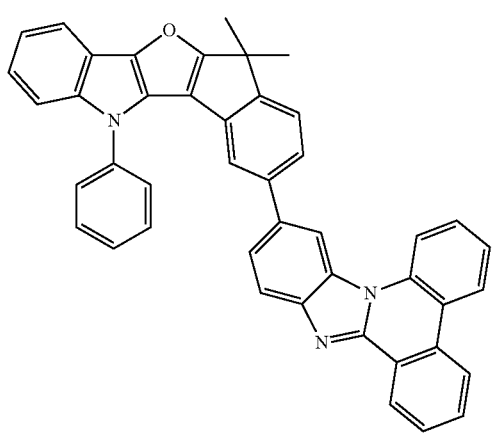
127
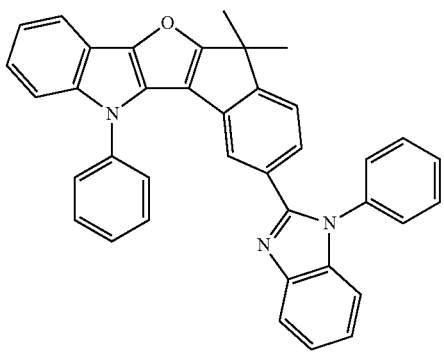
128
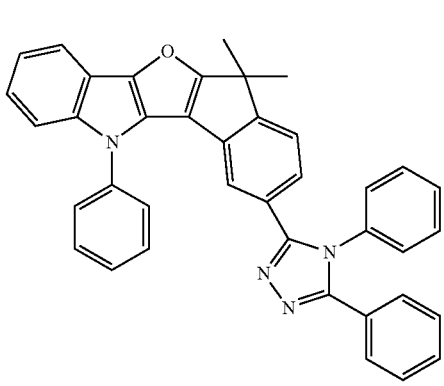
129
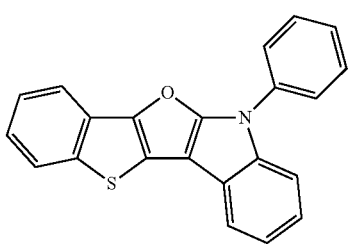
130

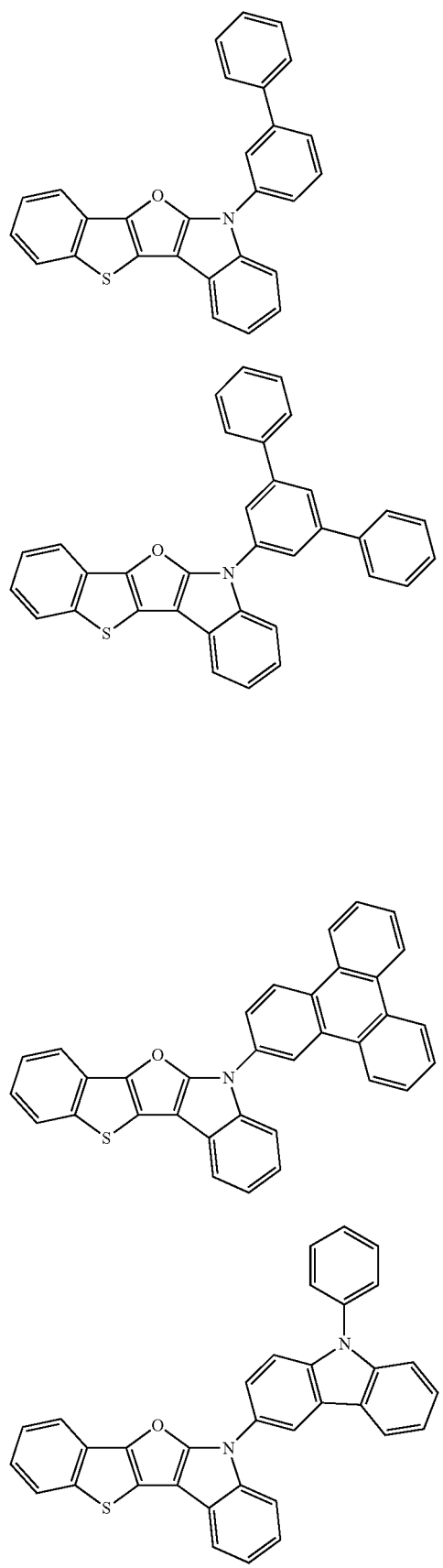
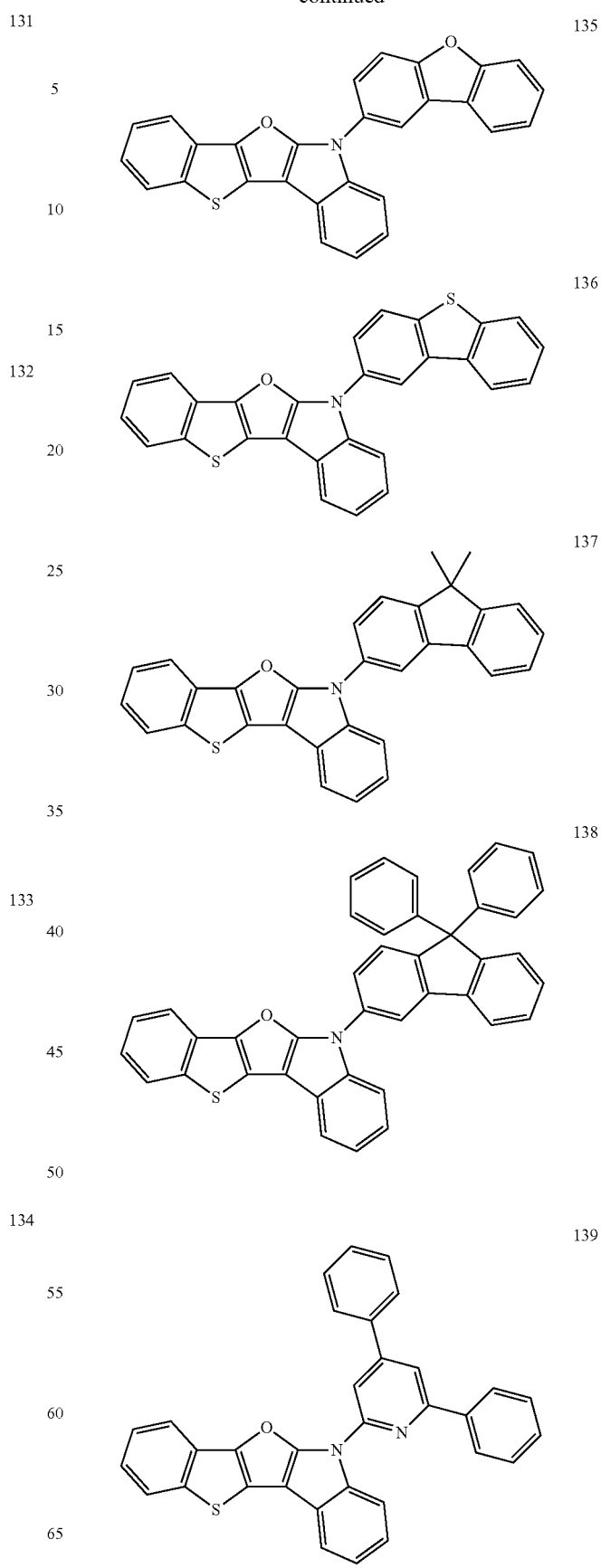

140
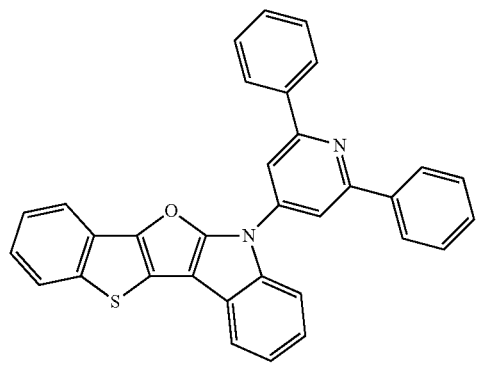
141
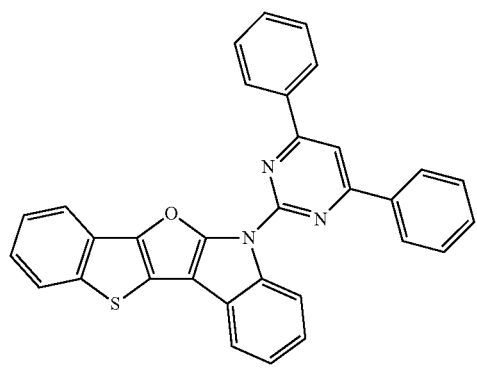
142
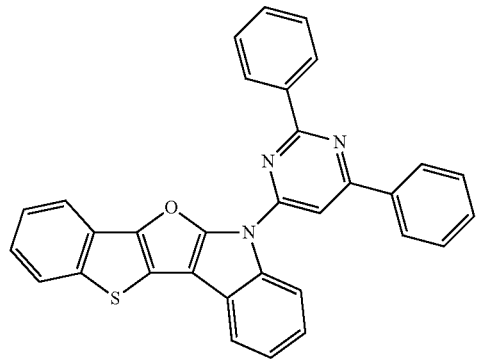
143
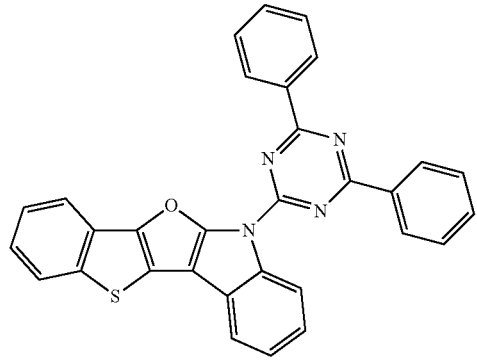
144
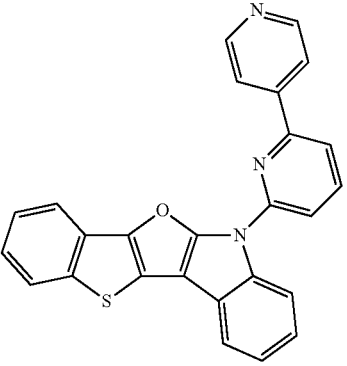
145
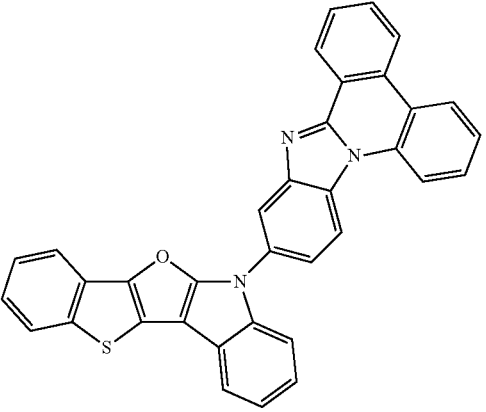
146
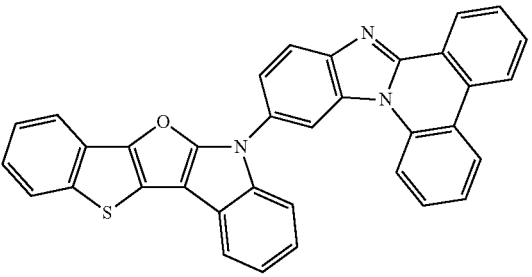
147
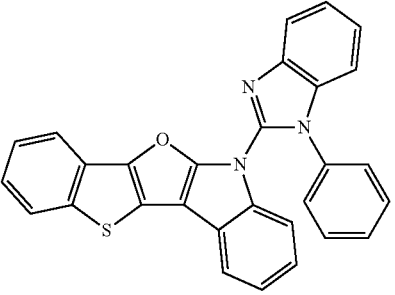

-continued
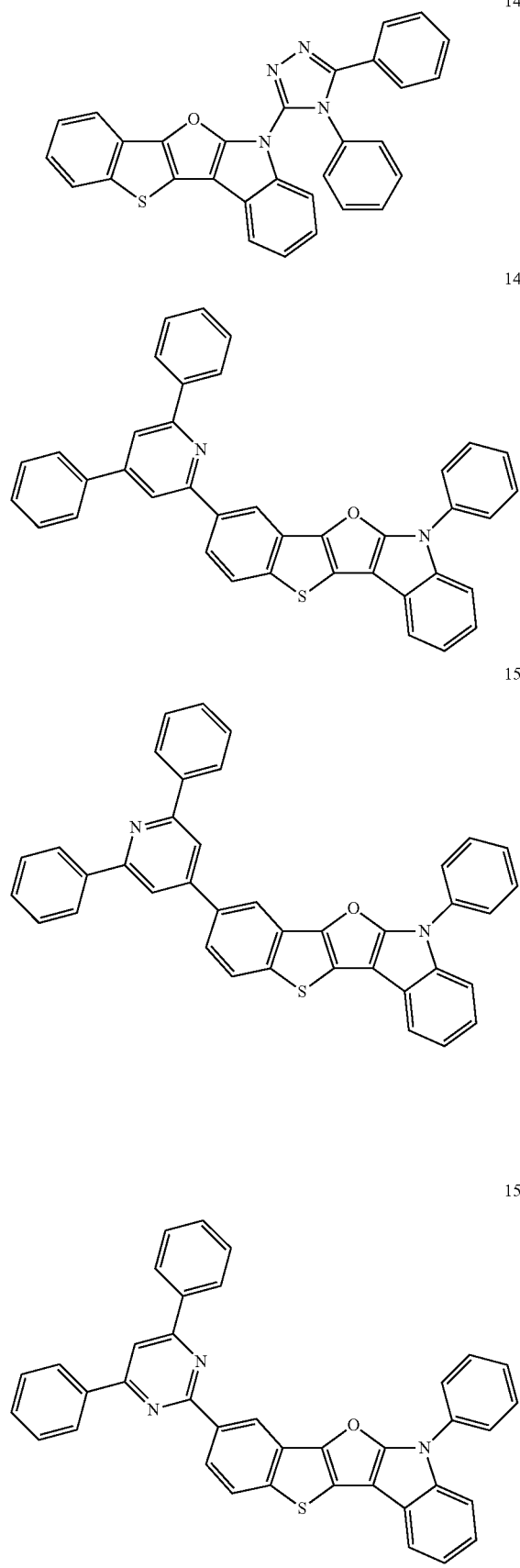
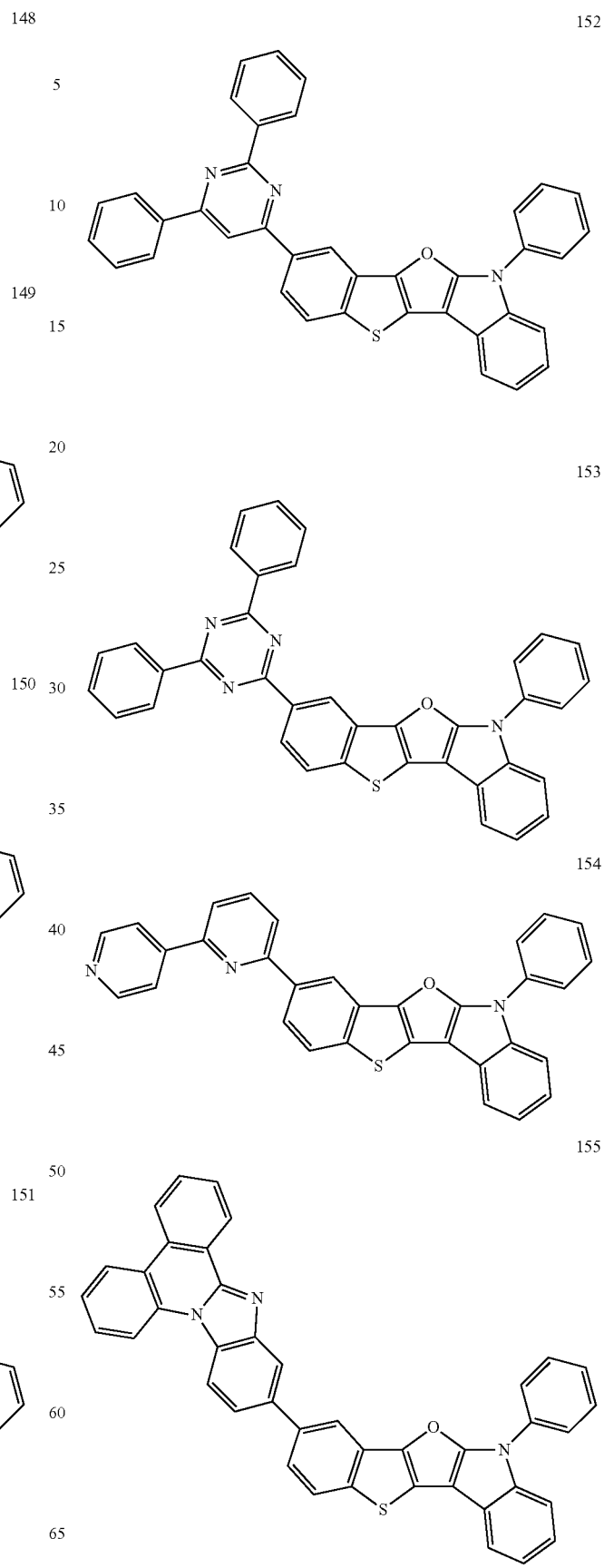

156
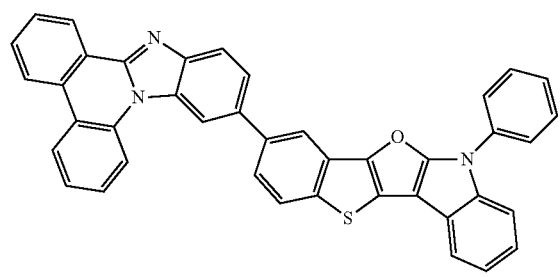
157
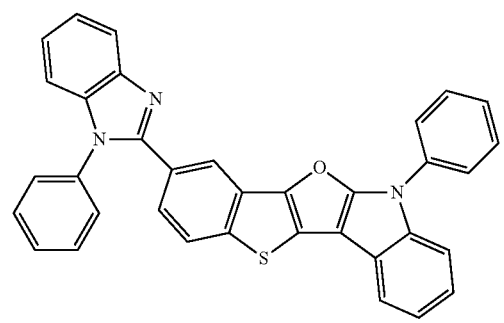
158
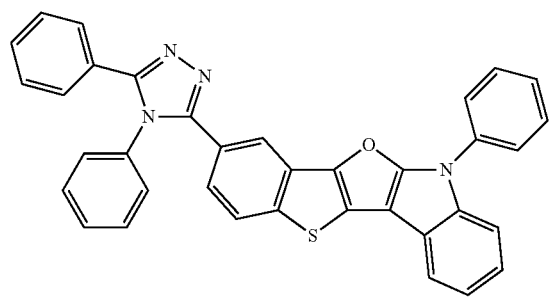
159
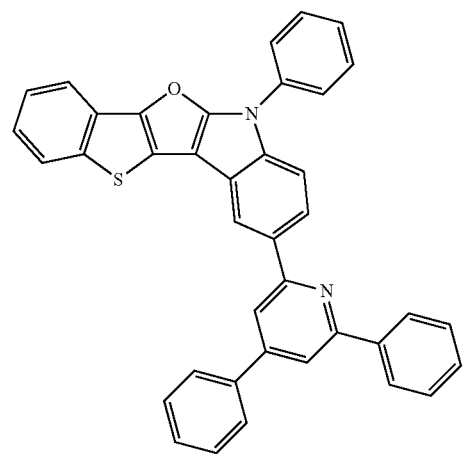
160
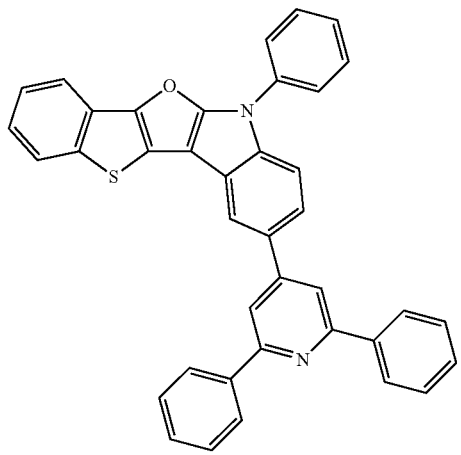
161
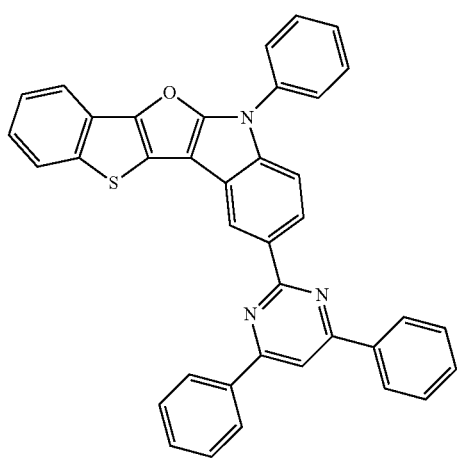
162

163 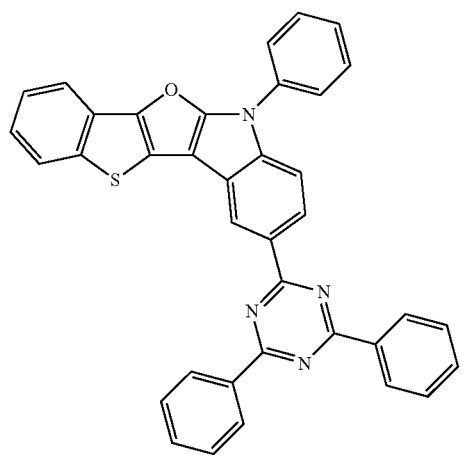
164 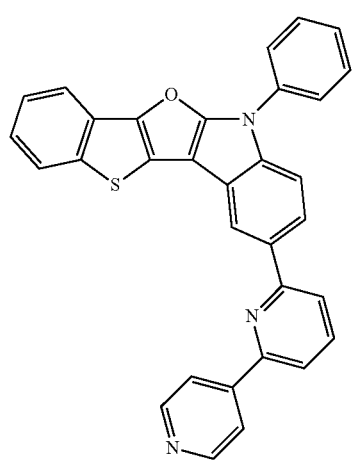
165 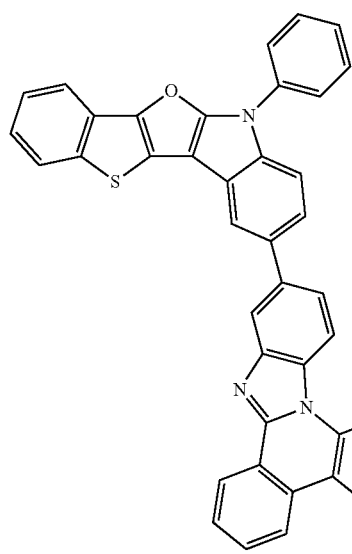
166 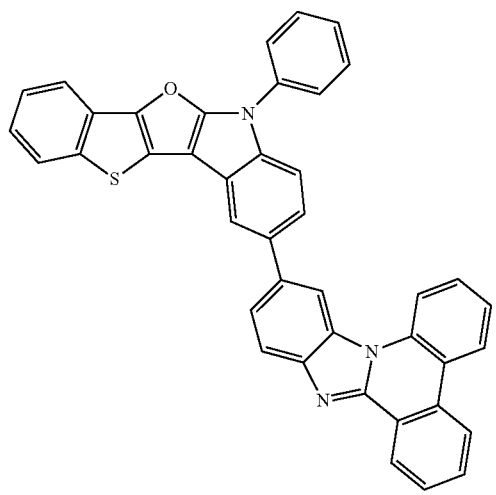
167 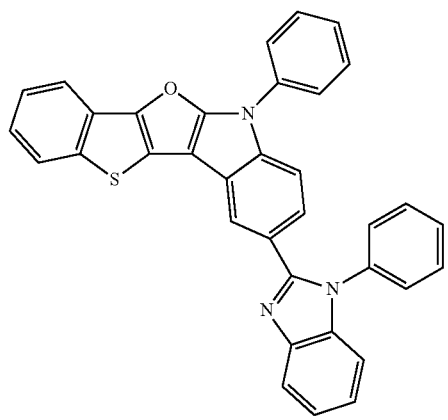
168 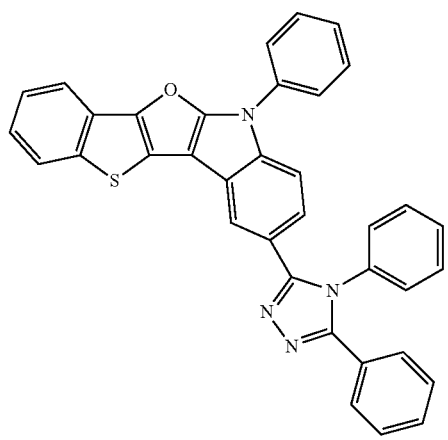
169 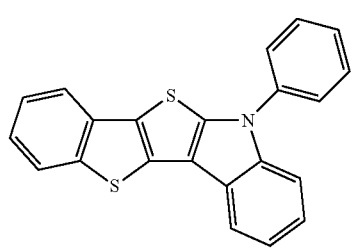

US 10,032,985 B2
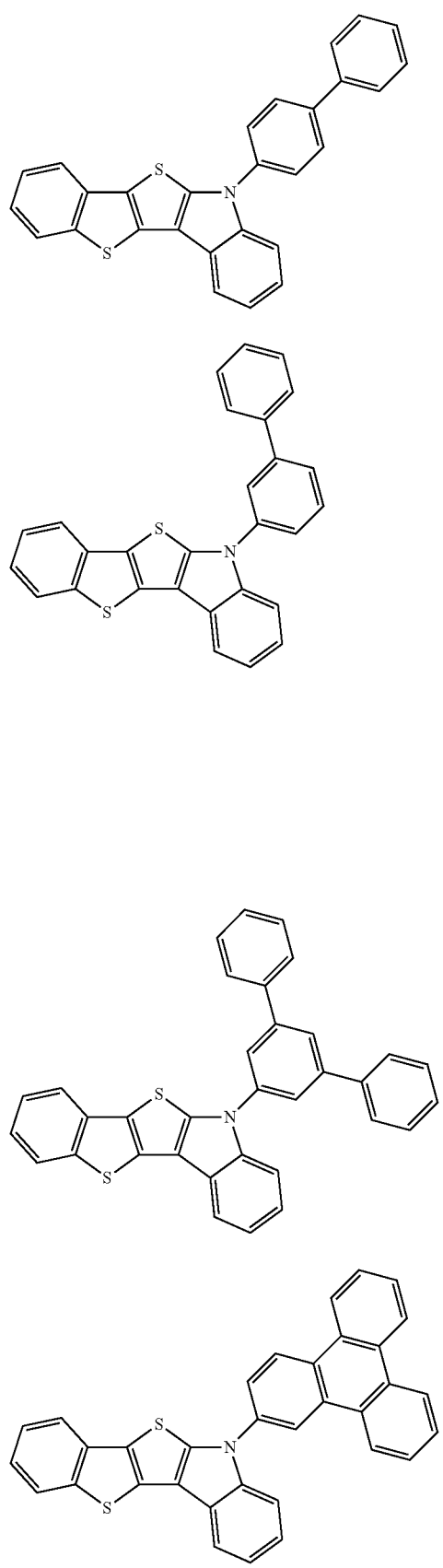
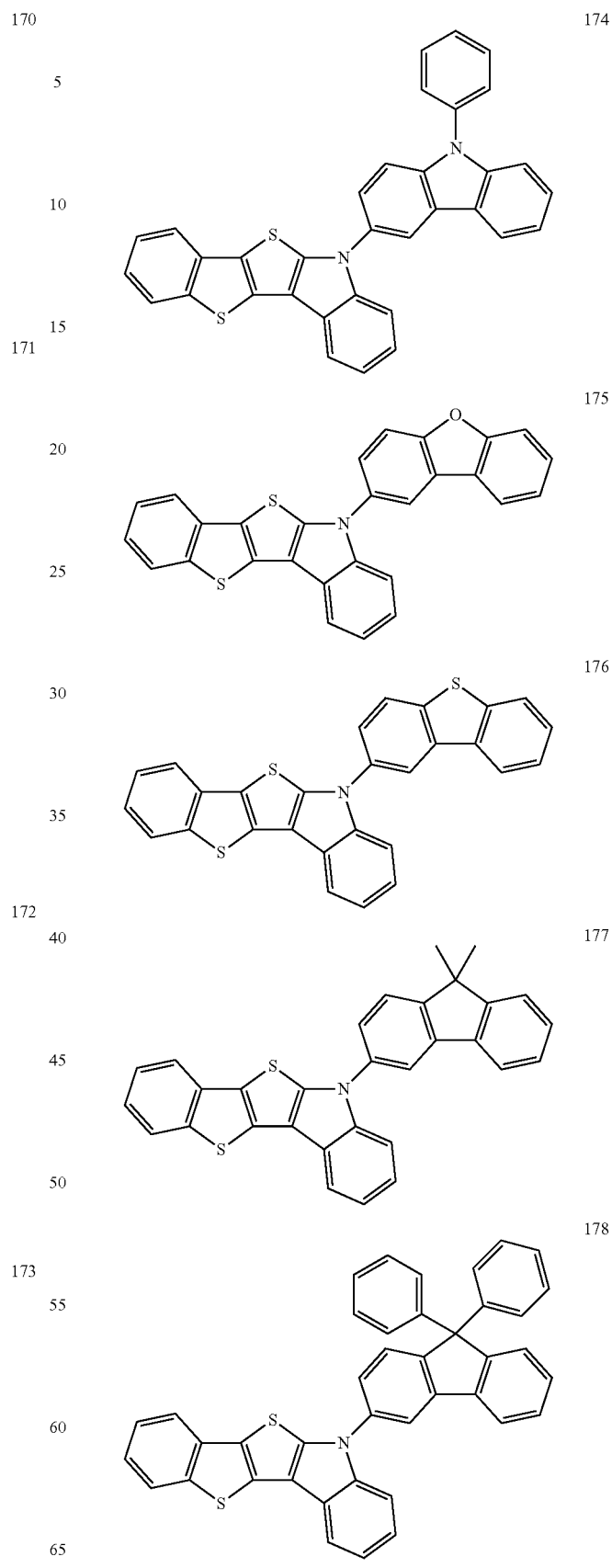

179
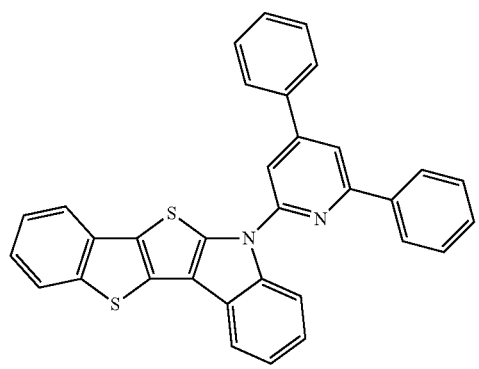
180
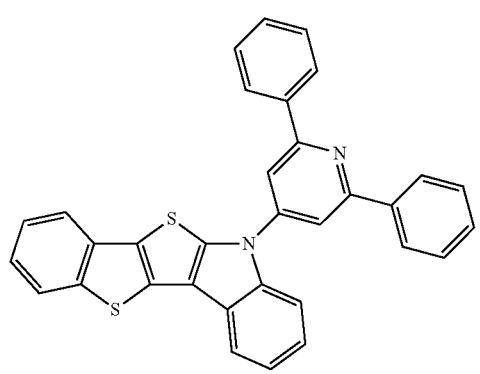
181
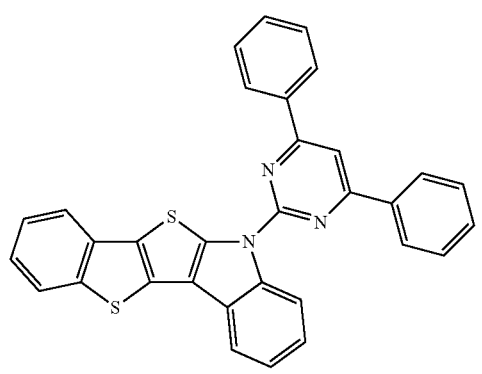
182
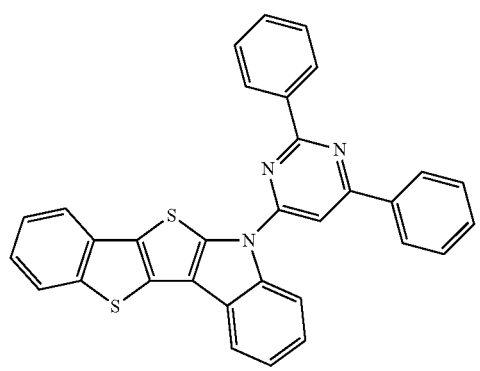
183
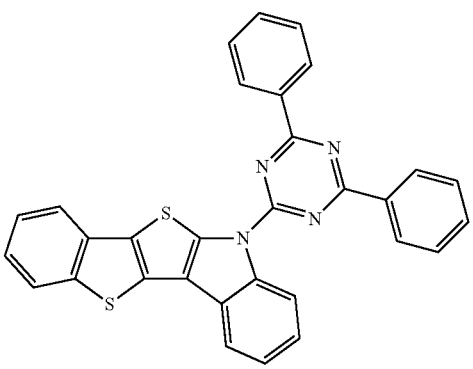
184
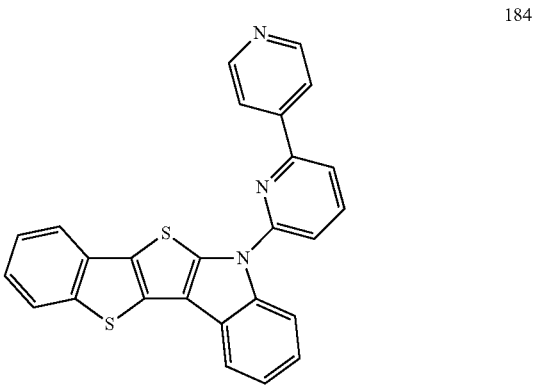
185
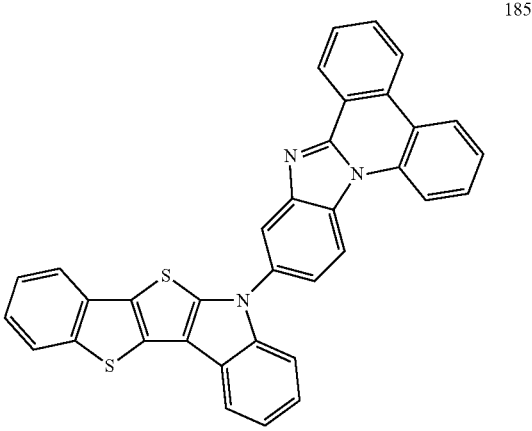
186
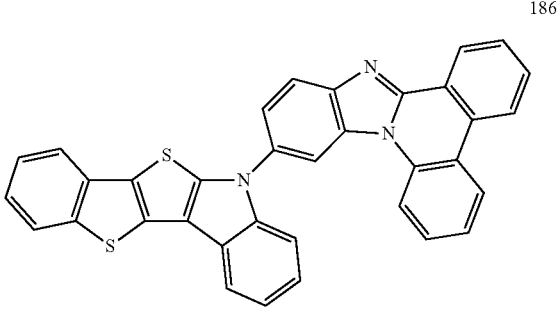

-continued
187
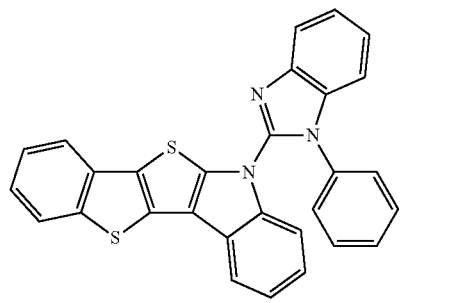
188
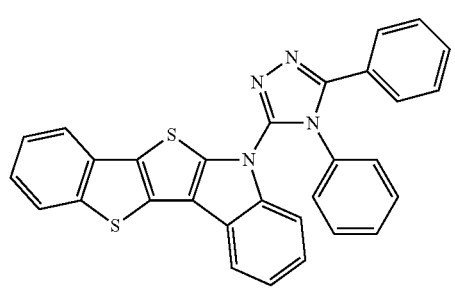
189
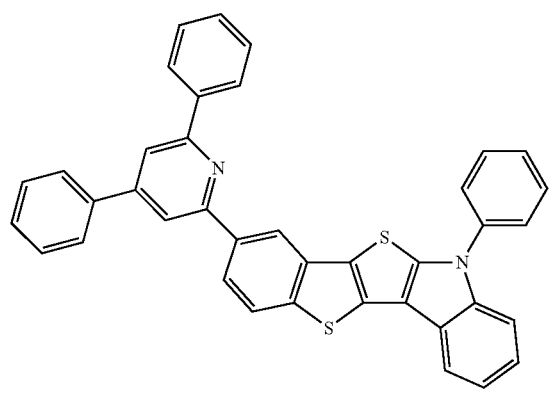
190
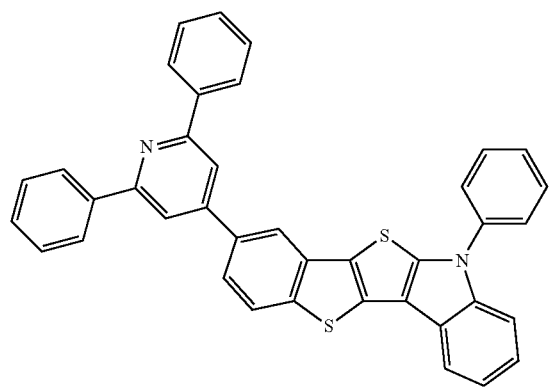
-continued
191
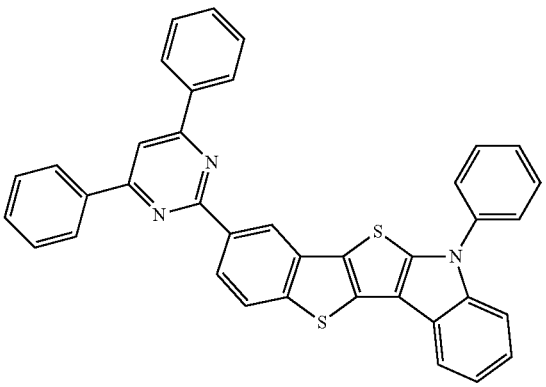
192
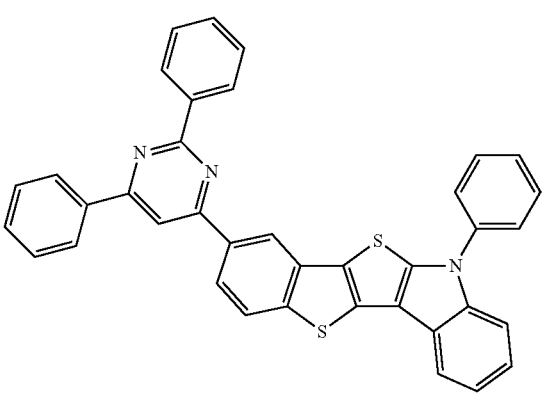
193
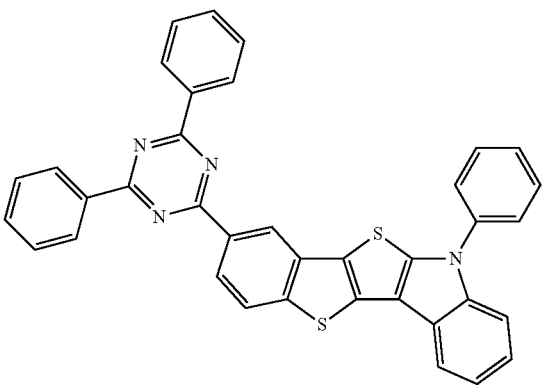
194
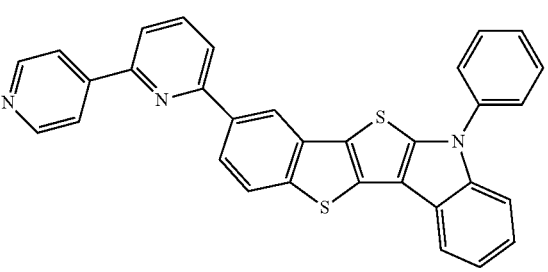

195
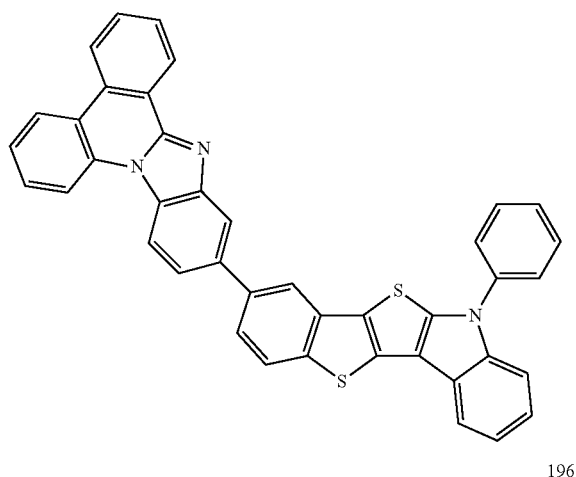
196
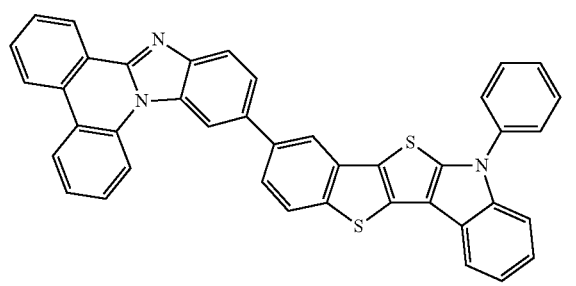
197
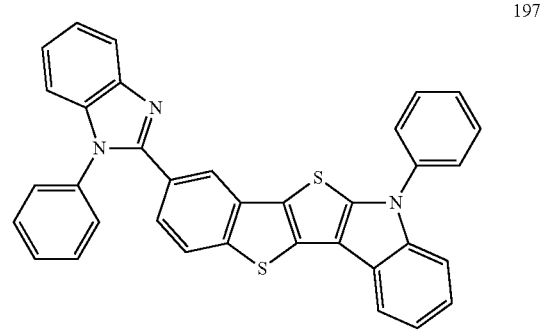
198
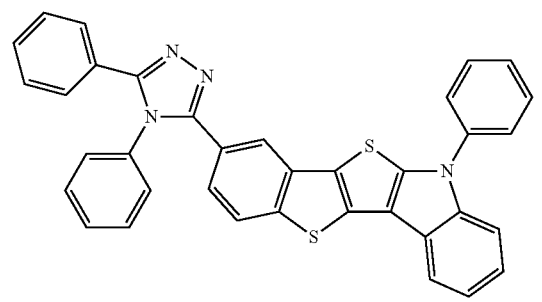
199
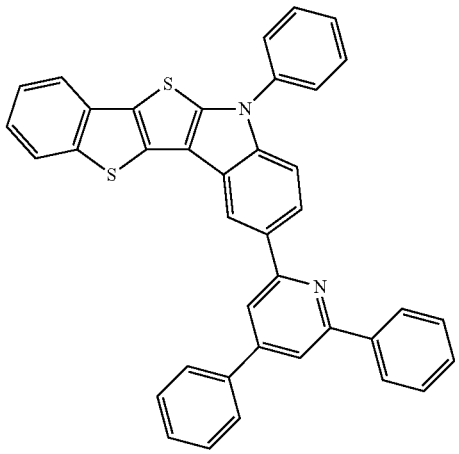
200
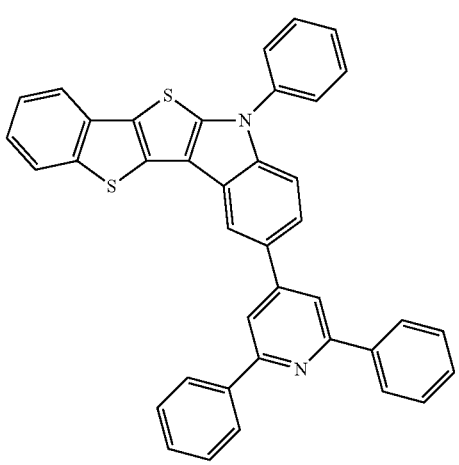
201
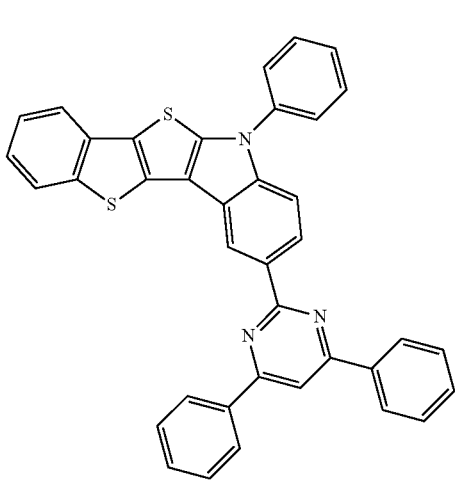

202
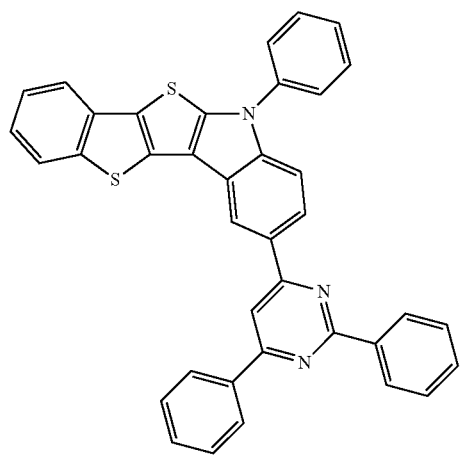
203
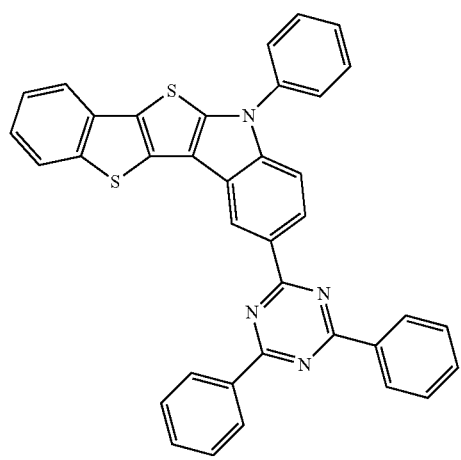
204
205
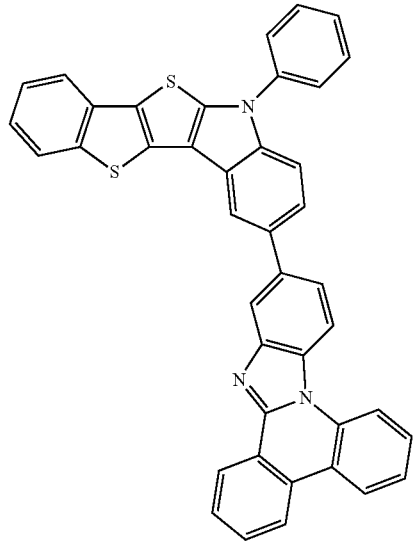
206
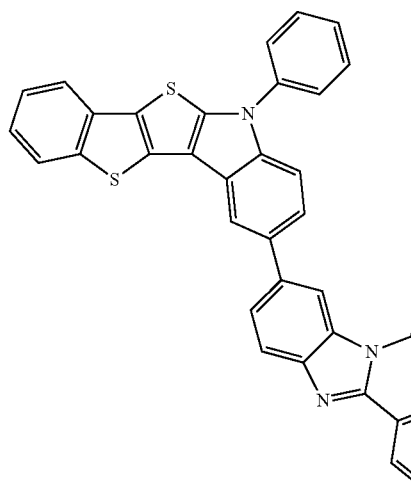
207
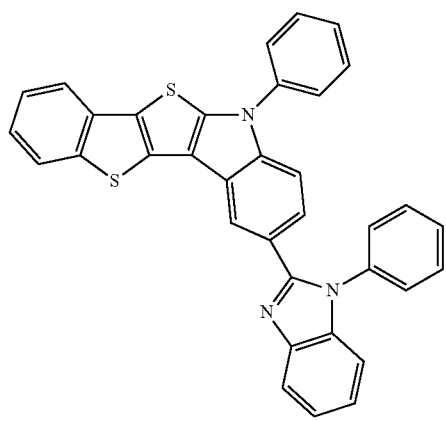

-continued

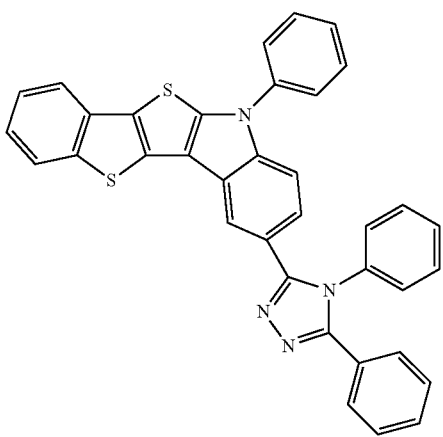
208

In Formula 1,
when $X_2$ is $N[(L_4)_{a4}\text{-}(R_4)_{b4}]$,
i) $X_1$ is $C[(L_2)_{a2}\text{-}(R_2)_{b2}][(L_3)_{a3}\text{-}(R_3)_{b3}]$ or $Si[(L_2)_{a2}\text{-}(R_2)_{b2}][(L_3)_{a3}\text{-}(R_3)_{b3}]$, and $X_3$ is selected from $N[(L_7)_{a7}\text{-}(R_7)_{b7}]$, $C[(L_8)_{a8}\text{-}(R_8)_{b8}][(L_9)_{a9}\text{-}(R_9)_{b9}]$, $Si[(L_8)_{a8}\text{-}(R_8)_{b8}][(L_9)_{a9}\text{-}(R_9)_{b9}]$, S, and O, or
ii) $X_1$ is selected from $N[(L_1)_{a1}\text{-}(R_1)_{b1}]$, S, and O, and $X_3$ is $C[(L_8)_{a8}\text{-}(R_8)_{b8}][(L_9)_{a9}\text{-}(R_9)_{b9}]$ or $Si[(L_8)_{a8}\text{-}(R_8)_{b8}][(L_9)_{a9}\text{-}(R_9)_{b9}]$. That is, in Formula 1, when $X_2$ is $N[(L_4)_{a4}\text{-}(R_4)_{b4}]$, at least one of $X_1$ and $X_3$ includes C or Si. Since various substituents are capable of being introduced to the condensed cyclic compound, as described above, controlling molecular energy levels is facilitated.

Also, in Formula 1, ring C and ring E may be condensed in anti-syn locations, respectively, relative to ring D (see Formula 1″ below). Thus, the resultant structure may be an asymmetric molecular structure. Due to the asymmetric structure, the condensed cyclic compound has low crystallinity, and thus excellent film-formation characteristics.

compound represented by Formula 1, low driving voltage, high efficiency, high brightness, and long lifespan.

The condensed cyclic compound of Formula 1 may be used between a pair of electrodes of an organic light-emitting device. For example, the condensed cyclic compound may be included in at least one group selected from
i) a hole transport region (including, for example, at least one of a hole injection layer, a hole transport layer, a buffer layer, and an electron blocking layer) that is disposed between the first electrode and the emission layer, and
ii) an electron transport region (including, for example, at least one group selected from a hole blocking layer, an electron transport layer, and an electron injection layer) that is disposed between the emission layer and the second electrode.

For example, the condensed cyclic compound represented by Formula 1 may be included in the emission layer. In this regard, the emission layer may further include a dopant, and the condensed cyclic compound included in the emission layer may act as a host. The emission layer may be a green emission layer emitting green light, and the dopant may be a phosphorescent dopant.

The expression "(an organic layer) includes at least one condensed cyclic compounds" used herein may include a case in which "(an organic layer) includes one condensed cyclic compound of Formula 1" and a case in which "(an organic layer) includes two or more different condensed cyclic compounds of Formula 1".

For example, the organic layer may include, as the condensed cyclic compound, only Compound 1. In this regard, Compound 1 may be situated in an emission layer of the organic light-emitting device. In another embodiment, the organic layer may include, as the condensed cyclic compound, Compound 1 and Compound 2. In this regard, Compound 1 and Compound 2 may be situated in either an identical layer (for example, Compound 1 and Compound 2 all may be situated in an emission layer), or different layers.

Formula 1″

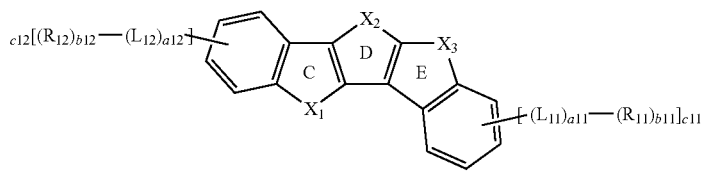

Synthesis methods of the condensed cyclic compound represented by Formula 1 may be apparent to one of ordinary skill in the art by referring to Synthesis Examples provided below.

The condensed cyclic compound represented by Formula 1 is suitable for use in an organic layer of an organic light-emitting device, for example, for use as a host in an emission layer of the organic layer. Thus, another aspect provides an organic light-emitting device that includes:
a first electrode;
a second electrode; and
an organic layer that is disposed between the first electrode and the second electrode, wherein
the organic layer includes an emission layer and at least one of the condensed cyclic compounds represented by Formula 1.

The organic light-emitting device may have, due to the inclusion of an organic layer including the condensed cyclic The first electrode may be an anode, which is a hole injection electrode, and the second electrode may be a cathode, which is an electron injection electrode. Alternatively, the first electrode may be a cathode, which is an electron injection electrode, or the second electrode may be an anode, which is a hole injection electrode.

For example, the first electrode may be an anode, and the second electrode may be a cathode, and the organic layer includes
i) a hole transport region that is disposed between the first electrode and the emission layer and includes at least one of a hole injection layer, a hole transport layer, and an electron blocking layer, and
ii) an electron transport region that is disposed between the emission layer and the second electrode and includes at least one group selected from a hole blocking layer, an electron transport layer, and an electron injection layer.

The term "organic layer" used herein refers to a single layer and/or a plurality of layers disposed between the first electrode and the second electrode of an organic light-emitting device. The "organic layer" may include, in addition to an organic compound, an organometallic complex including metal.

The FIGURE, is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

In the FIGURE, a substrate may be additionally disposed under the first electrode 11 or above the second electrode 19. Any substrate that is used in general organic light-emitting devices may be used. The substrate may be a glass substrate or transparent plastic substrate, each of which has excellent mechanical strength, thermal stability, transparency, surface smoothness, ease of handling, and water repellency.

The first electrode 11 may be formed by depositing or sputtering a material for forming the first electrode on the substrate. The first electrode 11 may be an anode. The material for the first electrode 11 may be selected from materials with a high work function to make holes be easily injected. The first electrode 13 may be a reflective electrode or a transmissive electrode. The material for the first electrode 11 may be an indium tin oxide (ITO), indium zinc oxide (IZO), tin oxide ($SnO_2$), or zinc oxide (ZnO). According to another embodiment, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers.

An organic layer 15 may be disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. According to another embodiment, the hole transport region may have a structure of hole injection layer/hole transport layer or hole injection layer/hole transport layer/electron blocking layer, which are sequentially stacked in this stated order from the first electrode 11.

When the hole injection layer (HIL) includes a hole injection layer, the hole injection layer may be formed on the first electrode 11 by using any one of various methods, for example, vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, for example, about 3,5000 rpm to about 5,000 rpm, and a temperature at which a heat treatment is performed to remove a solvent after coating may be from about 80° C. to about 200° C., for example, about 120° C. to about 200° C. However, the coating conditions are not limited thereto.

Conditions for a hole transport layer and an electron blocking layer may be understood by referring to conditions for forming the hole injection layer.

The hole transport region may include at least one compound selected from m-MTDATA, TDATA, 2-TNATA, NPB, 13-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

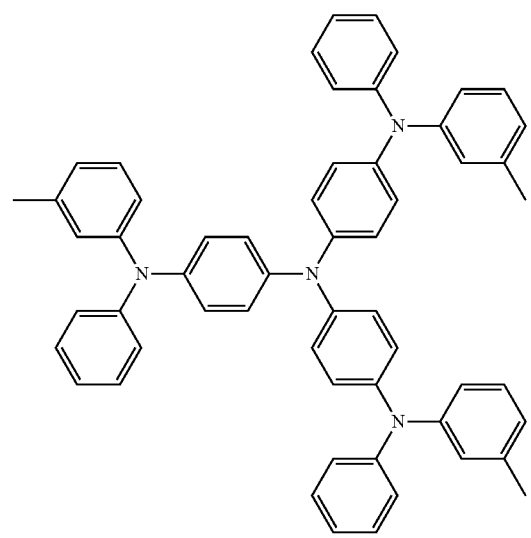

m-MTDATA

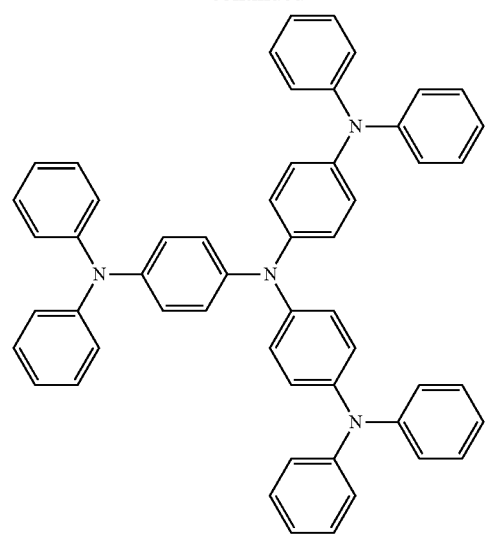
TDATA
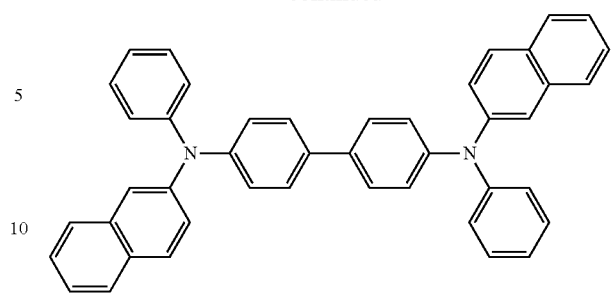
β-NPB
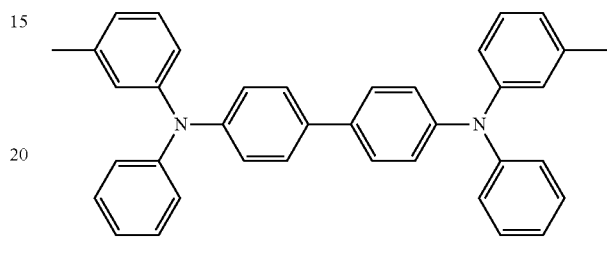
TPD
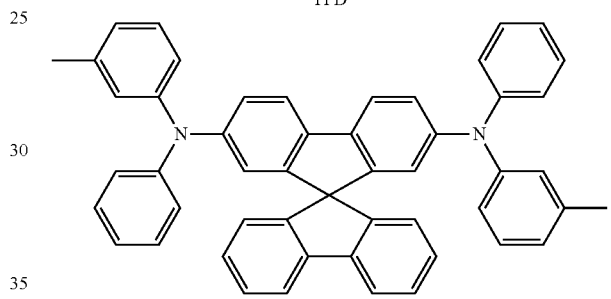
Spiro-TPD
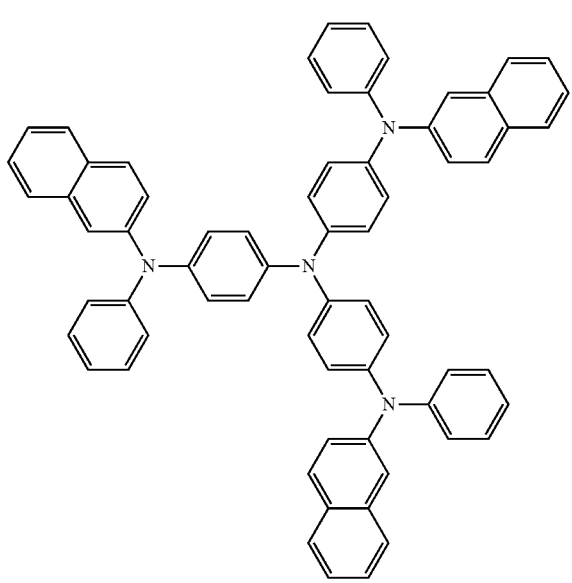
2-TNATA
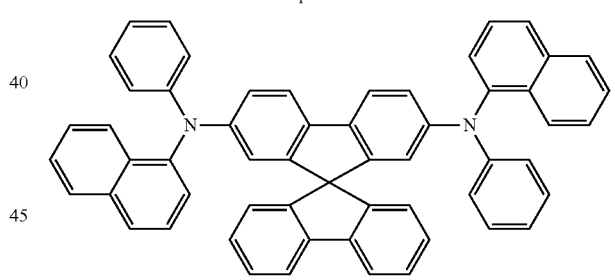
Spiro-NPB
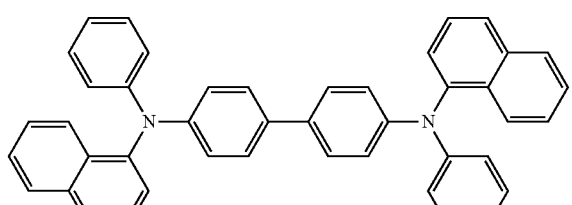
NPB
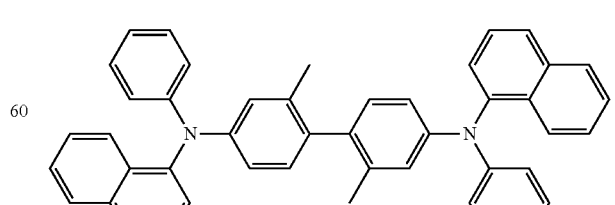
α-NPB

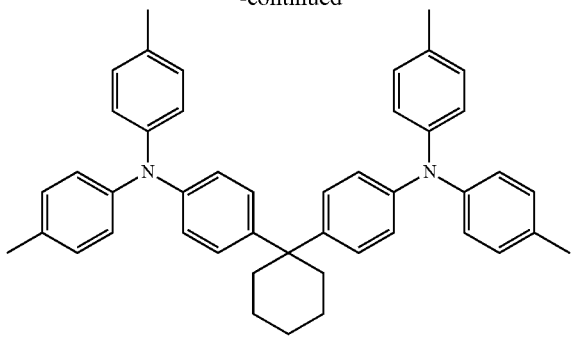

TAPC

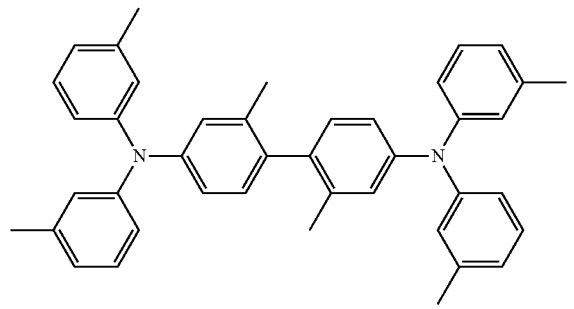

HMTPD

Formula 201

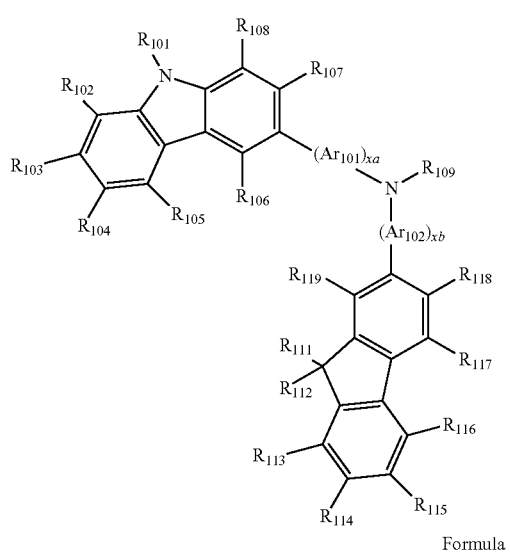

Formula 202

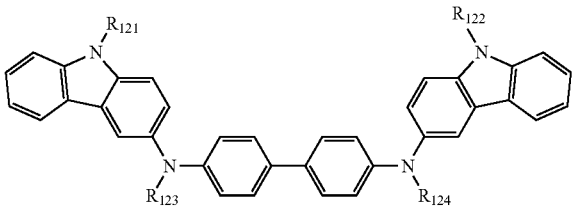

$Ar_{101}$ and $Ar_{102}$ in Formula 201 may be each independently phenylene group, pentalenylene group, indenylene group, naphthylene group, azulenylene group, heptalenylene group, acenaphthylene group, fluorenylene group, penalenylene group, phenanthrenylene group, anthracenylene group, fluoranthenylene group, triphenylenylene group, pyrenylene group, chrysenylenylene group, naphthacenylene group, picenylene group, perylenylene group, or pentacenylene; or phenylene group, pentalenylene group, indenylene group, naphthylene group, azulenylene group, heptalenylene group, acenaphthylene group, fluorenylene group, penalenylene group, phenanthrenylene group, anthracenylene group, fluoranthenylene group, triphenylenylene group, pyrenylene group, chrysenylenylene group, naphthacenylene group, picenylene group, perylenylene group, or pentacenylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group.

xa and xb in Formula 201 may be each independently an integer of 0 to 5, or 0, 1 or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may be each independently hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl (for example, methyl group, ethyl group, propyl group, butyl group, pentyl group, or hexyl group), or a $C_1$-$C_{10}$ alkoxy (for example, methoxy group, ethoxy group, propoxy group, butoxy group, or pentoxy group);

a $C_1$-$C_{10}$ alkyl group or a $C_1$-$C_{10}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof;

phenyl group, naphthyl group, anthracenyl group, fluorenyl group, or pyrenyl group; or phenyl group, naphthyl group, anthracenyl group, fluorenyl group, or pyrenyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group, but they are not limited thereto.

$R_{109}$ in Formula 201 may be one group selected from phenyl group, naphthyl group, anthracenyl group, biphenyl group, and pyridinyl group, each substituted with at least one group selected from phenyl group, naphthyl group, anthracenyl group, biphenyl and pyridinyl; and a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy.

According to an embodiment, the compound represented by Formula 201 may be represented by Formula 201A below, but is not limited thereto:

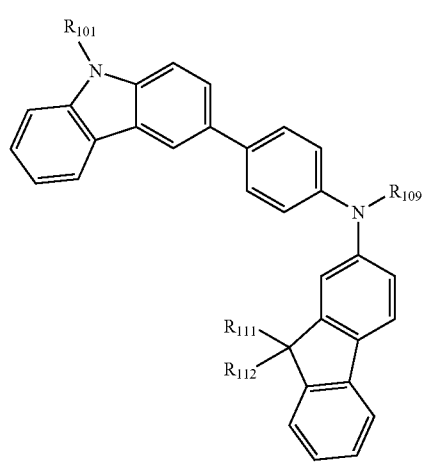

Formula 201A $R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

HT1

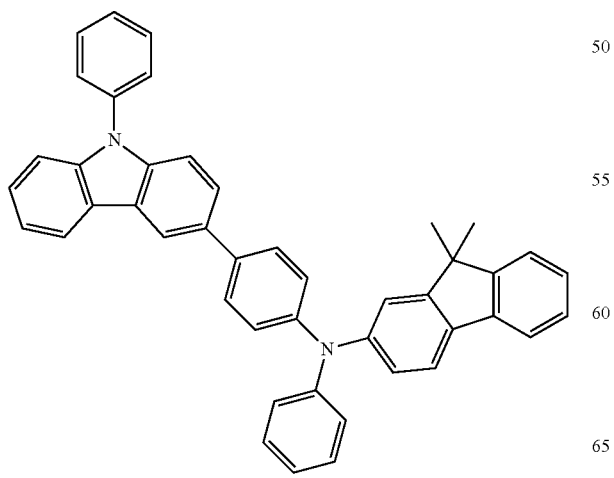

HT2

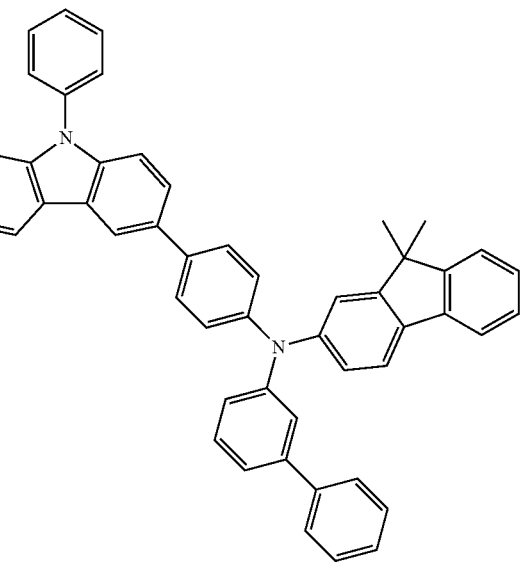

HT3

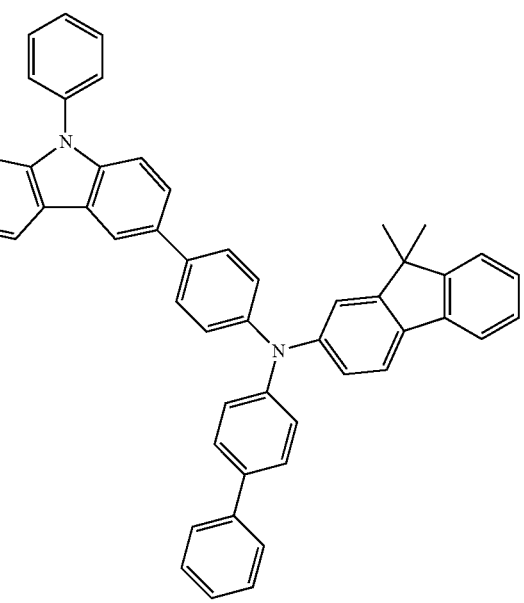

HT4
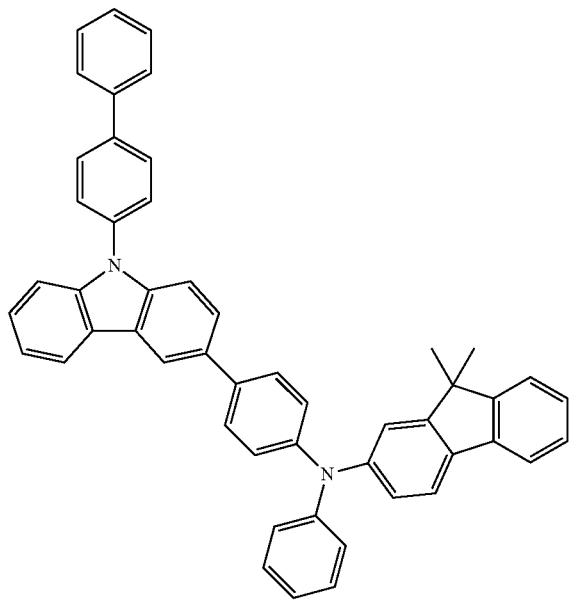
HT5
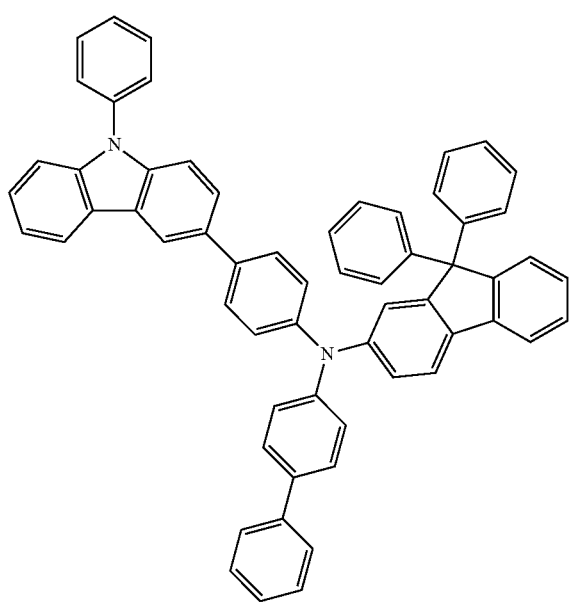
HT6
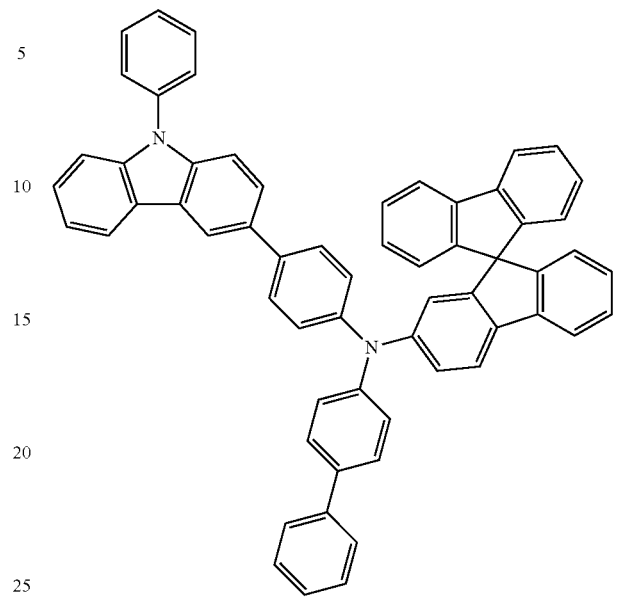
HT7
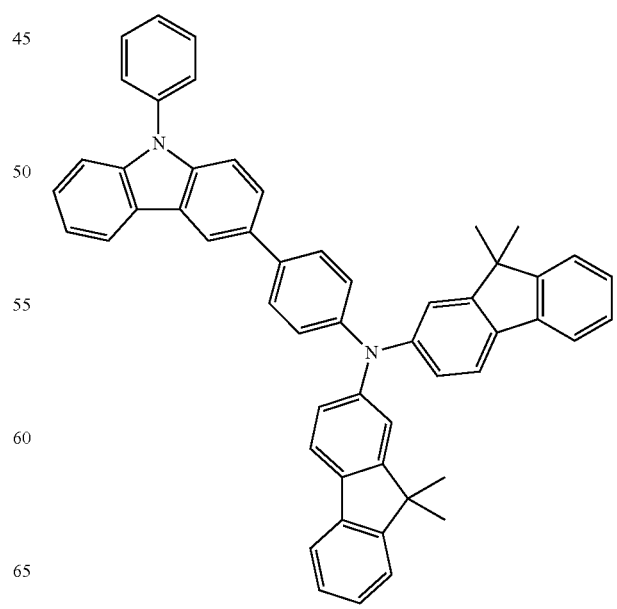

HT8
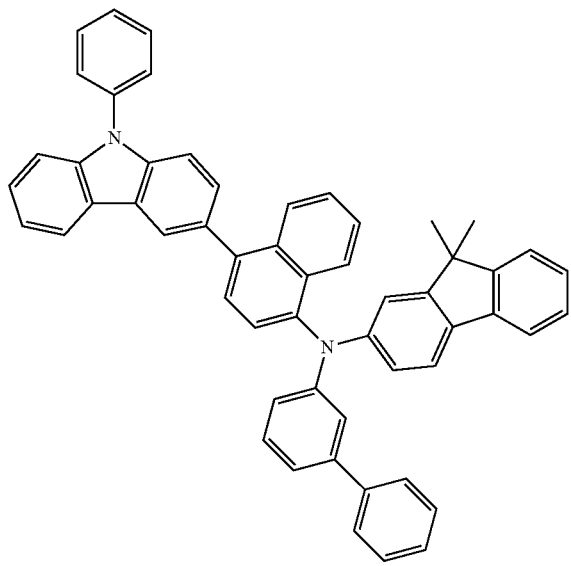
HT9
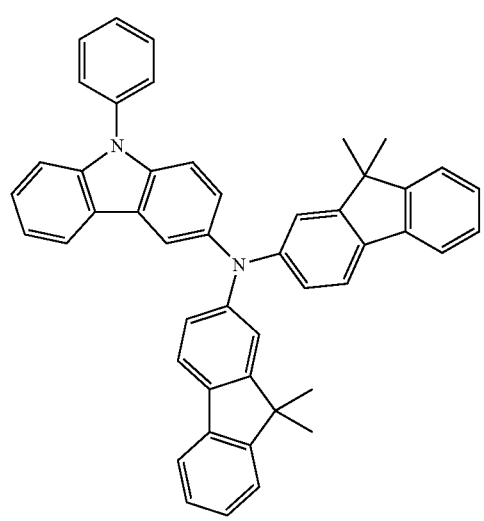
HT10
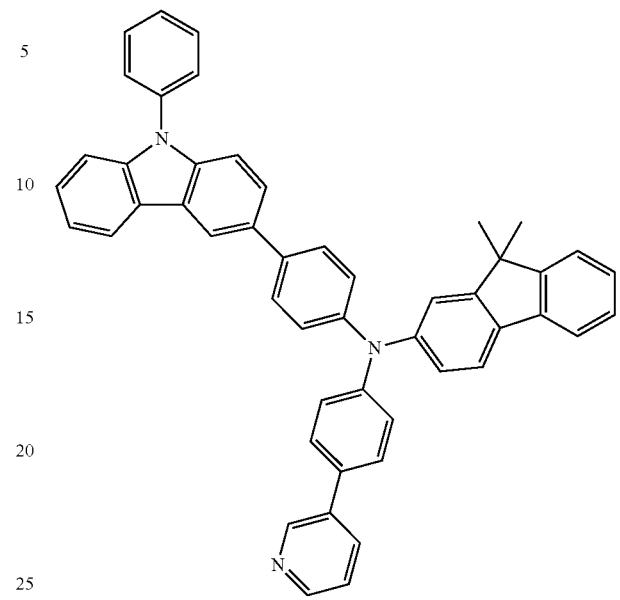
HT11
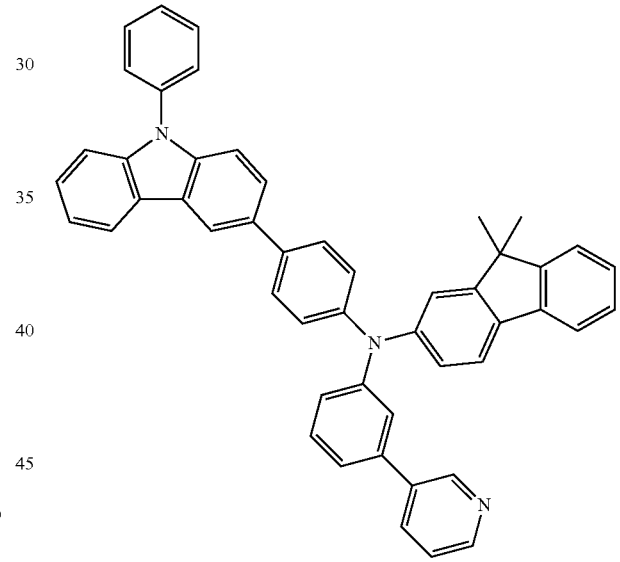
HT12
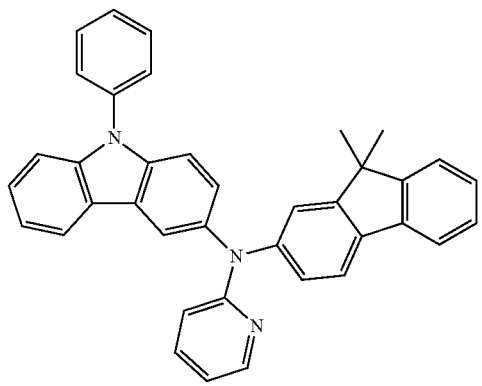

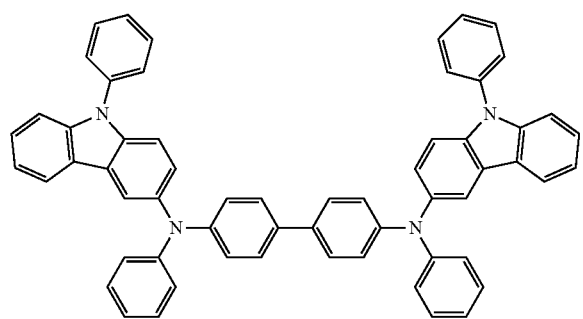
HT13

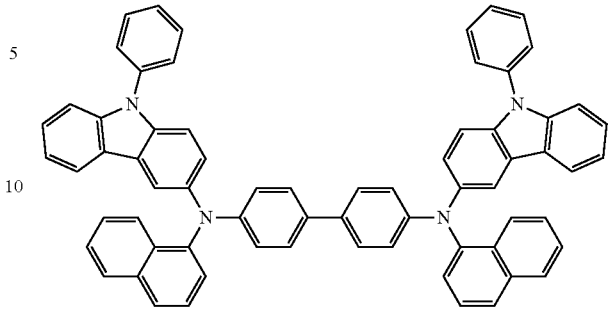
HT17

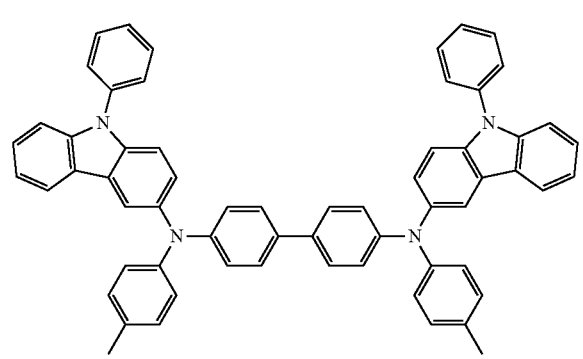
HT14

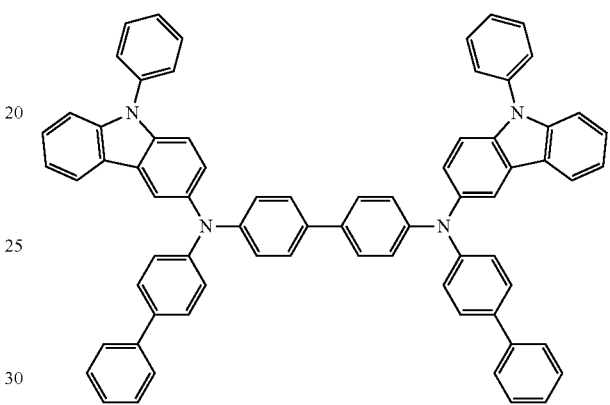
HT18

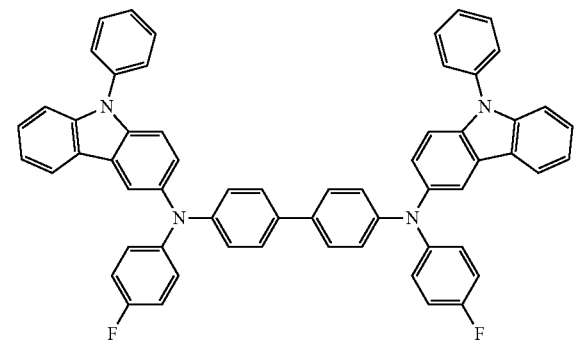
HT15

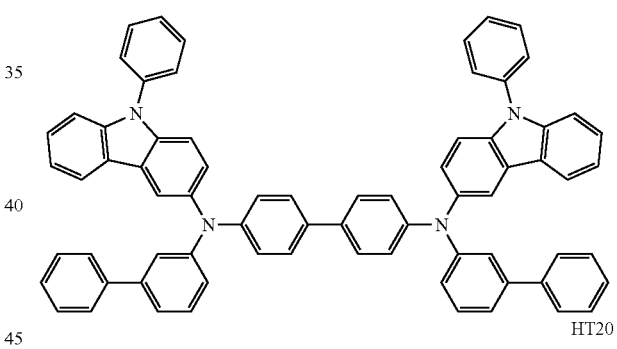
HT19

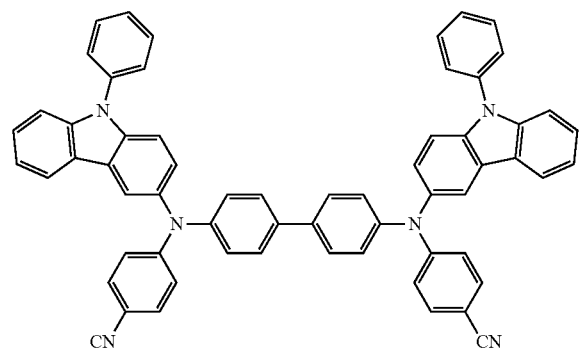
HT16

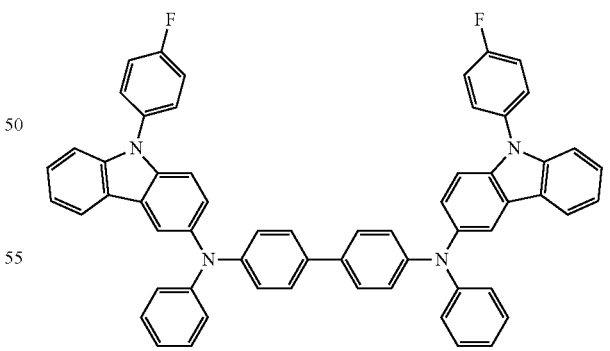
HT20

A thickness of the hole transport region may be in a range of about 100 Å to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto.

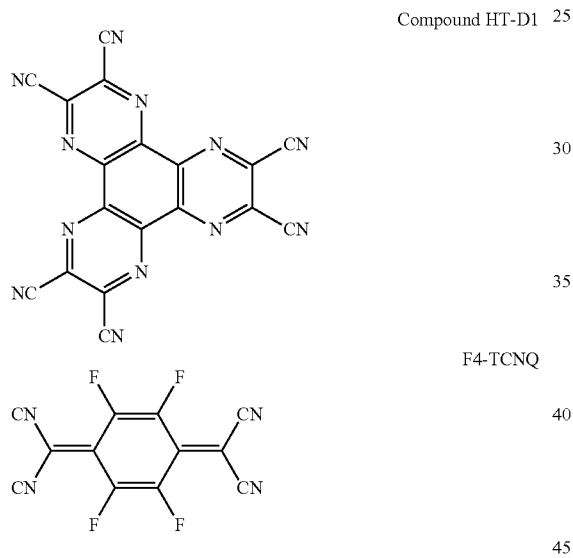

Compound HT-D1

F4-TCNQ

The hole transport region may include a buffer layer.

Also, the buffer layer may compensate for an optical resonance distance according to a wavelength of light emitted from the emission layer. Thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant. The host may include at least one condensed cyclic compound represented by Formula 1.

The host may further include, in addition to the condensed cyclic compound represented by Formula 1, at least one of TPBi, TBADN, AND (also referred to as "DNA"), CBP, CDBP, and TCP.

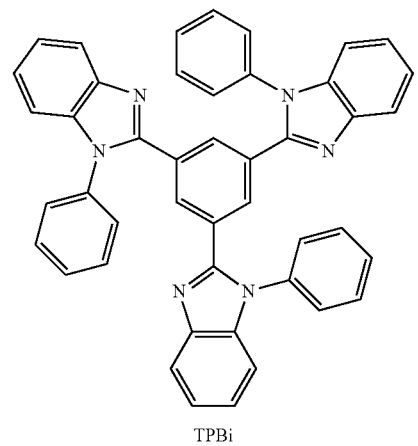

TPBi

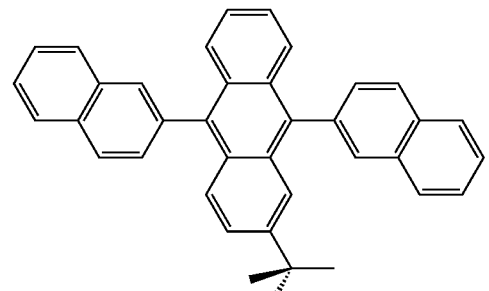

TBADN

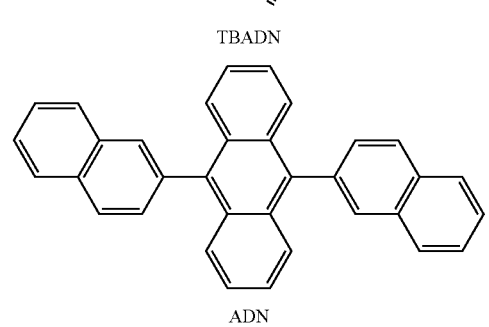

ADN

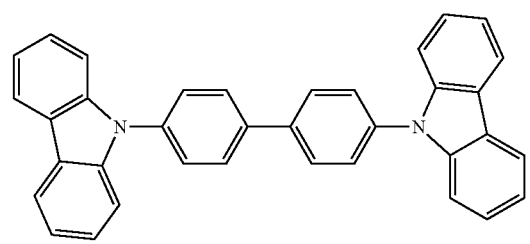

CBP

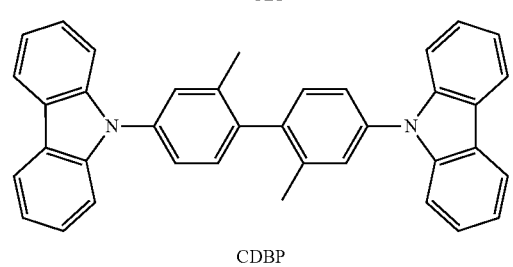

CDBP

-continued

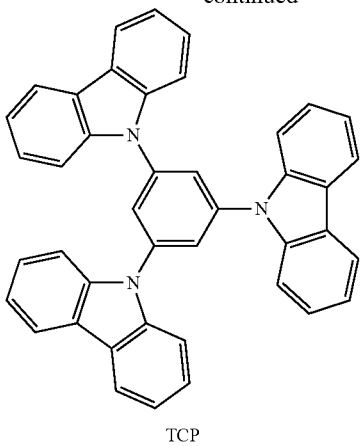

TCP

According to another embodiment, the host may further include, the condensed cyclic compound represented by Formula 1, a compound represented by Formula 301 below:

Formula 301

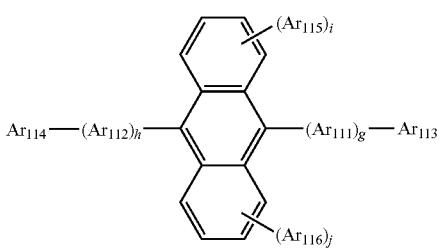

$Ar_{111}$ and $Ar_{112}$ in Formula 301 may be each independently phenylene group, naphthylene group, phenanthrenylene group, or pyrenylene; and phenylene group, naphthylene group, phenanthrenylene group, fluorenyl group, or pyrenylene group, each substituted with at least one group selected from phenyl group, naphthyl group, and anthracenyl group.

$Ar_{113}$ to $Ar_{116}$ in Formula 301 may be each independently a $C_1$-$C_{10}$ alkyl group; phenyl group, naphthyl group, phenanthrenyl group, or pyrenyl group; or phenyl group, naphthyl group, phenanthrenyl group, fluorenyl group, or pyrenyl group, each substituted with at least one group selected from phenyl group, naphthyl group, and anthracenyl group.

g, h, 1, and j in Formula 301 may be each independently an integer of 0 to 4, for example, an integer of 0, 1, or 2.

$Ar_{113}$ and $Ar_{116}$ in Formula 301 may be each independently a $C_1$-$C_{10}$ alkyl group substituted with at least one group selected from phenyl group, naphthyl group, or anthracenyl group;

phenyl group, naphthyl group, anthracenyl group, pyrenyl group, phenanthrenyl group, or fluorenyl group;

phenyl group, naphthyl group, anthracenyl group, pyrenyl group, phenanthrenyl group, or fluorenyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, phenyl group, naphthyl group, anthracenyl group, pyrenyl group, phenanthrenyl group, and fluorenyl; or

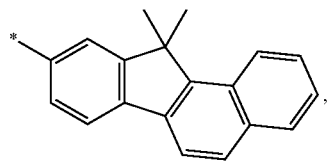 [SMILES: *c1ccc2c(c1)C(C)(C)c1c-2ccc2ccccc12]

but they are not limited thereto.

According to another embodiment, the host may further include, the condensed cyclic compound represented by Formula 1, a compound represented by Formula 302 below:

Formula 302

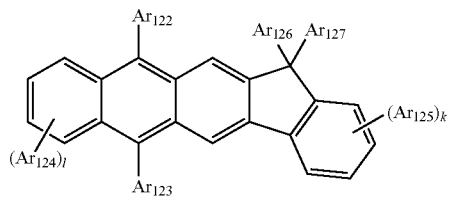

$Ar_{122}$ to $Ar_{125}$ in Formula 302 are the same as described in detail in connection with $Ar_{113}$ in Formula 301.

$Ar_{126}$ and $Ar_{127}$ in Formula 302 may each be independently a $C_1$-$C_{10}$ alkyl group (for example, methyl group, ethyl group, or propyl group).

k and 1 in Formula 302 may be each independently an integer of 0 to 4. For example, k and 1 may be 0, 1, or 2.

The compound represented by Formula 301 and the compound represented by Formula 302 may include Compounds H1 to H42 illustrated below, but are not limited thereto.

H1

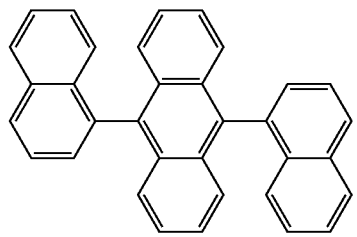

H2

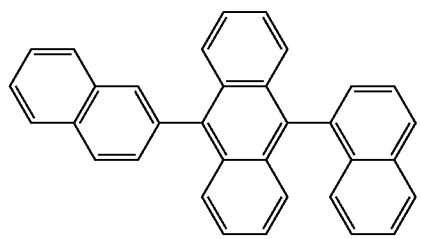

127
-continued
H3
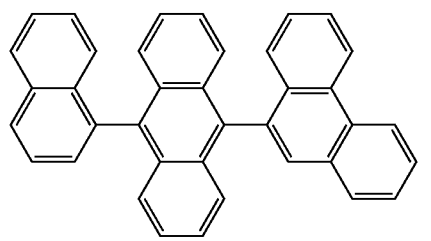
H4
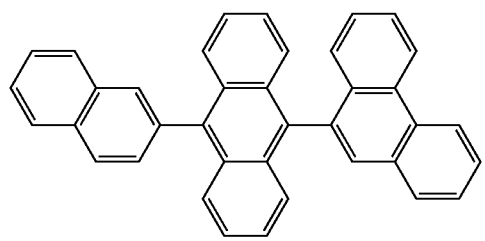
H5
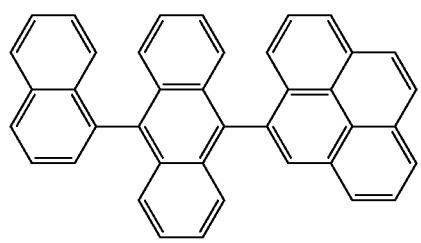
H6
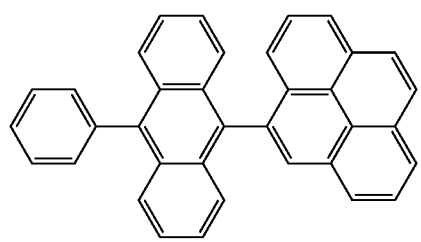
H7
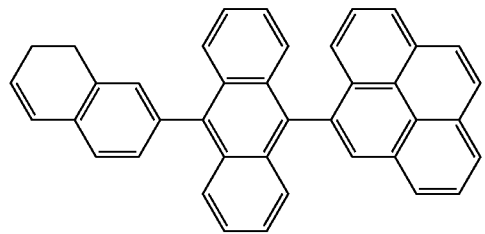
H8
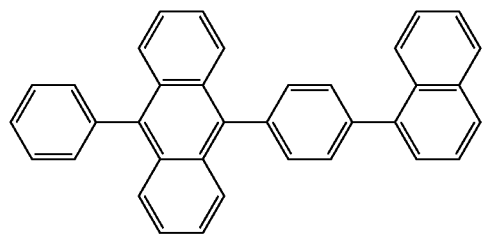
128
-continued
H9
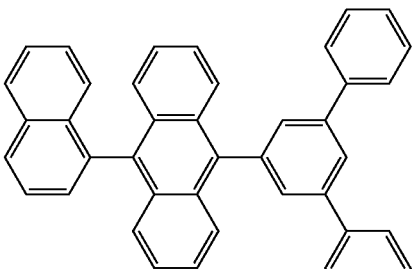
H10
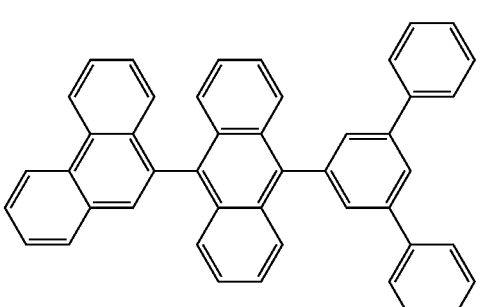
H11
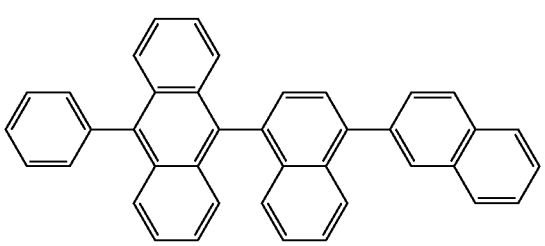
H12
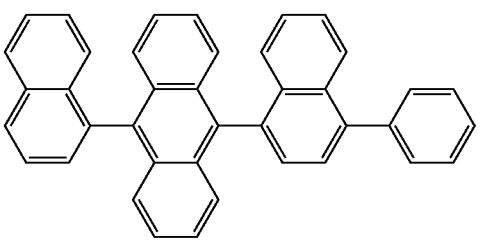
H13
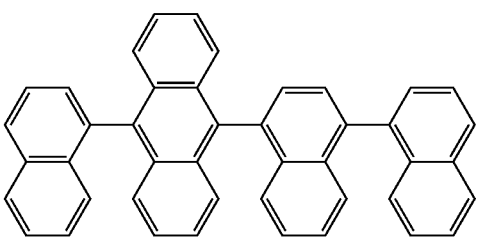
H14
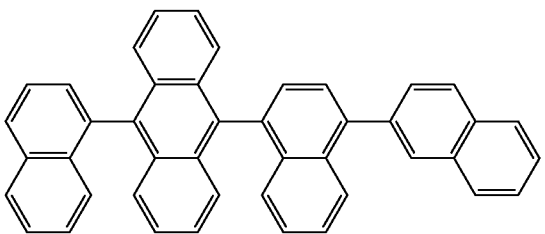

H15
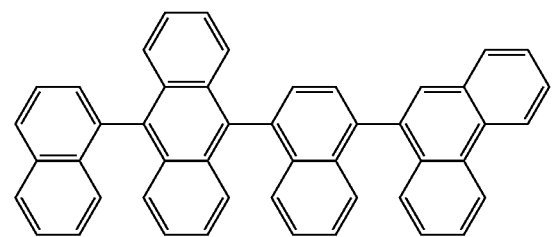
H16
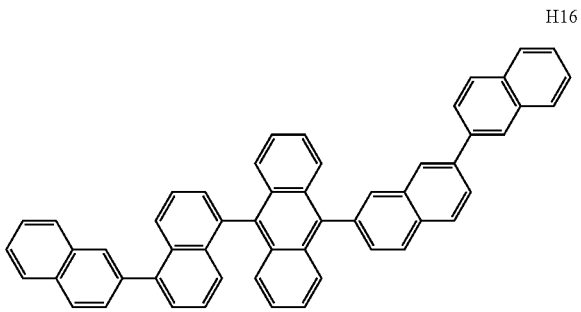
H17
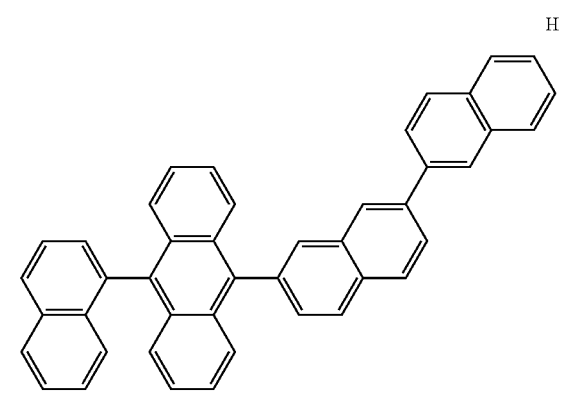
H18
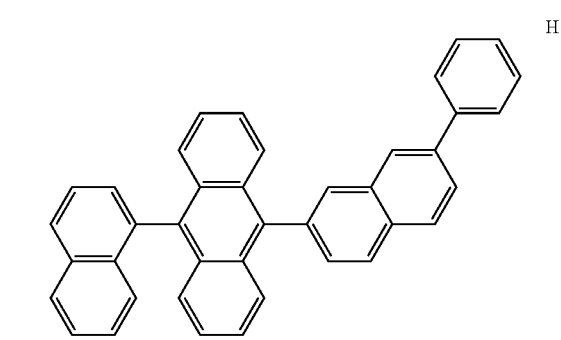
H19
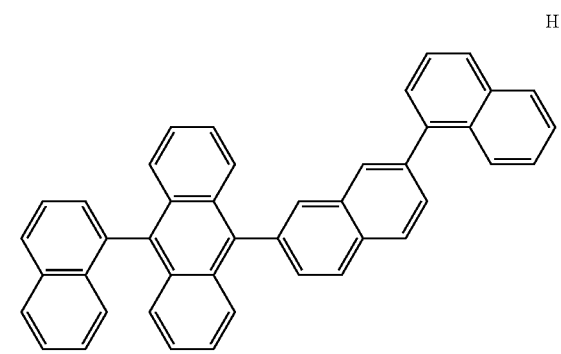
H20
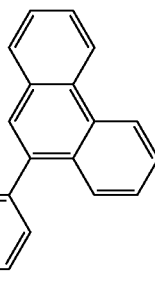
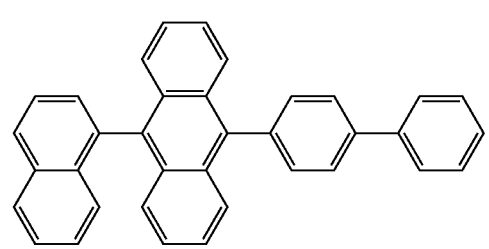
H21
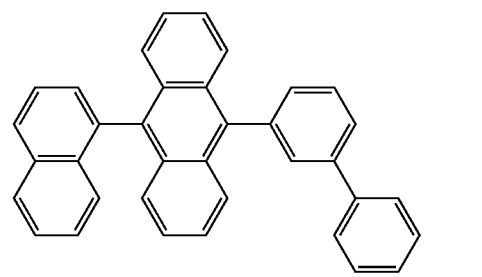
H22
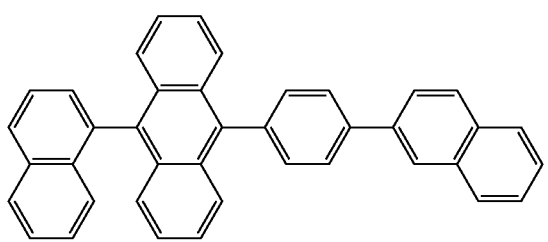
H23
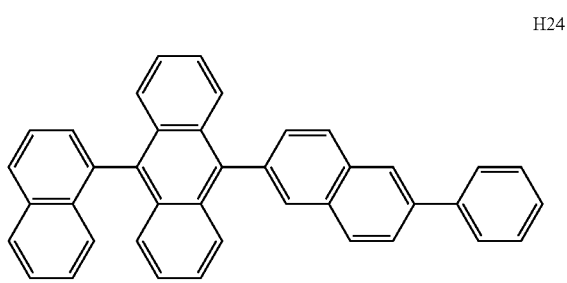
H24

H25
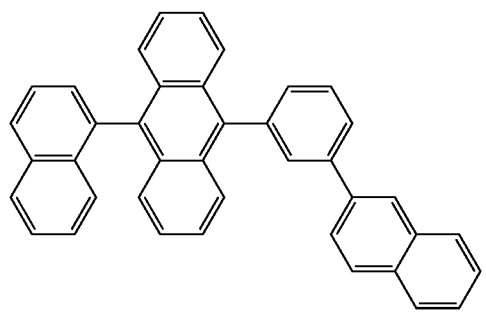
H26
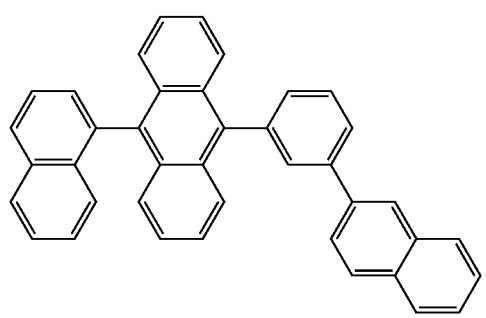
H27
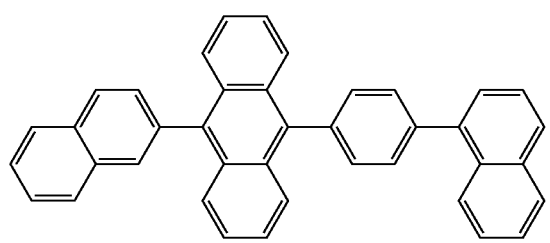
H28
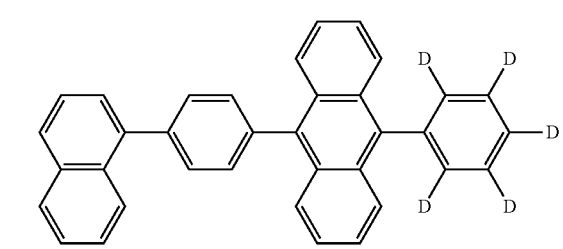
H29
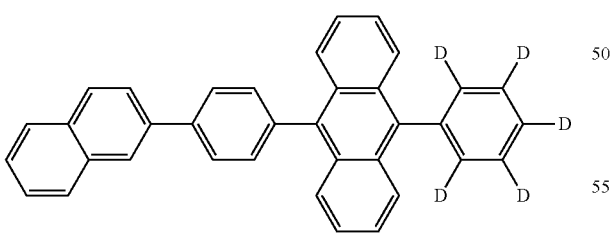
H30
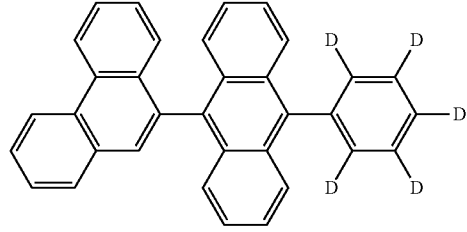
H31
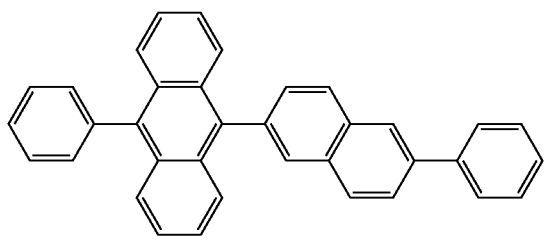
H32
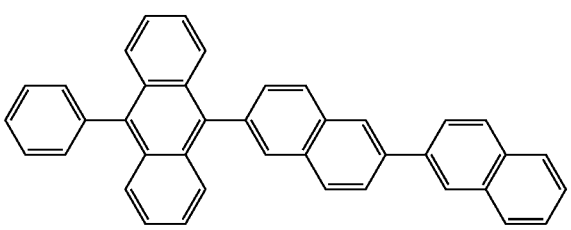
H33
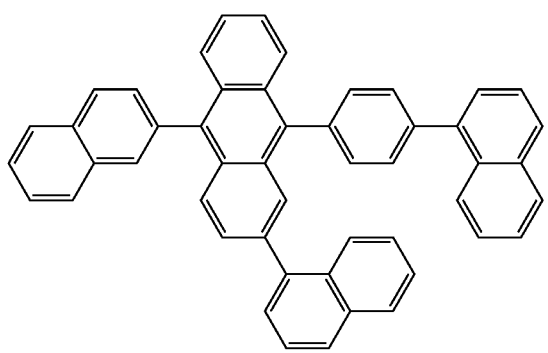
H34
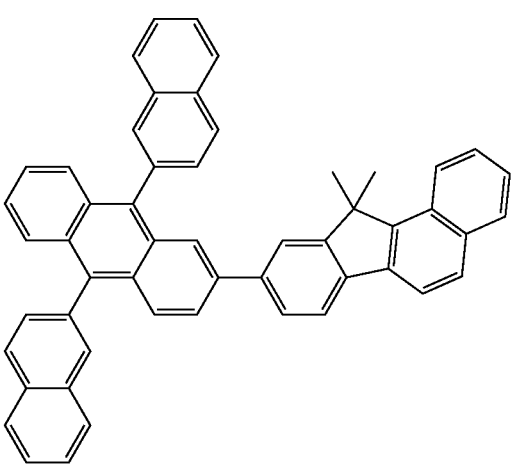

H35
H36
H37
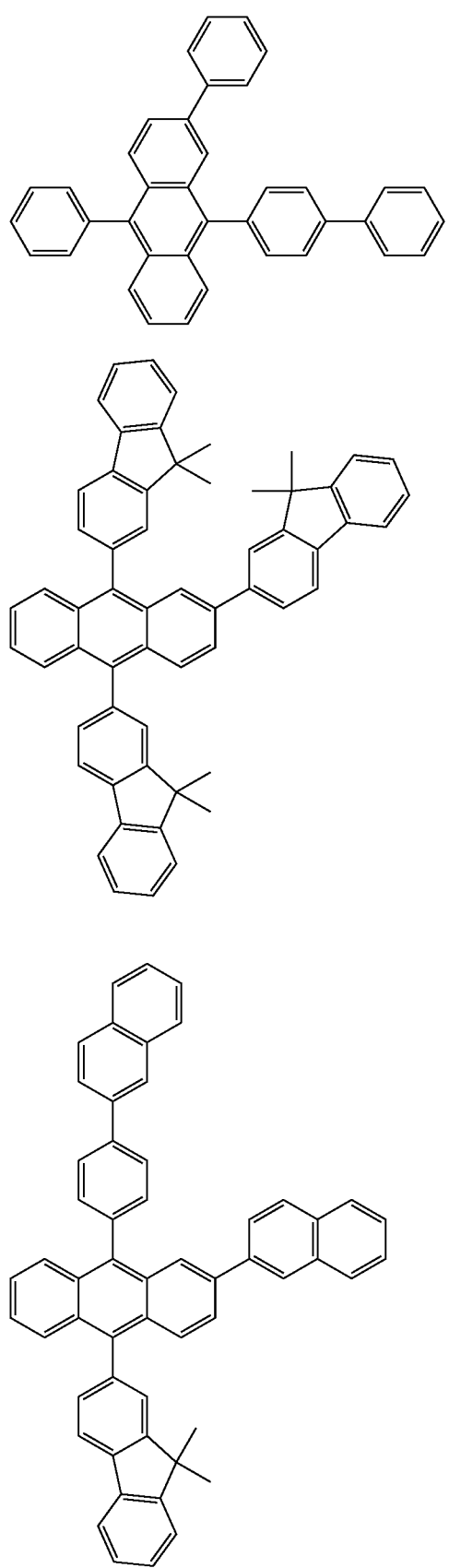
H38
H39
H40
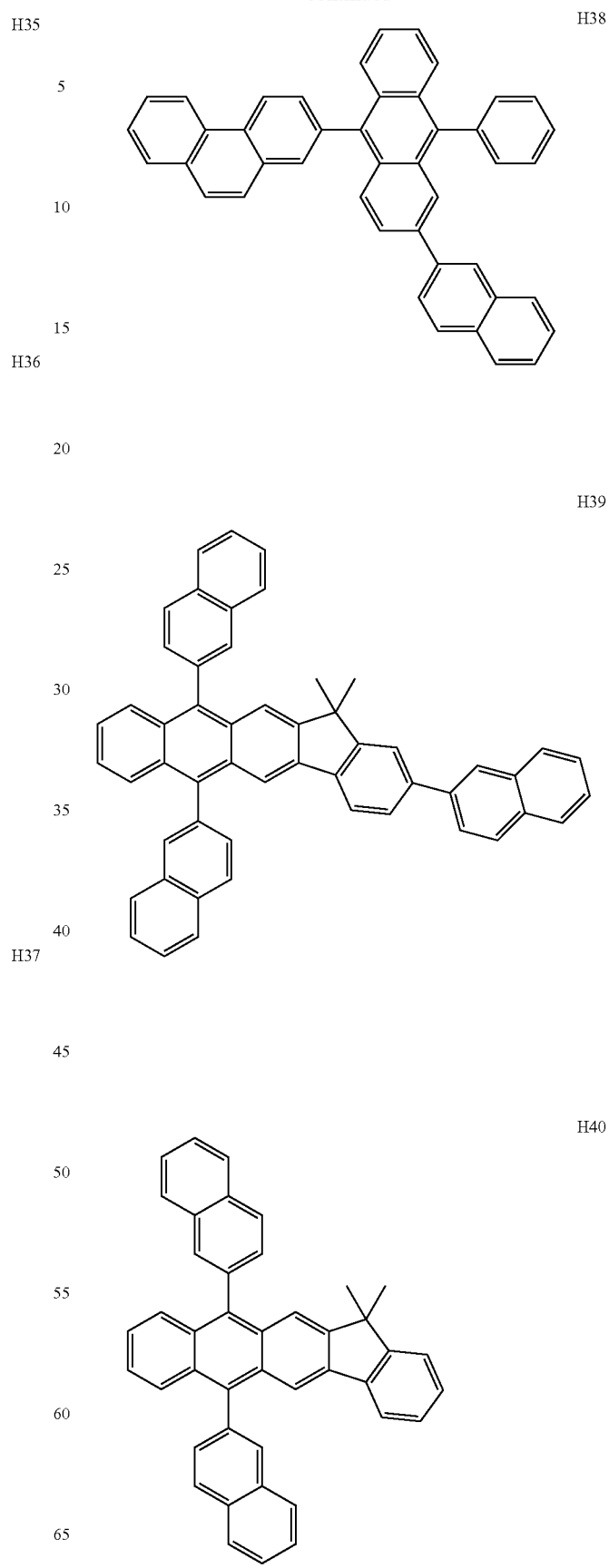

H41
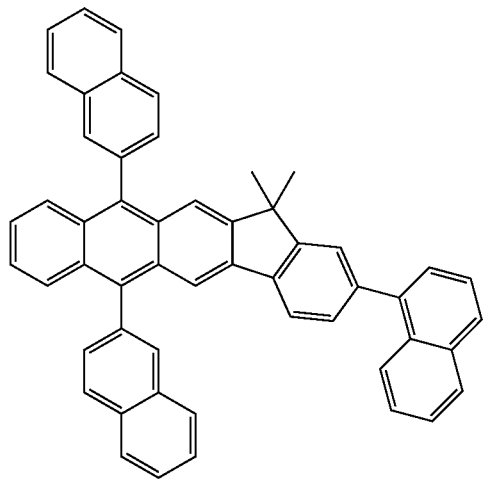
H42
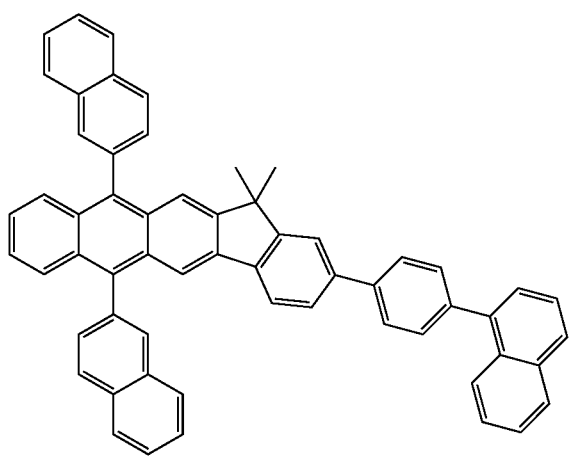
H44
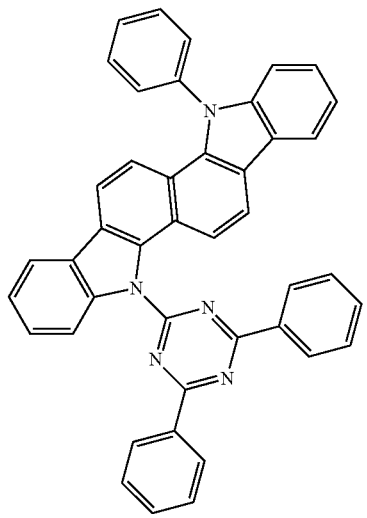
H45
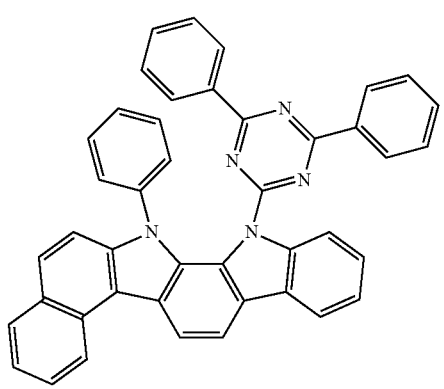
According to another embodiment, the host may include, in addition to the condensed cyclic compound represented by Formula 1, at least one of Compounds H43 to H49 below, but is not limited thereto:
H43
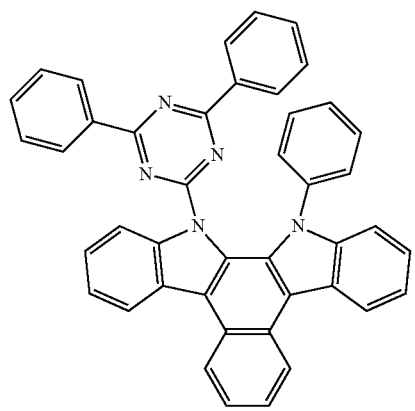
H46
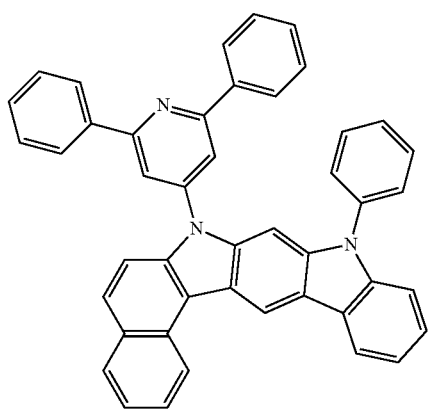

-continued

H47
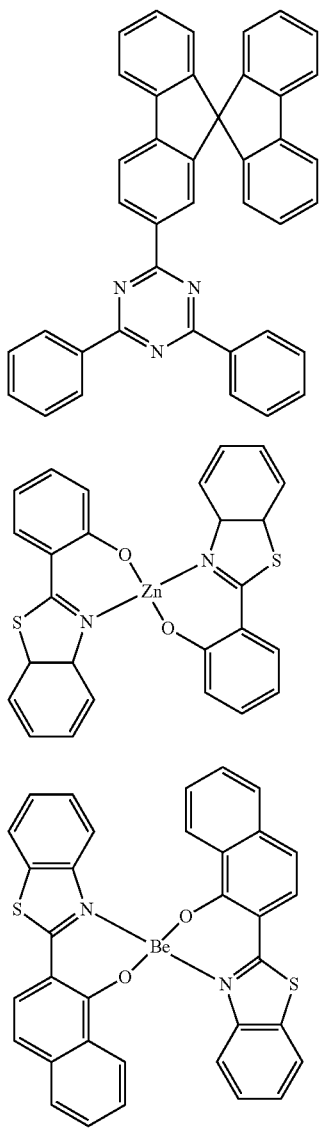

H48

H49

When the organic light-emitting device is a full color organic light-emitting device, the emission layer may be patterned into a red emission layer, a green emission layer, and a blue emission layer. According to another embodiment, due to a stack structure including a red emission layer, a green emission layer, and/or a blue emission layer, the emission layer may emit white light. A host in the red emission layer, the green emission layer, and the blue emission layer may include the condensed cyclic compound represented by Formula 1. According to an embodiment, the host in the green emission layer may include the condensed cyclic compound represented by Formula 1.

A dopant in the emission layer may be a fluorescent dopant that emits light according to a fluorescent emission mechanism or a phosphorescent dopant that emits light according to a phosphorescent emission mechanism.

According to an embodiment, the emission layer may include a host including the condensed cyclic compound represented by Formula 1 and a phosphorescent dopant. The phosphorescent dopant may include an organometallic complex including a transition metal (for example, iridium (Ir), platinum (Pt), osmium (Os), or rhodium (Rh)).

The phosphorescent dopant may include at least one of Compounds PD1 to PD74 below, but is not limited thereto (Compound PD1 below is Ir(ppy)$_3$):

PD1
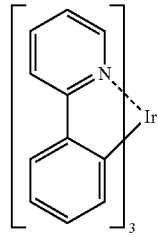

PD2
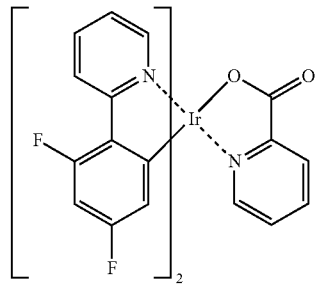

PD3
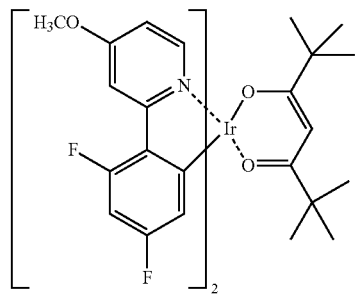

PD4
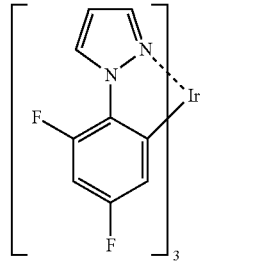

PD5
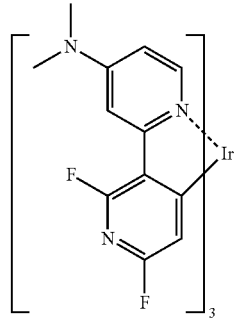

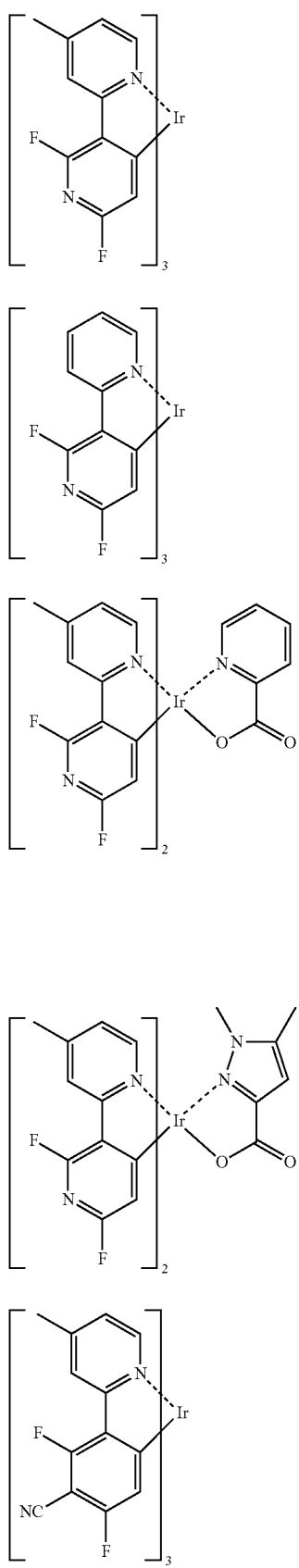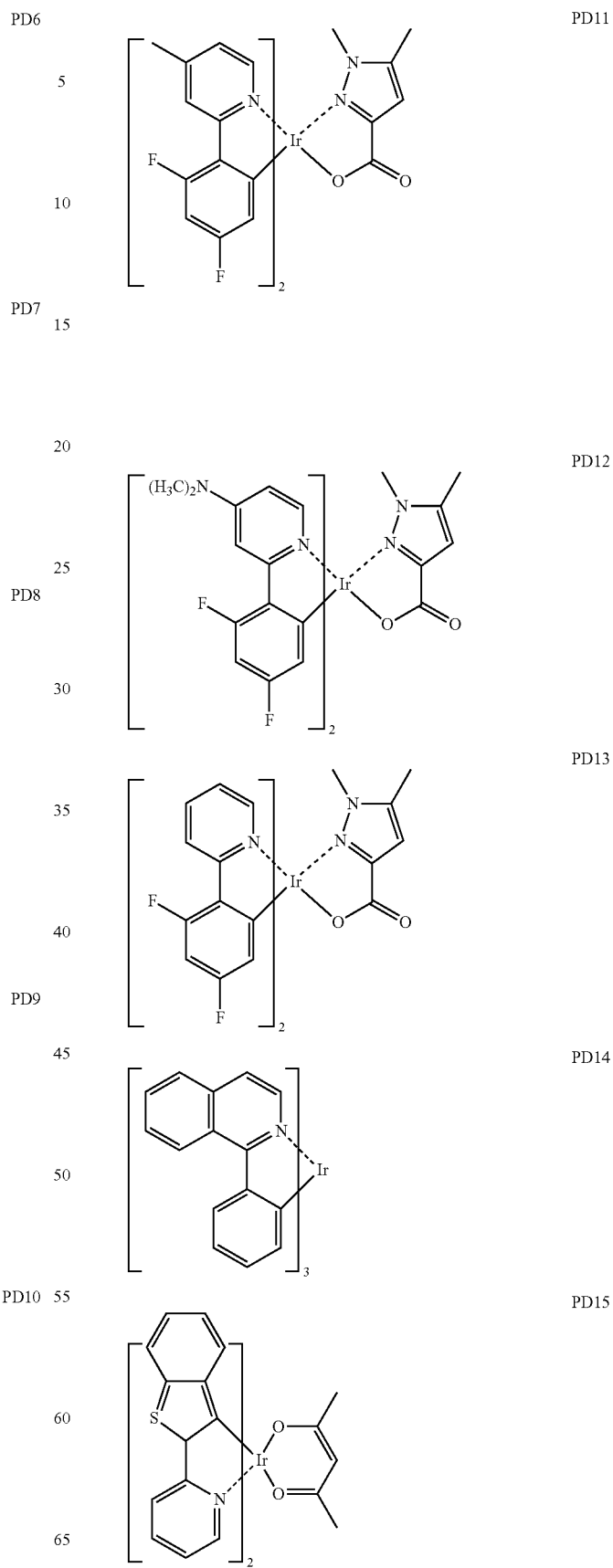

PD16
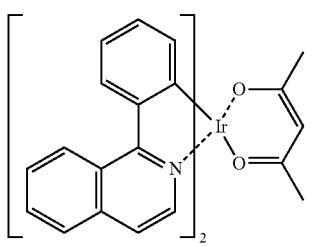
PD17
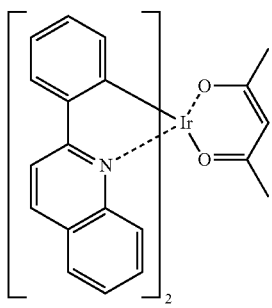
PD18
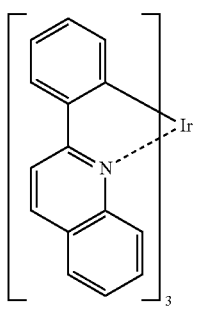
PD19
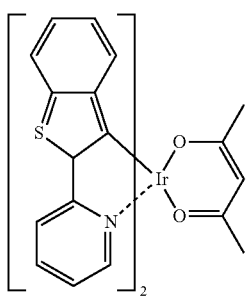
PD20
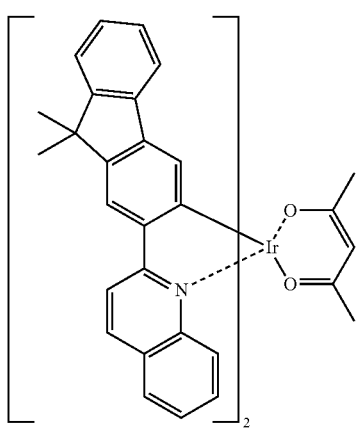
PD21
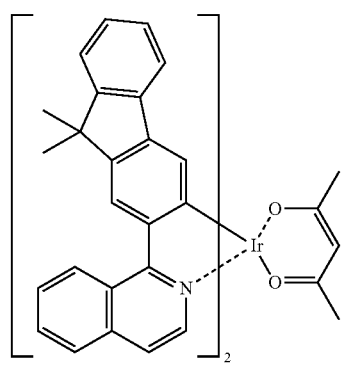
PD22
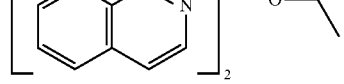
PD23
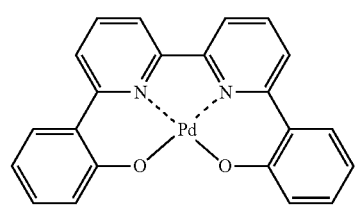
PD24
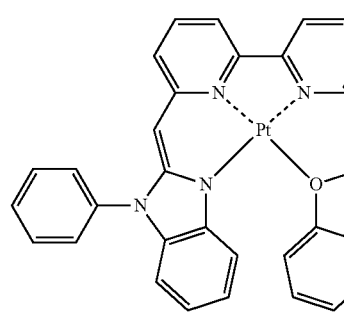
PD25
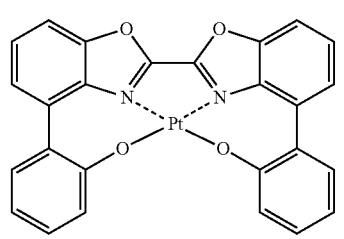

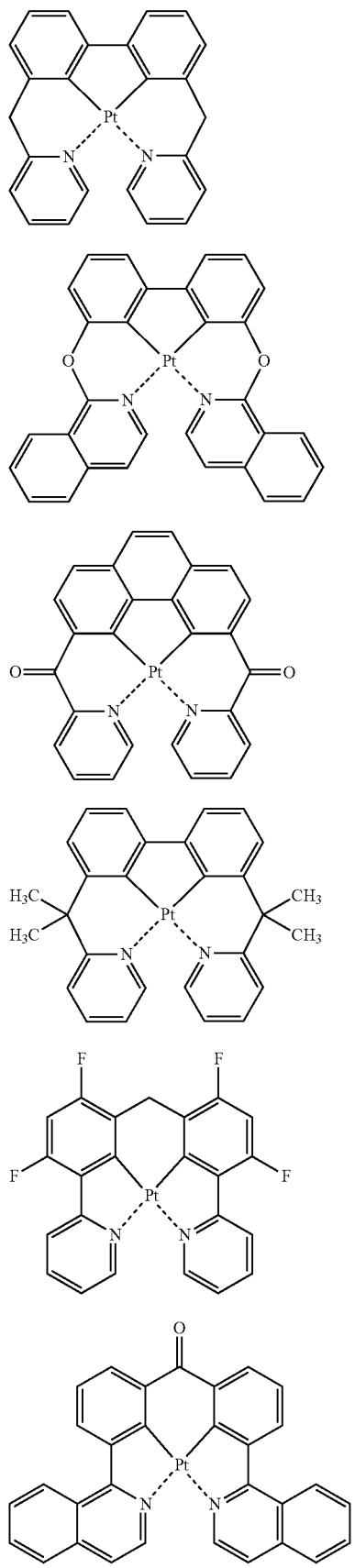
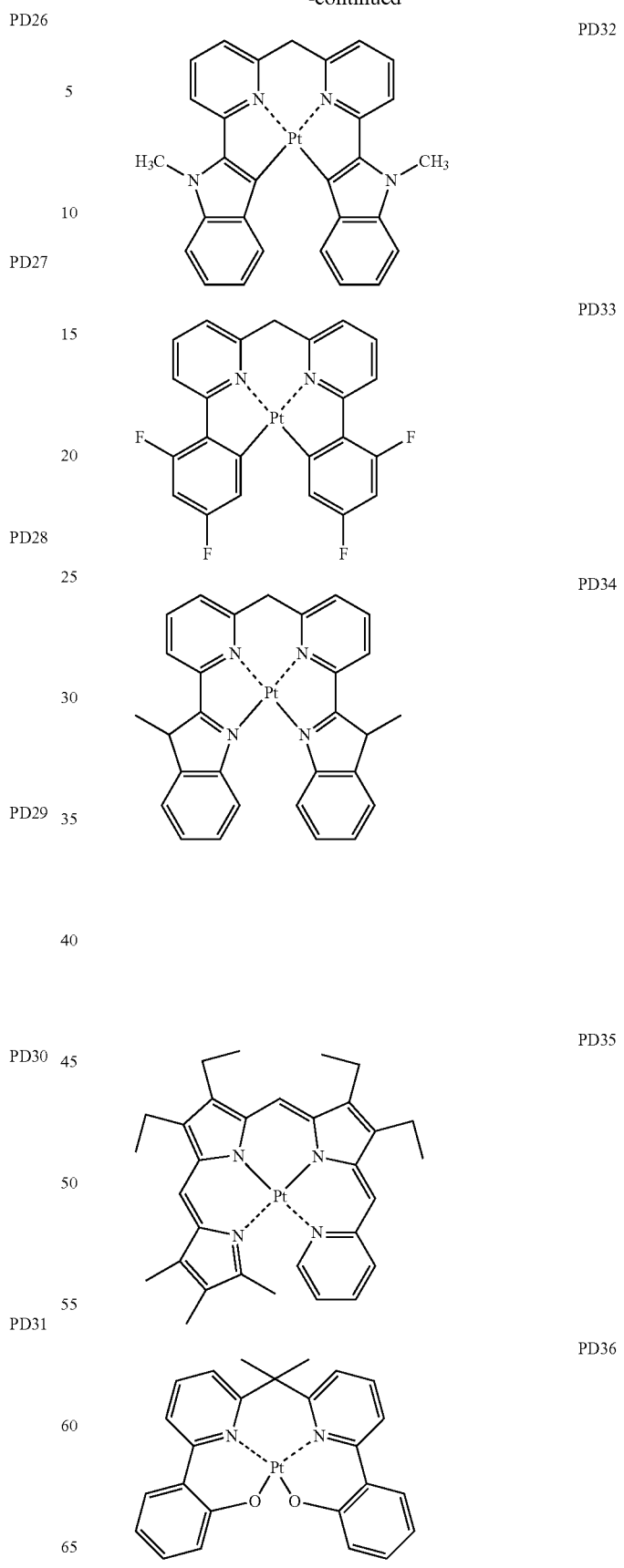

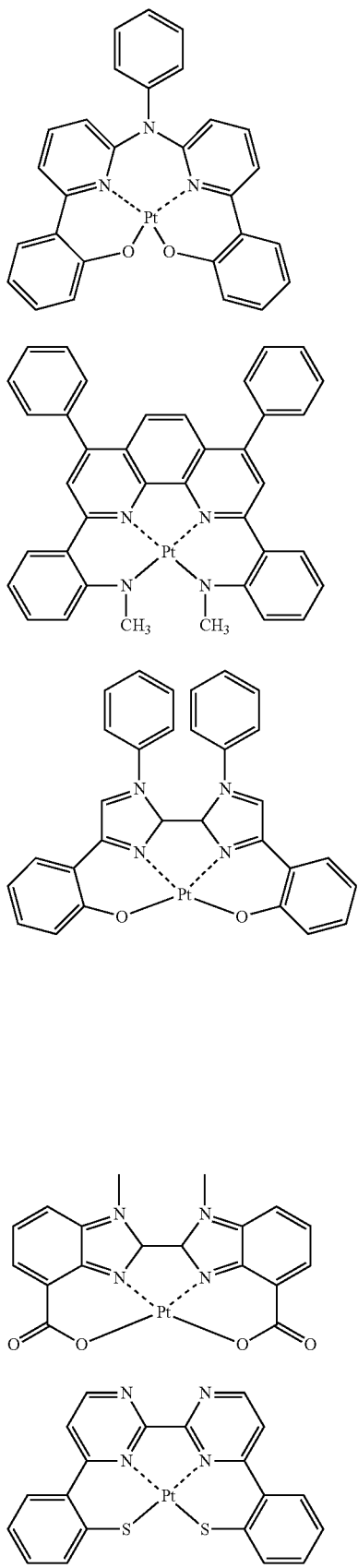
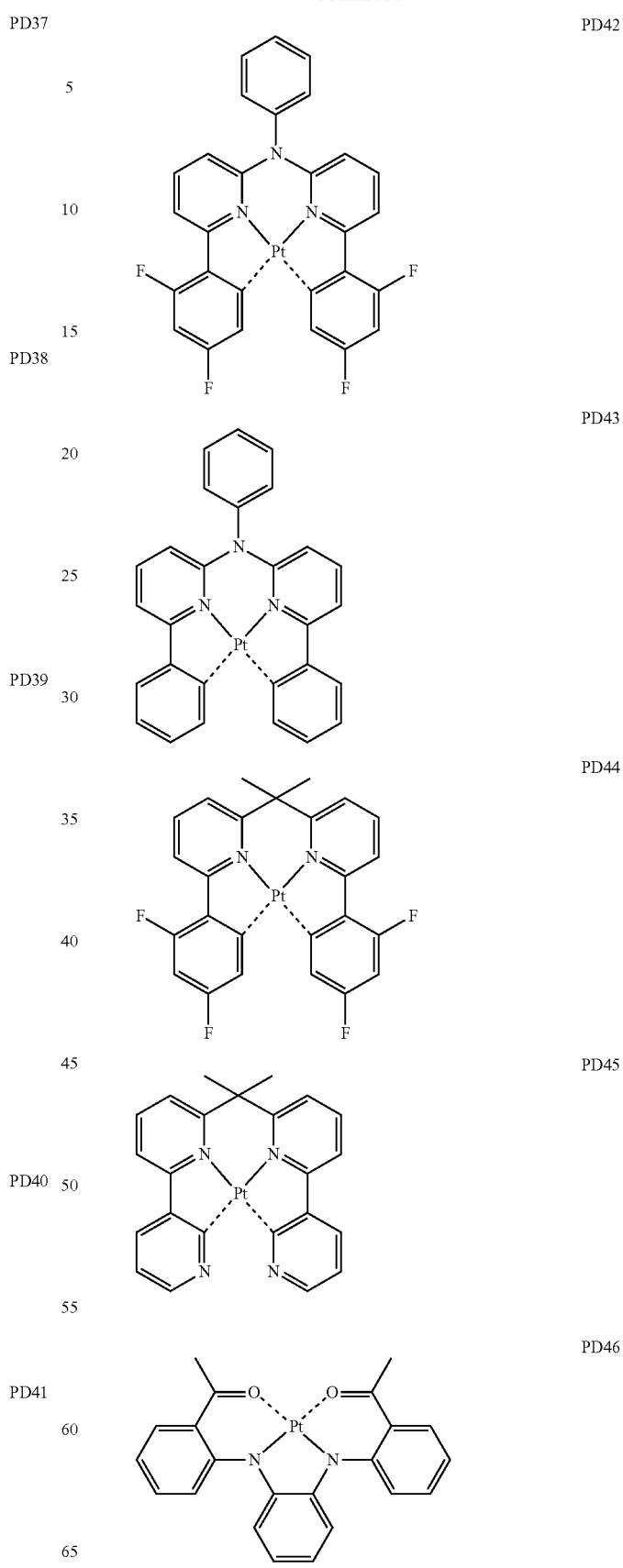

PD47 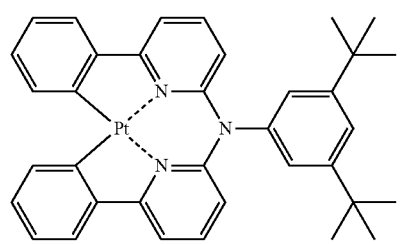
PD48 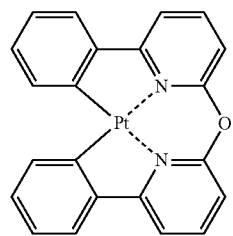
PD49 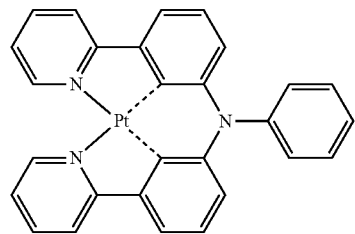
PD50 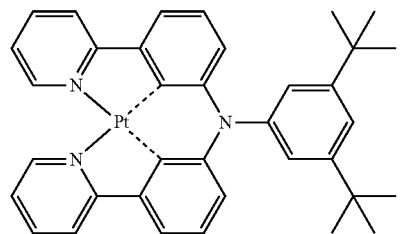
PD51 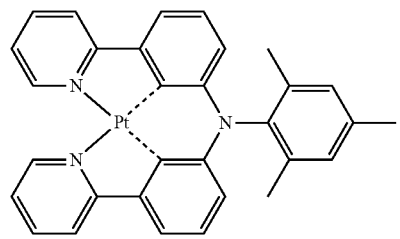
PD52 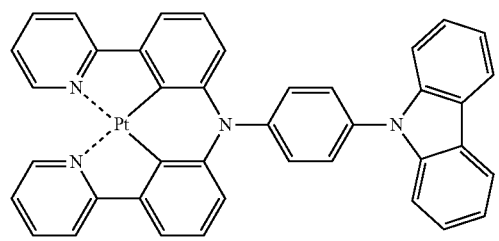
PD53 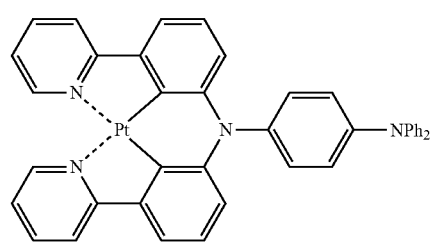
PD54 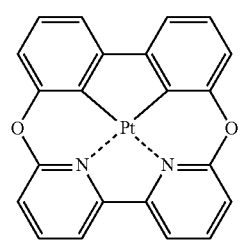
PD55 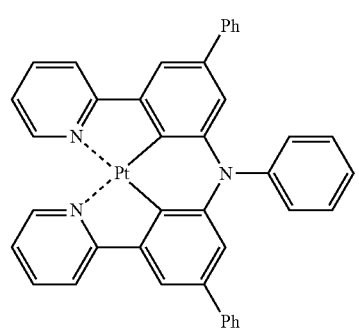
PD56 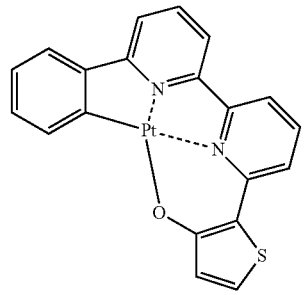
PD57 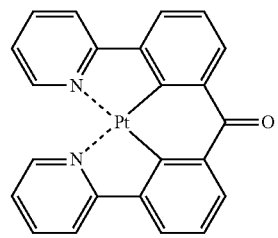

PD58
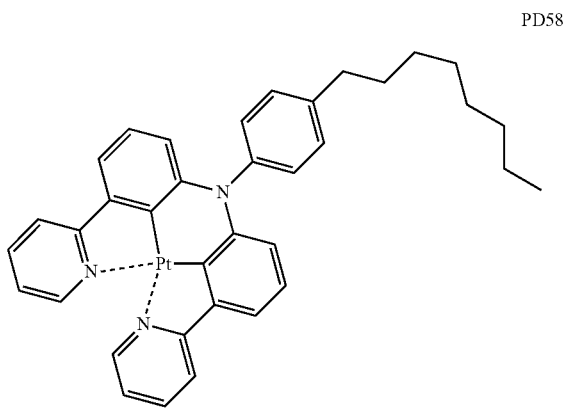
PD59
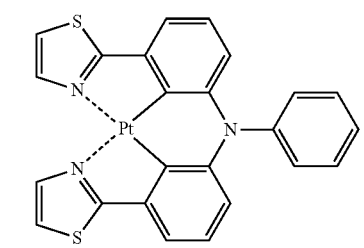
PD60
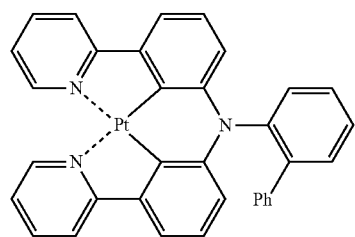
PD61
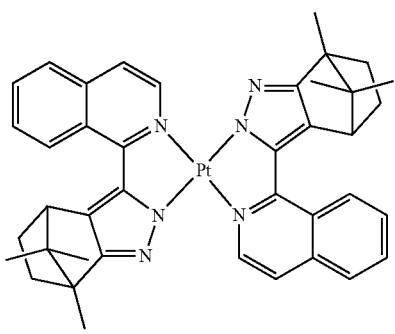
PD62
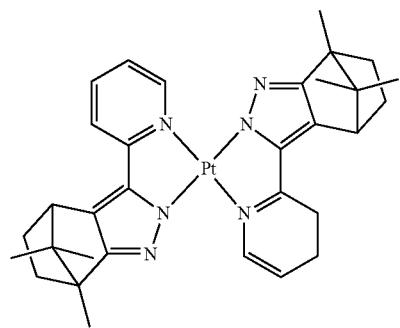
PD63
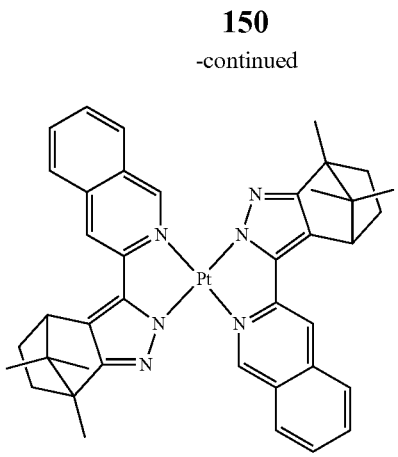
PD64
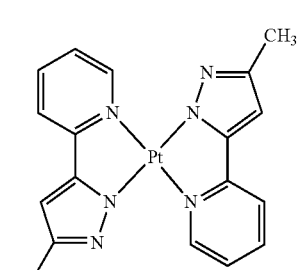
PD65
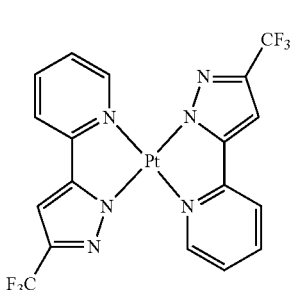
PD66
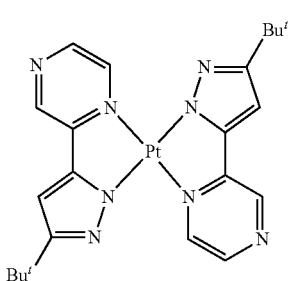
PD67
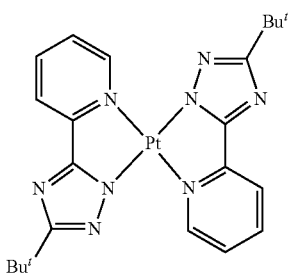

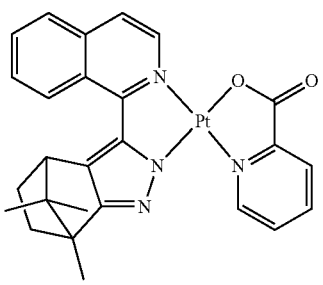
PD68
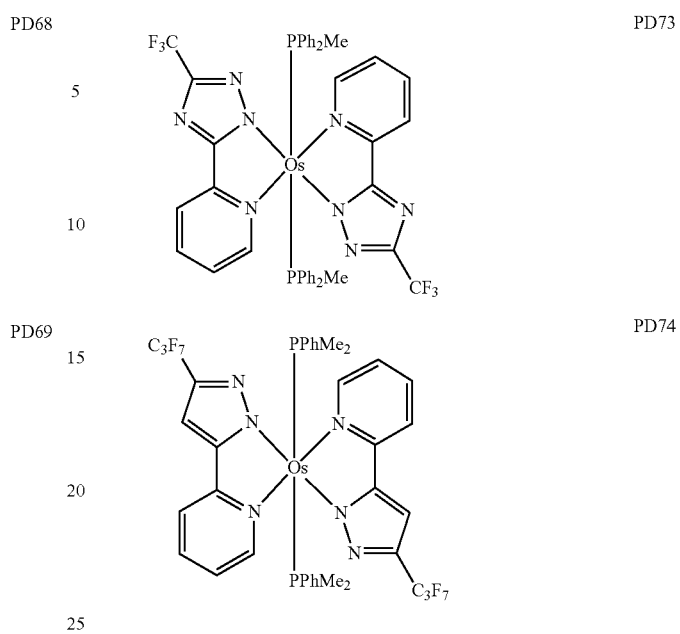
PD73
PD69
PD74
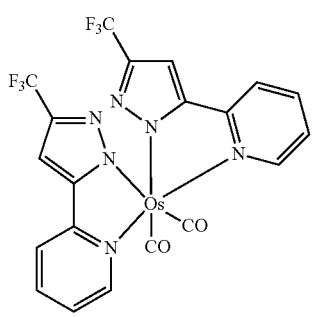
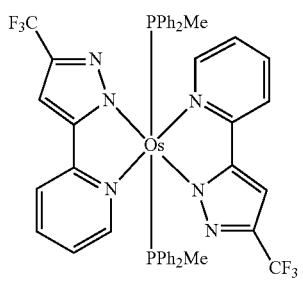
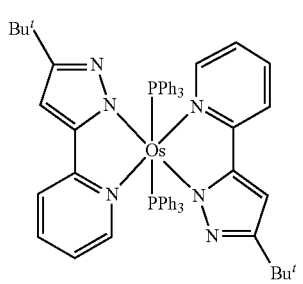
According to another embodiment, the phosphorescent dopant may include PtOEP or Compound PhGD illustrated below:
PD70
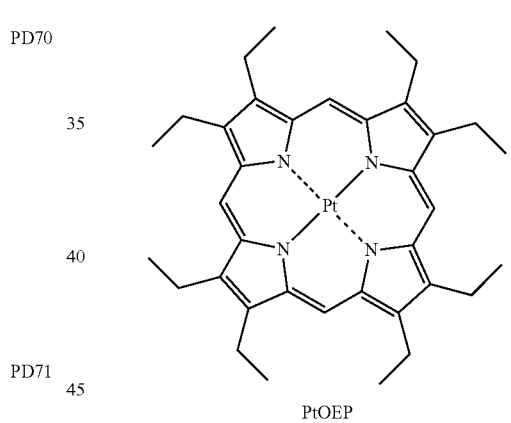
PtOEP
PD71
PD72
PhGD
The fluorescent dopant may include at least one compound selected from DPAVBi, BDAVBi, TBPe, DCM, DCJTB, Coumarin 6, and C545T.

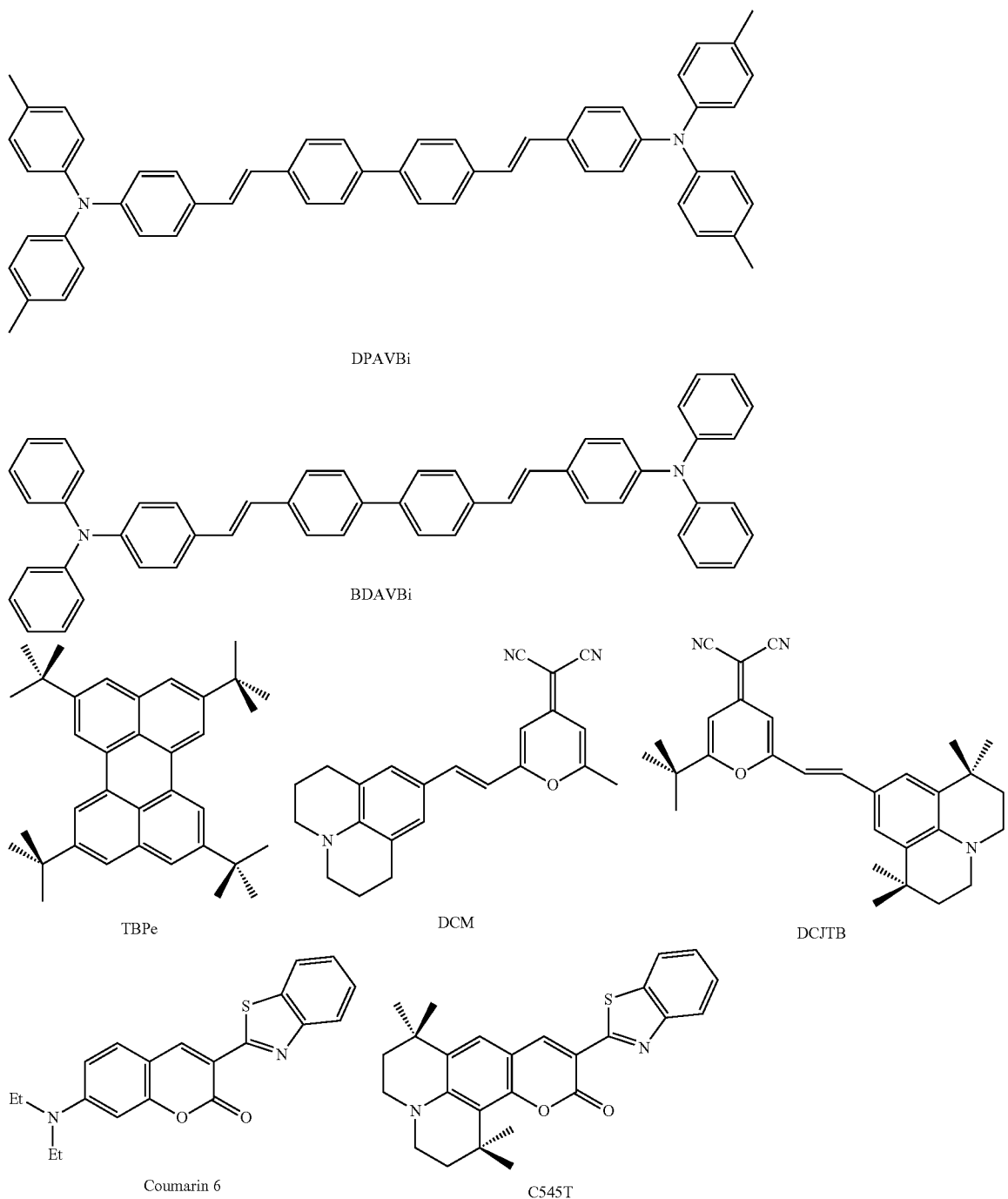

When the emission layer includes a host and a dopant, an amount of the dopant may be in a range of about 0.01 to about 15 parts by weight, for example, about 0.1 to about 15 parts by weight, based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one layer selected from a hole blocking layer, an electron transport layer, and an electron injection layer.

For example, the electron transport region may have a structure of hole blocking layer/electron transport layer/electron injection layer or electron transport layer/electron injection layer, but the structure of the electron transport region is not limited thereto. The electron transport layer may have a single-layered structure or a multi-layer structure including two or more different materials.

Conditions for forming the hole blocking layer, electron transport layer, and electron injection layer of the electron transport region may be understood by referring to the conditions for forming the hole injection layer.

When the electron transport layer includes a hole blocking layer, the hole blocking layer may include, for example, at least one of BCP, Bphen, and BAlq but is not limited thereto.

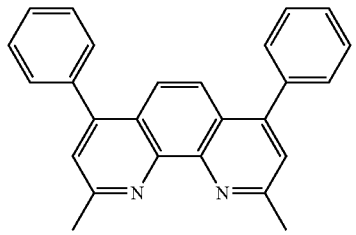

BCP

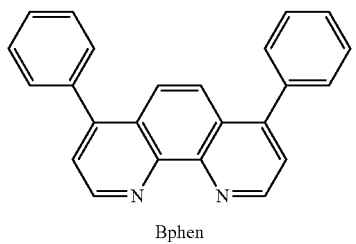

Bphen

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to the condensed cyclic compound represented by Formula 1, at least one compound selected from BCP, Bphen, $Alq_3$, BAlq, TAZ, and NTAZ.

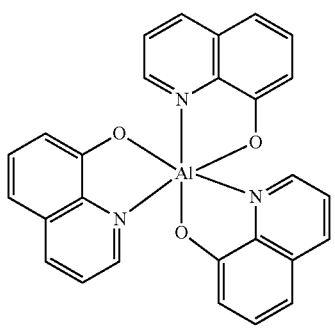

$Alq_3$

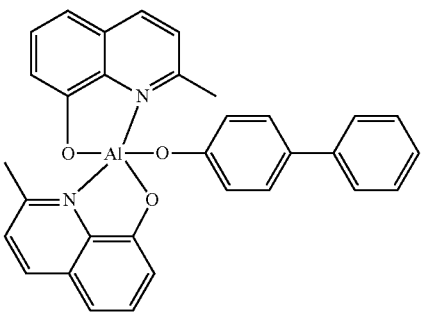

BAlq

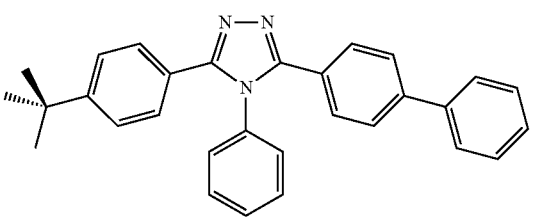

TAZ

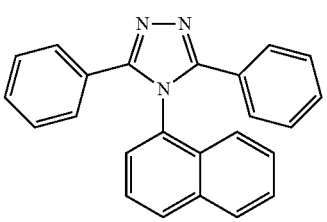

NTAZ

According to another embodiment, the electron transport layer may include at least one of ET1 and ET2, but are not limited thereto:

ET1

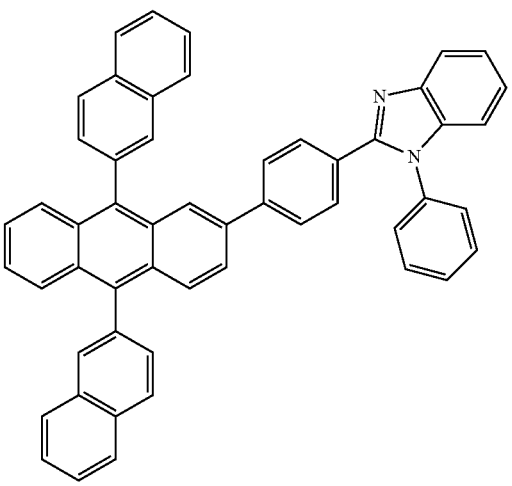

ET2

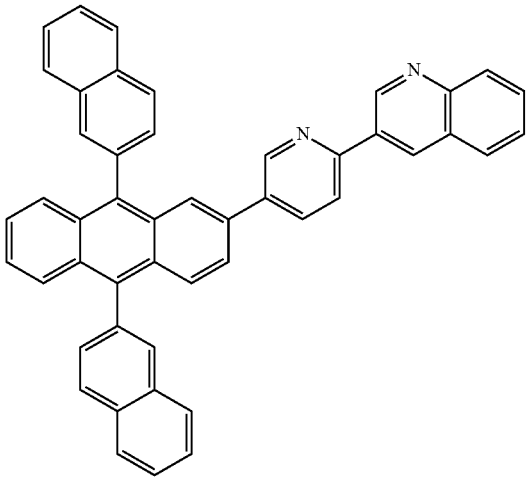

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

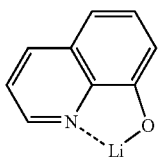

ET-D2

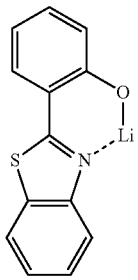

The electron transport region may include an electron injection layer (EIL) that allows electrons to be easily provided from a second electrode 19.

The electron injection layer may include at least one compound selected from, LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within the range described above, the electron injection layer may have satisfactory electron transport characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to the FIGURE, but is not limited thereto.

A $C_1$-$C_{60}$ alkyl group used herein refers to a linear or branched aliphatic hydrocarbon monovalent group having 1 to 60 carbon atoms. Detailed examples thereof are methyl group, ethyl group, propyl group, isobutyl group, sec-butyl group, tert-butyl group, pentyl group, iso-amyl group, and hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by -$OA_{101}$ (wherein $A_{101}$ is the $C_1$-$C_{60}$ alkyl group). Detailed examples thereof are methoxy group, ethoxy group, and isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group. Detailed examples thereof are ethenyl group, propenyl group, and butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group having at least one carbon triple bond in the middle or at the terminal of the $C_2$-$C_{60}$ alkyl group. Detailed examples thereof are ethynyl group, and propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms. Detailed examples thereof are cyclopropyl group, cyclobutyl group, cyclopentyl group, cyclohexyl group, and cycloheptyl group. A $C_3$-$C_{10}$ cycloalkylene group used herein refers to a divalent group having the same structure as the $C_3$-$C_{10}$ cycloalkyl group.

A $C_3$-$C_{10}$ heterocycloalkyl group used herein refers to a monovalent monocyclic group having at least one hetero atom selected from N, O, P, and S as a ring-forming atom and 3 to 10 carbon atoms. Detailed examples thereof are tetrahydrofuranyl group and tetrahydrothiophenyl group. A $C_3$-$C_{10}$ heterocycloalkylene group used herein refers to a divalent group having the same structure as the $C_3$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromacity. Detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_3$-$C_{10}$ heterocycloalkenyl group used herein refers to a monovalent monocyclic group that has at least one heteroatom selected from N, O, P, and S as a ring-forming atom, 3 to 10 carbon atoms, and at least one double bond in its ring. Detailed examples of the $C_3$-$C_{10}$ heterocycloalkenyl group are 2,3-dihydrofuranyl group and 2,3-dihydrothiophenyl group. A $C_3$-$C_{10}$ heterocycloalkenylene group used herein refers to a divalent group having the same structure as the $C_3$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl and the $C_6$-$C_{60}$ arylene each include two or more rings, the rings may be fused to each other.

A $C_2$-$C_{60}$ heteroaryl group used herein refers to a monovalent group having a carbocyclic aromatic system that has at least one heteroatom selected from N, O, P, and S as a ring-forming atom, and 2 to 60 carbon atoms. A $C_2$-$C_{60}$ heteroarylene group used herein refers to a divalent group having a carbocyclic aromatic system that has at least one heteroatom selected from N, O, P, and S as a ring-forming atom, and 2 to 60 carbon atoms. Detailed examples of the $C_2$-$C_{60}$ heteroaryl group are pyridinyl group, pyrimidinyl group, pyrazinyl group, pyridazinyl group, triazinyl group, quinolinyl group, and isoquinolinyl group. When the $C_2$-$C_{60}$ heteroaryl group and the $C_2$-$C_{60}$ heteroarylene group each include two or more rings, the rings may be fused to each other.

The $C_6$-$C_{60}$ aryloxy used herein indicates -$OA_{102}$ (wherein $A_{102}$ is the $C_6$-$C_{60}$ aryl group), the $C_6$-$C_{60}$ arylthio indicates -$SA_{103}$ (wherein $A_{103}$ is the $C_6$-$C_{60}$ aryl group), and the $C_7$-$C_{60}$ arylalkyl indicates -$A_{104}A_{105}$ (wherein $A_{104}$ is the $C_6$-$C_{60}$ aryl group and $A_{105}$ is the $C_1$-$C_{60}$ alkyl group).

The $C_2$-$C_{60}$ heteroaryloxy used herein indicates -$OA_{106}$ (wherein $A_{106}$ is the $C_2$-$C_{60}$ heteroaryl group), the $C_2$-$C_{60}$ heteroarylthio indicates $SA_{107}$ (wherein $A_{107}$ is the $C_2$-$C_{60}$ heteroaryl group), and the $C_3$-$C_{60}$ heteroarylalkyl indicates -$A_{108}A_{109}$ (wherein $A_{108}$ is the $C_2$-$C_{60}$ heteroaryl group and $A_{109}$ is the $C_1$-$C_{60}$ alkyl group).

A monovalent non-aromatic condensed polycyclic group used herein refers to a monovalent group that has two or more rings condensed to each other, only carbon atoms (for example, the number of carbon atoms may be in a range of 8 to 60) as a ring forming atoms, wherein the molecular structure as a whole is non-aromatic. A detailed example of the monovalent non-aromatic condensed polycyclic group is fluorenyl. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group that has two or more rings condensed to each other, has a heteroatom selected from N, O P, and S, other than carbon atoms (for example, the number of carbon atoms may be in a range of 2 to 60), as a ring forming atoms, wherein the molecular structure as a whole is non-aromatic. An example of the monovalent non-aromatic condensed heteropolycyclic group is carbazolyl. A divalent non-aromatic condensed heteropolycyclic group used herein refers to a divalent group having the same structure as the monovalent non-aromatic condensed heteropolycyclic group.

A substituent of at least one of the substituted $C_3$-$C_{10}$ cycloalkylene group, the substituted $C_3$-$C_{10}$ cycloalkenylene group, the substituted $C_6$-$C_{60}$ arylene group, the substituted bivalent non-aromatic condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, a substituted or unsubstituted $C_7$-$C_{60}$ arylalkyl group, the substituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, cyclopentyl group, cyclohexyl group, cycloheptyl group, cyclopentenyl group, cycloheptenyl group, phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrycenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthylidinyl group, quinoxalinyl group, quinazolinyl group, cynolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, —$N(Q_{11})(Q_{12})$, —$Si(Q_{13})(Q_{14})(Q_{15})$, and —$B(Q_{16})(Q_{17})$;

cyclopentyl group, cyclohexyl group, cycloheptyl group, cyclopentenyl group, cycloheptenyl group, phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, and imidazopyridinyl;

cyclopentyl group, cyclohexyl group, cycloheptyl group, cyclopentenyl group, cycloheptenyl group, phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrycenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthylidinyl group, quinoxalinyl group, quinazolinyl group, cynolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, and imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, phenyl group, naphthyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, cyclopentyl group, cyclohexyl group, cycloheptyl group, cyclopentenyl group, cycloheptenyl group, phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrycenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthylidinyl group, quinoxalinyl group, quinazolinyl group, cynolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group or imidazopyrimidinyl group.

Hereinafter, a compound and an organic light-emitting device according to embodiments is described in detail with reference to Synthesis Example and Examples. However, the organic light-emitting device is not limited thereto. The wording "B was used instead of A" used in describing Synthesis Examples means that a molar equivalent of A was identical to a molar equivalent of B.

EXAMPLE

Synthesis Example 1

Synthesis of Compound 1

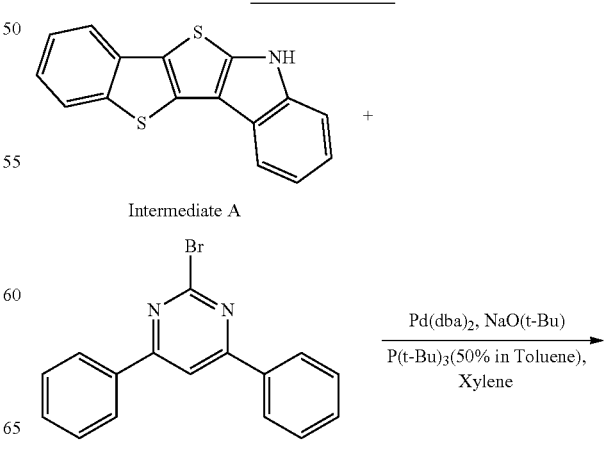

Reaction Scheme 1

Intermediate A

Pd(dba)$_2$, NaO(t-Bu)
P(t-Bu)$_3$(50% in Toluene),
Xylene

-continued

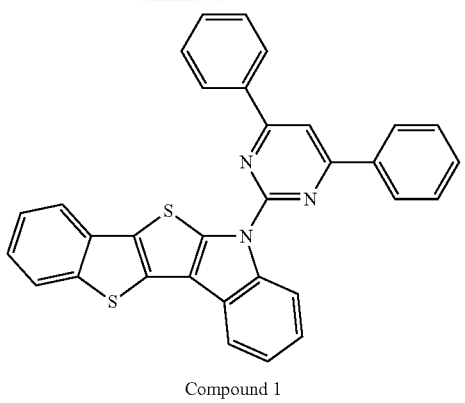

Compound 1

12.0 g (42.9 mmol) of Intermediate A, 16 g (51.5 mmol) of 2-bromo-4,6-diphenylpyrimidine, 8.3 g (85.9 mmol) of sodium t-butoxide, 2.5 g (4.3 mmol) of Pd(dba)$_2$ (bis(dibenzylideneacetone)palladium(0)), and 4.1 mL (50% in toluene) of tri t-butylphosphine were added to 200 mL of xylene in a 500 mL round flask, and then, the mixture was refluxed in a nitrogen stream for 15 hours while heating. The obtained mixture was added to 1,000 mL of methanol and the crystallized solid powder was obtained by filtering and then, the result was dissolved in dichlorobenzene and filtered by using silica gel/celite, and an appropriate amount of an organic solvent used herein was removed therefrom, and then, the result was re-crystallized by using methanol to obtain Compound 1 (14.2 g, yield of 65%). Elementary analysis results of Compound 1 are as follows:

calcd. $C_{32}H_{19}N_3S_2$: C, 75.41; H, 3.76; N, 8.25; S, 12.58; found: C, 75.38; H, 3.74; N, 8.22; S, 12.57

Synthesis Example 2

Synthesis of Compound 2

Reaction Scheme 2

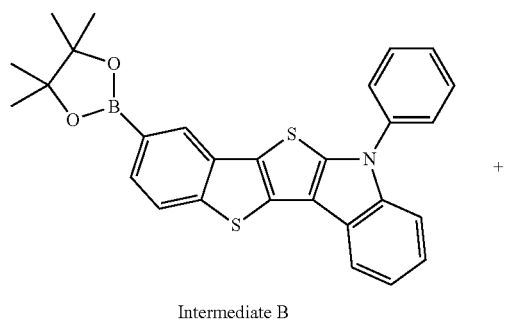

Intermediate B

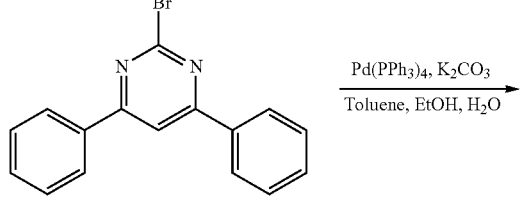

-continued

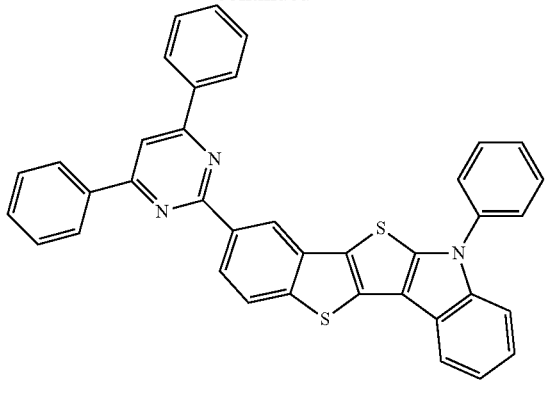

Compound 2

15.0 g (31.2 mmol) of Intermediate B, 10.7 g (34.3 mmol) of 2-bromo-4,6-diphenylpyrimidine, 8.6 g (62.3 mmol) of potassium carbonate, and 1.8 g (1.6 mmol) of tetrakis (triphenylphosphine)palladium(0) (Pd(PPh$_3$)$_4$) were added to 350 mL of toluene group, 150 mL of water, and 150 mL of ethanol in 1000 mL flask, and then, the mixture was refluxed in a nitrogen stream for 6 hours while heating. The obtained mixture was added to 1,500 mL of methanol and the crystallized solid powder was obtained by filtering and then, the result was dissolved in monochlorobenzene and filtered by using silica gel/celite, and an appropriate amount of an organic solvent used herein was removed therefrom, and then, the result was re-crystallized by using methanol to obtain Compound 2 (11.3 g, yield of 62%). Elementary analysis results of Compound 2 are as follows:

calcd. $C_{38}H_{23}N_3S_2$: C, 77.92; H, 3.96; N, 7.17; S, 10.95; found: C, 77.88; H, 3.97; N, 7.18; S, 10.93

Synthesis Example 3

Synthesis of Compound 3

Reaction Scheme 3

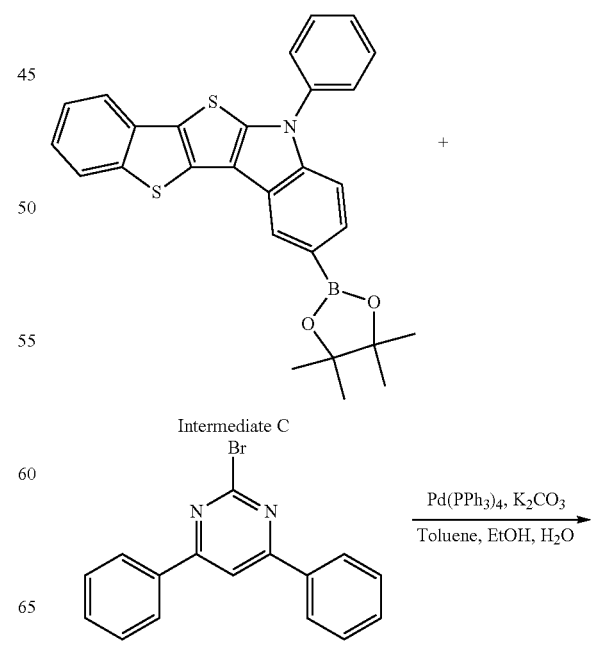

Intermediate C

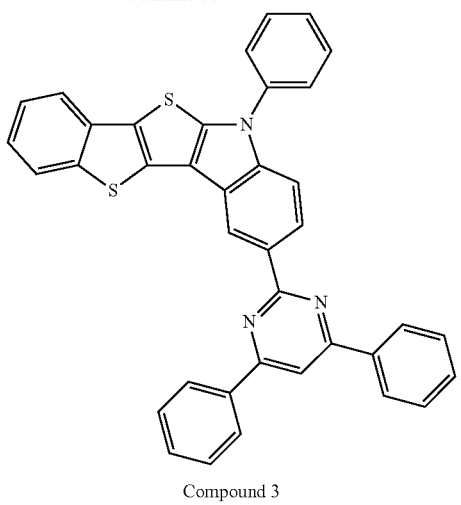

Compound 3

15.5 g (32.2 mmol) of Intermediate C, 11.0 g (35.4 mmol) of 2-bromo-4,6-diphenylpyrimidine, 8.9 g (64.4 mmol) of potassium carbonate, and 1.9 g (1.6 mmol) of tetrakis(triphenylphosphine)palladium(0) (Pd(PPh$_3$)$_4$) were added to 350 mL of toluene group, 150 mL of water, and 150 mL of ethanol in 1,000 mL flask, and then, the mixture was refluxed in a nitrogen stream for 6 hours while heating. The obtained mixture was added to 1,500 mL of methanol and the crystallized solid powder was obtained by filtering and then, the result was dissolved in monochlorobenzene and filtered by using silica gel/celite, and an appropriate amount of an organic solvent used herein was removed therefrom, and then, the result was re-crystallized by using methanol to obtain Compound 3 (12.1 g, yield of 64%). Elementary analysis results of Compound 3 are as follows:

calcd. C$_{38}$H$_{23}$N$_3$S$_2$: C, 77.92; H, 3.96; N, 7.17; S, 10.95; found: C, 77.91; H, 3.98; N, 7.16; S, 10.94

Synthesis Example 4

Synthesis of Compound 4

Reaction Scheme 4

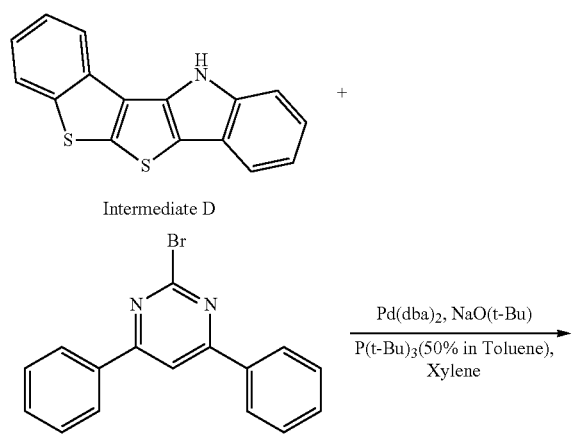

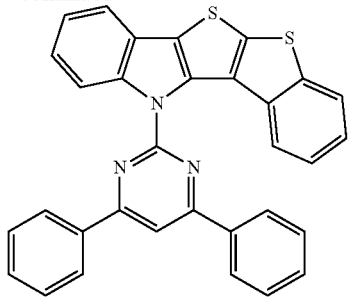

Compound 4

13.0 g (46.2 mmol) of Intermediate D, 17.2 g (55.4 mmol) of 2-bromo-4,6-diphenylpyrimidine, 8.9 g (92.4 mmol) of sodium t-butoxide, 2.7 g (4.6 mmol) of Pd(dba)$_2$, and 3.7 mL (50% in toluene) of tri t-butylphosphine were added to 230 mL of xylene in a 500 mL round flask, and then, the mixture was refluxed in a nitrogen stream for 15 hours while heating. The obtained mixture was added to 1,000 mL of methanol and the crystallized solid powder was obtained by filtering and then, the result was dissolved in dichlorobenzene and filtered by using silica gel/celite, and an appropriate amount of an organic solvent used herein was removed therefrom, and then, the result was re-crystallized by using methanol to obtain Compound 4 (14.1 g, yield of 60%). Elementary analysis results and NMR analysis results of Compound 4 are as follows:

calcd. C$_{32}$H$_{19}$N$_3$S$_2$: C, 75.41; H, 3.76; N, 8.25; S, 12.58; C, 75.39; H, 3.75; N, 8.26; S, 12.57

300 MHz (CDCl$_3$, ppm): δ 8.65 (dd, 1H), 8.16 (s, 1H), 8.07 (m, 4H), 7.80 (d, 1H), 7.75 (dd, 1H), 7.34~7.49 (m, 8H), 7.14 (m, 2H), 6.85 (t, 1H)

Synthesis Example 5

Synthesis of Compound 5

Reaction Scheme 5

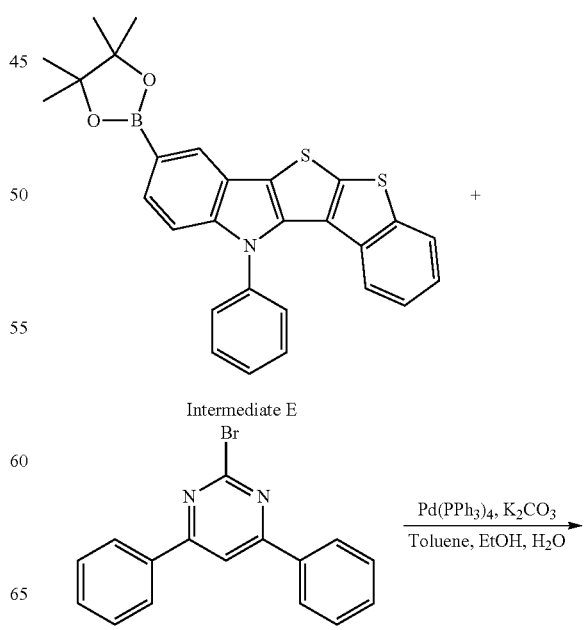

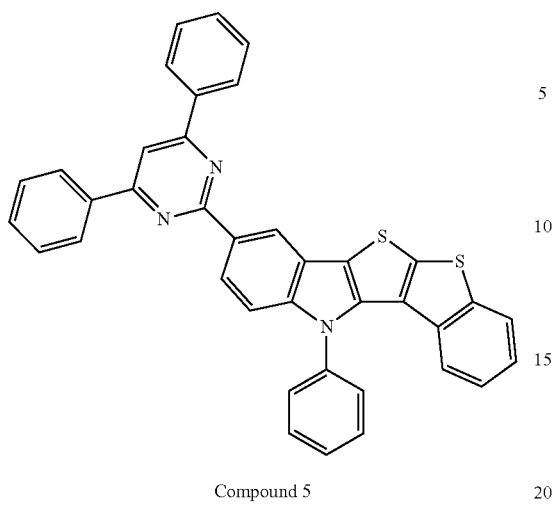

Compound 5

17.0 g (35.3 mmol) of Intermediate E, 12.1 g (38.8 mmol) of 2-bromo-4,6-diphenylpyrimidine, 9.8 g (70.6 mmol) of potassium carbonate, and 2.0 g (1.8 mmol) of tetrakis (triphenylphosphine)palladium(0) (Pd(PPh$_3$)$_4$) were added to 350 mL of toluene group, 150 mL of water, and 150 mL of ethanol in 1,000 mL flask, and then, the mixture was refluxed in a nitrogen stream for 6 hours while heating. The obtained mixture was added to 1,500 mL of methanol and the crystallized solid powder was obtained by filtering and then, the result was dissolved in monochlorobenzene and filtered by using silica gel/celite, and an appropriate amount of an organic solvent used herein was removed therefrom, and then, the result was re-crystallized by using methanol to obtain Compound 5 (12.2 g, yield of 59%). Elementary analysis results of Compound 5 are as follows:

calcd. C$_{38}$H$_{23}$N$_3$S$_2$: C, 77.92; H, 3.96; N, 7.17; S, 10.95; found: C, 77.93; H, 3.95; N, 7.16; S, 10.96

Synthesis Example 6

Synthesis of Compound 6

Reaction Scheme 6

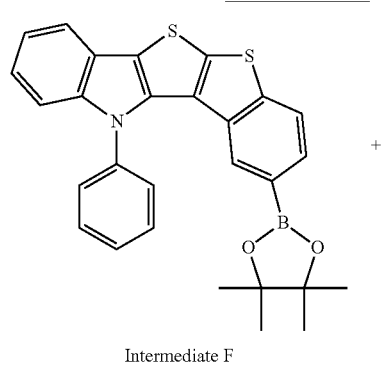

Intermediate F

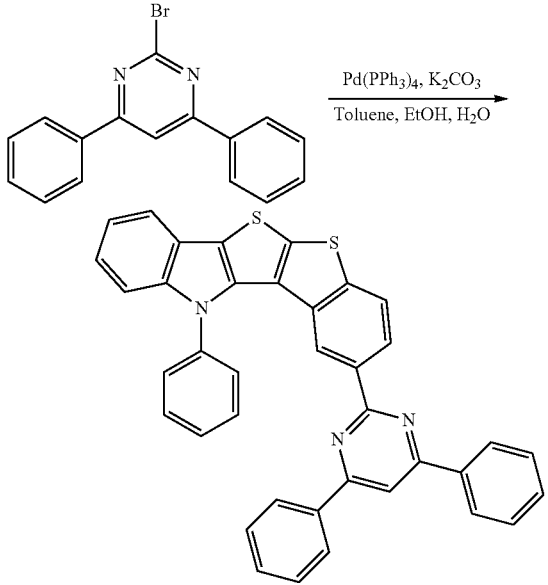

Compound 6

17.9 g (37.2 mmol) of Intermediate F, 13.9 g (44.6 mmol) of 2-bromo-4,6-diphenylpyrimidine, 10.3 g (74.4 mmol) of potassium carbonate, and 3.1 g (1.9 mmol) of tetrakis (triphenylphosphine)palladium(0) (Pd(PPh$_3$)$_4$) were added to 350 mL of toluene group, 150 mL of water, and 150 mL of ethanol in 1,000 mL flask, and then, the mixture was refluxed in a nitrogen stream for 6 hours while heating. The obtained mixture was added to 1,500 mL of methanol and the crystallized solid powder was obtained by filtering and then, the result was dissolved in monochlorobenzene and filtered by using silica gel/celite, and an appropriate amount of an organic solvent used herein was removed therefrom, and then, the result was re-crystallized by using methanol to obtain Compound 6 (14.9 g, yield of 68%). Elementary analysis results and NMR analysis results of Compound 6 are as follows:

calcd. C$_{38}$H$_{23}$N$_3$S$_2$: C, 77.92; H, 3.96; N, 7.17; S, 10.95; found: C, 77.90; H, 3.95; N, 7.18; S, 10.94

300 MHz (CDCl$_3$, ppm): δ 8.46 (dd, 1H), 8.18 (m, 4H), 7.94 (s, 1H), 7.92 (d, 1H), 7.79 (dd, 1H), 7.61 (m, 7H), 7.55 (m, 2H), 7.35 (dd, 1H), 7.27 (m, 2H), 7.16 (d, 1H), 7.13 (d, 1H), 6.68 (t, 1H)

Synthesis Example 7

Synthesis of Compound 7

Reaction Scheme 7

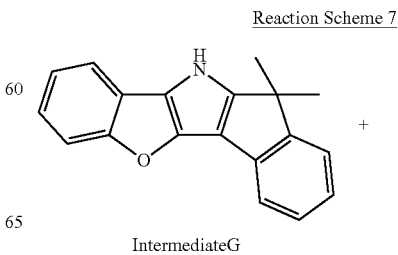

IntermediateG

-continued

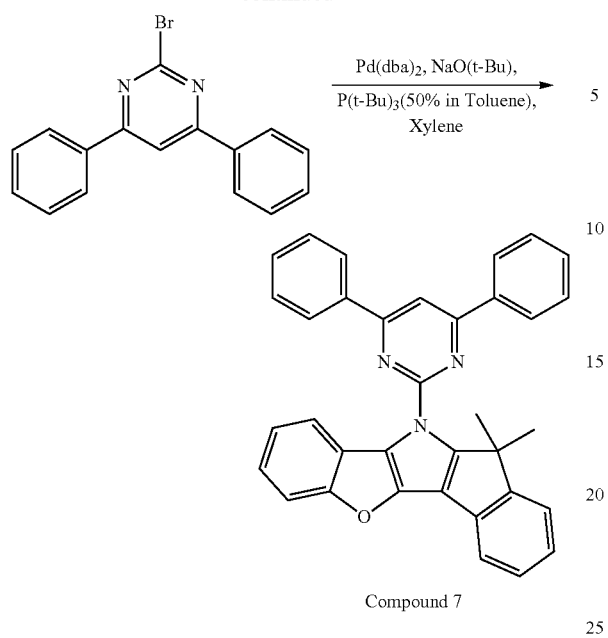

Compound 7

12.0 g (43.9 mmol) of Intermediate G, 16.4 g (52.7 mmol) of 2-bromo-4,6-diphenylpyrimidine, 8.4 g (87.8 mmol) of sodium t-butoxide, 4.0 g (4.4 mmol) of Pd(dba)$_2$, and 4.3 mL (50% in toluene) of tri t-butylphosphine were added to 250 mL of xylene in a 500 mL round flask, and then, the mixture was refluxed in a nitrogen stream for 15 hours while heating. The obtained mixture was added to 1,000 mL of methanol and the crystallized solid powder was obtained by filtering and then, the result was dissolved in dichlorobenzene and filtered by using silica gel/celite, and an appropriate amount of an organic solvent used herein was removed therefrom, and then, the result was re-crystallized by using methanol to obtain Compound 7 (12.2 g, yield of 55%). Elementary analysis results of Compound 7 re as follows:

calcd. $C_{35}H_{25}N_3O$: C, 83.48; H, 5.00; N, 8.34; O, 3.18; found: C, 83.45; H, 5.02; N, 8.33; O, 3.19

Synthesis Example 8

Synthesis of Compound 8

Reaction Scheme 8

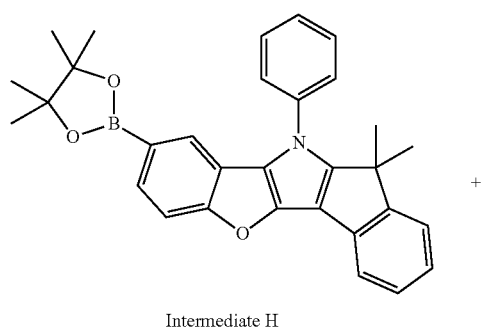

Intermediate H

-continued

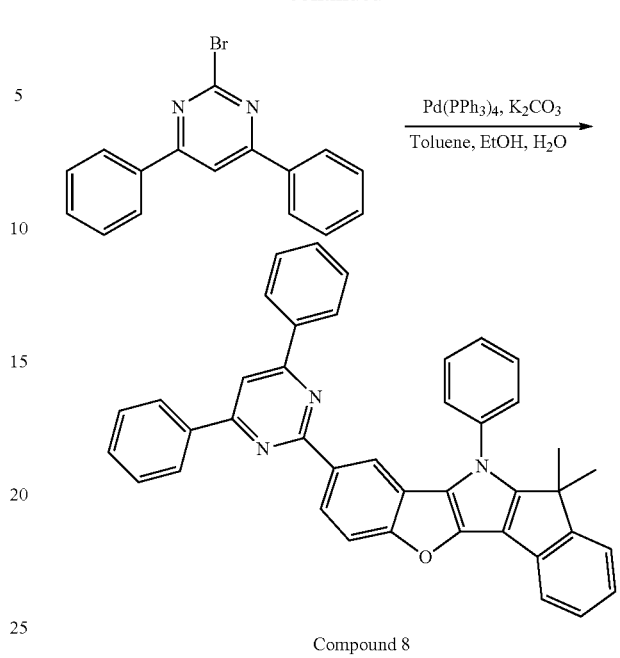

Compound 8

16.5 g (34.7 mmol) of Intermediate H, 11.9 g (38.2 mmol) of 2-bromo-4,6-diphenylpyrimidine, 9.6 g (69.4 mmol) of potassium carbonate, and 2.0 g (1.7 mmol) of tetrakis (triphenylphosphine)palladium(0) (Pd(PPh$_3$)$_4$) were added to 350 mL of toluene group, 150 mL of water, and 150 mL of ethanol in 1,000 mL flask, and then, the mixture was refluxed in a nitrogen stream for 6 hours while heating. The obtained mixture was added to 1,500 mL of methanol and the crystallized solid powder was obtained by filtering and then, the result was dissolved in monochlorobenzene and filtered by using silica gel/celite, and an appropriate amount of an organic solvent used herein was removed therefrom, and then, the result was re-crystallized by using methanol to obtain Compound 8 (12.3 g, yield of 61%). Elementary analysis results of Compound 8 are as follows:

calcd. $C_{41}H_{29}N_3O$: C, 84.95; H, 5.04; N, 7.25; O, 2.76; found: C, 84.92; H, 5.02; N, 7.26; O, 2.79

Synthesis Example 9

Synthesis of Compound 9

Reaction Scheme 9

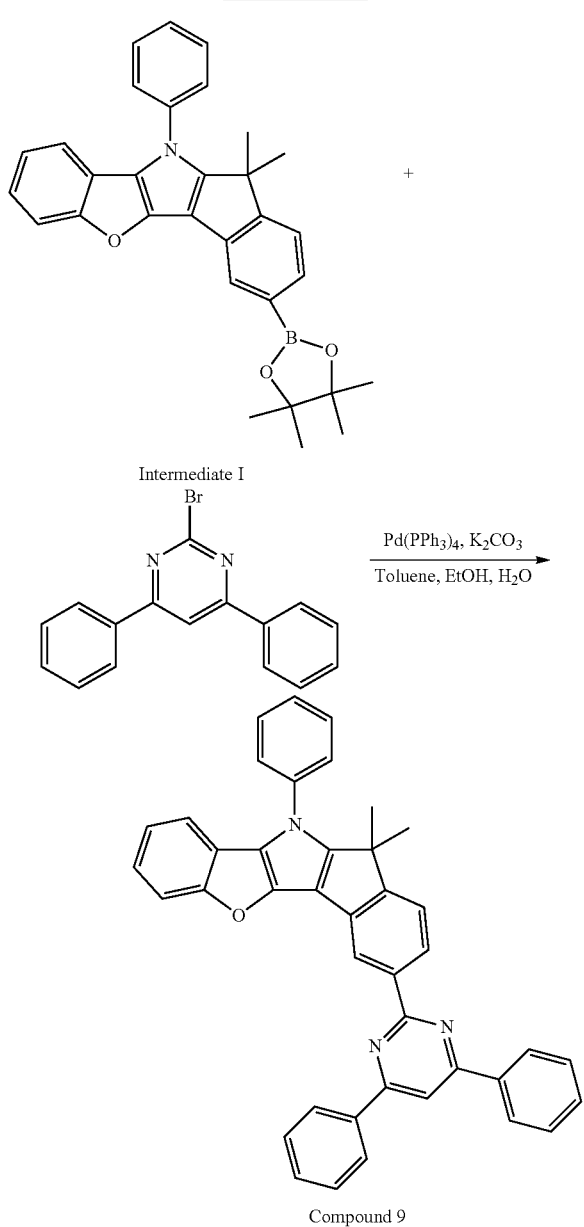

Compound 9

18.0 g (37.2 mmol) of Intermediate I, 13.0 g (41.7 mmol) of 2-bromo-4,6-diphenylpyrimidine, 10.5 g (75.7 mmol) of potassium carbonate, and 2.2 g (1.9 mmol) of tetrakis(triphenylphosphine)palladium(0) (Pd(PPh$_3$)$_4$) were added to 350 mL of toluene group, 150 mL of water, and 150 mL of ethanol in 1000 mL flask, and then, the mixture was refluxed in a nitrogen stream for 6 hours while heating. The obtained mixture was added to 1,500 mL of methanol and the crystallized solid powder was obtained by filtering and then, the result was dissolved in monochlorobenzene and filtered by using silica gel/celite, and an appropriate amount of an organic solvent used herein was removed therefrom, and then, the result was re-crystallized by using methanol to obtain Compound 9 (12.7 g, yield of 58%). Elementary analysis results of Compound 9 are as follows:

calcd. $C_{41}H_{29}N_3O$: C, 84.95; H, 5.04; N, 7.25; O, 2.76; found: C, 84.94; H, 5.02; N, 7.27; O, 2.78

Synthesis Example 10

Synthesis of Compound 10

Reaction Scheme 10

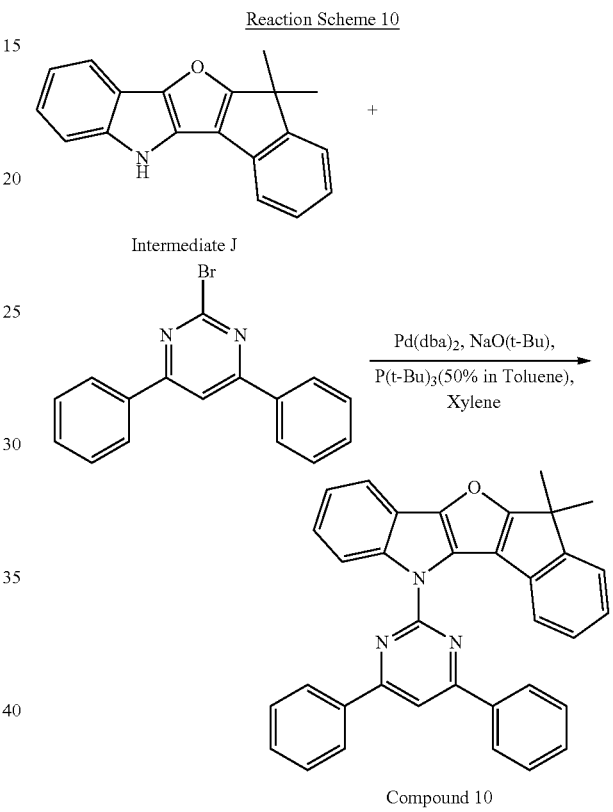

Compound 10

13.5 g (49.4 mmol) of Intermediate J, 18.4 g (59.3 mmol) of 2-bromo-4,6-diphenylpyrimidine, 9.5 g (98.8 mmol) of sodium t-butoxide, 4.5 g (4.9 mmol) of Pd(dba)$_2$, and 4.8 mL (50% in toluene) of tri t-butylphosphine were added to 300 mL of xylene in a 500 mL round flask, and then, the mixture was refluxed in a nitrogen stream for 15 hours while heating. The obtained mixture was added to 1,000 mL of methanol and the crystallized solid powder was obtained by filtering and then, the result was dissolved in dichlorobenzene and filtered by using silica gel/celite, and an appropriate amount of an organic solvent used herein was removed therefrom, and then, the result was re-crystallized by using methanol to obtain Compound 10 (14.4 g, yield of 58%). Elementary analysis results of Compound 10 are as follows:

calcd. $C_{35}H_{25}N_3O$: C, 83.48; H, 5.00; N, 8.34; O, 3.18; found: C, 83.49; H, 5.01; N, 8.32; O, 3.16

Synthesis Example 11

Synthesis of Compound 11

Reaction Scheme 11

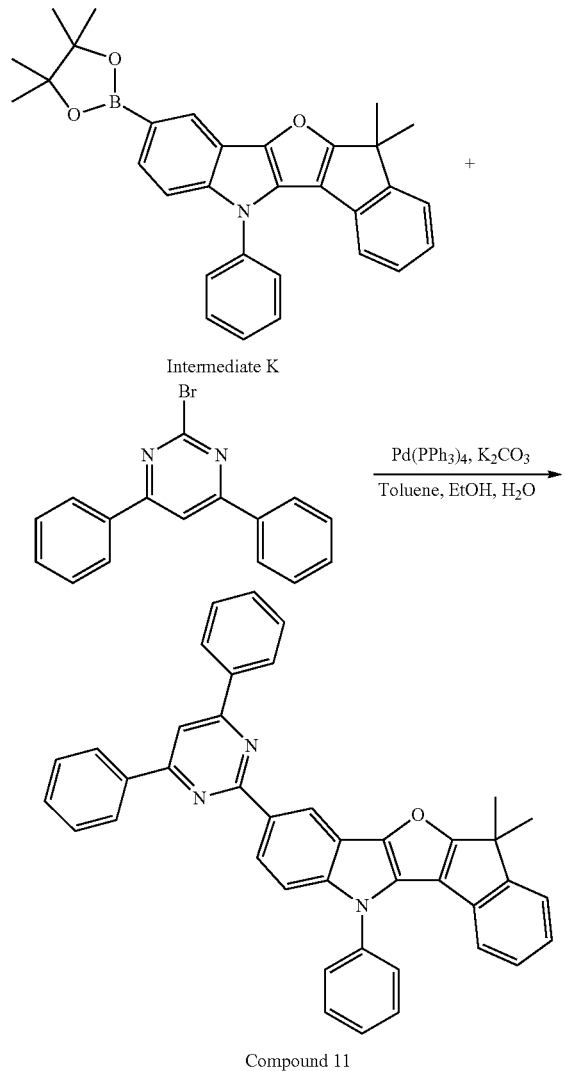

Compound 11

15.0 g (31.6 mmol) of Intermediate K, 10.8 g (34.7 mmol) of 2-bromo-4,6-diphenylpyrimidine, 8.7 g (63.1 mmol) of potassium carbonate, and 1.8 g (1.6 mmol) of tetrakis (triphenylphosphine)palladium(0) (Pd(PPh$_3$)$_4$) were added to 350 mL of toluene group, 150 mL of water, and 150 mL of ethanol in 1,000 mL flask, and then, the mixture was refluxed in a nitrogen stream for 6 hours while heating. The obtained mixture was added to 1,500 mL of methanol and the crystallized solid powder was obtained by filtering and then, the result was dissolved in monochlorobenzene and filtered by using silica gel/celite, and an appropriate amount of an organic solvent used herein was removed therefrom, and then, the result was re-crystallized by using methanol to obtain Compound 11 (11.5 g, yield of 63%). Elementary analysis results of Compound 11 are as follows:

calcd. C$_{41}$H$_{29}$N$_3$O: C, 84.95; H, 5.04; N, 7.25; O, 2.76; found: C, 84.96; H, 5.01; N, 7.27; O, 2.77

Synthesis Example 12

Synthesis of Compound 12

Reaction Scheme 12

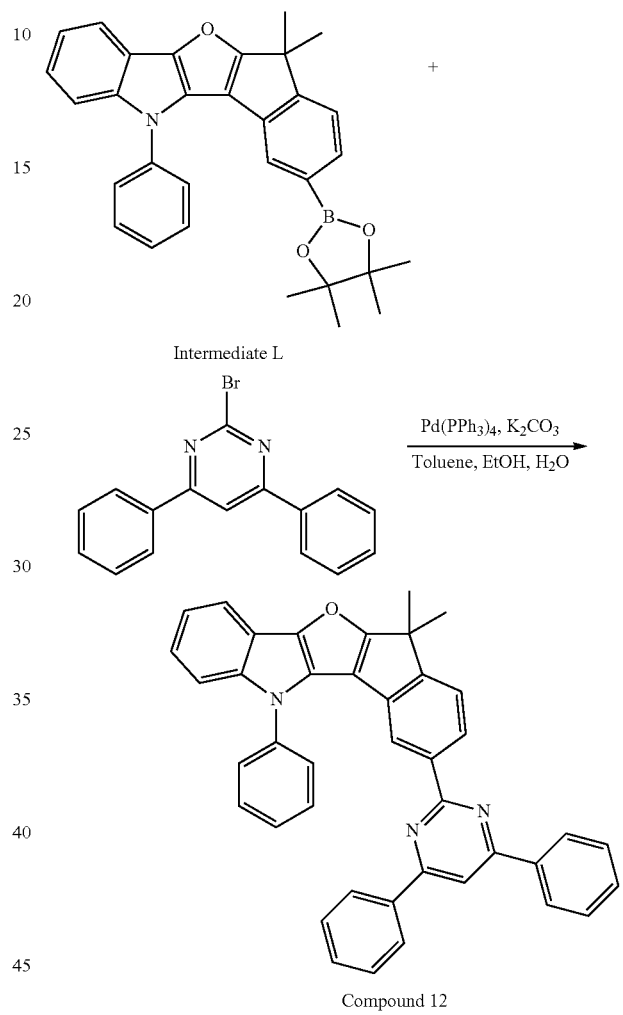

Compound 12

15.0 g (31.6 mmol) of Intermediate L, 10.8 g (34.7 mmol) of 2-bromo-4,6-diphenylpyrimidine, 8.7 g (63.1 mmol) of potassium carbonate, and 1.8 g (1.6 mmol) of tetrakis (triphenylphosphine)palladium(0) (Pd(PPh$_3$)$_4$) were added to 350 mL of toluene group, 150 mL of water, and 150 mL of ethanol in 1,000 mL flask, and then, the mixture was refluxed in a nitrogen stream for 6 hours while heating. The obtained mixture was added to 1,500 mL of methanol and the crystallized solid powder was obtained by filtering and then, the result was dissolved in monochlorobenzene and filtered by using silica gel/celite, and an appropriate amount of an organic solvent used herein was removed therefrom, and then, the result was re-crystallized by using methanol to obtain Compound 12 (11.3 g, yield of 62%). Elementary analysis results of Compound 12 are as follows:

calcd. C$_{41}$H$_{29}$N$_3$O: C, 84.95; H, 5.04; N, 7.25; O, 2.76; found: C, 84.93; H, 5.02; N, 7.26; O, 2.75

Evaluation Example 1

Evaluation on HOMO, LUMO, and Triplets (T1) Energy Level of Compounds 1 to 12

HOMO, LUMO and T1 energy levels of Compounds 1 to 12 were evaluated according to the method indicated in Table 1, and results thereof are shown in Table 2.

TABLE 1

| | |
|---|---|
| HOMO energy level evaluation method | Each compound was diluted in $CHCl_3$ to a concentration of $1 \times 10^{-5}$ M, and then, UV absorption spectrum thereof was measured at room temperature by using Shimadzu UV-350 Spectrometer. A HOMO energy level of the compound was calculated by using an optical band gap (Eg) measured by the edge of the absorption spectrum. |
| LUMO energy level evaluation method | Cyclic voltammetry (CV) (electrolyte: 0.1M $Bu_4NClO_4$/solvent: $CH_2Cl_2$/electrode: 3 electrode system (working electrode: GC, reference electrode: Ag/AgCl, auxiliary electrode: Pt)) were used to obtain a potential (V)-current (A) graph of each compound, and then, from reduction onset of the graph, the LUMO energy level of each compound was calculated. |
| T1 energy level evaluation method | A mixture (each compound was dissolved in an amount of 1 mg in 3 cc of toluene) of toluene and each compound was loaded into a quartz cell, and then, the resultant quartz cell was loaded into liquid nitrogen (77° K) and a photoluminescence spectrum thereof was measured by using a device for measuring photoluminescence, and the obtained spectrum was compared with a photoluminescence spectrum measured at room temperature, and peaks appearing only at low temperature were analyzed to calculate T1 energy levels. |

TABLE 2

| Compound No. | HOMO (eV) (calc.) | LUMO (eV) (calc.) | T1 energy level (eV) |
|---|---|---|---|
| Compound 1 | −5.116 | −1.914 | 2.604 |
| Compound 2 | −5.059 | −1.652 | 2.688 |
| Compound 3 | −5.084 | −1.581 | 2.689 |
| Compound 4 | −5.142 | −1.914 | 2.648 |
| Compound 5 | −5.152 | −1.557 | 2.686 |
| Compound 6 | −5.117 | −1.732 | 2.701 |
| Compound 7 | −4.941 | −1.918 | 2.429 |
| Compound 8 | −4.952 | −1.616 | 2.736 |
| Compound 9 | −4.929 | −1.548 | 2.648 |
| Compound 10 | −4.966 | −1.813 | 2.646 |
| Compound 11 | −5.029 | −1.534 | 2.680 |
| Compound 12 | −4.989 | −1.662 | 2.611 |

From Table 2, it was confirmed that Compounds 1 to 12 have electric characteristics that are suitable for use as a material for forming an organic light-emitting device.

Example 1

An ITO glass substrate was cut to a size of 50 mm×50 mm×0.5 mm and then, sonicated in acetone isopropyl alcohol and pure water, each for 15 minutes, and then, washed by exposure to UV ozone for 30 minutes. m-MTDATA was vacuum-deposited on the resultant ITO structure at a deposition speed of 1 Å/sec to form a hole injection layer having a thickness of 600 Å, and α-NPB was vacuum-deposited on the hole injection layer at a deposition speed of 1 Å/sec to form a hole transport layer having a thickness of 300 Å. Subsequently, $Ir(ppy)_3$(dopant) and Compound 1 (host) were co-deposited on the hole transport layer at deposition speeds of 0.1 Å/sec and 1 Å/sec, respectively, to form an emission layer having a thickness of 400 Å, and aluminum (III) bis(2-methyl-8-quinolinato)-4-phenylphenolate (BAlq) was vacuum-deposited on the emission layer at a deposition speed of 1 Å/sec to form a hole blocking layer having a thickness of 50 Å, and then, $Alq_3$ was vacuum-deposited on the hole blocking layer to form an electron transport layer having a thickness of 300 Å. LiF and Al were sequentially vacuum-deposited on the electron transport layer at thicknesses of 10 Å (electron injection layer) and Al 2,000 Å(cathode), respectively, thereby completing manufacturing of an organic light-emitting device.

Example 2

An organic light-emitting device was manufactured in the same manner as in Example 1, except that in forming an emission layer, as a host, Compound 4 was used instead of Compound 1.

Example 3

An organic light-emitting device was manufactured in the same manner as in Example 1, except that in forming an emission layer, as a host, Compound 6 was used instead of Compound 1.

Comparative Example 1

An organic light-emitting device was manufactured in the same manner as in Example 1, except that in forming an emission layer, as a host, Compound A illustrated below was used instead of Compound 1.

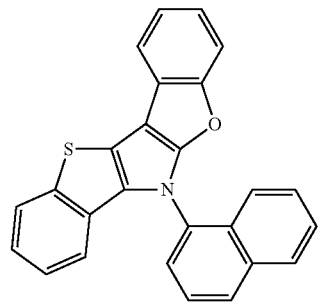

Compound A

Comparative Example 2

An organic light-emitting device was manufactured in the same manner as in Example 1, except that in forming an emission layer, as a host, Compound B illustrated below was used instead of Compound 1.

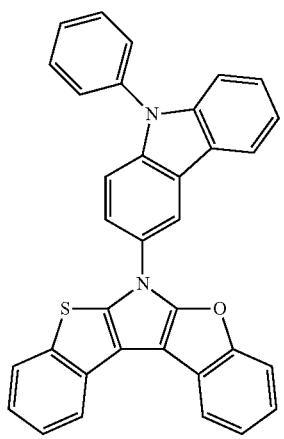

Compound B

Evaluation Example 2

Evaluation on Characteristics of an Organic Light-emitting Device

According to the methods indicated in Table 3 below, efficiency, power efficiency, and brightness of the organic light-emitting devices of Examples 1 to 3 and Comparative Examples 1 and 2 were evaluated, and results thereof are shown in Table 4 below.

TABLE 3

| | |
|---|---|
| Change in current density according to voltage | Regarding an organic light-emitting device, a current flowing in a unit device was measured by using a current-voltage meter while a voltage was raised from −5 V to 10 V, and the measured current value was divided by area |
| Change in brightness according to voltage | Regarding an organic light-emitting device, a brightness of a green emission region was measured by using a brightness meter (Minolta Cs-1000A) while a voltage was raised from −5 V to 10 V |
| Emission Efficiency Measurement | Current efficiency (cd/A) was calculated at the same current density (10 mA/cm²) by using the current density, brightness, and voltage which were measured as described above. |

TABLE 4

| | Host | Dopant | Driving voltage (V) | Efficiency (cd/A) | Power efficiency (lm/W) | Brightness (cd/m²) |
|---|---|---|---|---|---|---|
| Example 1 | Compound 1 | Ir(ppy)₃ | 4.7 | 32 | 21.4 | 3500 |
| Example 2 | Compound 4 | Ir(ppy)₃ | 4.5 | 28 | 19.5 | 3500 |
| Example 3 | Compound 6 | Ir(ppy)₃ | 4.8 | 30 | 19.6 | 3500 |
| Comparative Example 1 | Compound A | Ir(ppy)₃ | 5.5 | 33 | 18.8 | 3500 |
| Comparative Example 2 | Compound B | Ir(ppy)₃ | 5.6 | 32 | 18.0 | 3500 |

From Table 4, it was confirmed that the organic light-emitting devices of Examples 1 to 3 had a lower driving voltage and a higher power efficiency than the organic light-emitting devices of Comparative Examples 1 and 2.

The condensed cyclic compound according to embodiments has excellent electric characteristics and thermal stability. Accordingly, an organic light-emitting device including the condensed cyclic compound may have a low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula 1 below:

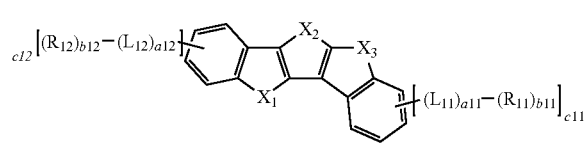

Formula 1 wherein in Formula 1, $X_1$ is $N[(L_1)_{a1}-(R_1)_{b1}]$, $C[(L_2)_{a2}-(R_2)_{b2}][(L_3)_{a3}-(R_3)_{b3}]$, $Si[(L_2)_{a2}-(R_2)_{b2}][(L_3)_{a3}-(R_3)_{b3}]$, S, or O;

$X_2$ is $N[(L_4)_{a4}-(R_4)_{b4}]$, $C[(L_5)_{a5}-(R_5)_{b5}][(L_6)_{a6}-(R_6)_{b6}]$, $Si[(L_5)_{a5}-(R_5)_{b5}][(L_6)_{a6}-(R_6)_{b6}]$, S, or O;

$X_3$ is $N[(L_7)_{a7}-(R_7)_{b7}]$, $C[(L_8)_{a8}-(R_8)_{b8}][(L_9)_{a9}-(R_9)_{b9}]$, $Si[(L_8)_{a8}-(R_8)_{b8}][(L_9)_{a9}-(R_9)_{b9}]$, S, or O;

when $X_2$ is $N[(L_4)_{a4}-(R_4)_{b4}]$, i) $X_1$ is $C[(L_2)_{a2}-(R_2)_{b2}][(L_3)_{a3}-(R_3)_{b3}]$ or $Si[(L_2)_{a2}-(R_2)_{b2}][(L_3)_{a3}-(R_3)_{b3}]$, and $X_3$ is $N[(L_7)_{a7}-(R_7)_{b7}]$, $C[(L_8)_{a8}-(R_8)_{b8}][(L_9)_{a9}-(R_9)_{b9}]$, $Si[(L_8)_{a8}-(R_8)_{b8}][(L_9)_{a9}-(R_9)_{b9}]$, S, or O, or ii) $X_1$ is $N[(L_1)_{a1}-(R_1)_{b1}]$, S, or O, and $X_3$ is $C[(L_8)_{a8}-(R_8)_{b8}][(L_9)_{a9}-(R_9)_{b9}]$ or $Si[(L_8)_{a8}-(R_8)_{b8}][(L_9)_{a9}-(R_9)_{b9}]$;

provided that i) a combination of $X_1$ is $C[(L_2)_{a2}-(R_2)_{b2}][(L_3)_{a3}-(R_3)_{b3}]$, $X_2$ is S, and $X_3$ is $C[(L_8)_{a8}-(R_8)_{b8}][(L_9)_{a9}-(R_9)_{b9}]$, ii) a combination of $X_1$ is S, $X_2$ is S, and $X_3$ is S, and iii) a combination of $X_1$ is $CH_2$, $X_2$ is O, and $X_3$ is $CH_2$ are excluded;

$L_1$ to $L_9$, $L_{11}$, and $L_{12}$ are each independently a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted bivalent non-aromatic condensed polycyclic group, or a substituted or unsubstituted divalent non-aromatic hetero-condensed polycyclic group, a1 to a9, a11, and a12 are each independently selected from an integer from 0 to 5;

$R_1$, $R_4$, and $R_7$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, or a substituted or unsubstituted monovalent non-aromatic condensed heteropolycyclic group;

$R_2$, $R_3$, $R_5$, $R_6$, $R_8$, $R_9$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), or —B($Q_6$)($Q_7$);

b1 to b9, b11, and b12 are each independently selected from an integer from 1 to 10;

c11 and c12 are each independently 1, 2, 3, or 4;

when c11 is 2 or more, at least two *-($L_{11}$)$_{a11}$-($R_{11}$)$_{b11}$ are identical or different;

when c12 is 2 or more, at least two *-($L_{12}$)$_{a12}$-($R_{12}$)$_{b12}$ are identical or different;

at least one of the substituted $C_3$-$C_{10}$ cycloalkylene group, the substituted $C_3$-$C_{10}$ heterocycloalkylene group, the substituted $C_3$-$C_{10}$ cycloalkenylene group substituted $C_3$-$C_{10}$ heterocycloalkenylene group substituted $C_6$-$C_{60}$ arylene group substituted $C_2$-$C_{60}$ heteroarylene group substituted bivalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, a substituted or unsubstituted $C_7$-$C_{60}$ arylalkyl group, the substituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, the substituted monovalent non-aromatic condensed polycyclic group, and the substituted monovalent non-aromatic condensed heteropolycyclic group is substituted with a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$ $C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycylic group, —N($Q_{21}$)($Q_{22}$), —Si($Q_{23}$)($Q_{24}$)($Q_{25}$), and —B($Q_{26}$)($Q_{27}$); or —N($Q_{31}$)($Q_{32}$), —Si($Q_{33}$)($Q_{34}$)($Q_{35}$), or —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group; or a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group.

2. The condensed cyclic compound of claim 1, wherein the condensed cyclic compound is represented by one of Formulae 1(1) to 1(83) and 1(85) to 1(115) in which $X_1$, $X_2$, and $X_3$ are:

| Formula No. | $X_1$ | $X_2$ | $X_3$ |
|---|---|---|---|
| 1(1) | C[($L_2$)$_{a2}$-($R_2$)$_{b2}$][($L_3$)$_{a3}$-($R_3$)$_{b3}$] | N[($L_4$)$_{a4}$-($R_4$)$_{b4}$] | N[($L_7$)$_{a7}$-($R_7$)$_{b7}$] |
| 1(2) | C[($L_2$)$_{a2}$-($R_2$)$_{b2}$][($L_3$)$_{a3}$-($R_3$)$_{b3}$] | N[($L_4$)$_{a4}$-($R_4$)$_{b4}$] | C[($L_8$)$_{a8}$-($R_8$)$_{b8}$][($L_9$)$_{a9}$-($R_9$)$_{b9}$] |
| 1(3) | C[($L_2$)$_{a2}$-($R_2$)$_{b2}$][($L_3$)$_{a3}$-($R_3$)$_{b3}$] | N[($L_4$)$_{a4}$-($R_4$)$_{b4}$] | Si[($L_8$)$_{a8}$-($R_8$)$_{b8}$][($L_9$)$_{a9}$-($R_9$)$_{b9}$] |
| 1(4) | C[($L_2$)$_{a2}$-($R_2$)$_{b2}$][($L_3$)$_{a3}$-($R_3$)$_{b3}$] | N[($L_4$)$_{a4}$-($R_4$)$_{b4}$] | S |
| 1(5) | C[($L_2$)$_{a2}$-($R_2$)$_{b2}$][($L_3$)$_{a3}$-($R_3$)$_{b3}$] | N[($L_4$)$_{a4}$-($R_4$)$_{b4}$] | O |
| 1(6) | Si[($L_2$)$_{a2}$-($R_2$)$_{b2}$][($L_3$)$_{a3}$-($R_3$)$_{b3}$] | N[($L_4$)$_{a4}$-($R_4$)$_{b4}$] | N[($L_7$)$_{a7}$-($R_7$)$_{b7}$] |
| 1(7) | Si[($L_2$)$_{a2}$-($R_2$)$_{b2}$][($L_3$)$_{a3}$-($R_3$)$_{b3}$] | N[($L_4$)$_{a4}$-($R_4$)$_{b4}$] | C[($L_8$)$_{a8}$-($R_8$)$_{b8}$][($L_9$)$_{a9}$-($R_9$)$_{b9}$] |
| 1(8) | Si[($L_2$)$_{a2}$-($R_2$)$_{b2}$][($L_3$)$_{a3}$-($R_3$)$_{b3}$] | N[($L_4$)$_{a4}$-($R_4$)$_{b4}$] | Si[($L_8$)$_{a8}$-($R_8$)$_{b8}$][($L_9$)$_{a9}$-($R_9$)$_{b9}$] |
| 1(9) | Si[($L_2$)$_{a2}$-($R_2$)$_{b2}$][($L_3$)$_{a3}$-($R_3$)$_{b3}$] | N[($L_4$)$_{a4}$-($R_4$)$_{b4}$] | S |

-continued

| Formula No. | X₁ | X₂ | X₃ |
|---|---|---|---|
| 1(10) | Si[(L₂)$_{a2}$-(R₂)$_{b2}$][(L₃)$_{a3}$-(R₃)$_{b3}$] | N[(L₄)$_{a4}$-(R₄)$_{b4}$] | O |
| 1(11) | N[(L₁)$_{a1}$-(R₁)$_{b1}$] | N[(L₄)$_{a4}$-(R₄)$_{b4}$] | C[(L₈)$_{a8}$-(R₈)$_{b8}$][(L₉)$_{a9}$-(R₉)$_{b9}$] |
| 1(12) | N[(L₁)$_{a1}$-(R₁)$_{b1}$] | N[(L₄)$_{a4}$-(R₄)$_{b4}$] | Si[(L₈)$_{a8}$-(R₈)$_{b8}$][(L₉)$_{a9}$-(R₉)$_{b9}$] |
| 1(13) | S | N[(L₄)$_{a4}$-(R₄)$_{b4}$] | C[(L₈)$_{a8}$-(R₈)$_{b8}$][(L₉)$_{a9}$-(R₉)$_{b9}$] |
| 1(14) | S | N[(L₄)$_{a4}$-(R₄)$_{b4}$] | Si[(L₈)$_{a8}$-(R₈)$_{b8}$][(L₉)$_{a9}$-(R₉)$_{b9}$] |
| 1(15) | O | N[(L₄)$_{a4}$-(R₄)$_{b4}$] | C[(L₈)$_{a8}$-(R₈)$_{b8}$][(L₉)$_{a9}$-(R₉)$_{b9}$] |
| 1(16) | O | N[(L₄)$_{a4}$-(R₄)$_{b4}$] | Si[(L₈)$_{a8}$-(R₈)$_{b8}$][(L₉)$_{a9}$-(R₉)$_{b9}$] |
| 1(17) | N[(L₁)$_{a1}$-(R₁)$_{b1}$] | C[(L₅)$_{a5}$-(R₅)$_{b5}$][(L₆)$_{a6}$-(R₆)$_{b6}$] | N[(L₇)$_{a7}$-(R₇)$_{b7}$] |
| 1(18) | N[(L₁)$_{a1}$-(R₁)$_{b1}$] | C[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(19) | N[(L₁)$_{a1}$-(R₁)$_{b1}$] | C[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(20) | N[(L₁)$_{a1}$-(R₁)$_{b1}$] | C[(L₅)$_{a5}$-(R₅)$_{b5}$][(L₆)$_{a6}$-(R₆)$_{b6}$] | S |
| 1(21) | N[(L₁)$_{a1}$-(R₁)$_{b1}$] | C[(L₅)$_{a5}$-(R₅)$_{b5}$][(L₆)$_{a6}$-(R₆)$_{b6}$] | O |
| 1(22) | C[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | N[(L₇)$_{a7}$-(R₇)b₇] |
| 1(23) | C[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(24) | C[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(25) | C[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | S |
| 1(26) | C[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | O |
| 1(27) | Si[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | N[(L₇)$_{a7}$-(R₇)$_{b7}$] |
| 1(28) | Si[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(29) | Si[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(30) | Si[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | S |
| 1(31) | Si[(L₂)$_{a2}$-(R₂)$_{b2}$][(L₃)$_{a3}$-(R₃)$_{b3}$] | C[(L₅)$_{a5}$-(R₅)$_{b5}$][(L₆)$_{a6}$-(R₆)$_{b6}$] | O |
| 1(32) | S | C[(L₅)$_{a5}$-(R₅)$_{b5}$][(L₆)$_{a6}$-(R₆)$_{b6}$] | N[(L₇)$_{a7}$-(R₇)$_{b7}$] |
| 1(33) | S | C[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(34) | S | C[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(35) | S | C[(L₅)$_{a5}$-(R₅)$_{b5}$][(L₆)$_{a6}$-(R₆)$_{b6}$] | S |
| 1(36) | S | C[(L₅)$_{a5}$-(R₅)$_{b5}$][(L₆)$_{a6}$-(R₆)$_{b6}$] | O |
| 1(37) | O | C[(L₅)$_{a5}$-(R₅)$_{b5}$][(L₆)$_{a6}$-(R₆)$_{b6}$] | N[(L₇)$_{a7}$-(R₇)$_{b7}$] |
| 1(38) | O | C[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(39) | O | C[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(40) | O | C[(L₅)$_{a5}$-(R₅)$_{b5}$][(L₆)$_{a6}$-(R₆)$_{b6}$] | S |
| 1(41) | O | C[(L₅)$_{a5}$-(R₅)$_{b5}$][(L₆)$_{a6}$-(R₆)$_{b6}$] | O |
| 1(42) | N[(L₁)$_{a1}$-(R₁)$_{b1}$] | Si[(L₅)$_{a5}$-(R₅)$_{b5}$][(L₆)$_{a6}$-(R₆)$_{b6}$] | N[(L₇)$_{a7}$-(R₇)$_{b7}$] |
| 1(43) | N[(L₁)$_{a1}$-(R₁)$_{b1}$] | Si[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(44) | N[(L₁)$_{a1}$-(R₁)$_{b1}$] | Si[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(45) | N[(L₁)$_{a1}$-(R₁)$_{b1}$] | Si[(L₅)$_{a5}$-(R₅)$_{b5}$][(L₆)$_{a6}$-(R₆)$_{b6}$] | S |
| 1(46) | N[(L₁)$_{a1}$-(R₁)$_{b1}$] | Si[(L₅)$_{a5}$-(R₅)$_{b5}$][(L₆)$_{a6}$-(R₆)$_{b6}$] | O |
| 1(47) | C[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | N[(L₇)$_{a7}$-(R₇)$_{b7}$] |
| 1(48) | C[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(49) | C[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(50) | C[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | S |
| 1(51) | C[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | O |
| 1(52) | Si[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | N[(L₇)$_{a7}$-(R₇)$_{b7}$] |
| 1(53) | Si[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(54) | Si[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(55) | Si[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | S |
| 1(56) | Si[(L₂)$_{a2}$-(R₂)$_{b2}$][(L₃)$_{a3}$-(R₃)$_{b3}$] | Si[(L₅)$_{a5}$-(R₅)$_{b5}$][(L₆)$_{a6}$-(R₆)$_{b6}$] | O |
| 1(57) | S | Si[(L₅)$_{a5}$-(R₅)$_{b5}$][(L₆)$_{a6}$-(R₆)$_{b6}$] | N[(L₇)$_{a7}$-(R₇)$_{b7}$] |
| 1(58) | S | Si[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(59) | S | Si[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(60) | S | Si[(L₅)$_{a5}$-(R₅)$_{b5}$][(L₆)$_{a6}$-(R₆)$_{b6}$] | S |
| 1(61) | S | Si[(L₅)$_{a5}$-(R₅)$_{b5}$][(L₆)$_{a6}$-(R₆)$_{b6}$] | O |
| 1(62) | O | Si[(L₅)$_{a5}$-(R₅)$_{b5}$][(L₆)$_{a6}$-(R₆)$_{b6}$] | N[(L₇)$_{a7}$-(R₇)$_{b7}$] |
| 1(63) | O | Si[(L₅)$_{a5}$-(R₅)$_{b5}$][(L₆)$_{a6}$-(R₆)$_{b6}$] | C[(L₈)$_{a8}$-(R₈)$_{b8}$][(L₉)$_{a9}$-(R₉)$_{b9}$] |
| 1(64) | O | Si[(L₅)$_{a5}$-(R₅)$_{b5}$][(L₆)$_{a6}$-(R₆)$_{b6}$] | Si[(L₈)$_{a8}$-(R₈)$_{b8}$][(L₉)$_{a9}$-(R₉)$_{b9}$] |
| 1(65) | O | Si[(L₅)$_{a5}$-(R₅)$_{b5}$][(L₆)$_{a6}$-(R₆)$_{b6}$] | S |
| 1(66) | O | Si[(L₅)$_{a5}$-(R₅)$_{b5}$][(L₆)$_{a6}$-(R₆)$_{b6}$] | O |
| 1(67) | N[(L₁)$_{a1}$-(R₁)$_{b1}$] | S | N[(L₇)$_{a7}$-(R₇)$_{b7}$] |
| 1(68) | N[(L₁)$_{a1}$-(R₁)$_{b1}$] | S | C[(L₈)$_{a8}$-(R₈)$_{b8}$][(L₉)$_{a9}$-(R₉)$_{b9}$] |
| 1(69) | N[(L₁)$_{a1}$-(R₁)$_{b1}$] | S | Si[(L₈)$_{a8}$-(R₈)$_{b8}$][(L₉)$_{a9}$-(R₉)$_{b9}$] |
| 1(70) | N[(L₁)$_{a1}$-(R₁)$_{b1}$] | S | S |
| 1(71) | N[(L₁)$_{a1}$-(R₁)$_{b1}$] | S | O |
| 1(72) | C[(L₂)$_{a2}$-(R₂)$_{b2}$][(L₃)$_{a3}$-(R₃)$_{b3}$] | S | N[(L₇)$_{a7}$-(R₇)$_{b7}$] |
| 1(73) | C[(L₂)$_{a2}$-(R₂)$_{b2}$][(L₃)$_{a3}$-(R₃)$_{b3}$] | S | Si[(L₈)$_{a8}$-(R₈)$_{b8}$][(L₉)$_{a9}$-(R₉)$_{b9}$] |
| 1(74) | C[(L₂)$_{a2}$-(R₂)$_{b2}$][(L₃)$_{a3}$-(R₃)$_{b3}$] | S | S |
| 1(75) | C[(L₂)$_{a2}$-(R₂)$_{b2}$][(L₃)$_{a3}$-(R₃)$_{b3}$] | S | O |
| 1(76) | Si[(L₂)$_{a2}$-(R₂)$_{b2}$][(L₃)$_{a3}$-(R₃)$_{b3}$] | S | N[(L₇)$_{a7}$-(R₇)$_{b7}$] |
| 1(77) | Si[(L₂)$_{a2}$-(R₂)$_{b2}$][(L₃)$_{a3}$-(R₃)$_{b3}$] | S | C[(L₈)$_{a8}$-(R₈)$_{b8}$][(L₉)$_{a9}$-(R₉)$_{b9}$] |
| 1(78) | Si[(L₂)$_{a2}$-(R₂)$_{b2}$][(L₃)$_{a3}$-(R₃)$_{b3}$] | S | Si[(L₈)$_{a8}$-(R₈)$_{b8}$][(L₉)$_{a9}$-(R₉)$_{b9}$] |
| 1(79) | Si[(L₂)$_{a2}$-(R₂)$_{b2}$][(L₃)$_{a3}$-(R₃)$_{b3}$] | S | S |
| 1(80) | Si[(L₂)$_{a2}$-(R₂)$_{b2}$][(L₃)$_{a3}$-(R₃)$_{b3}$] | S | O |
| 1(81) | S | S | N[(L₇)$_{a7}$-(R₇)$_{b7}$] |
| 1(82) | S | S | C[(L₈)$_{a8}$-(R₈)$_{b8}$][(L₉)$_{a9}$-(R₉)$_{b9}$] |
| 1(83) | S | S | Si[(L₈)$_{a8}$-(R₈)$_{b8}$][(L₉)$_{a9}$-(R₉)$_{b9}$] |
| 1(84) | S | S | S |
| 1(85) | S | S | O |

-continued

| Formula No. | $X_1$ | $X_2$ | $X_3$ |
|---|---|---|---|
| 1(86) | O | S | $N[(L_7)_{a7}-(R_7)_{b7}]$ |
| 1(87) | O | S | $C[(L_8)_{a8}-(R_8)_{b8}][(L_9)_{a9}-(R_9)_{b9}]$ |
| 1(88) | O | S | $Si[(L_8)_{a8}-(R_8)_{b8}][(L_9)_{a9}-(R_9)_{b9}]$ |
| 1(89) | O | S | S |
| 1(90) | O | S | O |
| 1(91) | $N[(L_1)_{a1}-(R_1)_{b1}]$ | O | $N[(L_7)_{a7}-(R_7)_{b7}]$ |
| 1(92) | $N[(L_1)_{a1}-(R_1)_{b1}]$ | O | $C[(L_8)_{a8}-(R_8)_{b8}][(L_9)_{a9}-(R_9)_{b9}]$ |
| 1(93) | $N[(L_1)_{a1}-(R_1)_{b1}]$ | O | $Si[(L_8)_{a8}-(R_8)_{b8}][(L_9)_{a9}-(R_9)_{b9}]$ |
| 1(94) | $N[(L_1)_{a1}-(R_1)_{b1}]$ | O | S |
| 1(95) | $N[(L_1)_{a1}-(R_1)_{b1}]$ | O | O |
| 1(96) | $C[(L_2)_{a2}-(R_2)_{b2}][(L_3)_{a3}-(R_3)_{b3}]$ | O | $N[(L_7)_{a7}-(R_7)_{b7}]$ |
| 1(97) | $C[(L_2)_{a2}-(R_2)_{b2}][(L_3)_{a3}-(R_3)_{b3}]$ | O | $C[(L_8)_{a8}-(R_8)_{b8}][(L_9)_{a9}-(R_9)_{b9}]$ |
| 1(98) | $C[(L_2)_{a2}-(R_2)_{b2}][(L_3)_{a3}-(R_3)_{b3}]$ | O | $Si[(L_8)_{a8}-(R_8)_{b8}][(L_9)_{a9}-(R_9)_{b9}]$ |
| 1(99) | $C[(L_2)_{a2}-(R_2)_{b2}][(L_3)_{a3}-(R_3)_{b3}]$ | O | S |
| 1(100) | $C[(L_2)_{a2}-(R_2)_{b2}][(L_3)_{a3}-(R_3)_{b3}]$ | O | O |
| 1(101) | $Si[(L_2)_{a2}-(R_2)_{b2}][(L_3)_{a3}-(R_3)_{b3}]$ | O | $N[(L_7)_{a7}-(R_7)b_7]$ |
| 1(102) | $Si[(L_2)_{a2}-(R_2)_{b2}][(L_3)_{a3}-(R_3)_{b3}]$, | O | $C[(L_8)_{a8}-(R_8)_{b8}][(L_9)_{a9}-(R_9)_{b9}]$ |
| 1(103) | $Si[(L_2)_{a2}-(R_2)_{b2}][(L_3)_{a3}-(R_3)_{b3}]$, | O | $Si[(L_8)_{a8}-(R_8)_{b8}][(L_9)_{a9}-(R_9)_{b9}]$ |
| 1(104) | $Si[(L_2)_{a2}-(R_2)_{b2}][(L_3)_{a3}-(R_3)_{b3}]$, | O | S |
| 1(105) | $Si[(L_2)_{a2}-(R_2)_{b2}][(L_3)_{a3}-(R_3)_{b3}]$, | O | O |
| 1(106) | S | O | $N[(L_7)_{a7}-(R_7)_{b7}]$ |
| 1(107) | S | O | $C[(L_8)_{a8}-(R_8)_{b8}][(L_9)_{a9}-(R_9)_{b9}]$ |
| 1(108) | S | O | $Si[(L_8)_{a8}-(R_8)_{b8}][(L_9)_{a9}-(R_9)_{b9}]$ |
| 1(109) | S | O | S |
| 1(110) | S | O | O |
| 1(111) | O | O | $N[(L_7)_{a7}-(R_7)_{b7}]$ |
| 1(112) | 0 | O | $C[(L_8)_{a8}-(R_8)_{b8}][(L_9)_{a9}-(R_9)_{b9}]$ |
| 1(113) | O | O | $Si[(L_8)_{a8}-(R_8)_{b8}][(L_9)_{a9}-(R_9)_{b9}]$ |
| 1(114) | O | O | S |
| 1(115) | O | O | O. |

3. The condensed cyclic compound of claim 1, wherein $X_2$ is selected from $C[(L_5)_{a5}-(R_5)_{b5}][(L_6)_{a6}-(R_6)_{b6}]$; $Si[(L_5)_{a5}-(R_5)_{b5}][(L_6)_{a6}-(R_6)_{b6}]$; S, and O.

4. The condensed cyclic compound of claim 1, wherein
$X_1=X_2$ and $X_2 \neq X_3$;
$X_1 \neq X_2$ and $X_2=X_3$; or
$X_1 \neq X_2 \neq X_3$.

5. The condensed cyclic compound of claim 1, wherein
$X_1$ is $N[(L_1)_{a1}-(R_1)_{b1}]$;
$X_2$ is $N[(L_4)_{a4}-(R_4)_{b4}]$; or
$X_3$ is $N[(L_7)_{a7}-(R_7)_{b7}]$.

6. The condensed cyclic compound of claim 2, wherein the condensed cyclic compound is represented by any one of Formulae 1(81), 1(70), 1(15), 1(92), or 1(106).

7. The condensed cyclic compound of claim 1, wherein $L_1$ to $L_9$, $L_{11}$, and $L_{12}$ are each independently phenylene group, pentalenylene group, indenylene group, naphthylene group, azulenylene group, heptalenylene group, indacenylene group, acenaphthylene group, fluorenylene group, spiro-fluorenylene group, benzofluorenylene group, dibenzofluorenylene group, phenalenylene group, phenanthrenylene group, anthracenylene group, fluoranthenylene group, triphenylenylene group, pyrenylene group, chrysenylene group, naphthacenylene group, picenylene group, perylenylene group, pentaphenylene group, hexacenylene group, pentacenylene group, rubicenylene group, coronenylene group, ovalenylene group, pyrrolylene group, thiophenylene group, furanylene group, imidazolylene group, pyrazolylene group, thiazolylene group, isothiazolylene group, oxazolylene group, isooxazolylene group, pyridinylene group, pyrazinylene group, pyrimidinylene group, pyridazinylene group, isoindolylene group, indolylene group, indazolylene group, purinylene group, quinolinylene group, isoquinolinylene group, benzoquinolinylene group, phthalazinylene group, naphthyridinylene group, quinoxalinylene group, quinazolinylene group, cinnolinylene group, carbazolylene group, phenanthridinylene group, acridinylene group, phenanthrolinylene group, phenazinylene group, benzoimidazolylene group, benzofuranylene group, benzothiophenylene group, isobenzothiazolylene group, benzooxazolylene group, isobenzooxazolylene group, triazolylene group, tetrazolylene group, oxadiazolylene group, triazinylene group, dibenzofuranylene group, dibenzothiophenylene group, benzocarbazolylene group, dibenzocarbazolylene group, or imidazopyridinylene group, or imidazopyrimidinylene group; or phenylene group, pentalenylene group, indenylene group, naphthylene group, azulenylene group, heptalenylene group, indacenylene group, acenaphthylene group, fluorenylene group, spiro-fluorenylene group, benzofluorenylene group, dibenzofluorenylene group, phenalenylene group, phenanthrenylene group, anthracenylene group, fluoranthenylene group, triphenylenylene group, pyrenylene group, chrysenylene group, naphthacenylene group, picenylene group, perylenylene group, pentaphenylene group, hexacenylene group, pentacenylene group, rubicenylene group, coronenylene group, ovalenylene group, pyrrolylene group, thiophenylene group, furanylene group, imidazolylene group, pyrazolylene group, thiazolylene group, isothiazolylene group, oxazolylene group, isooxazolylene group, pyridinylene group, pyrazinylene group, pyrimidinylene group, pyridazinylene group, isoindolylene group, indolylene group, indazolylene group, purinylene group, quinolinylene group, isoquinolinylene group, benzoquinolinylene group, phthalazinylene group, naphthyridinylene group, quinoxalinylene group, quinazolinylene group, cinnolinylene group, carbazolylene group, phenanthridinylene group, acridinylene group, phenanthrolinylene group, phenazinylene group, benzoimidazolylene group, benzofuranylene group, benzothiophenylene group, isobenzothiazolylene group, benzooxazolylene group, isobenzooxazolylene group, triazolylene group, tetrazolylene group, oxadiazolylene group, triazinylene group, dibenzofuranylene group, dibenzothiophenylene group, benzocarbazolylene group, dibenzocarbazolylene, imidazopyridinylene group, or imidazopyrimidinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyridinyl group, and —Si($Q_{33}$)($Q_{34}$)($Q_{35}$), wherein $Q_{33}$ to $Q_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group.

8. The condensed cyclic compound of claim 1, wherein $L_1$ to $L_9$, $L_{11}$, and $L_{12}$ are each independently represented by one of Formulae 2-1 to 2-33:

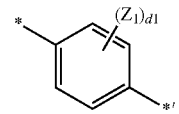
Formula 2-1

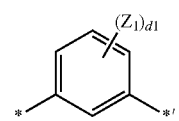
Formula 2-2

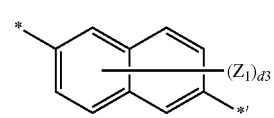
Formula 2-3

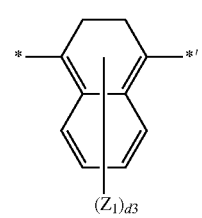
Formula 2-4

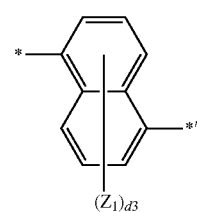
Formula 2-5

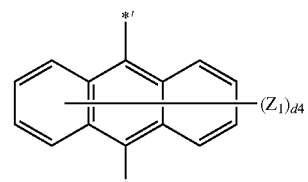
Formula 2-6

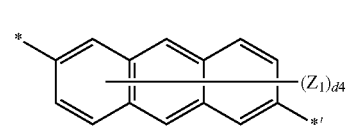
Formula 2-7

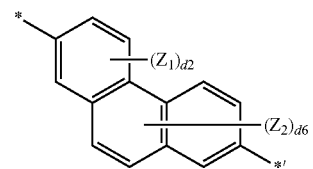
Formula 2-8

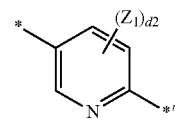
Formula 2-9

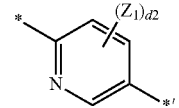
Formula 2-10

-continued
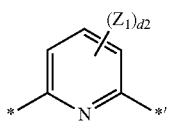
Formula 2-11
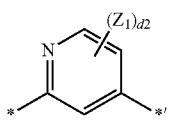
Formula 2-12
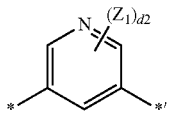
Formula 2-13
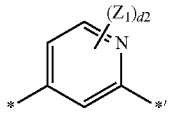
Formula 2-14
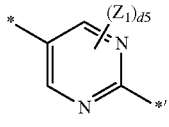
Formula 2-15
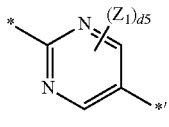
Formula 2-16
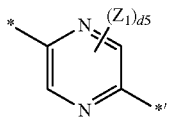
Formula 2-17
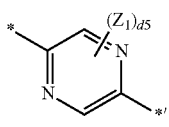
Formula 2-18
Formula 2-19
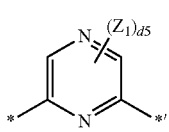
Formula 2-20
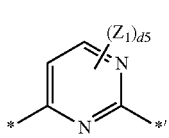
Formula 2-21
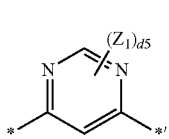
Formula 2-22
-continued
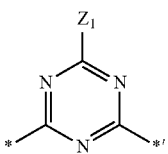
Formula 2-23
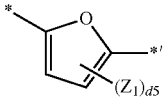
Formula 2-24
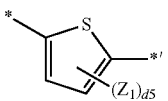
Formula 2-25
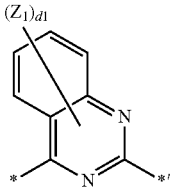
Formula 2-26
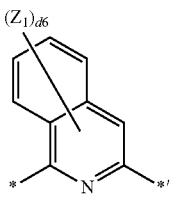
Formula 2-27
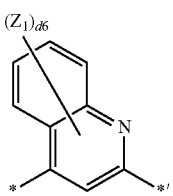
Formula 2-28
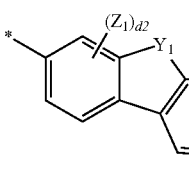
Formula 2-29
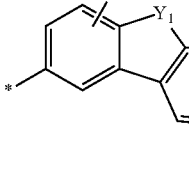
Formula 2-30
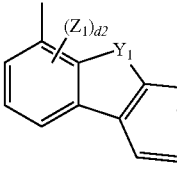
Formula 2-31

-continued

Formula 2-32

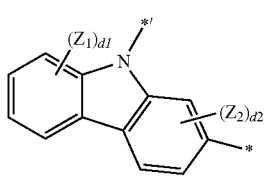

Formula 2-33

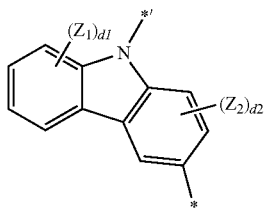

wherein in Formulae 2-1 to 2-33,
$Y_1$ is O, S, S(=O), S(=O)$_2$, C($Z_3$)($Z_4$), N($Z_5$), or Si($Z_6$)($Z_7$);
$Z_1$ to $Z_7$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, quinoxalinyl group, or —Si($Q_{33}$)($Q_{34}$)($Q_{35}$),
wherein $Q_{33}$ to $Q_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group;
d1 is an integer of 1 to 4;
d2 is an integer of 1 to 3;
d3 is an integer of 1 to 6;
d4 is an integer of 1 to 8;
d5 is 1 or 2;
d6 is an integer of 1 to 5; and
* and *' each indicates a binding site to a neighboring atom.

9. The condensed cyclic compound of claim 1, wherein $L_1$ to $L_9$, $L_{11}$, and $L_{12}$ are each independently represented by one of Formulae 3-1 to 3-59:

Formula 3-1

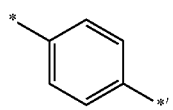

Formula 3-2

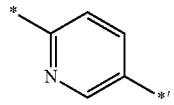

Formula 3-3

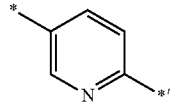

Formula 3-4

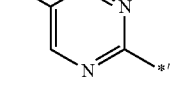

Formula 3-5

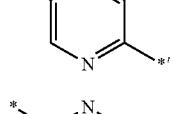

Formula 3-6

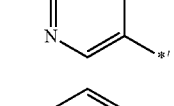

Formula 3-7

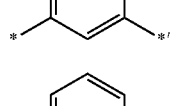

Formula 3-8

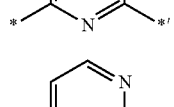

Formula 3-9

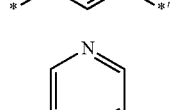

Formula 3-10

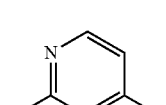

Formula 3-11

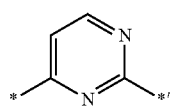

Formula 3-12

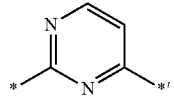

Formula 3-13

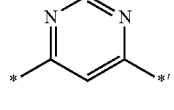

Formula 3-14

Formula 3-15

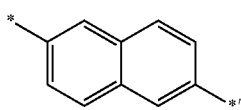
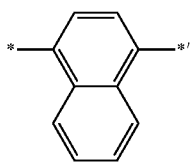
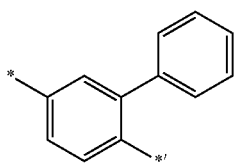
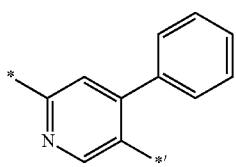
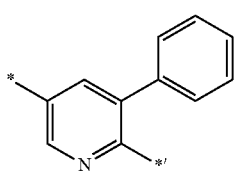
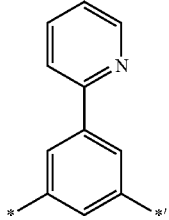
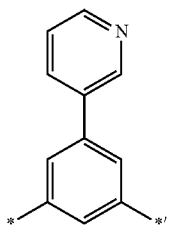
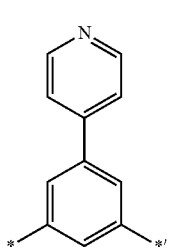
Formula 3-16
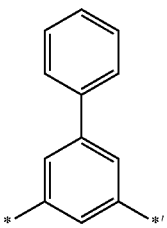
Formula 3-17
Formula 3-11 3-18
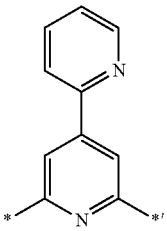
Formula 3-11 3-19
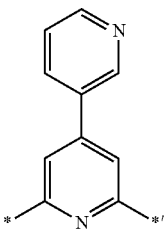
Formula 3-11 3-20
Formula 3-11 3-21
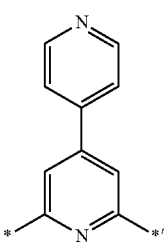
Formula 3-22
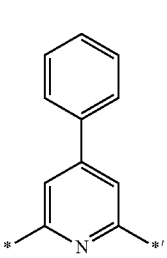
Formula 3-23
Formula 3-24
Formula 3-25
Formula 3-26
Formula 3-27
Formula 3-28
Formula 3-29
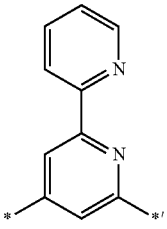

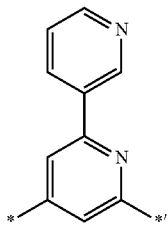
Formula 3-30
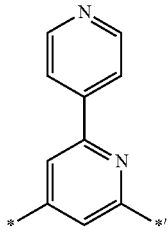
Formula 3-31
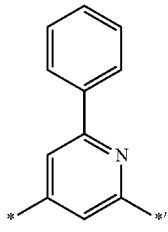
Formula 3-32
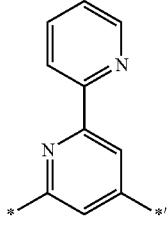
Formula 3-33
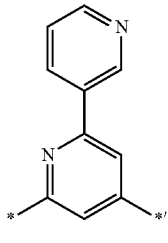
Formula 3-34
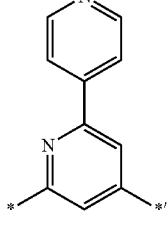
Formula 3-35
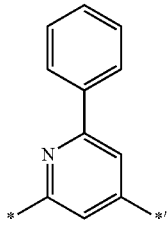
Formula 3-36
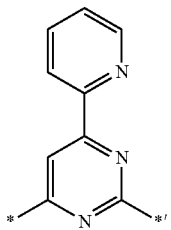
Formula 3-37
Formula 3-38
Formula 3-39
Formula 3-40
Formula 3-41
Formula 3-42

-continued
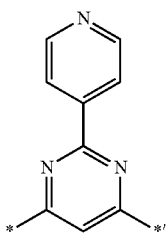
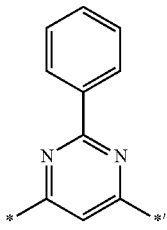
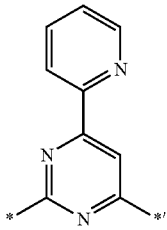
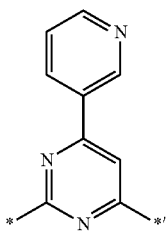
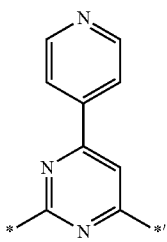
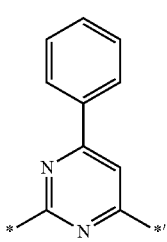
-continued
Formula 3-43
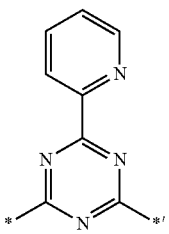
Formula 3-44
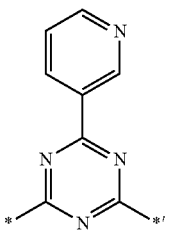
Formula 3-45
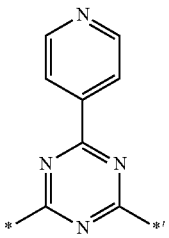
Formula 3-46
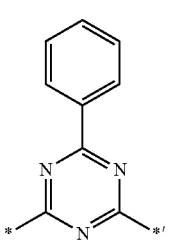
Formula 3-47
Formula 3-48
Formula 3-49
Formula 3-50
Formula 3-51
Formula 3-52
Formula 3-53
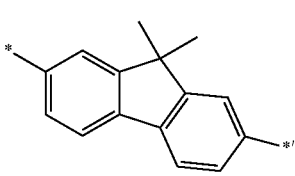
Formula 3-54
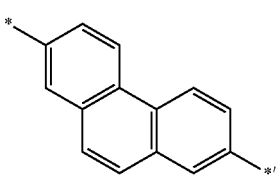
Formula 3-55
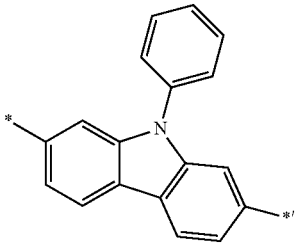

-continued

Formula 3-56
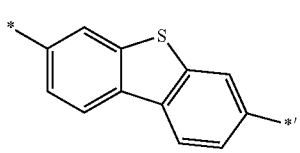

Formula 3-57
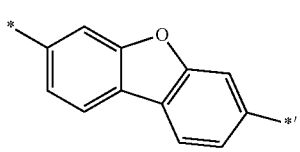

Formula 3-58
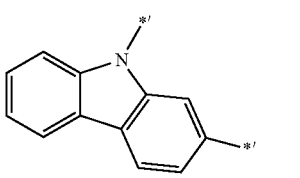

Formula 3-59
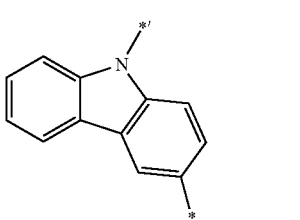

wherein in Formulae 3-1 to 3-57,

* and *' each indicates a binding site to a neighboring atom.

10. The condensed cyclic compound of claim 1, wherein a1 to a9, a11, and a12 are each independently 0, 1, or 2.

11. The condensed cyclic compound of claim 1, wherein $R_1$, $R_4$, and $R_7$ are each independently phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluoranthenyl group, triphenylenyl group, pyrenyl group, chrysenyl group, naphthacenyl group, picenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyrimidinyl group, or a group represented by

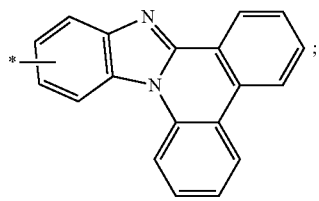

or phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyrimidinyl group, or a group represented by

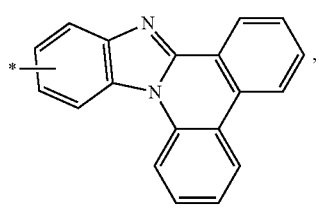

each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluoranthenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, and imidazopyrimidinyl group;

wherein $Q_{33}$ to $Q_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group.

12. The condensed cyclic compound of claim 1, wherein $R_2$, $R_3$, $R_5$, $R_6$, $R_8$, $R_9$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, phenyl group, naphthyl group, anthracenyl group, pyrenyl group, phenanthrenyl group, pyridinyl group, pyrimidinyl group, triazinyl group, quinolinyl group, isoquinolinyl group, and quinazolinyl;

phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluoranthenyl group, triphenylenyl group, pyrenyl group, chrysenyl group, naphthacenyl group, picenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyrimidinyl group, or a group represented by

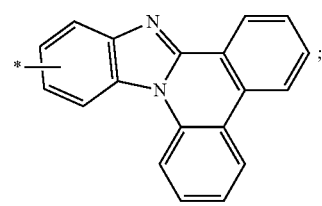

or phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, imidazopyrimidinyl group, or a group represented by

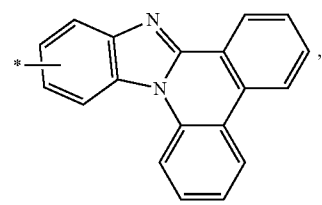

each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), phenyl group, pentalenyl group, indenyl group, naphthyl group, azulenyl group, heptalenyl group, indacenyl group, acenaphthyl group, fluorenyl group, spiro-fluorenyl group, benzofluorenyl group, dibenzofluorenyl group, phenalenyl group, phenanthrenyl group, anthracenyl group, fluorantenyl group, triphenylenyl group, pyrenyl group, chrysenyl group, naphthacenyl group, pycenyl group, perylenyl group, pentaphenyl group, hexacenyl group, pentacenyl group, rubicenyl group, coronenyl group, ovalenyl group, pyrrolyl group, thiophenyl group, furanyl group, imidazolyl group, pyrazolyl group, thiazolyl group, isothiazolyl group, oxazolyl group, isooxazolyl group, pyridinyl group, pyrazinyl group, pyrimidinyl group, pyridazinyl group, isoindolyl group, indolyl group, indazolyl group, purinyl group, quinolinyl group, isoquinolinyl group, benzoquinolinyl group, phthalazinyl group, naphthyridinyl group, quinoxalinyl group, quinazolinyl group, cinnolinyl group, carbazolyl group, phenanthridinyl group, acridinyl group, phenanthrolinyl group, phenazinyl group, benzoimidazolyl group, benzofuranyl group, benzothiophenyl group, isobenzothiazolyl group, benzooxazolyl group, isobenzooxazolyl group, triazolyl group, tetrazolyl group, oxadiazolyl group, triazinyl group, dibenzofuranyl group, dibenzothiophenyl group, benzocarbazolyl group, dibenzocarbazolyl group, imidazopyridinyl group, and imidazopyrimidinyl group;

wherein $Q_{33}$ to $Q_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group.

13. The condensed cyclic compound of claim 1, wherein $R_1$, $R_4$, and $R_7$ are each independently selected from Formulae 4-1 to 4-27 below;

$R_2$, $R_3$, $R_5$, $R_6$, $R_8$, $R_9$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, phenyl group, naphthyl group, anthracenyl group, pyrenyl group, phenanthrenyl group, pyridinyl group, pyrimidinyl group, triazinyl group, quinolinyl group, isoquinolinyl group, and quinazolinyl group; or one of Formulae 4-1 to 4-27:

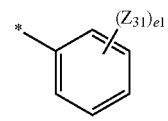

Formula 4-1

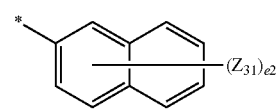

Formula 4-2

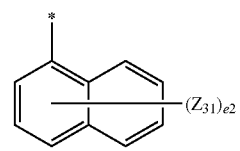

Formula 4-3

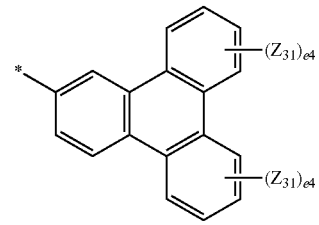

Formula 4-4

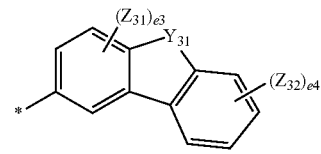

Formula 4-4

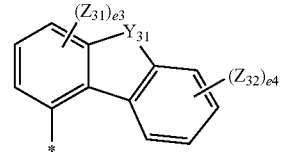

Formula 4-5

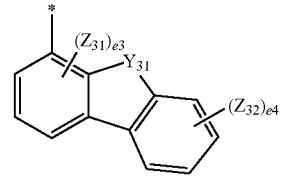

Formula 4-6

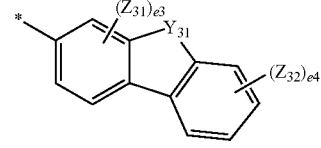

Formula 4-7

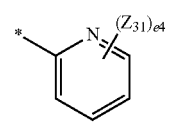

Formula 4-8

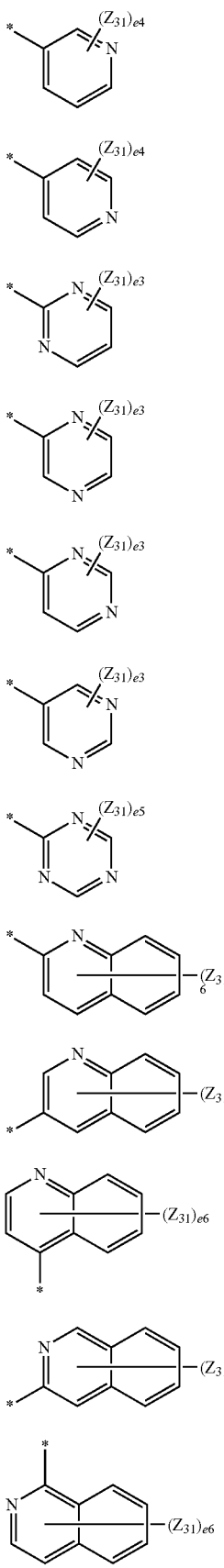
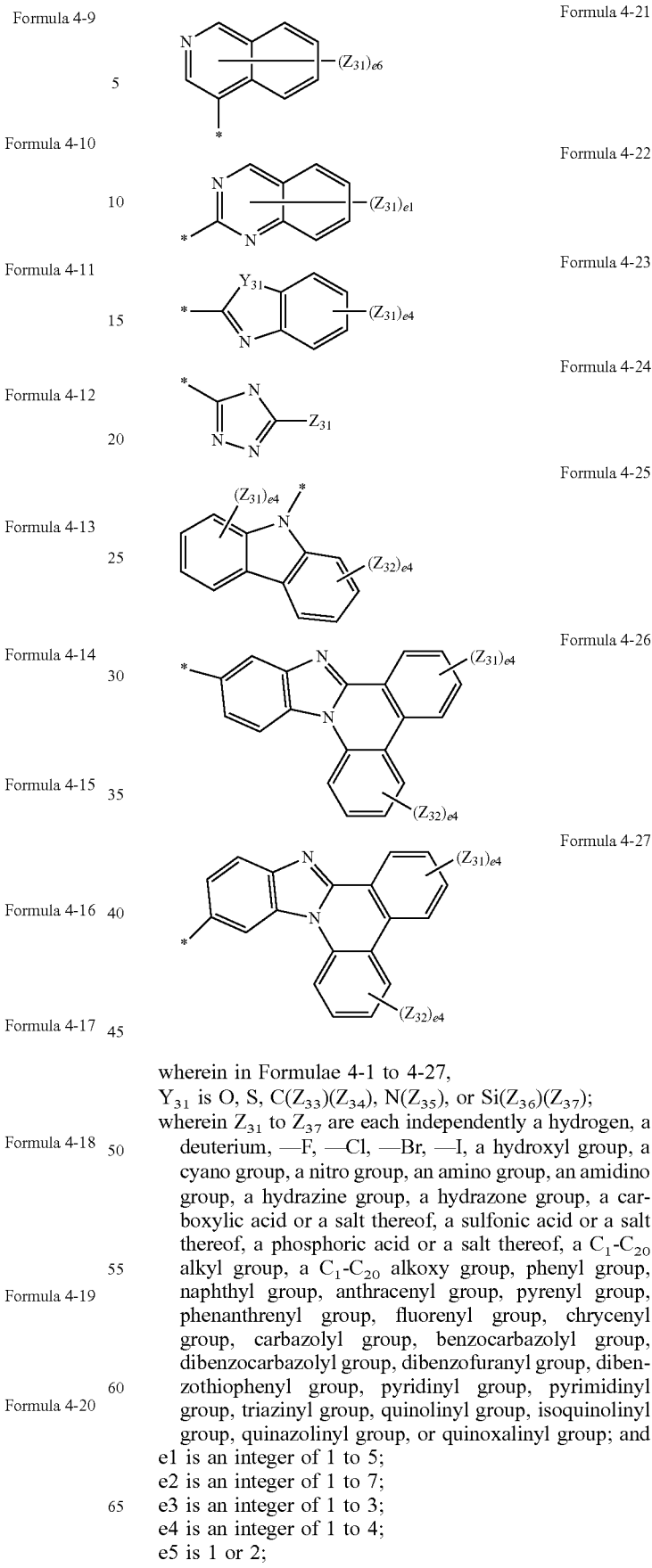

wherein in Formulae 4-1 to 4-27,
Y$_{31}$ is O, S, C(Z$_{33}$)(Z$_{34}$), N(Z$_{35}$), or Si(Z$_{36}$)(Z$_{37}$);
wherein Z$_{31}$ to Z$_{37}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, phenyl group, naphthyl group, anthracenyl group, pyrenyl group, phenanthrenyl group, fluorenyl group, chrycenyl group, carbazolyl group, benzocarbazolyl group, dibenzocarbazolyl group, dibenzofuranyl group, dibenzothiophenyl group, pyridinyl group, pyrimidinyl group, triazinyl group, quinolinyl group, isoquinolinyl group, quinazolinyl group, or quinoxalinyl group; and
e1 is an integer of 1 to 5;
e2 is an integer of 1 to 7;
e3 is an integer of 1 to 3;
e4 is an integer of 1 to 4;
e5 is 1 or 2;

e6 is an integer of 1 to 6; and

\* indicates a binding site to a neighboring atom.

14. The condensed cyclic compound of claim 1, wherein $R_1$, $R_4$, and $R_7$ are each independently represented by one of Formulae 5-1 to 5-51 below;

$R_2$, $R_3$, $R_5$, $R_6$, $R_8$, $R_9$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, phenyl group, naphthyl group, anthracenyl group, pyrenyl group, phenanthrenyl group, pyridinyl group, pyrimidinyl group, triazinyl group, quinolinyl group, isoquinolinyl group, and quinazolinyl; or one of Formulae 5-1 to 5-51:

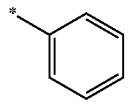

Formula 5-1

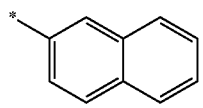

Formula 5-2

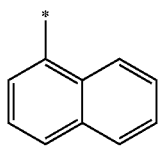

Formula 5-3

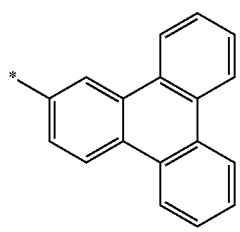

Formula 5-4

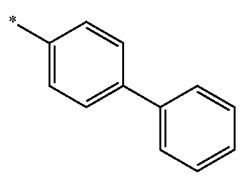

Formula 5-5

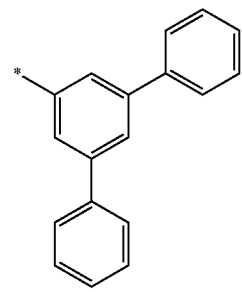

Formula 5-6

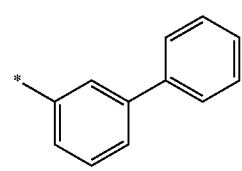

Formula 5-7

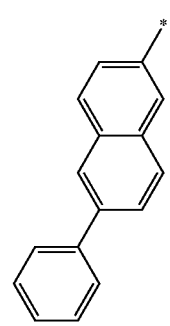

Formula 5-8

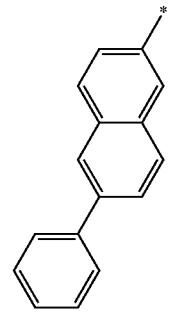

Formula 5-9

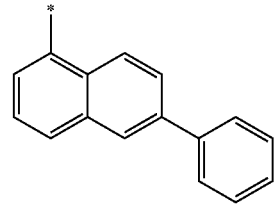

Formula 5-10

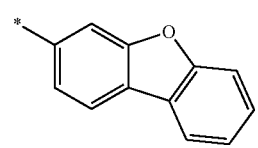

Formula 5-11

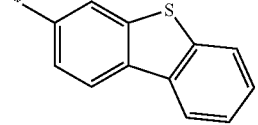

Formula 5-12

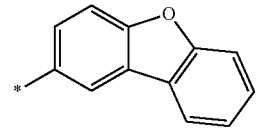

Formula 5-13

Formula 5-14
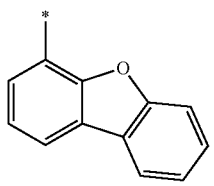
Formula 5-15
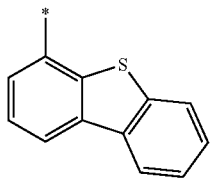
Formula 5-16
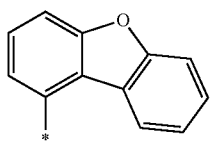
Formula 5-17
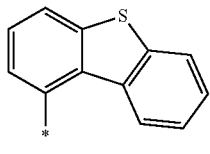
Formula 5-18
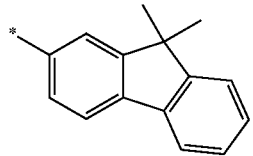
Formula 5-19
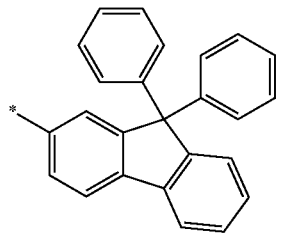
Formula 5-20
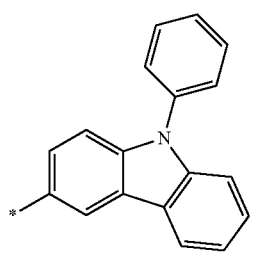
Formula 5-21
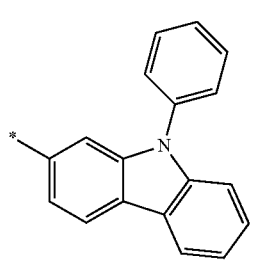
Formula 5-22
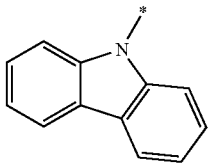
Formula 5-23
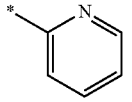
Formula 5-24
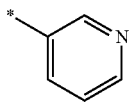
Formula 5-25
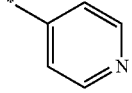
Formula 5-26
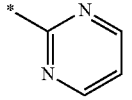
Formula 5-27
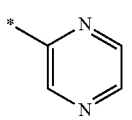
Formula 5-28
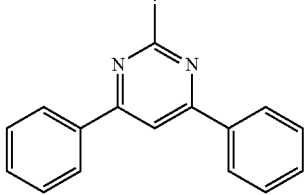
Formula 5-29
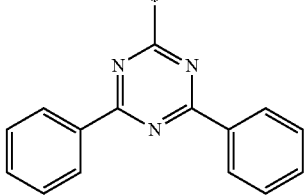
Formula 5-30
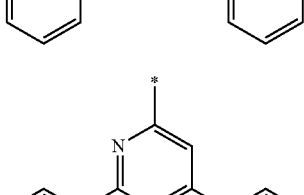
Formula 5-31
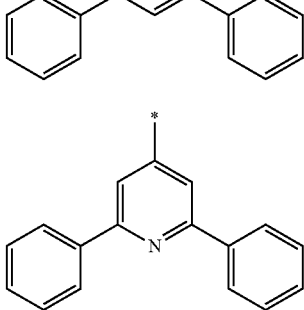

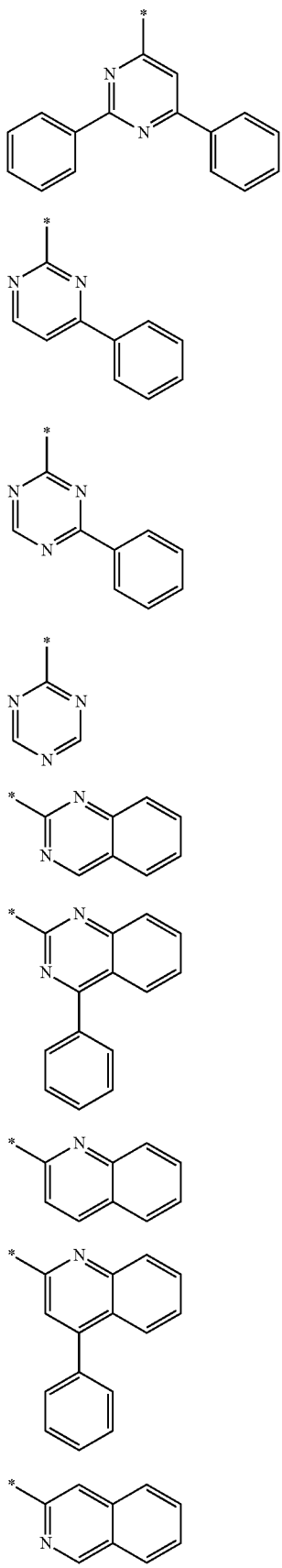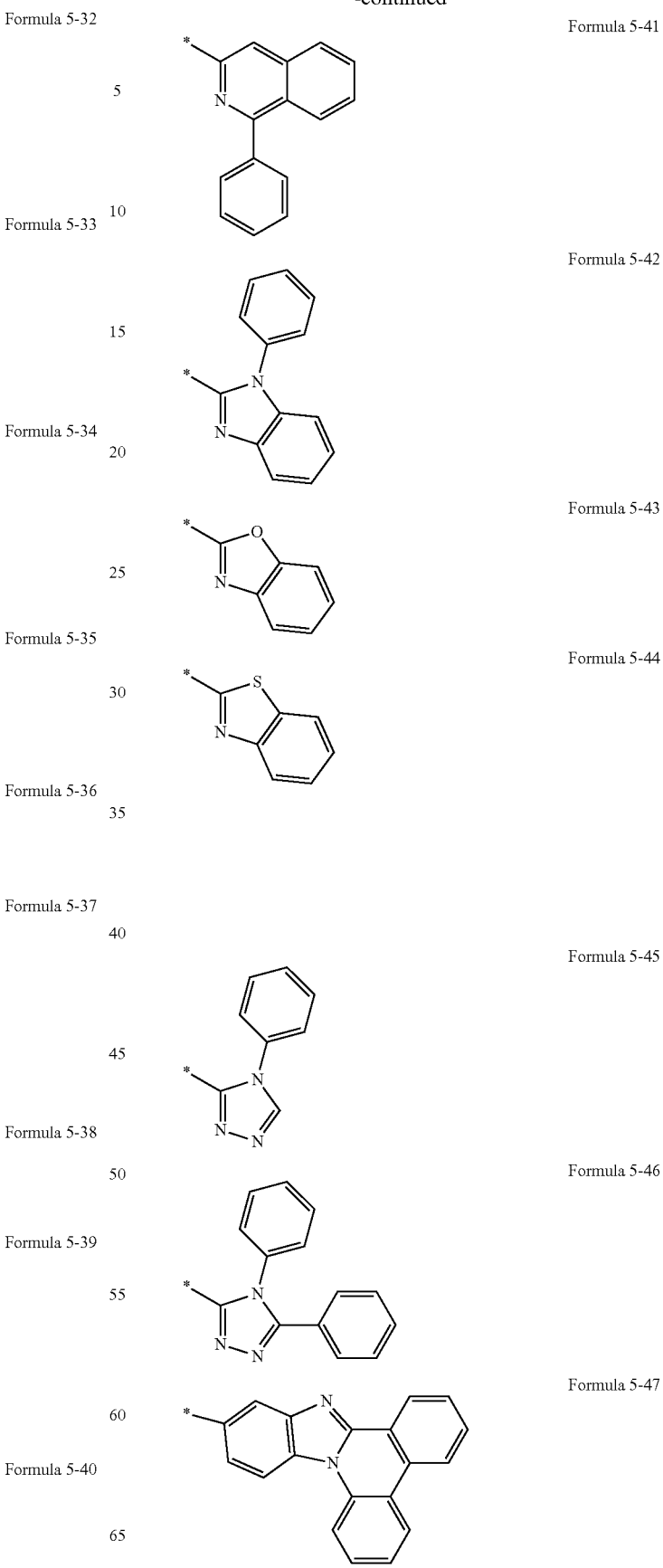
Formula 5-32
Formula 5-33
Formula 5-34
Formula 5-35
Formula 5-36
Formula 5-37
Formula 5-38
Formula 5-39
Formula 5-40
Formula 5-41
Formula 5-42
Formula 5-43
Formula 5-44
Formula 5-45
Formula 5-46
Formula 5-47

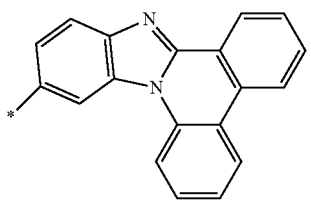
Formula 5-48

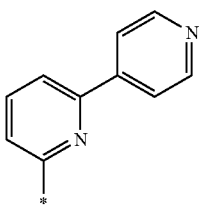
Formula 5-49

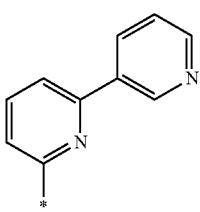
Formula 5-50

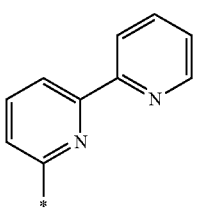
Formula 5-51 wherein in Formulae 5-1 to 5-51,

* indicates a binding site to a neighboring atom.

15. The condensed cyclic compound of claim 1, wherein the condensed cyclic compound represented by Formula 1A:

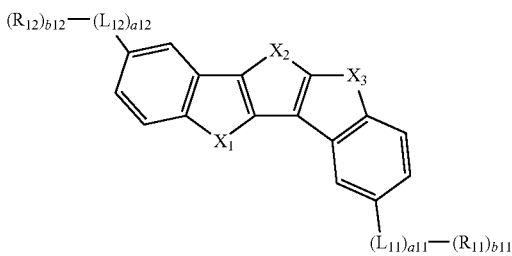
Formula 1A wherein in Formula 1A, substituents $X_1$ to $X_3$, $L_{11}$, $L_{12}$, $R_{11}$, $R_{12}$, a11, a12, b11, and b12 are the same as in claim 1.

16. The condensed cyclic compound of claim 1, wherein the condensed cyclic compound is represented by Formulae 1-1A, 1-2A, 1-3A, or 1A':

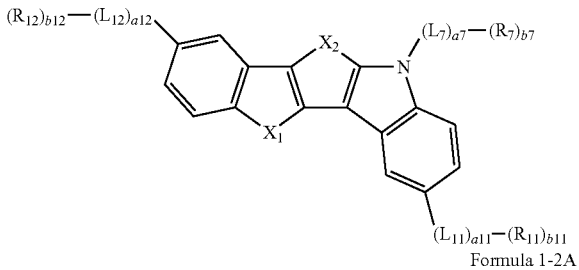
Formula 1-1A

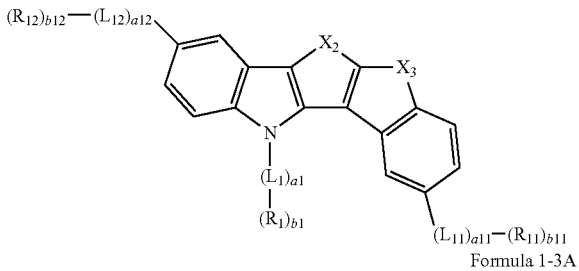
Formula 1-2A

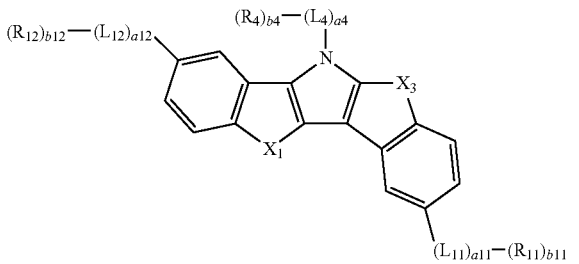
Formula 1-3A

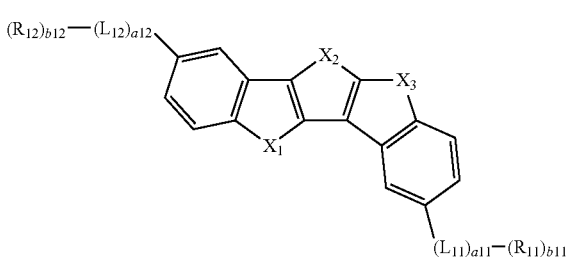
Formula 1A' wherein
in Formulae 1-1A, 1-2A, 1-3A, and 1A', $X_1$ is selected from $C[(L_2)_{a2}-(R_2)_{b2}][(L_3)_{a3}-(R_3)_{b3}]$, $Si[(L_2)_{a2}-(R_2)_{b2}][(L_3)_{a3}-(R_3)_{b3}]$, S, and O, $X_2$ is selected from $C[(L_5)_{a5}-(R_5)_{b5}][(L_6)_{a6}-(R_6)_{b6}]$, $Si[(L_5)_{a5}-(R_5)_{b5}][(L_6)_{a6}-(R_6)_{b6}]$, S, and O; $X_3$ is selected from $C[(L_8)_{a8}-(R_8)_{b8}][(L_9)_{a9}-(R_9)_{b9}]$, $Si[(L_8)_{a8}-(R_8)_{b8}][(L_9)_{a9}-(R_9)_{b9}]$, S, and O, at least one of $R_7$, $R_{11}$, and $R_{12}$ in Formula 1-1A, at least one of $R_1$, $R_{11}$, and $R_{12}$ in Formula 1-2A, at least one of $R_4$, $R_{11}$, and $R_{12}$ in Formula 1-3A, and at least one of $R_{11}$ and $R_{12}$ in Formula 1A' are each independently a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group; or
a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group.

17. The condensed cyclic compound of claim 16, wherein at least one of $R_7$, $R_{11}$, and $R_{12}$ in Formula 1-1A, at least one of $R_1$, $R_{11}$, and $R_{12}$ in Formula 1-2A, at least one of $R_4$, $R_{11}$, and $R_{12}$ in Formula 1-3A, and at least one of $R_{11}$ and $R_{12}$ in Formula 1A' are each independently a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a group represented by

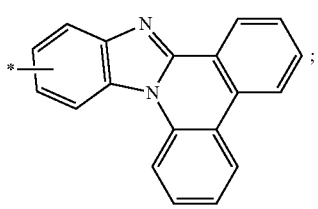

or a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or a group represented by

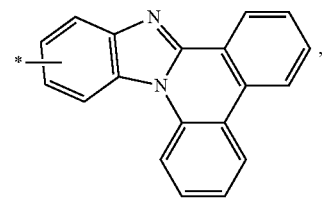

each substituted with at least one group selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a naphthyl group.

18. The condensed cyclic compound of claim 16, wherein in Formulae 1-1A, 1-2A, 1-3A, and 1A',
$L_1$ to $L_9$, $L_{11}$, and $L_{12}$ are each independently represented by one of Formulae 3-1 to 3-59;
a1 to a9, a11, and a12 are each independently 0 or 1;
$R_1$, $R_4$, $R_7$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a group represented by one of Formula 5-1 to 5-51; and
b1 to b9, b11, and b12 are 1:

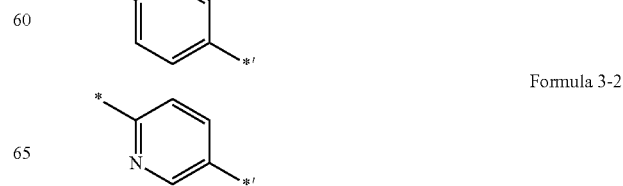

-continued
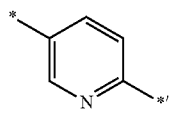
Formula 3-3
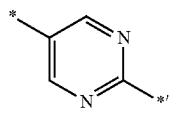
Formula 3-4
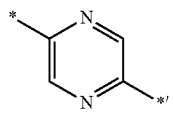
Formula 3-5
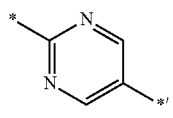
Formula 3-6
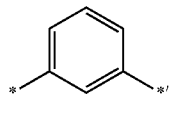
Formula 3-7
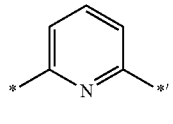
Formula 3-8
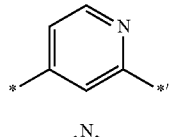
Formula 3-9
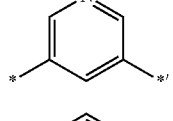
Formula 3-10
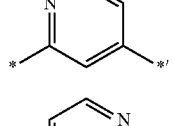
Formula 3-11
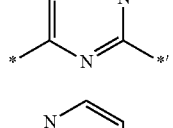
Formula 3-12
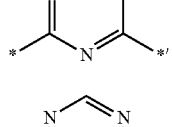
Formula 3-13
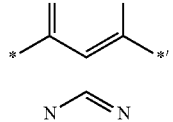
Formula 3-14
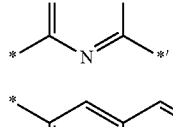
Formula 3-15
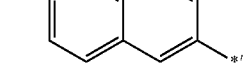
Formula 3-16
-continued
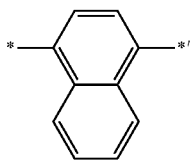
Formula 3-17
Formula 3-18
Formula 3-19
Formula 3-20
Formula 3-21
Formula 3-22
Formula 3-23
Formula 3-24

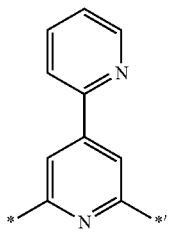
Formula 3-25
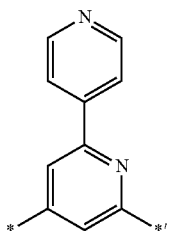
Formula 3-31
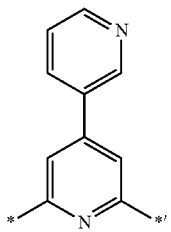
Formula 3-26
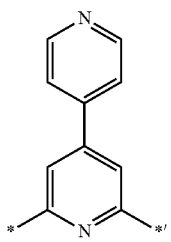
Formula 3-27
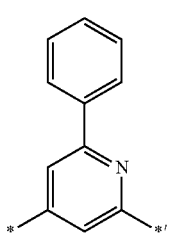
Formula 3-32
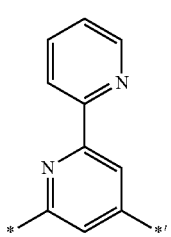
Formula 3-33
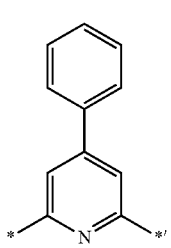
Formula 3-28
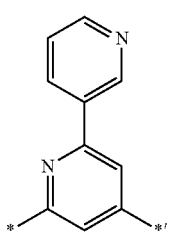
Formula 3-34
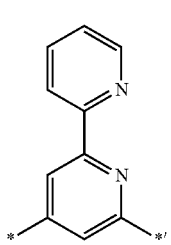
Formula 3-29
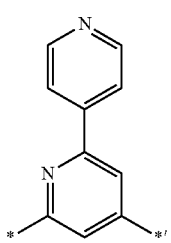
Formula 3-35
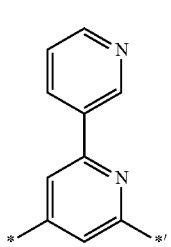
Formula 3-30
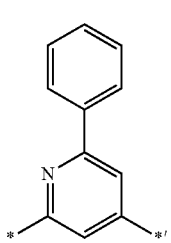
Formula 3-36

-continued
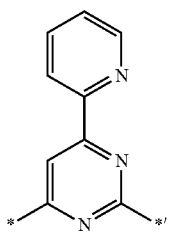
Formula 3-37
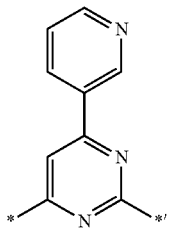
Formula 3-38
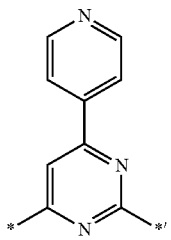
Formula 3-39
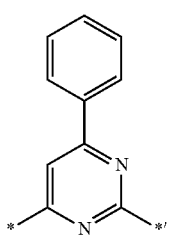
Formula 3-40
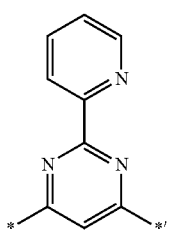
Formula 3-41
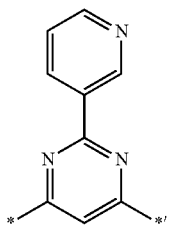
Formula 3-42
-continued
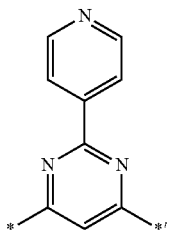
Formula 3-43
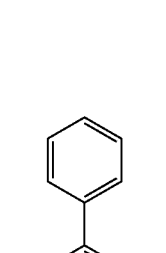
Formula 3-44
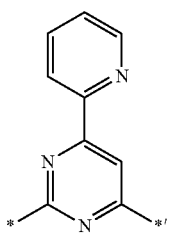
Formula 3-45
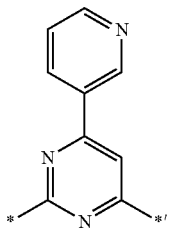
Formula 3-46
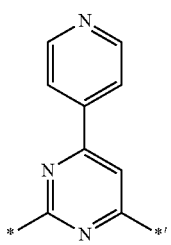
Formula 3-47
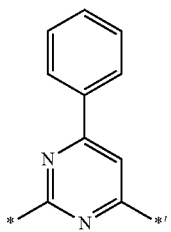
Formula 3-48

-continued
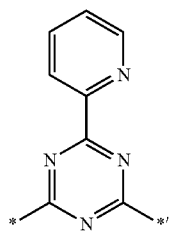
Formula 3-49
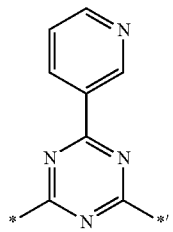
Formula 3-50
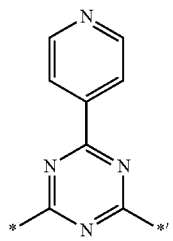
Formula 3-51
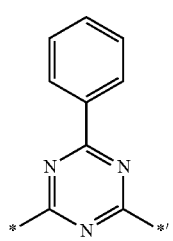
Formula 3-52
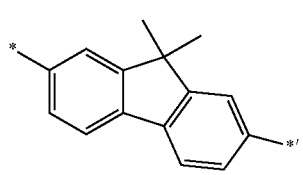
Formula 3-53
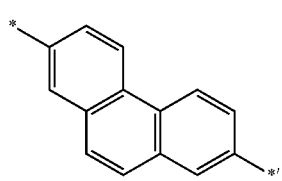
Formula 3-54
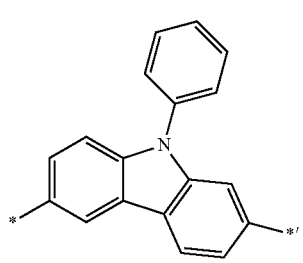
Formula 3-55
-continued
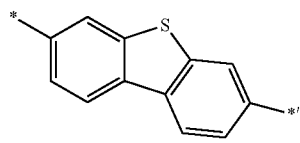
Formula 3-56
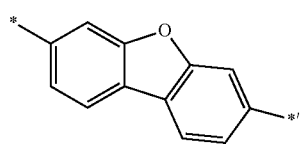
Formula 3-57
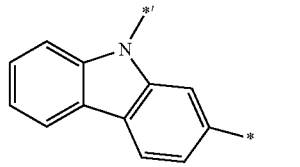
Formula 3-58
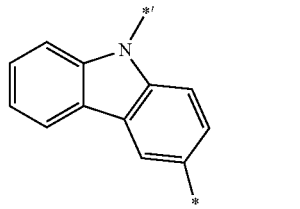
Formula 3-59
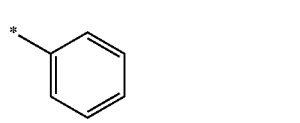
Formula 5-1
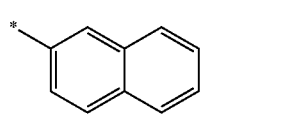
Formula 5-2
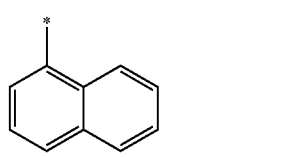
Formula 5-3
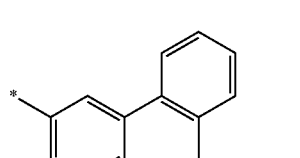
Formula 5-4
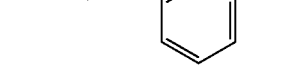
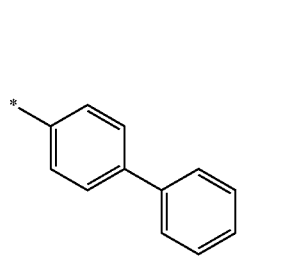
Formula 5-5

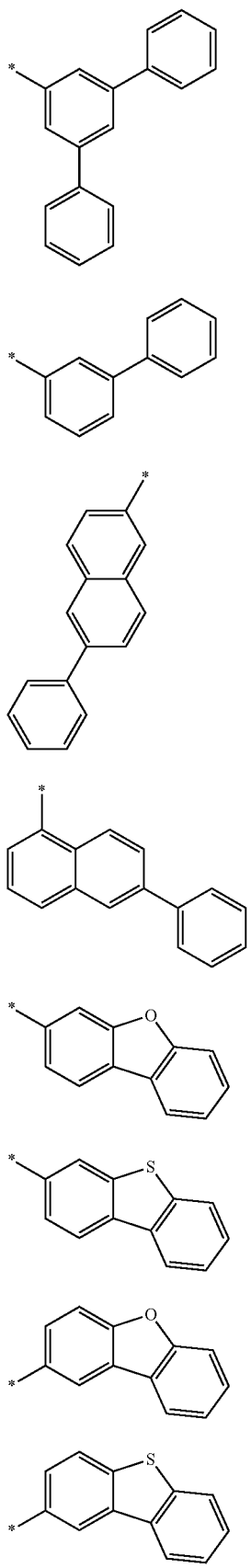
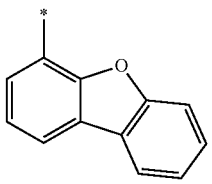
Formula 5-6
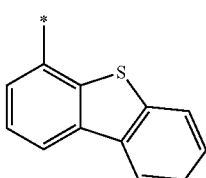
Formula 5-7
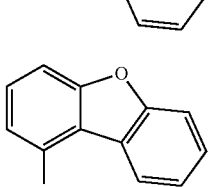
Formula 5-8
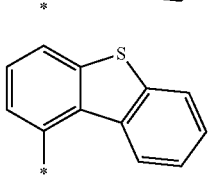
Formula 5-9
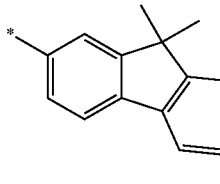
Formula 5-10
Formula 5-11
Formula 5-12
Formula 5-13
Formula 5-14
Formula 5-15
Formula 5-16
Formula 5-17
Formula 5-18
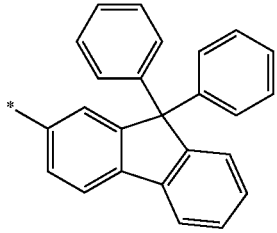
Formula 5-19
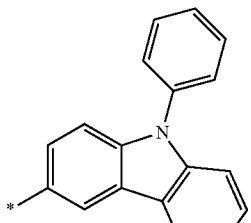
Formula 5-20
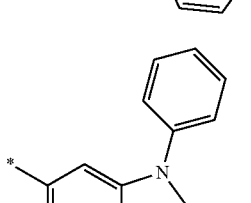
Formula 5-21

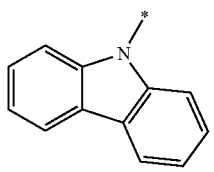
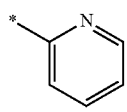
Formula 5-22
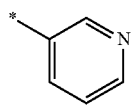
Formula 5-23
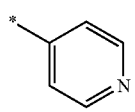
Formula 5-24
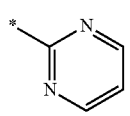
Formula 5-25
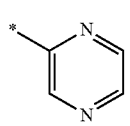
Formula 5-26
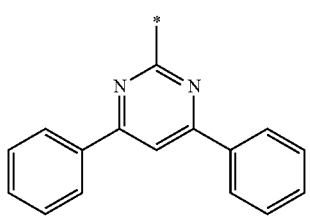
Formula 5-27
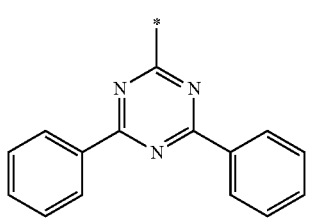
Formula 5-28
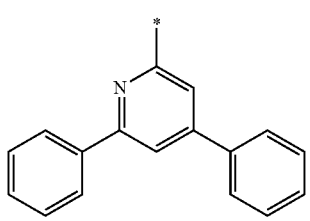
Formula 5-29
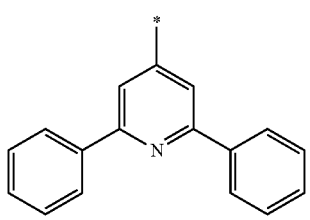
Formula 5-30
Formula 5-31
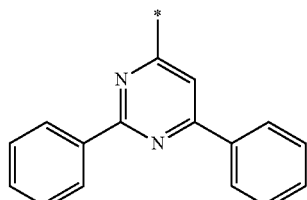
Formula 5-32
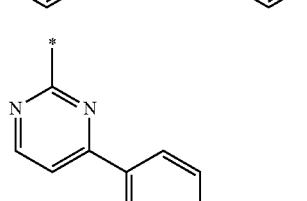
Formula 5-33
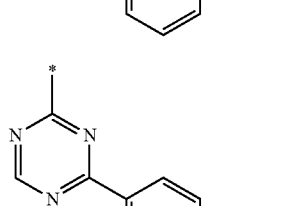
Formula 5-34
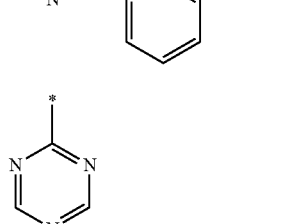
Formula 5-35
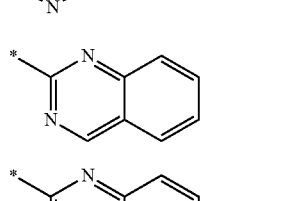
Formula 5-36
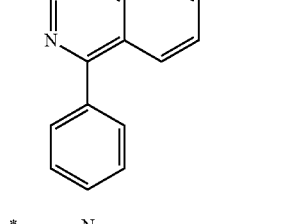
Formula 5-37
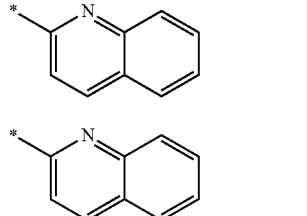
Formula 5-38
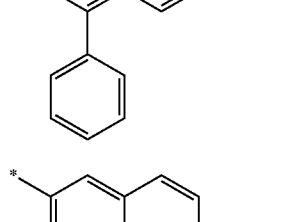
Formula 5-39
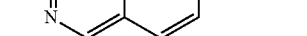
Formula 5-40

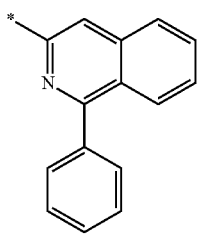
Formula 5-41

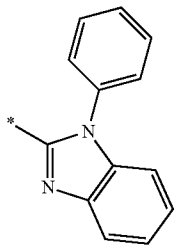
Formula 5-42

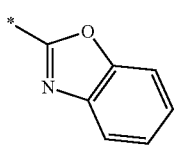
Formula 5-43

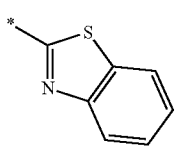
Formula 5-44

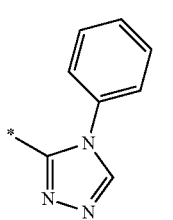
Formula 5-45

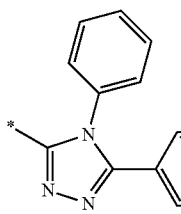
Formula 5-46

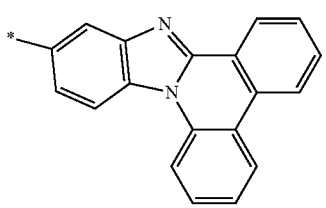
Formula 5-47

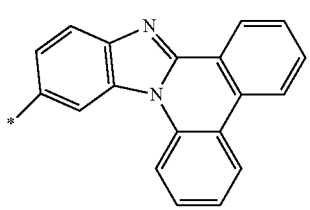
Formula 5-48

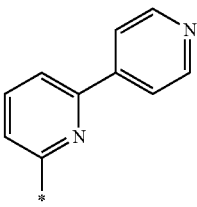
Formula 5-49

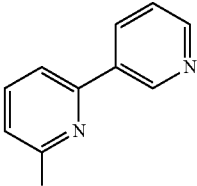
Formula 5-50

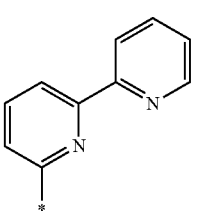
Formula 5-51 wherein in Formulae 3-1 to 3-59 and 5-1 to 5-51,
* and *' each indicates a binding site to a neighboring atom.

19. The condensed cyclic compound of claim 6, wherein in Formulae 1(81), 1(70), 1(15), 1(92), and 1(106),
$L_1$, $L_4$, $L_7$ to $L_9$, $L_{11}$, and $L_{12}$ are each independently represented by one of Formulae 3-1 to 3-59;
a1, a4, a7 to a9, a11, and a12 are each independently 0 or 1;
$R_1$, $R_4$, $R_7$, $R_{11}$, and $R_{12}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a group represented by one of Formula 5-1 to 5-51; and
b1 to b9, b11, and b12 are 1:

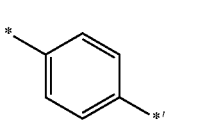
Formula 3-1

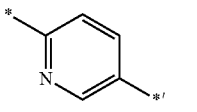
Formula 3-2

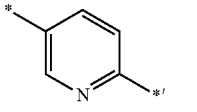
Formula 3-3

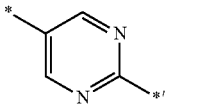
Formula 3-4

-continued
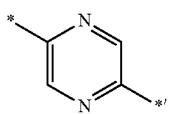
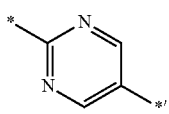
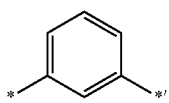
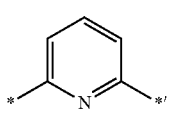
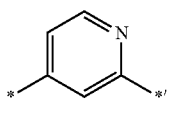
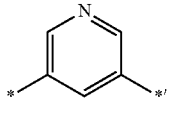
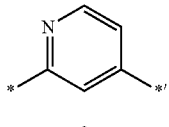
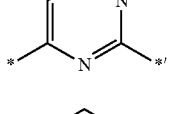
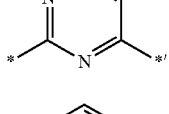
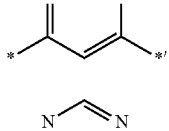
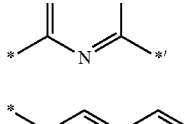
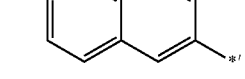
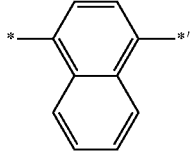
-continued
Formula 3-5
Formula 3-6
Formula 3-7
Formula 3-8
Formula 3-9
Formula 3-10
Formula 3-11
Formula 3-12
Formula 3-13
Formula 3-14
Formula 3-15
Formula 3-16
Formula 3-17
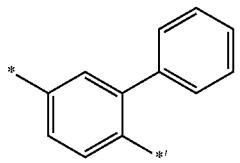
Formula 3-11 3-18
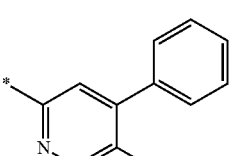
Formula 3-11 3-19
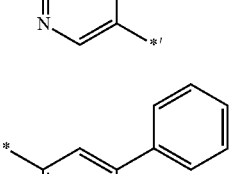
Formula 3-11 3-20
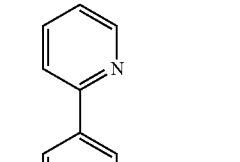
Formula 3-11 3-21
Formula 3-22
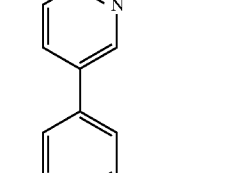
Formula 3-23
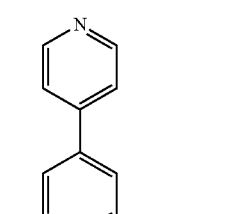
Formula 3-24
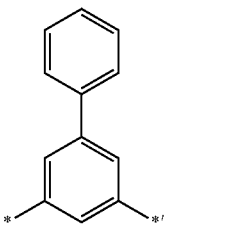

233
-continued
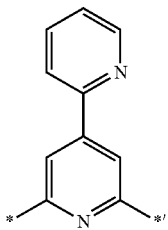
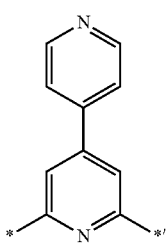
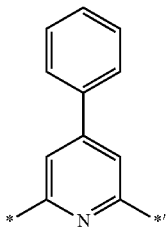
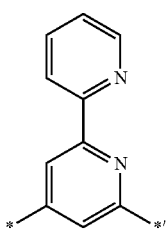
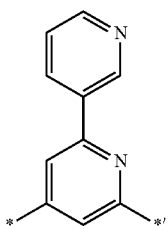
234
-continued
Formula 3-25
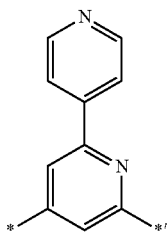
Formula 3-26
Formula 3-27
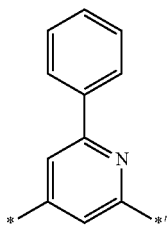
Formula 3-28
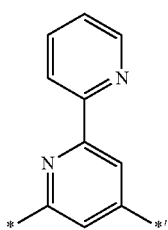
Formula 3-29
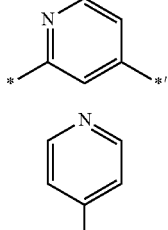
Formula 3-30
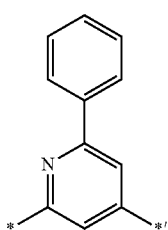
Formula 3-31
Formula 3-32
Formula 3-33
Formula 3-34
Formula 3-35
Formula 3-36
Formula 3-37
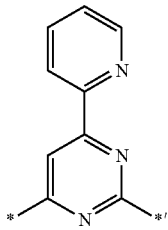

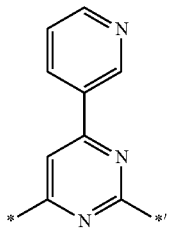
Formula 3-38
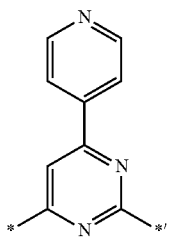
Formula 3-39
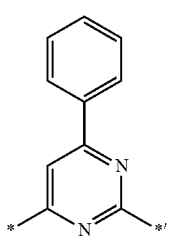
Formula 3-40
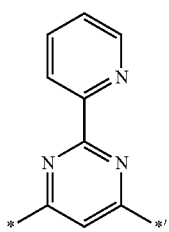
Formula 3-41
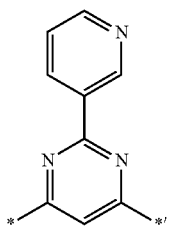
Formula 3-42
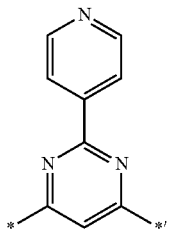
Formula 3-43
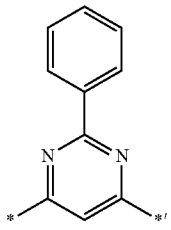
Formula 3-44
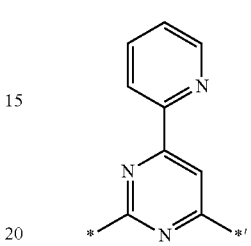
Formula 3-45
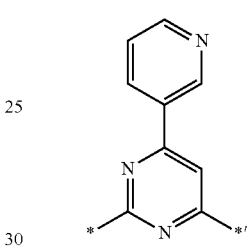
Formula 3-46
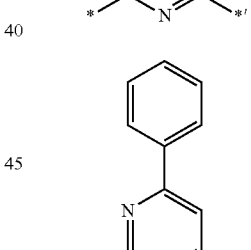
Formula 3-47
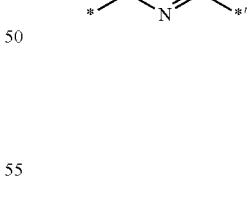
Formula 3-48
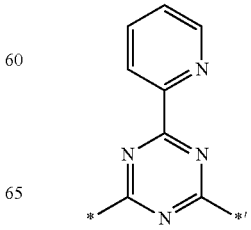
Formula 3-49

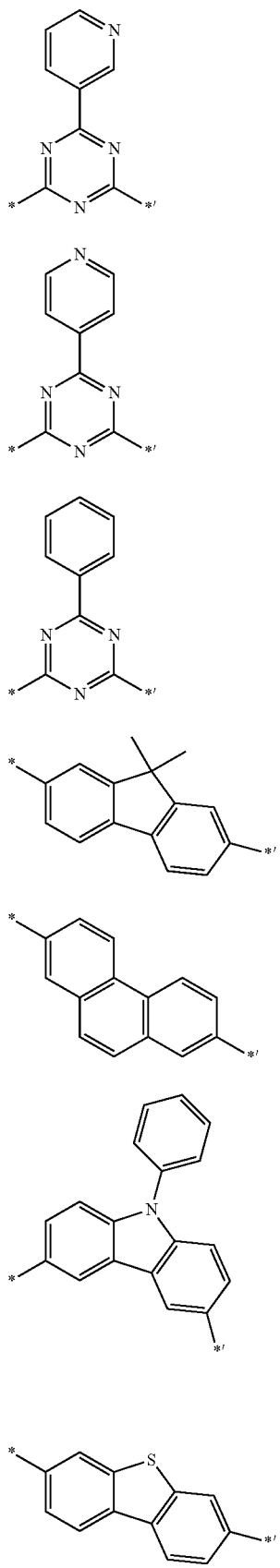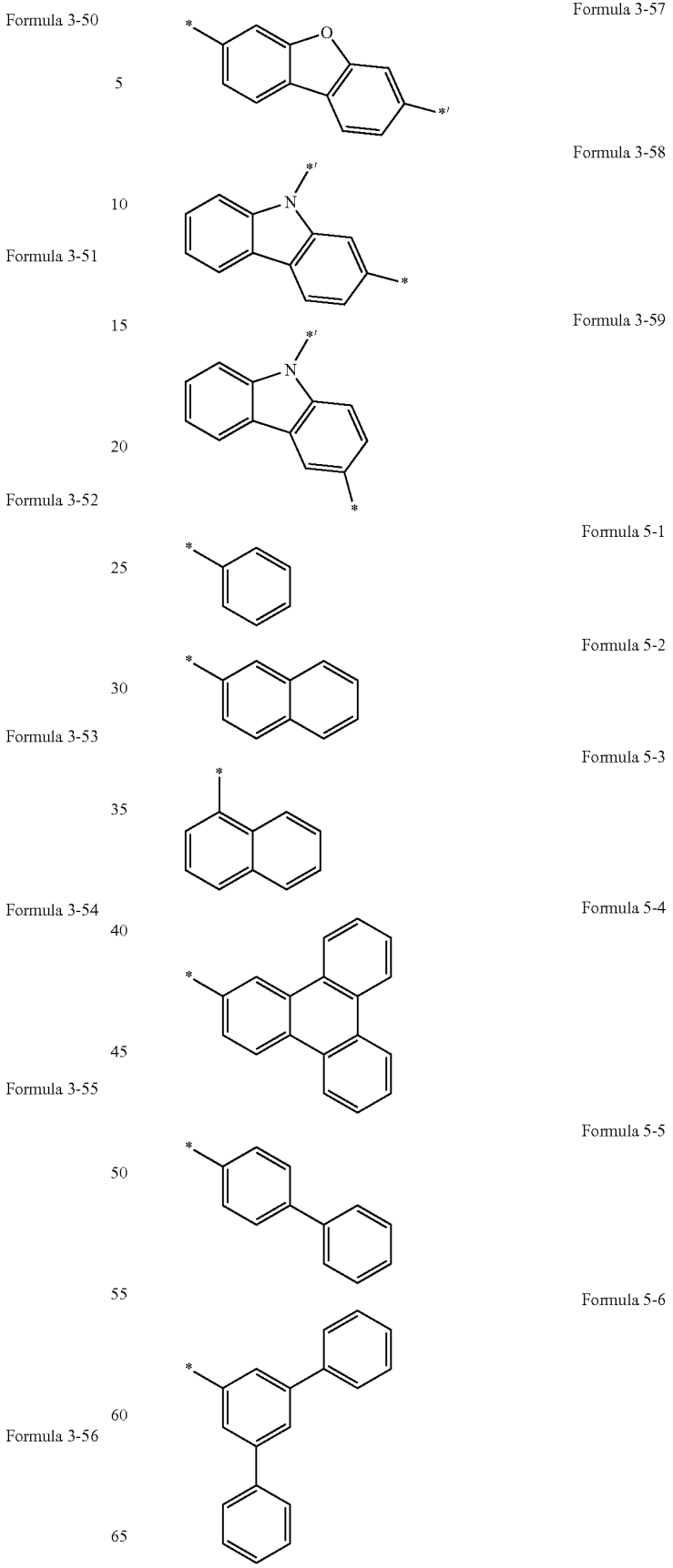

Formula 5-7
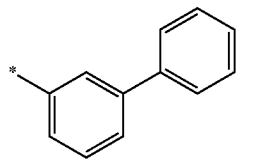
Formula 5-8
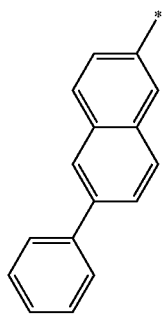
Formula 5-9
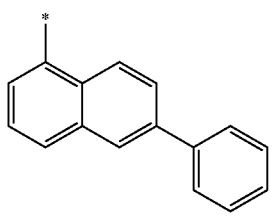
Formula 5-10
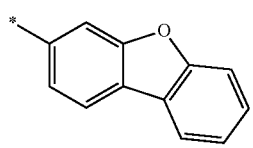
Formula 5-11
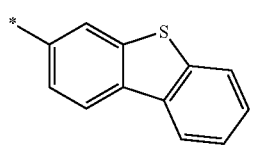
Formula 5-12
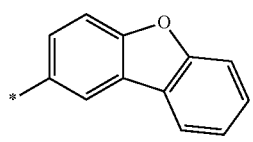
Formula 5-13
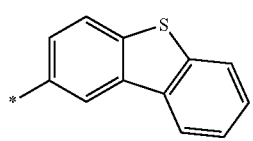
Formula 5-14
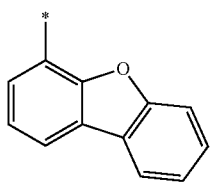
Formula 5-15
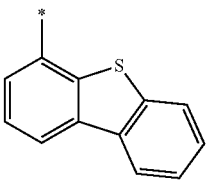
Formula 5-16
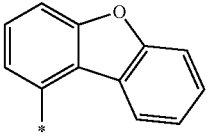
Formula 5-17
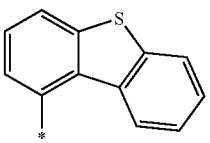
Formula 5-18
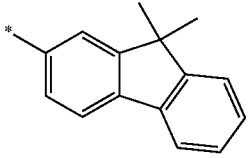
Formula 5-19
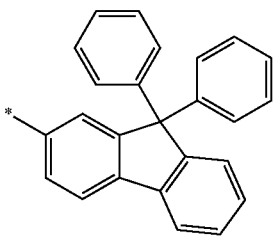
Formula 5-20
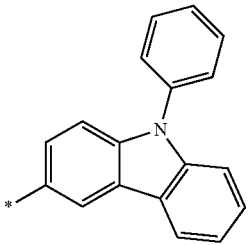
Formula 5-21
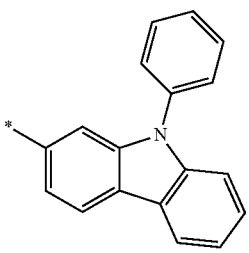
Formula 5-22
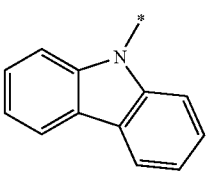

Formula 5-23
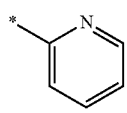
Formula 5-24
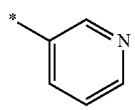
Formula 5-25
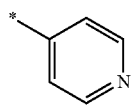
Formula 5-26
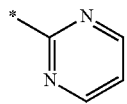
Formula 5-27
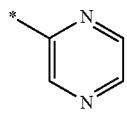
Formula 5-28
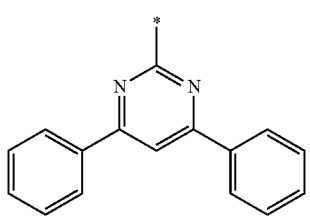
Formula 5-29
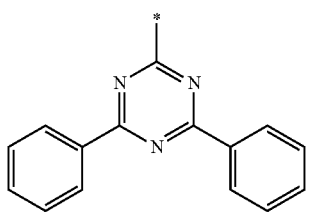
Formula 5-30
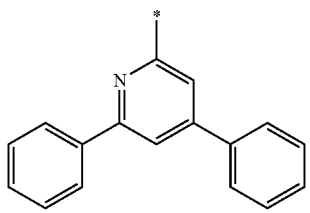
Formula 5-31
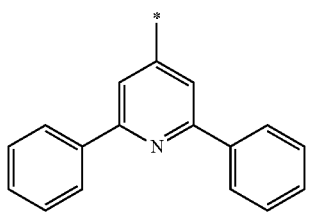
Formula 5-32
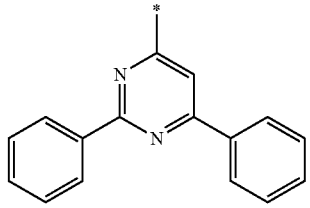
Formula 5-33
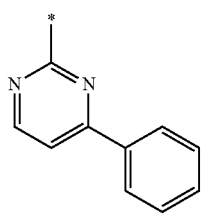
Formula 5-34
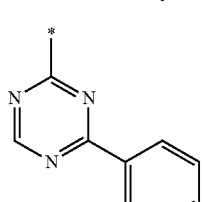
Formula 5-35
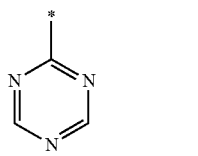
Formula 5-36
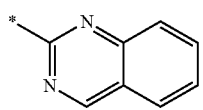
Formula 5-37
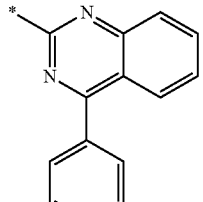
Formula 5-38
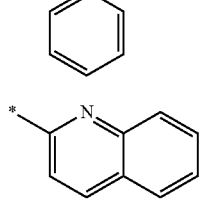
Formula 5-39
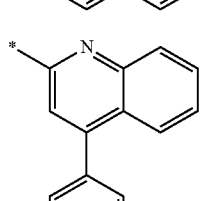
Formula 5-40
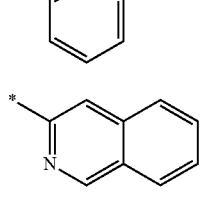

Formula 5-41 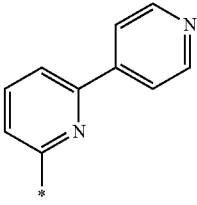
Formula 5-42 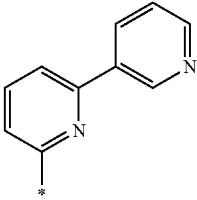
Formula 5-43 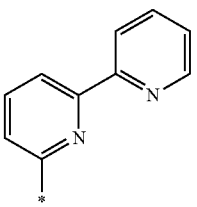
Formula 5-44 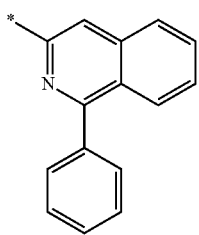
Formula 5-45 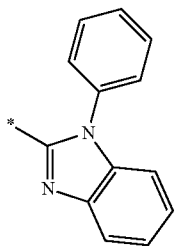
Formula 5-46 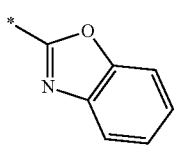
Formula 5-47 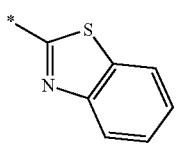
Formula 5-48 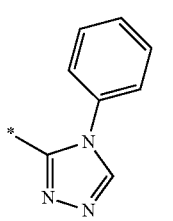
Formula 5-49
Formula 5-50
Formula 5-51
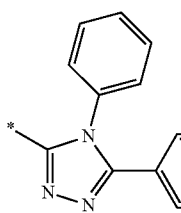
wherein in Formulae 3-1 to 3-59 and 5-1 to 5-51,
* and *¹ each indicates a binding site to a neighboring atom.
20. The condensed cyclic compound of claim 1, wherein the condensed cyclic compound is one of Compounds 1 to 208:
1
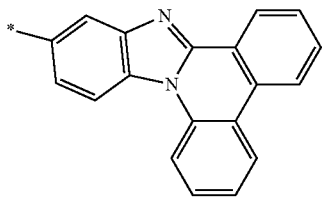
2
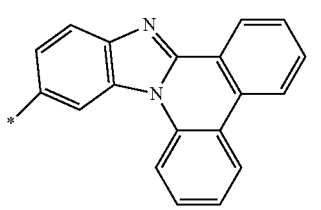

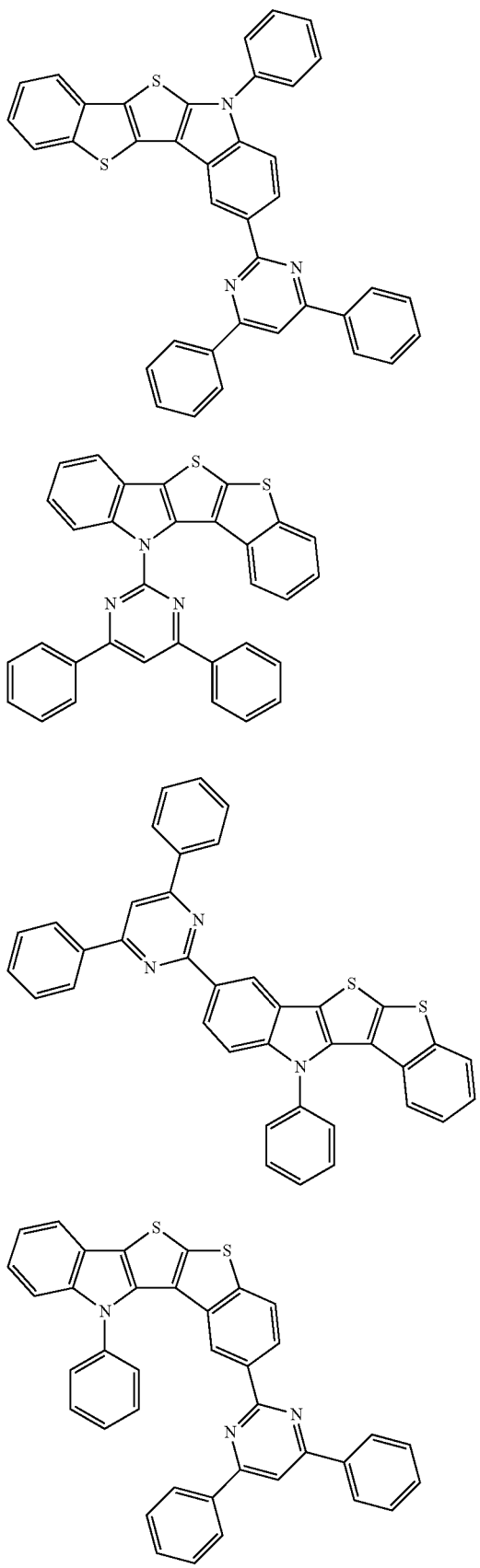
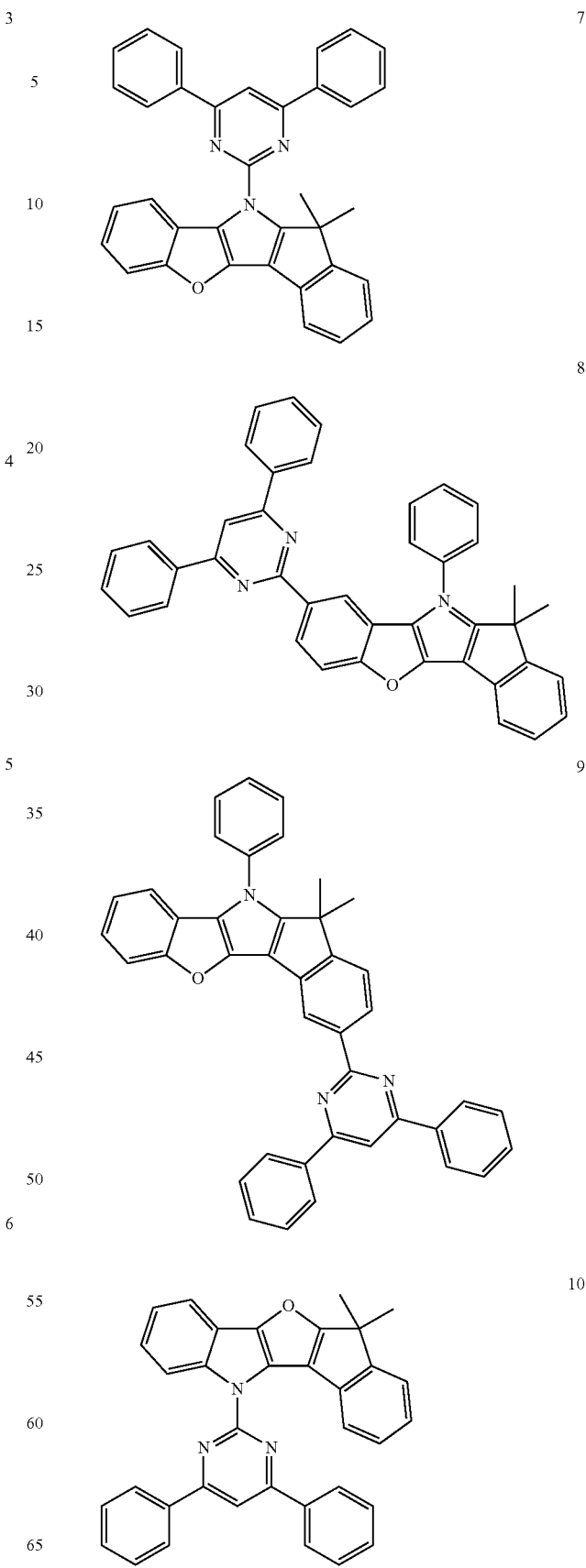

247
-continued
11
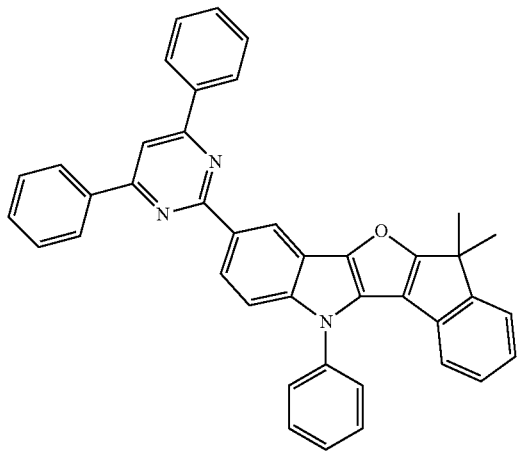
12
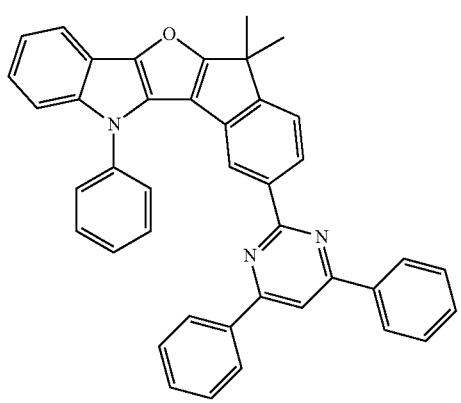
13
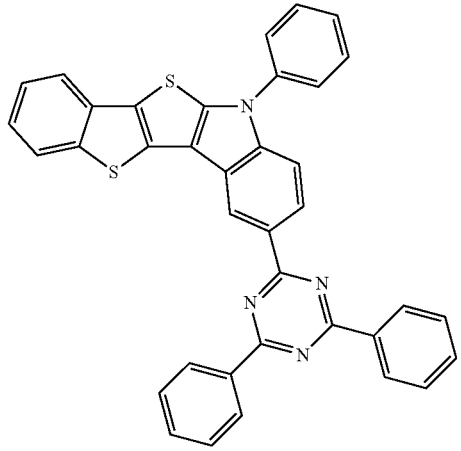
14
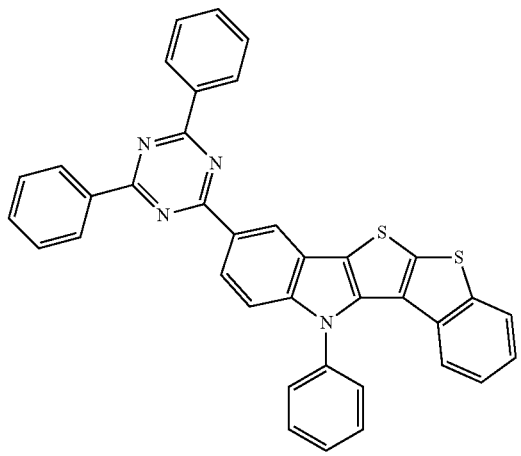
248
-continued
15
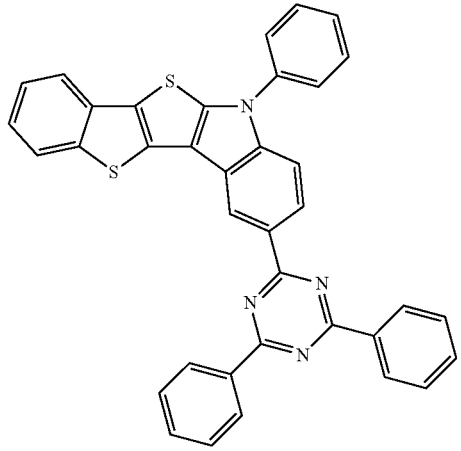
16
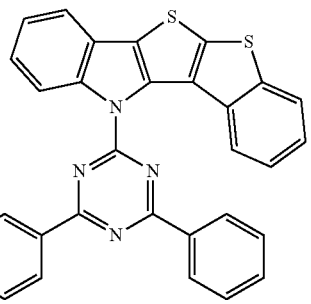
17
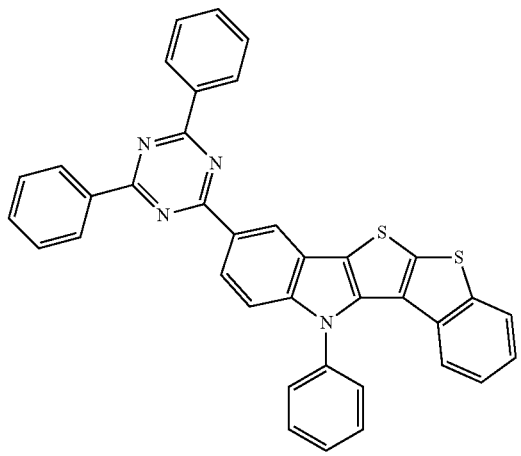
18
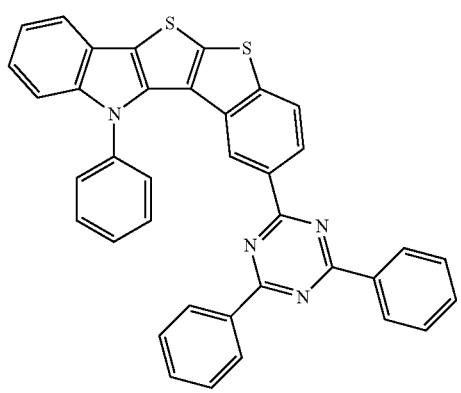

249
-continued
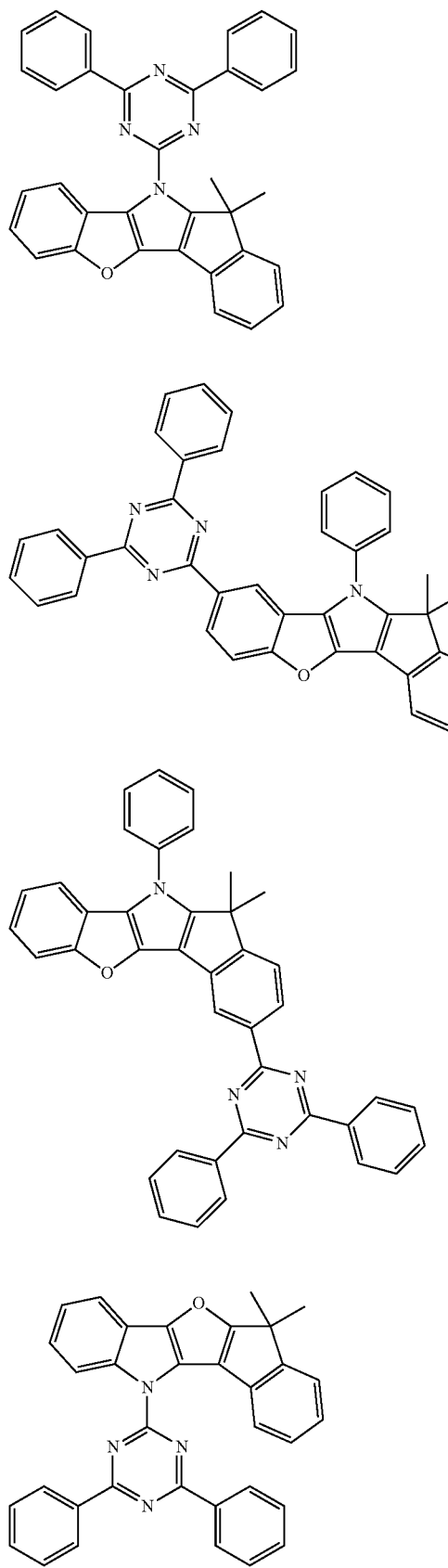
250
-continued
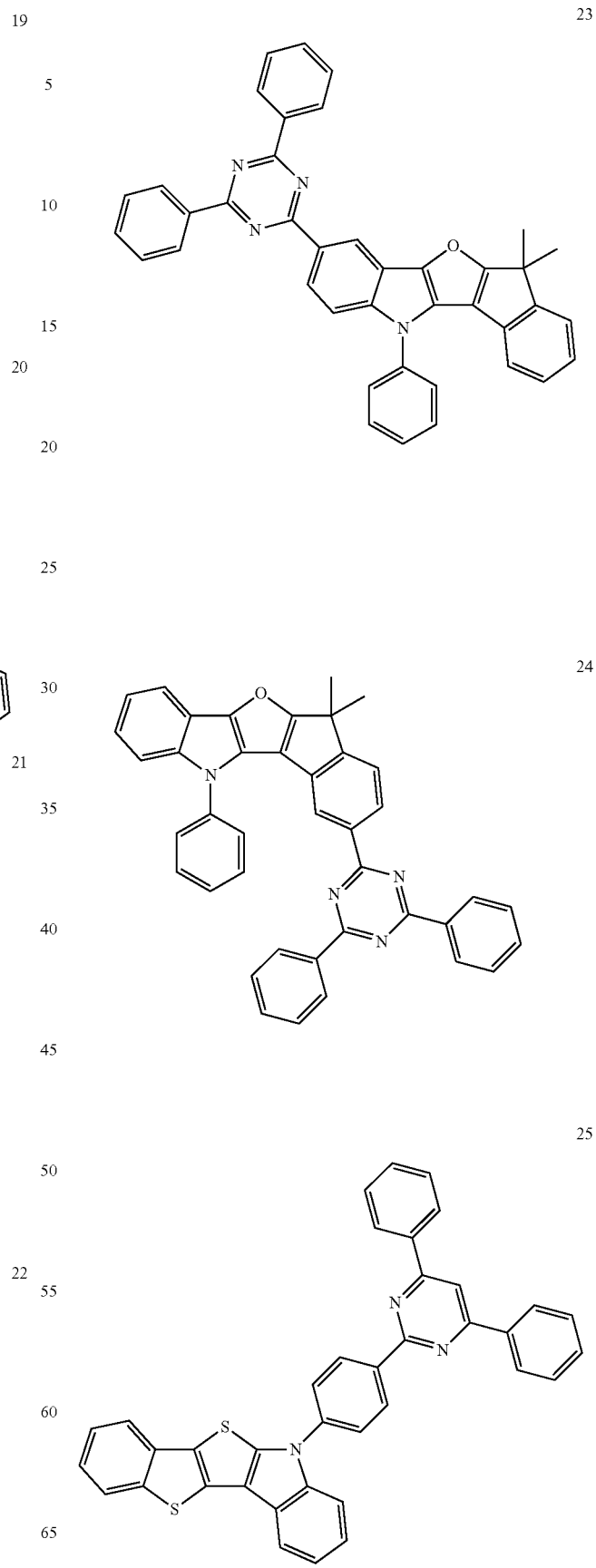

26
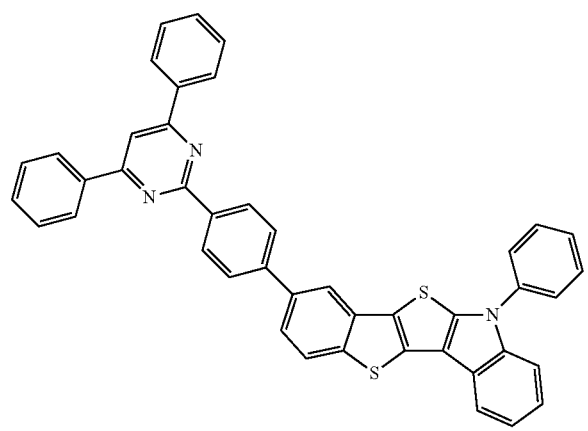
27
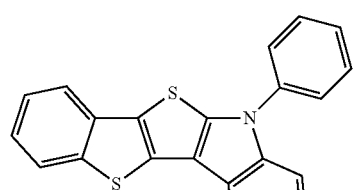
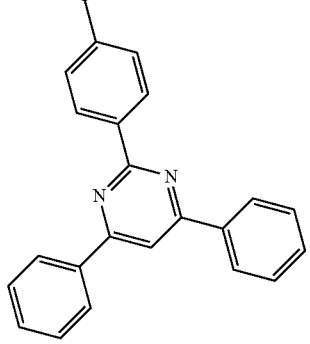
28
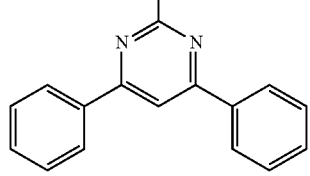
29
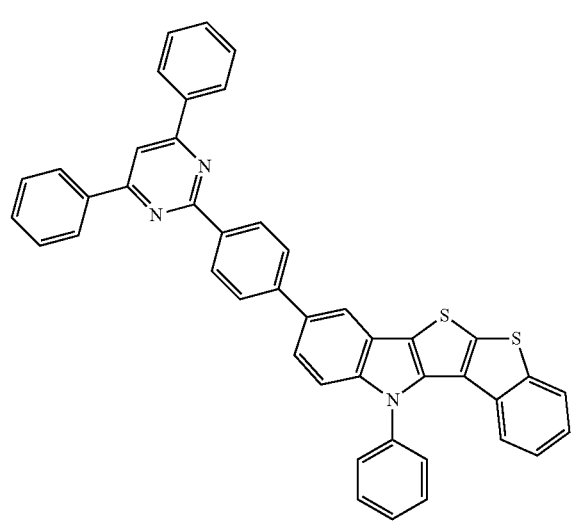
30
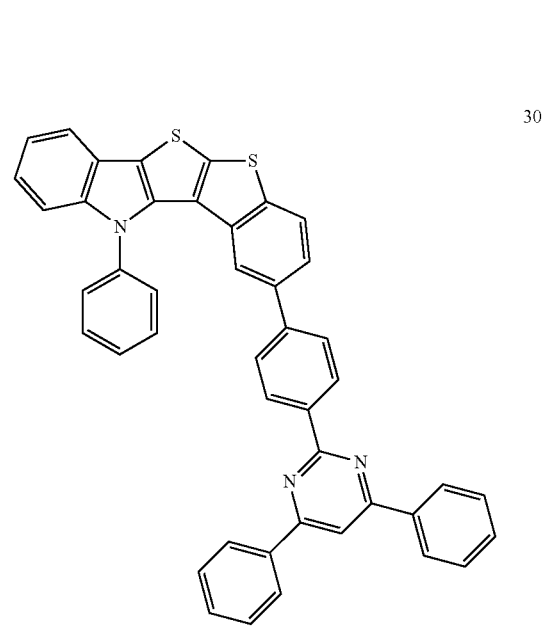
31
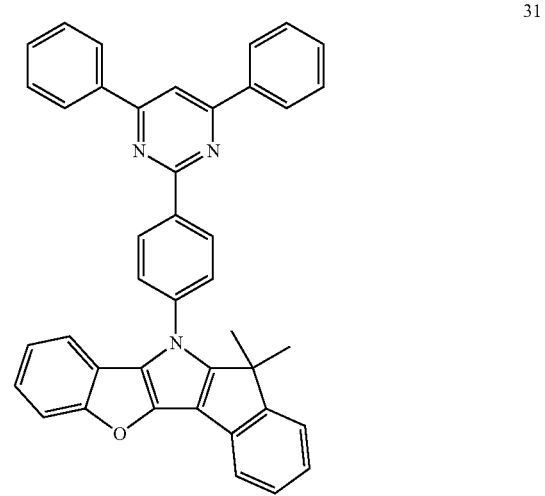

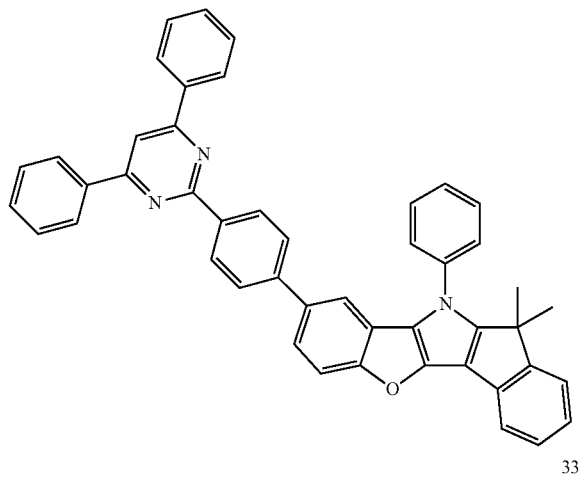
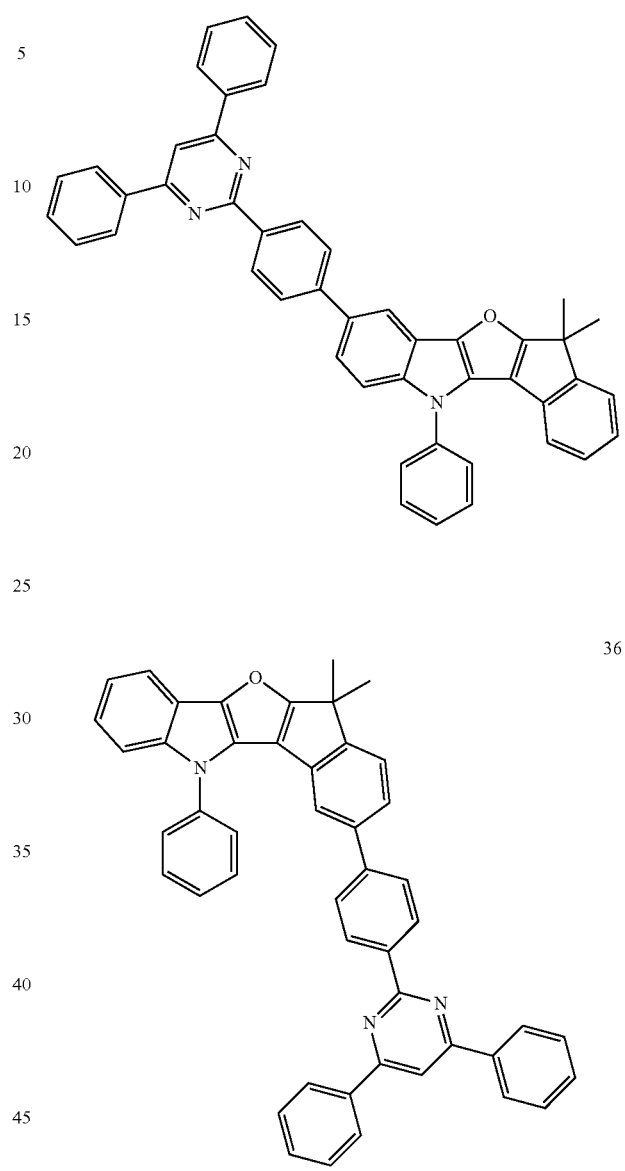
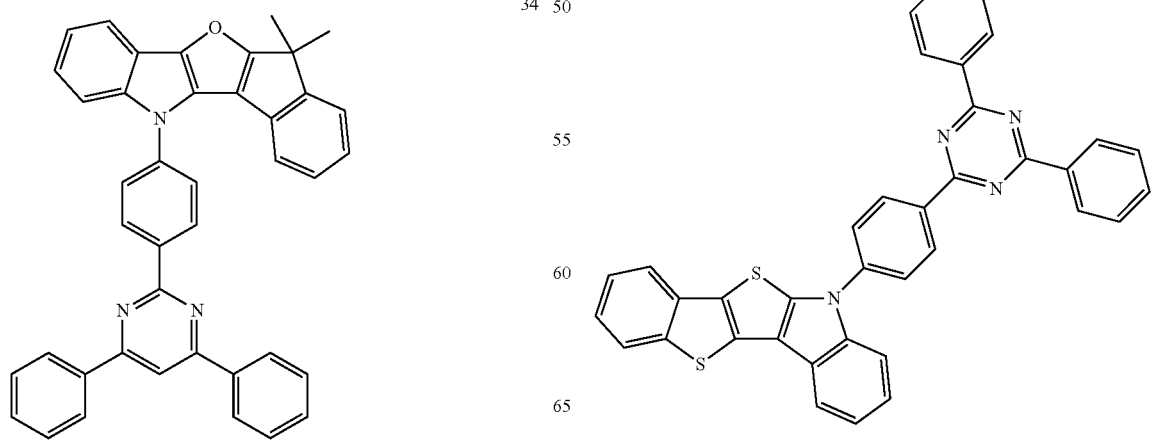

38
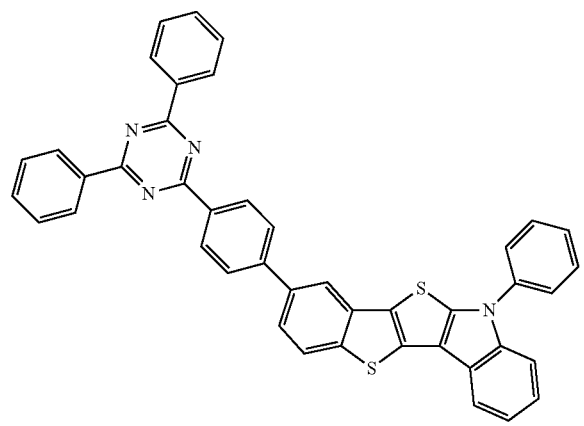
39
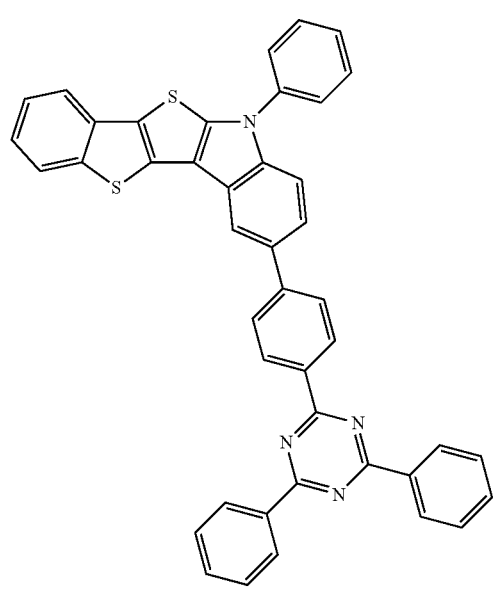
40
41
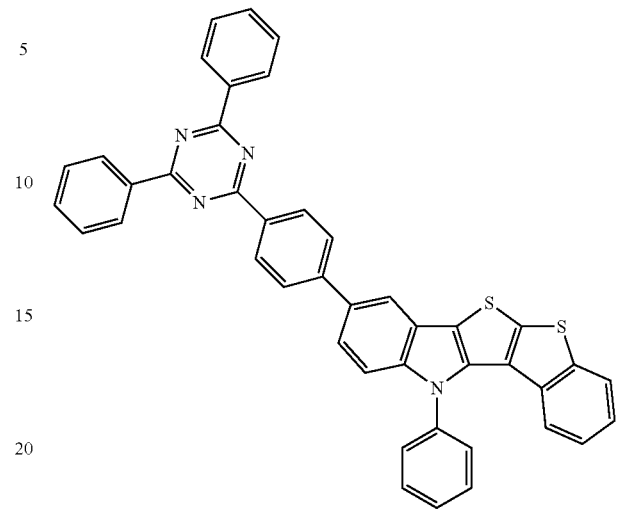
42
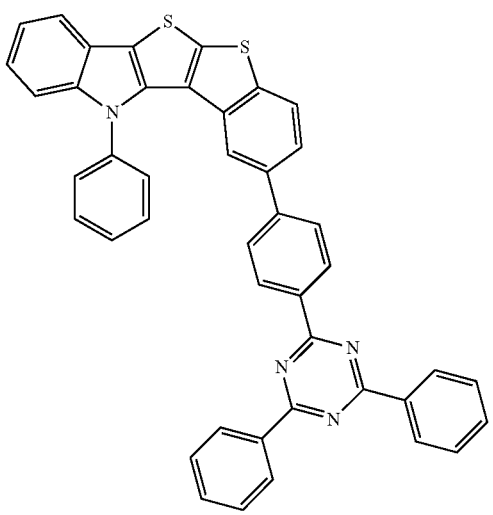
43
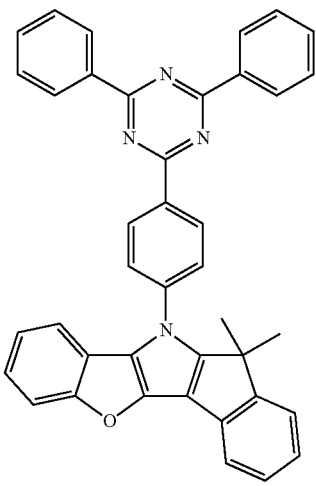

-continued
44
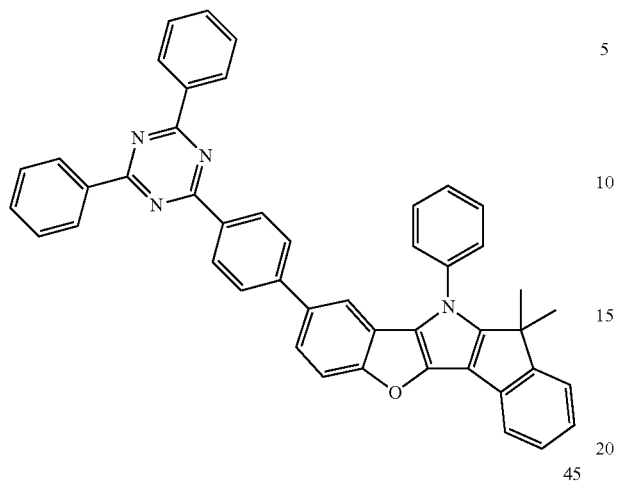
45
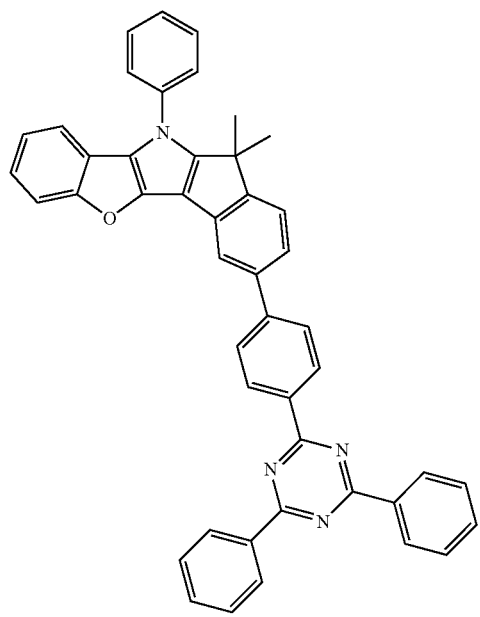
46
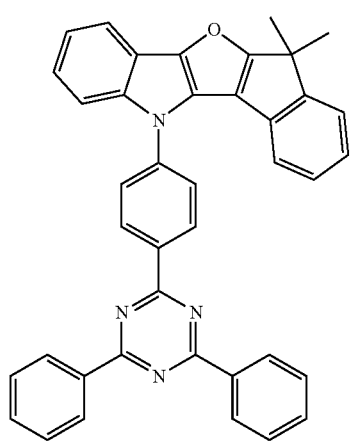
-continued
47
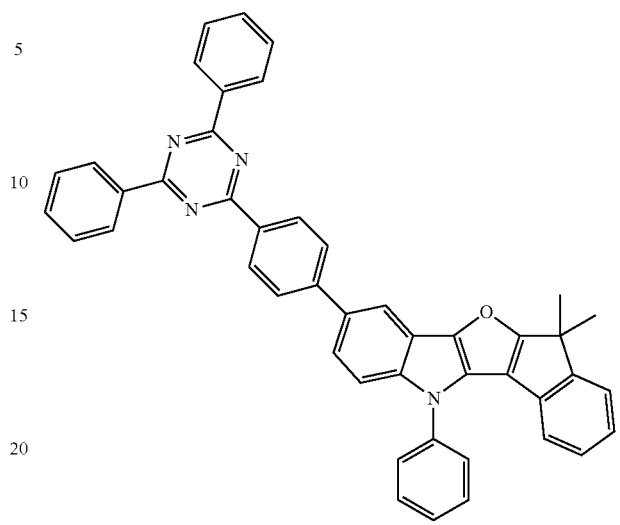
48
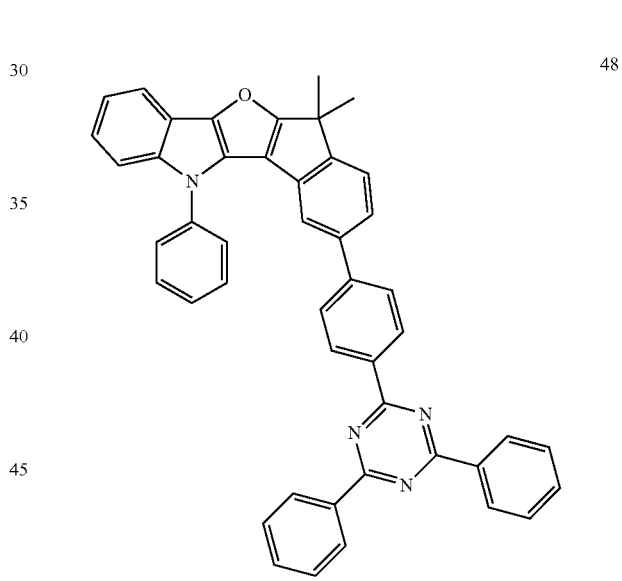
49
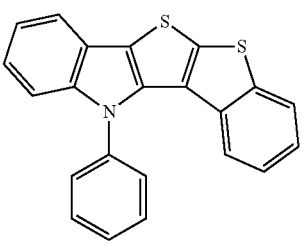

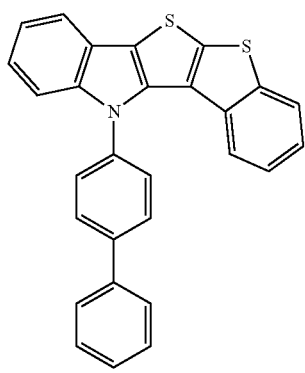
50
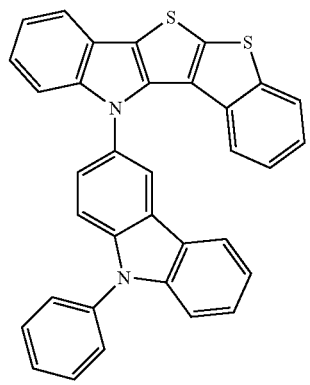
54
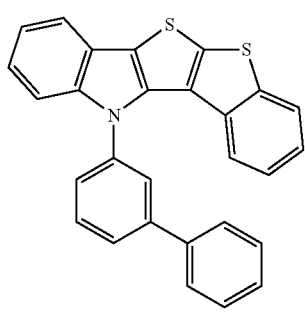
51
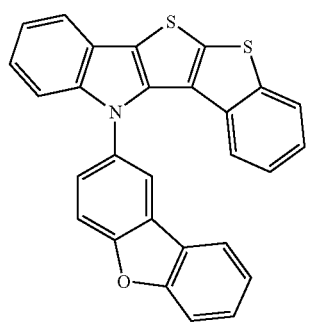
55
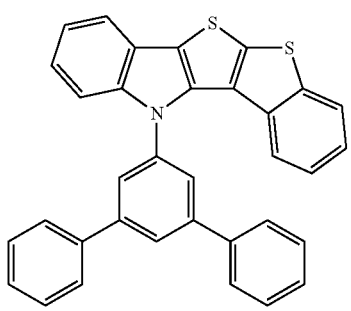
52
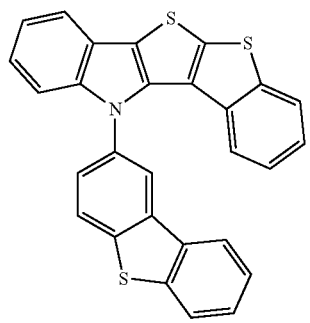
56
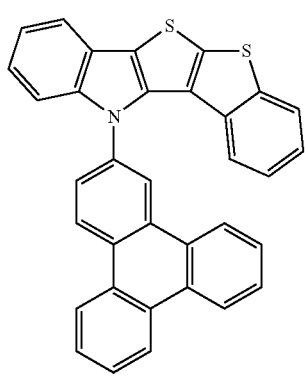
53
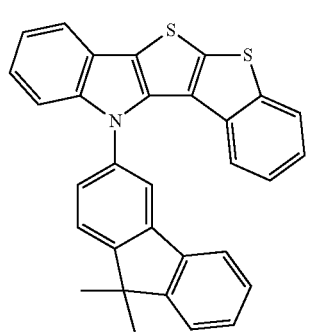
57

261
-continued
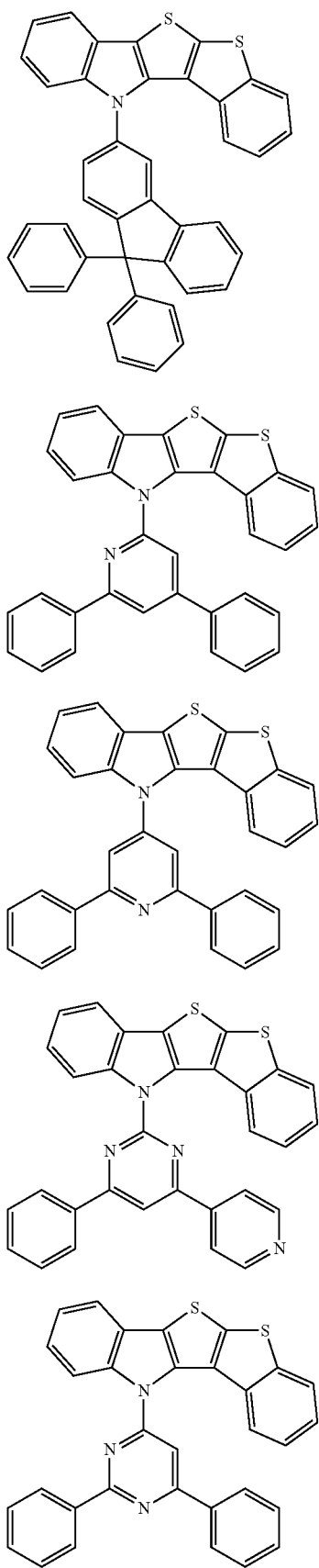
262
-continued
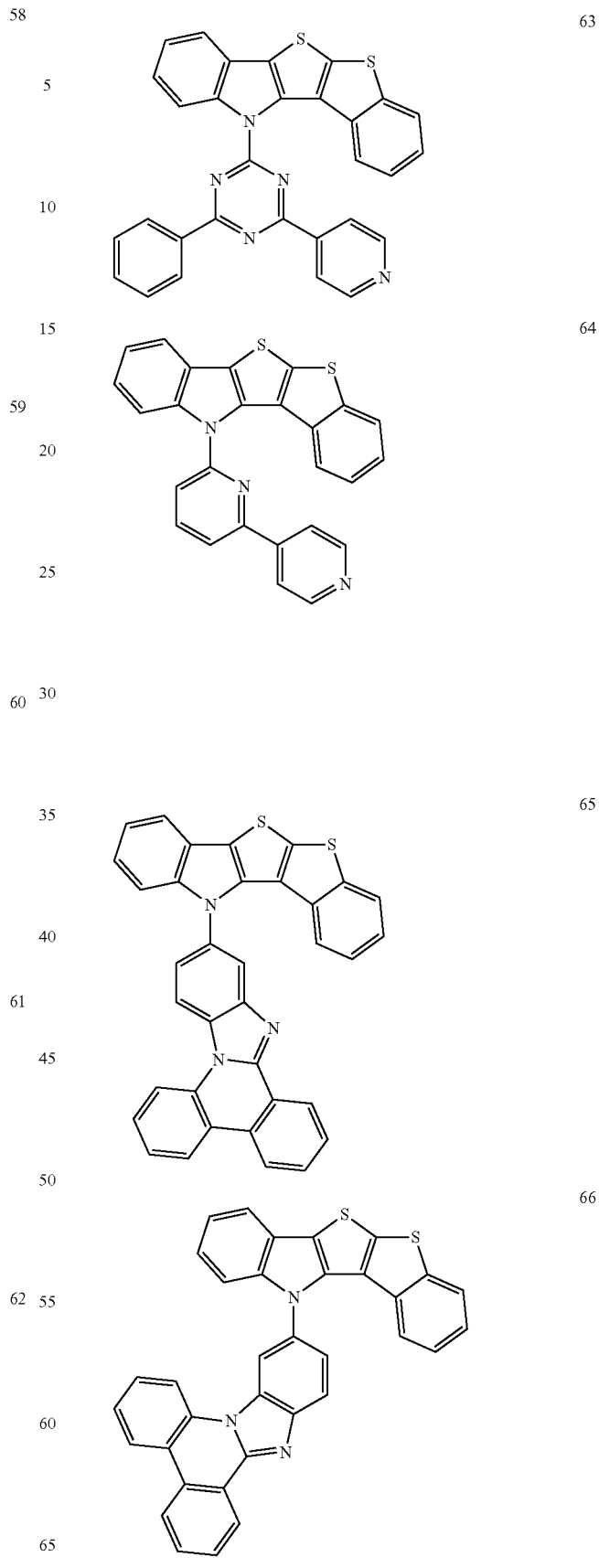

263
-continued
67
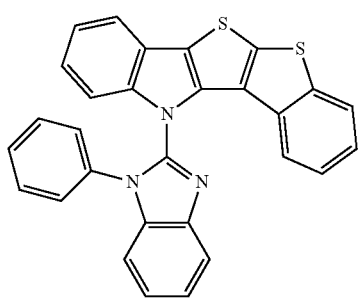
68
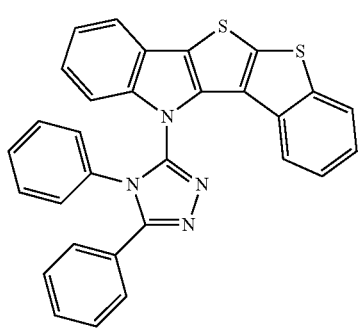
69
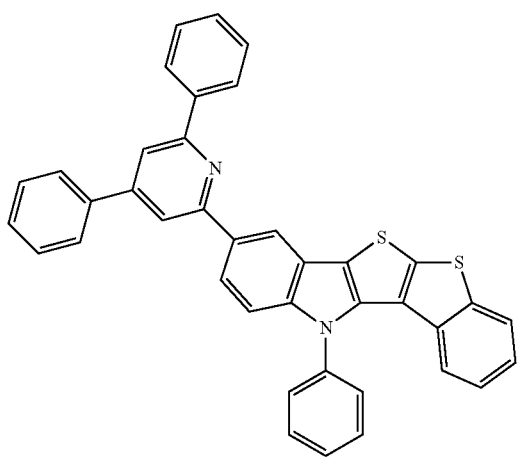
70
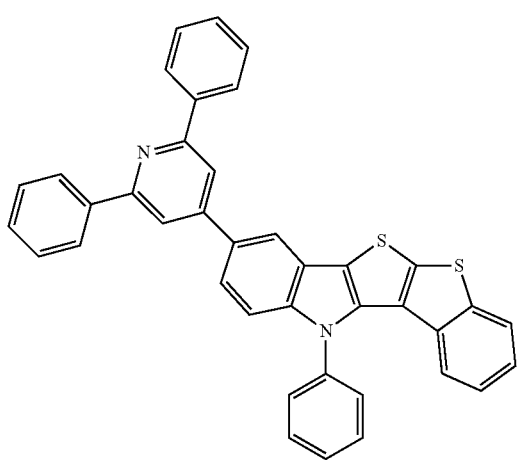
264
-continued
71
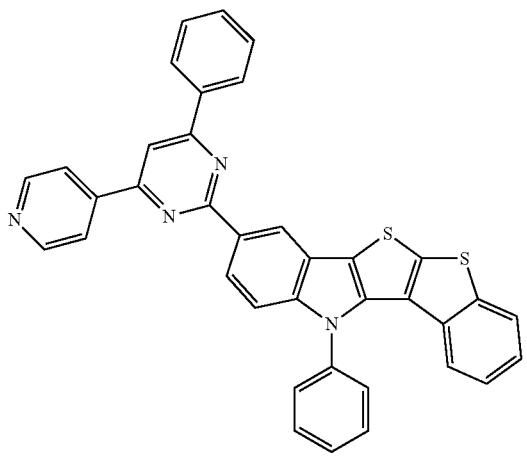
72
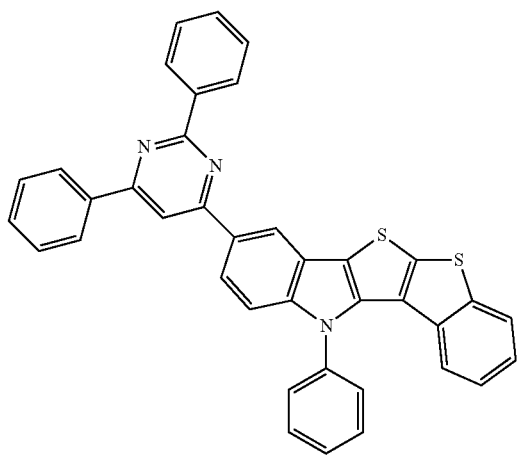
73
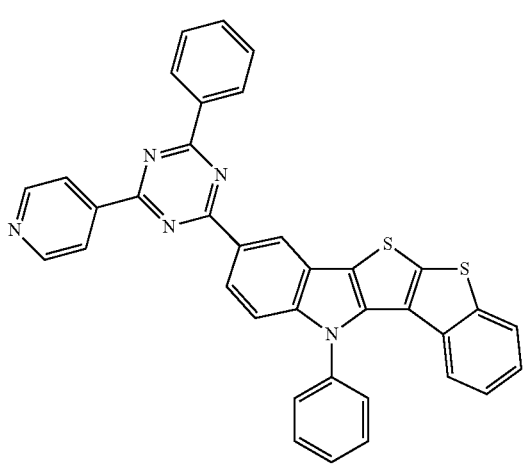

265
-continued
74
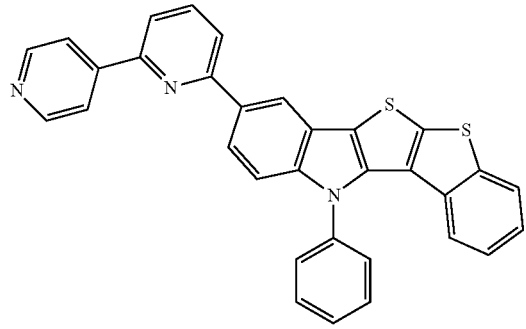
75
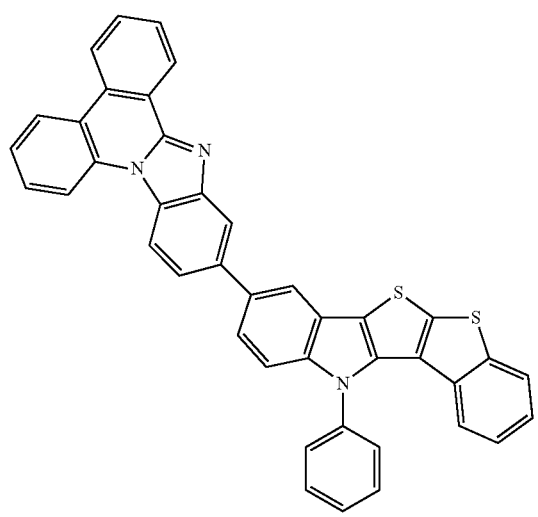
76
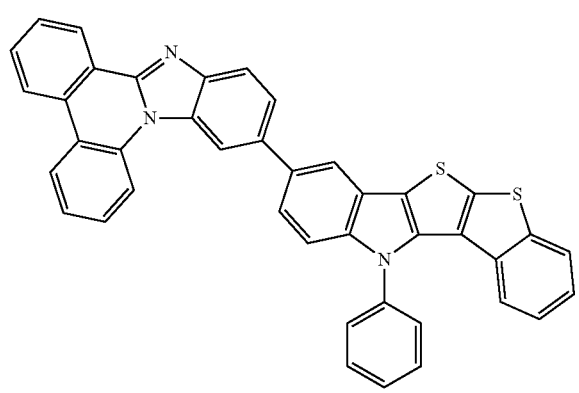
266
-continued
77
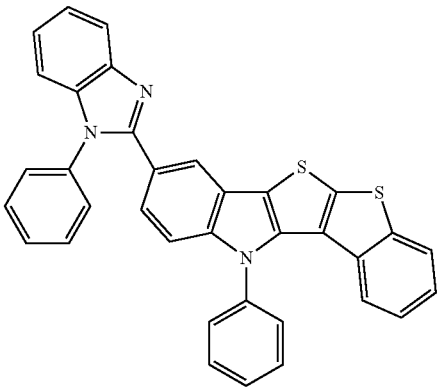
78
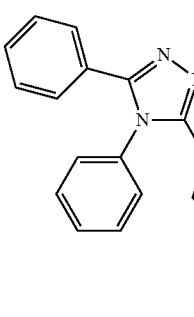
73
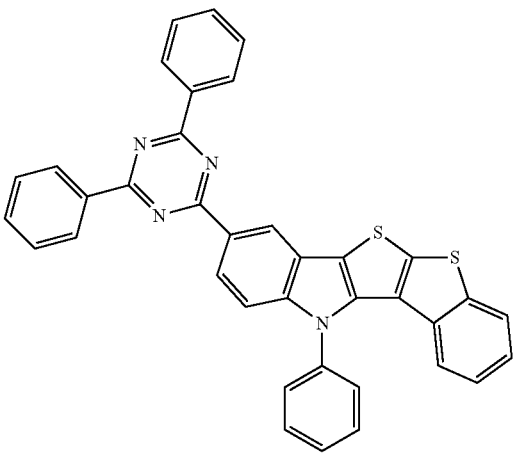
74

267
-continued
75
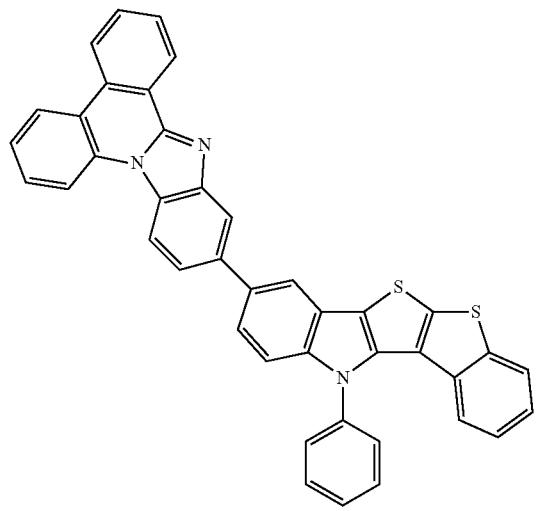
76
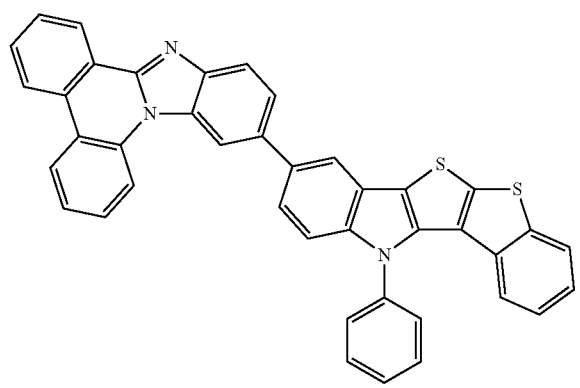
77
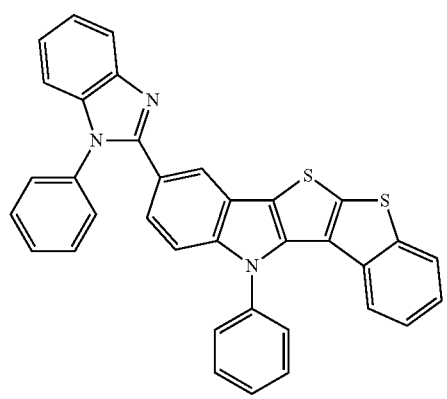
268
-continued
78
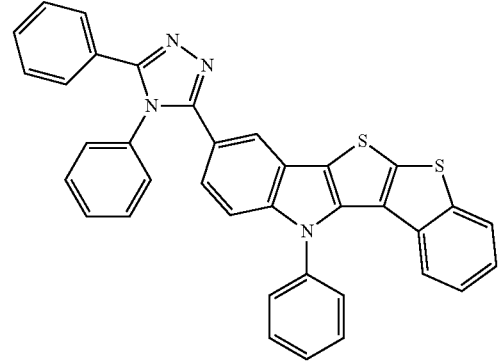
79
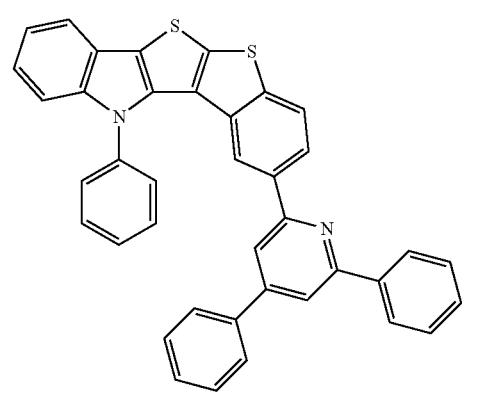
80
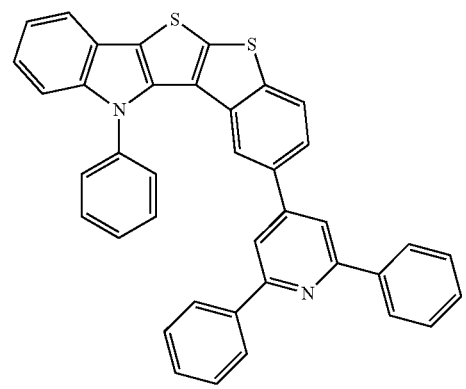
81
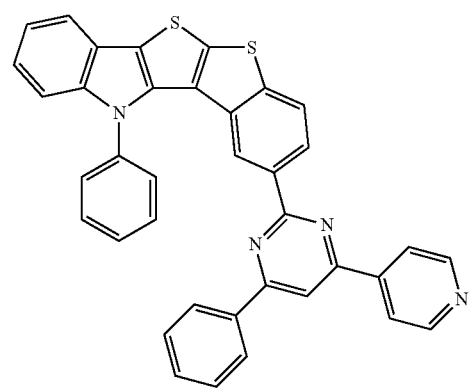

269
-continued
82
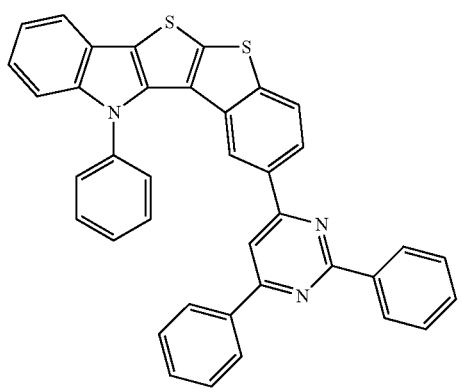
83
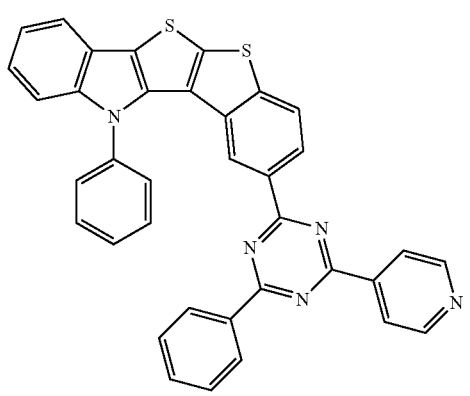
84
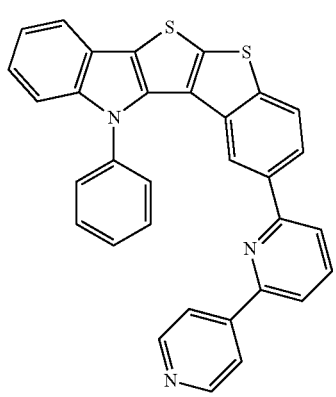
85
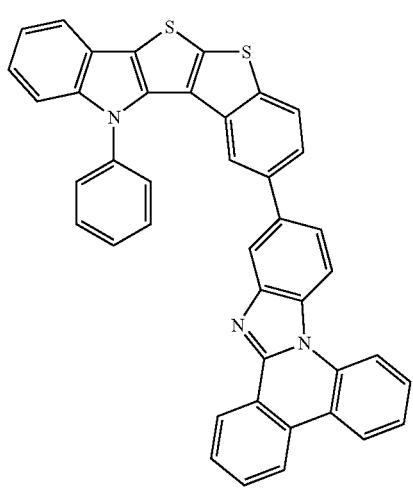
270
-continued
86
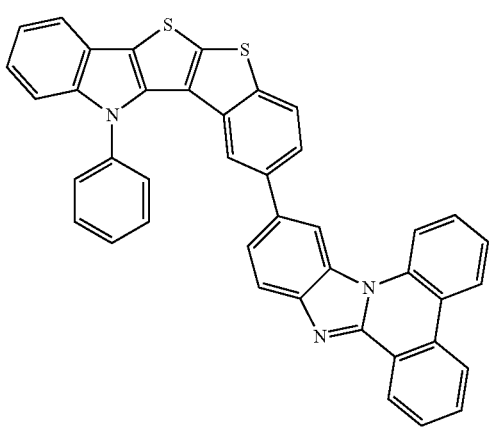
87
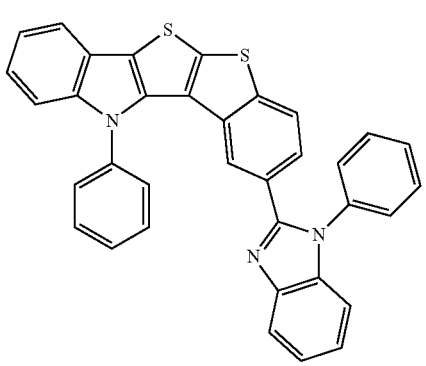
88
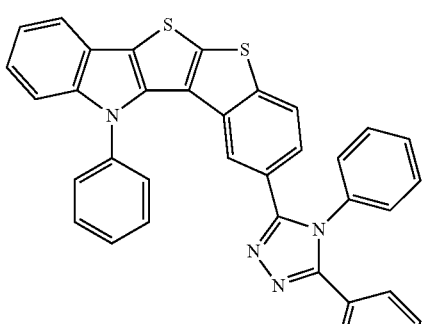
89
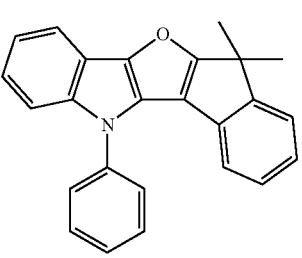

271
-continued
90
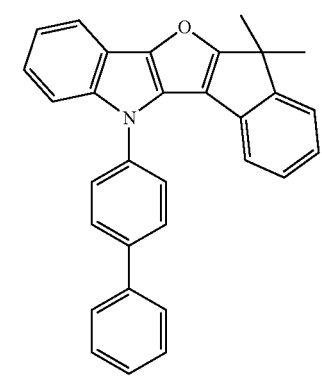
91
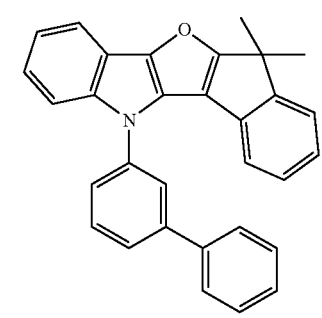
92
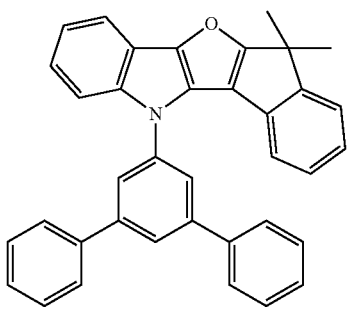
93
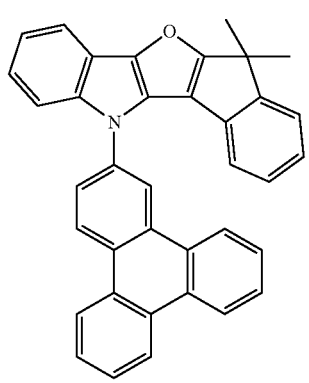
272
-continued
94
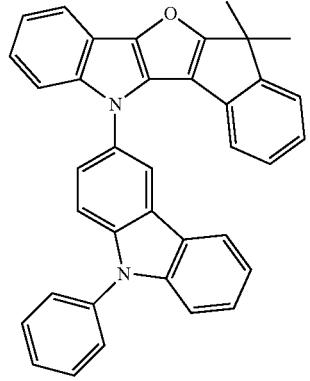
95
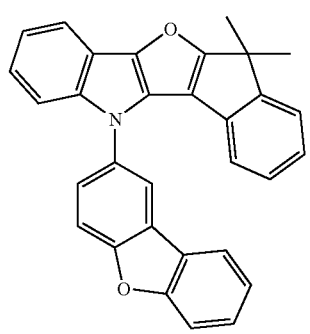
96
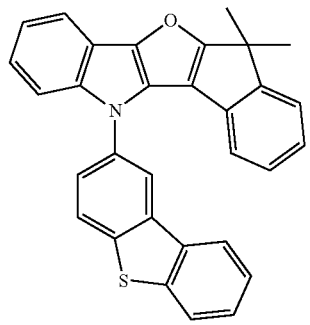
97
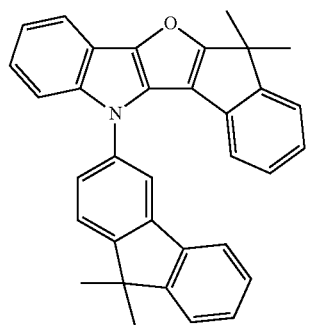

273
-continued
274
-continued
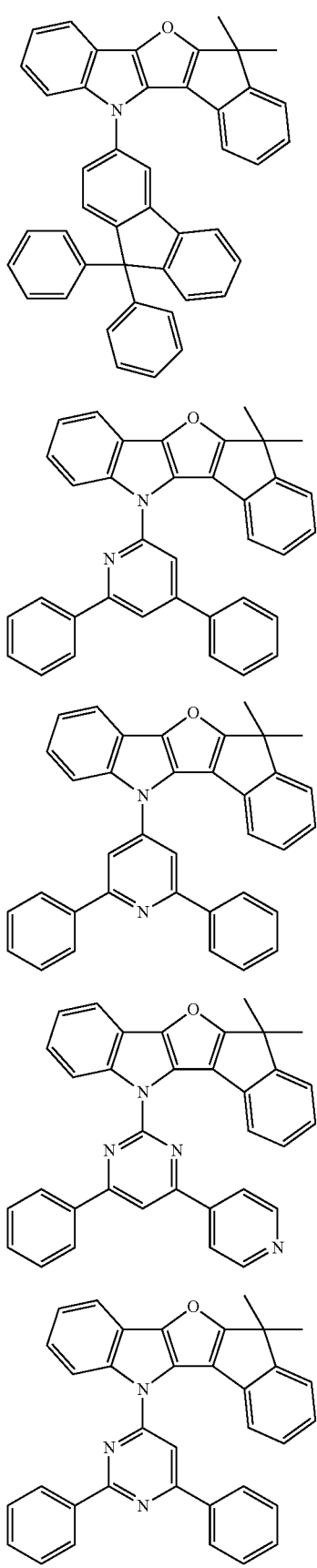
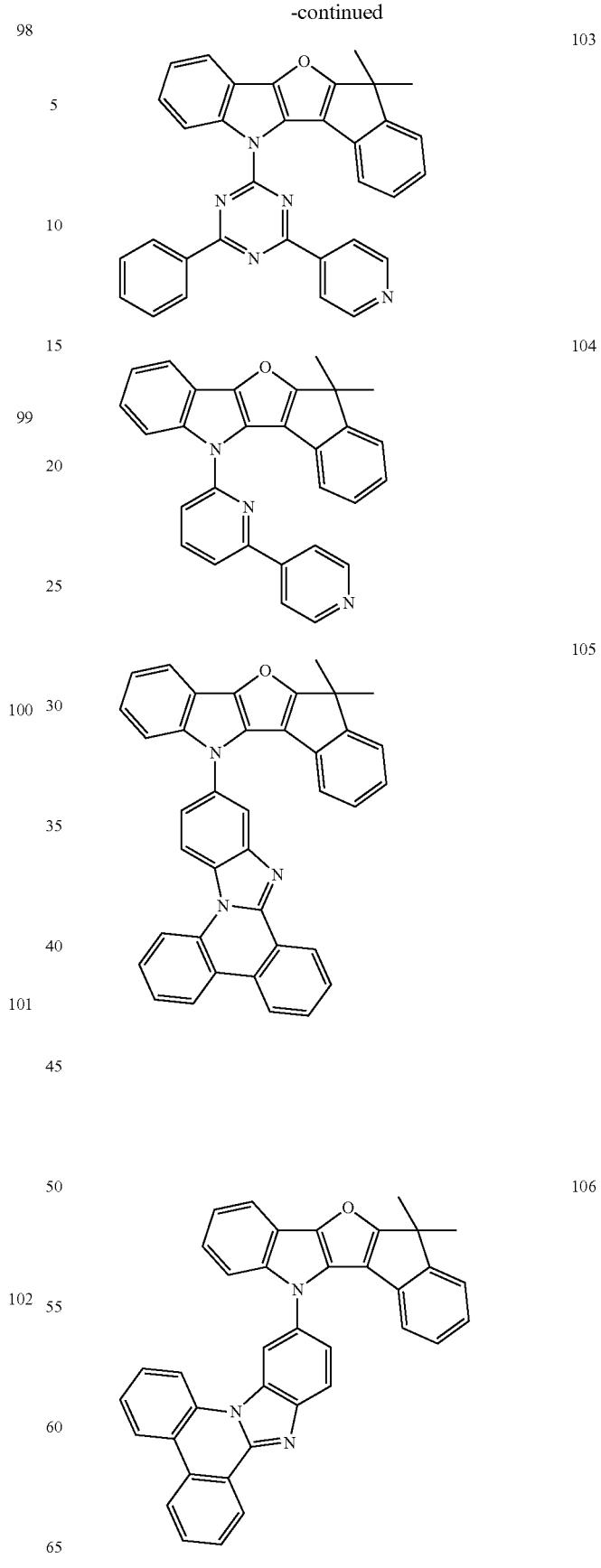

275
-continued
107
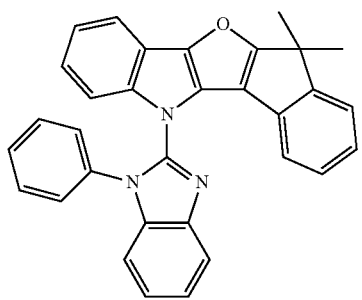
108
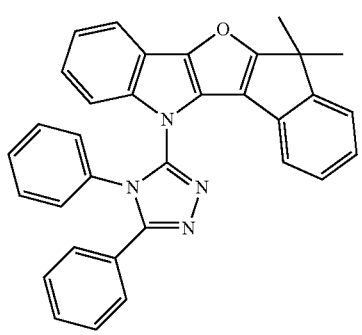
109
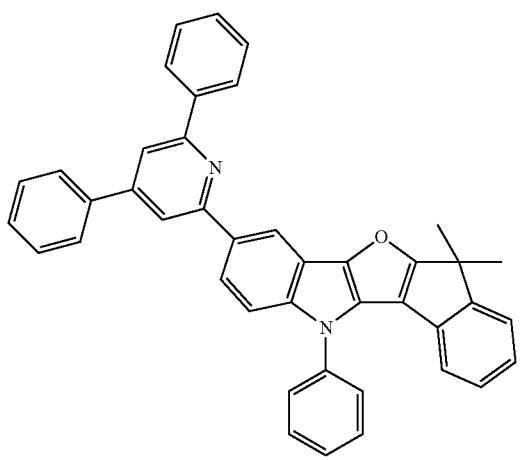
110
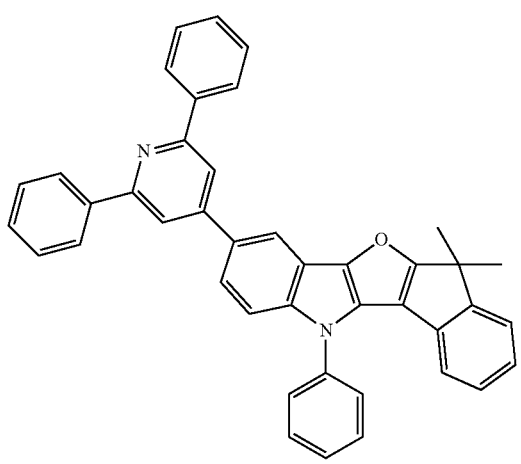
276
-continued
111
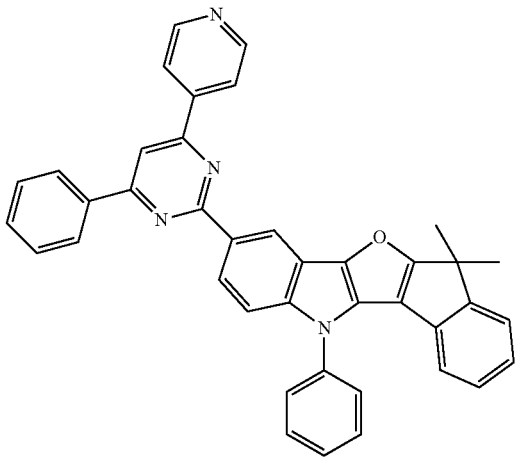
112
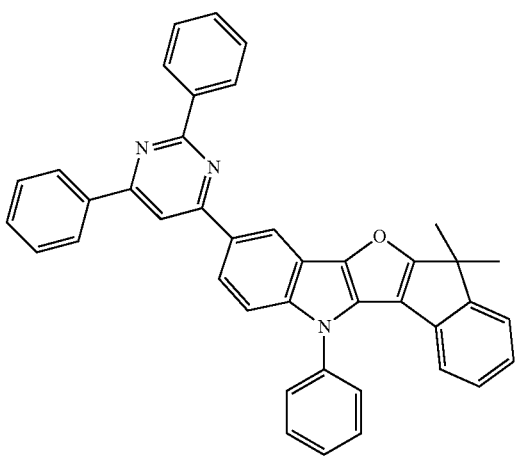
113
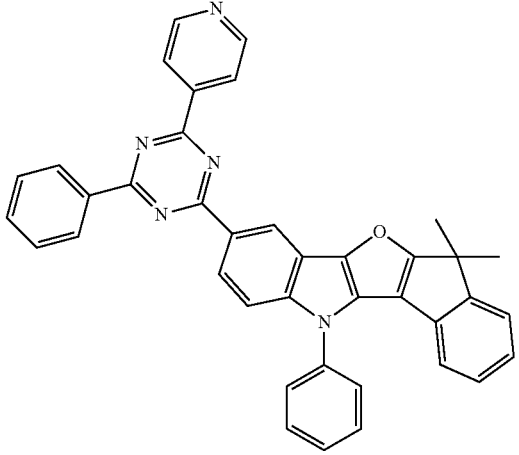

277
-continued
114
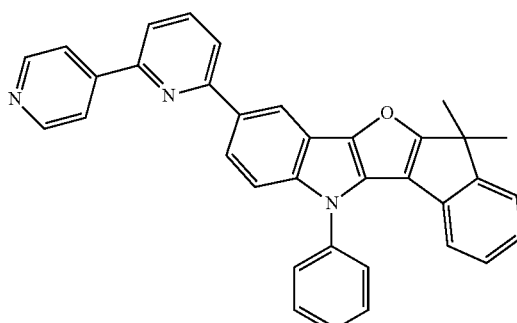
115
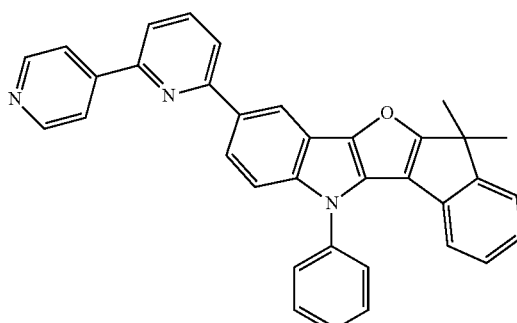
116
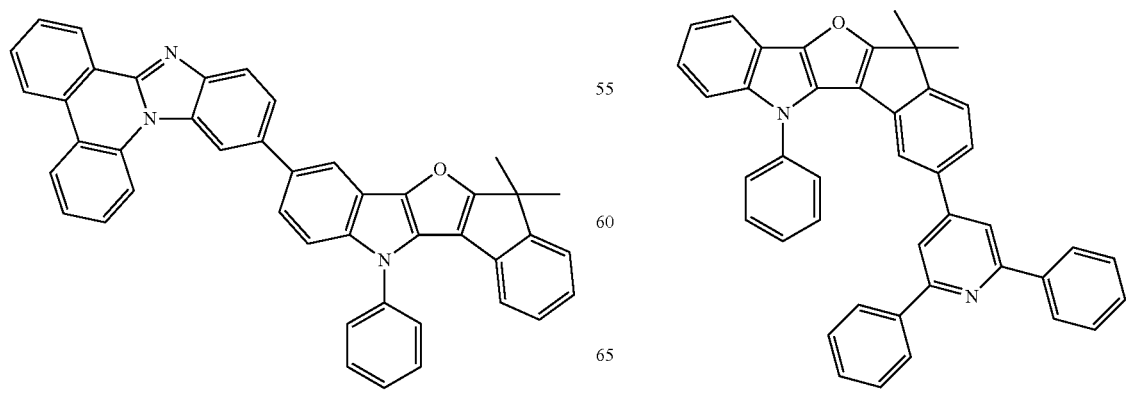
278
-continued
117
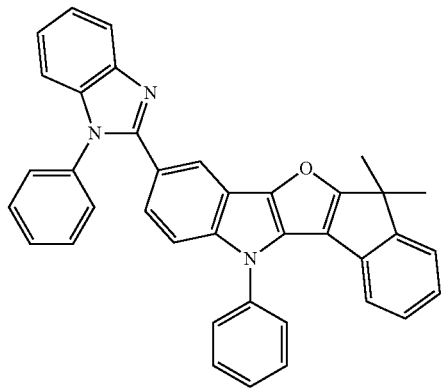
118
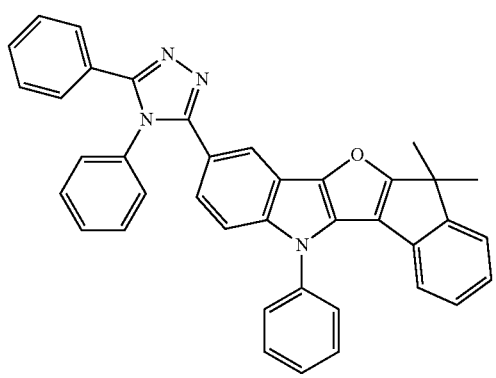
119
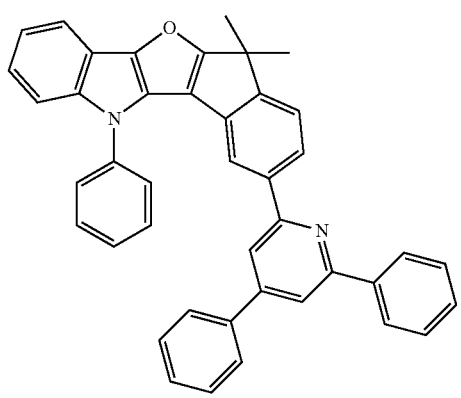
120
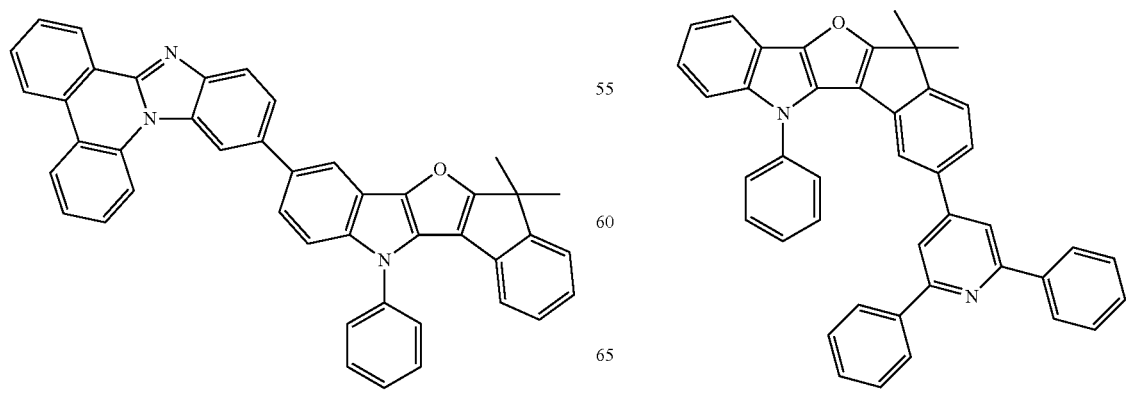

121 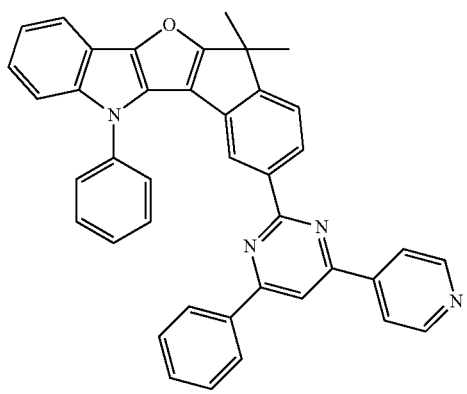
122 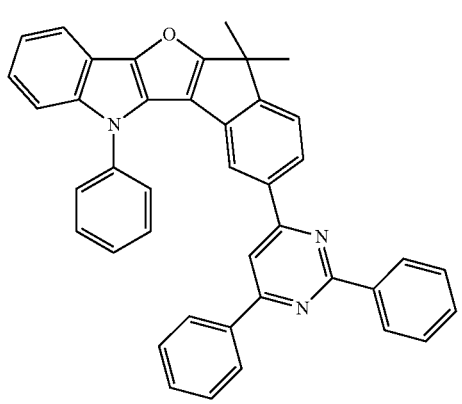
123 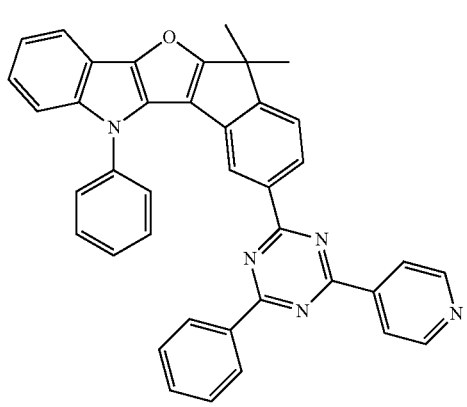
124 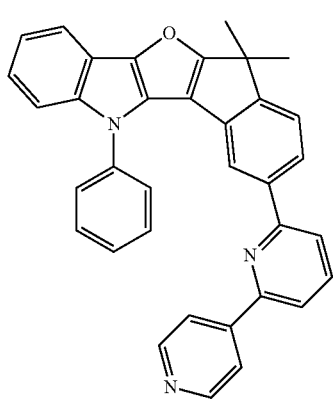
125 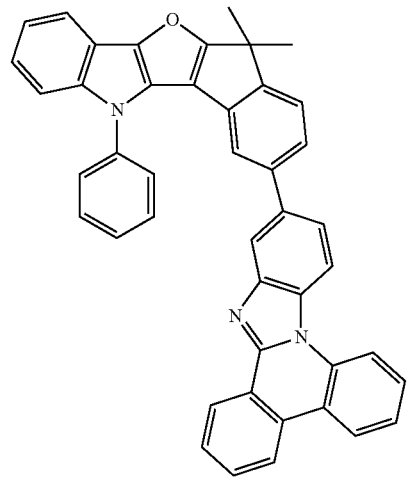
126 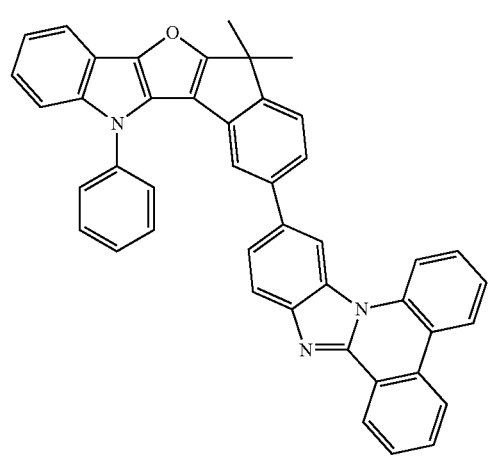
127 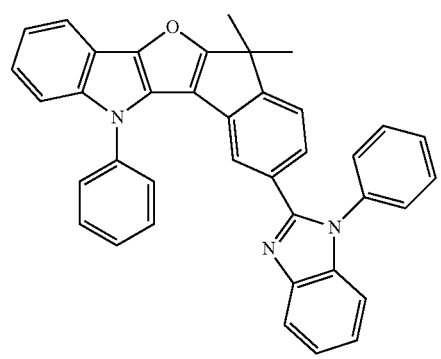
128 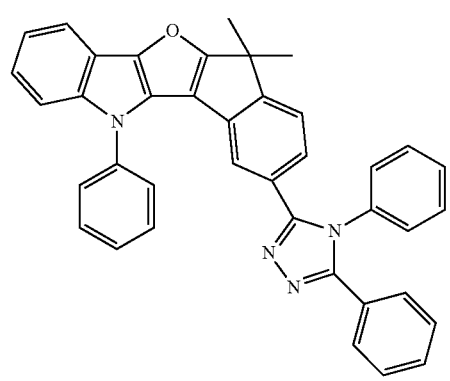

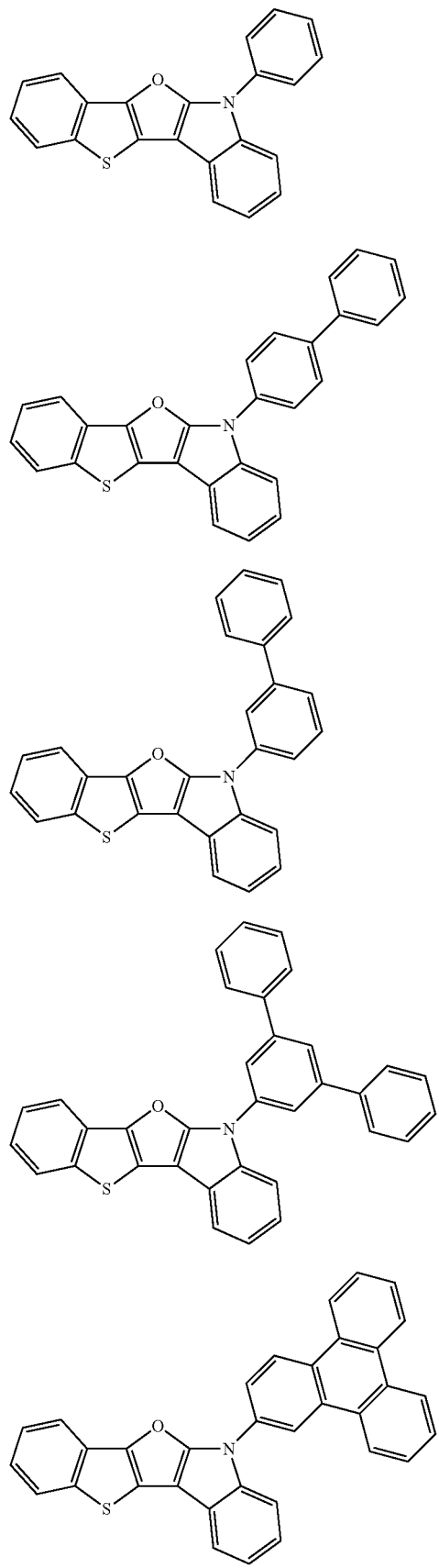
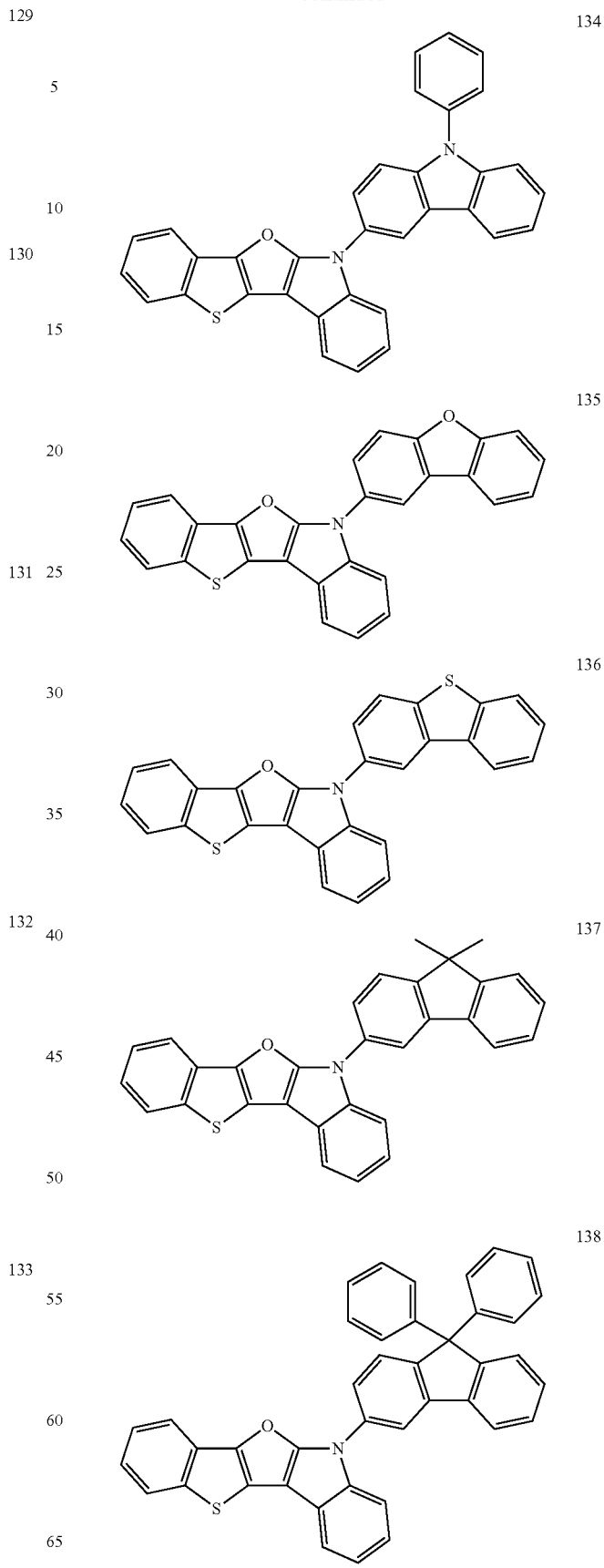

-continued
139
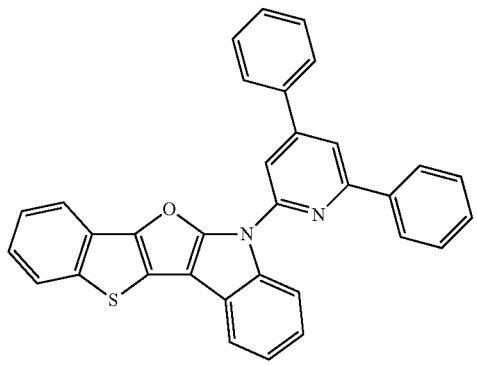
140
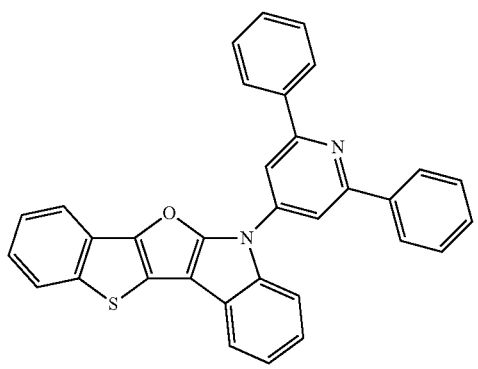
141
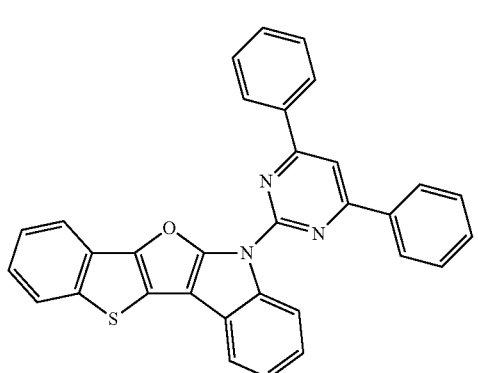
142
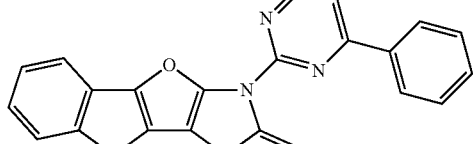
-continued
143
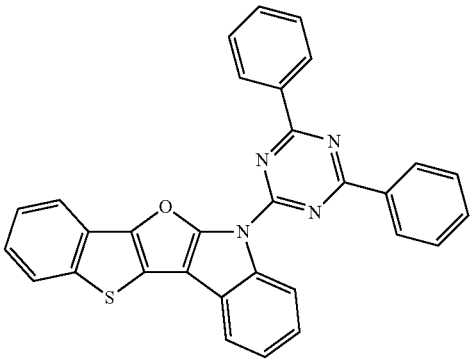
144
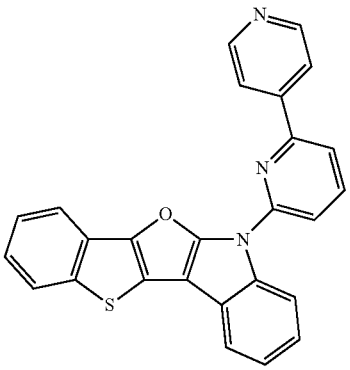
145
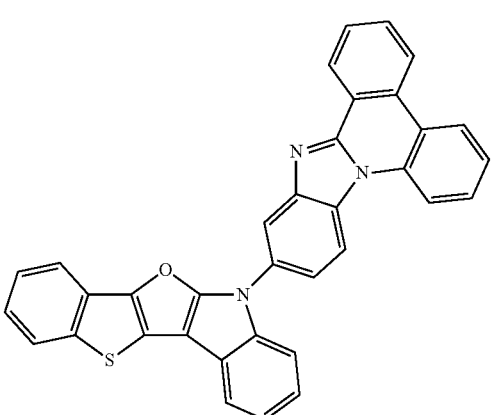
146
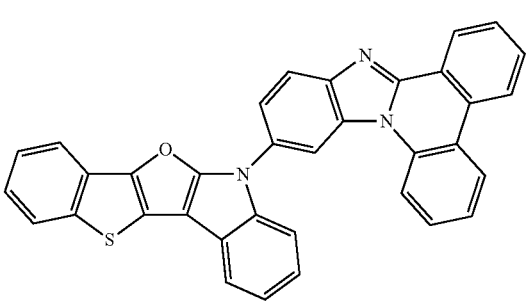

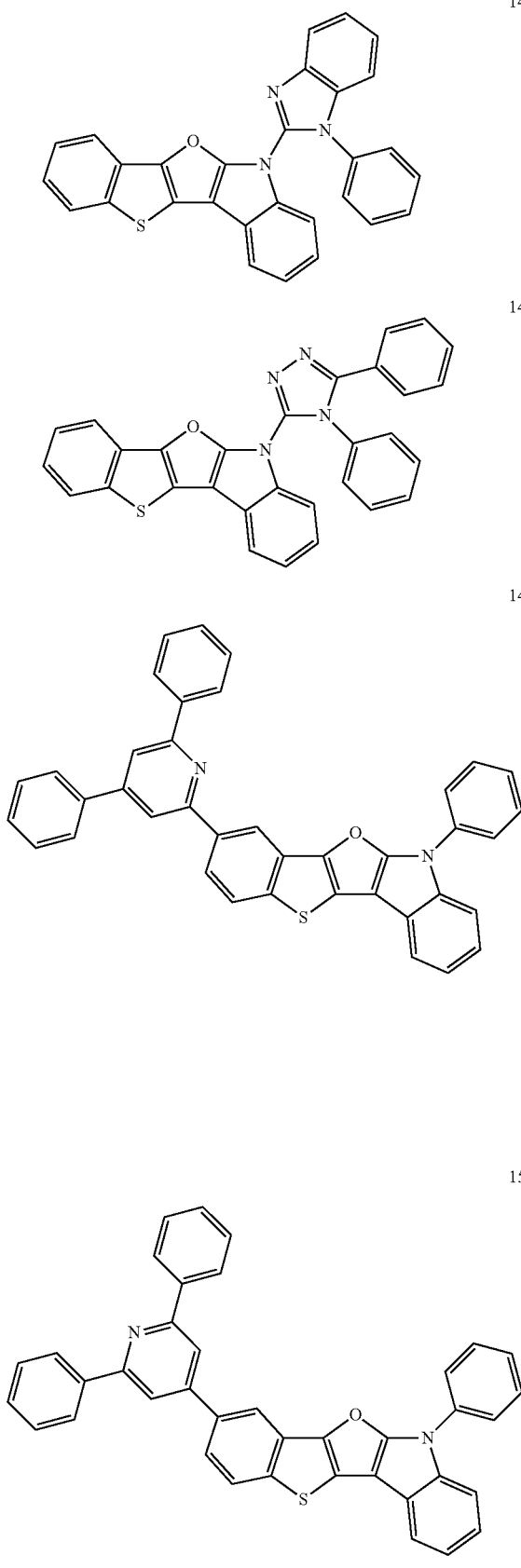
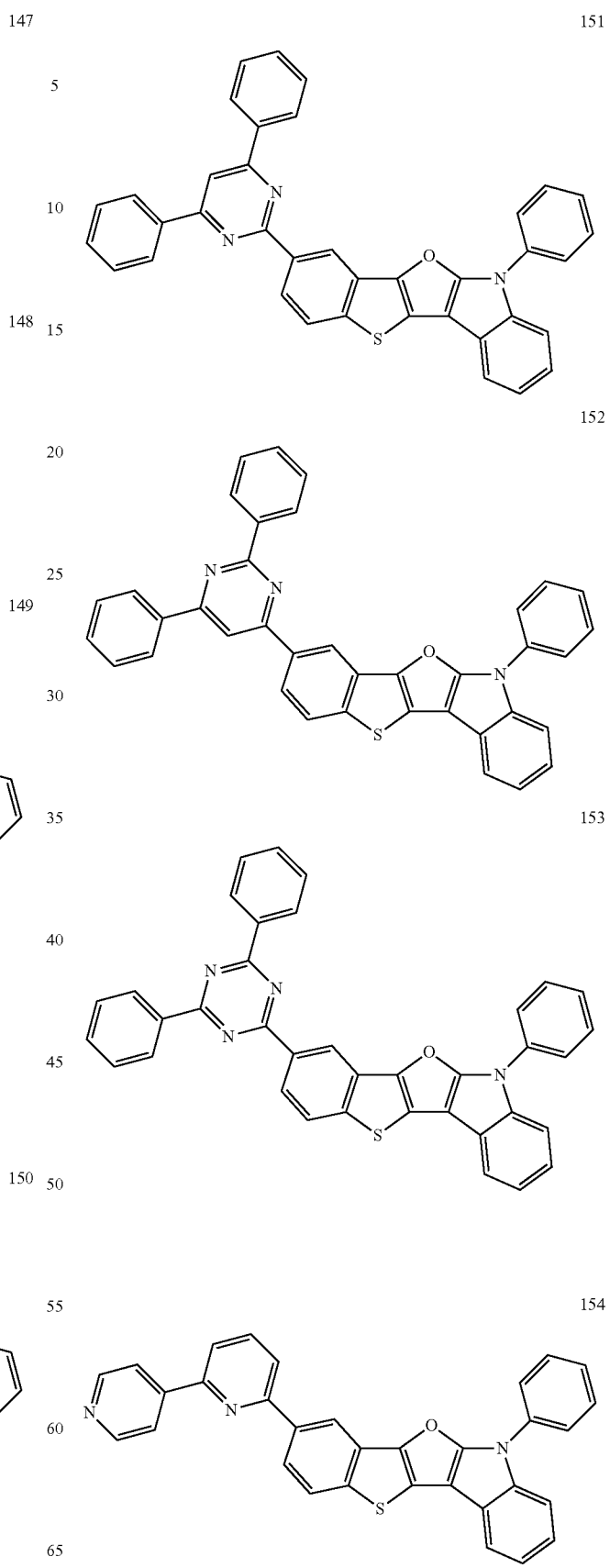

155
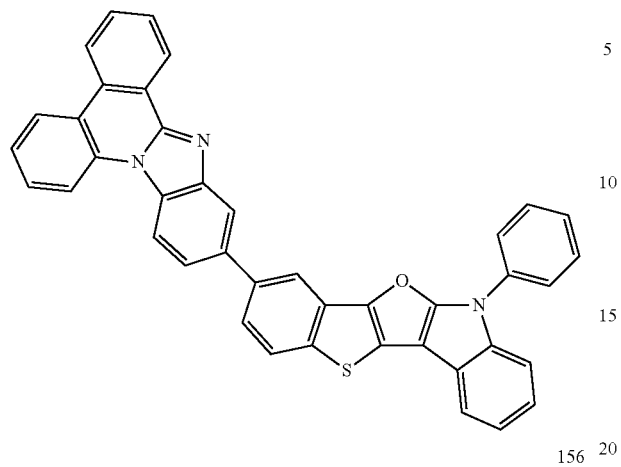
156
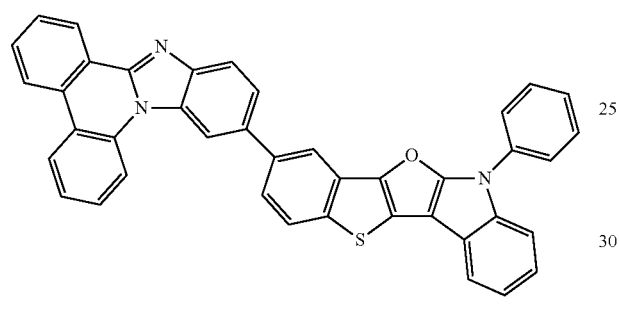
157
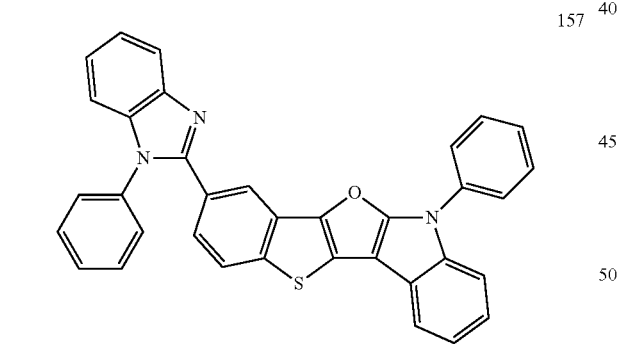
158
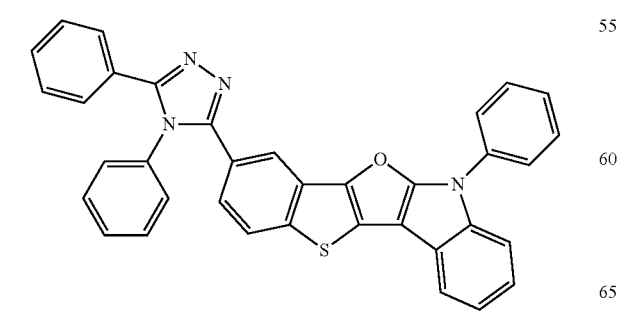
159
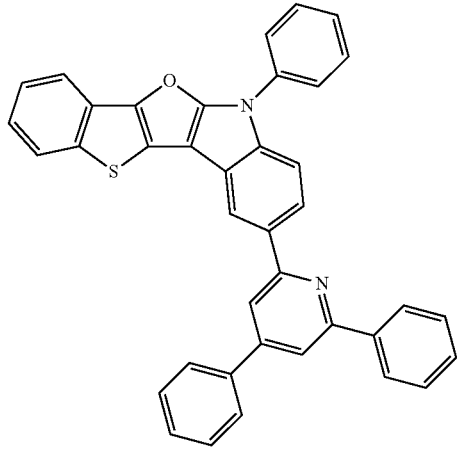
160
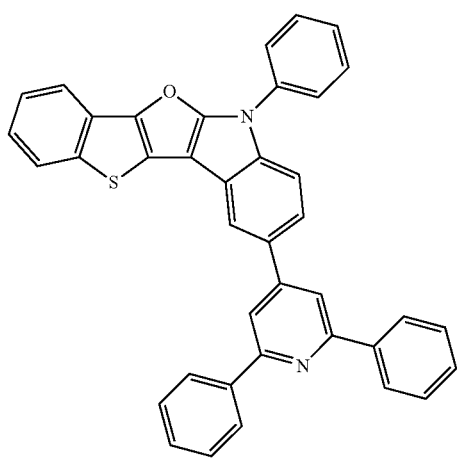
161
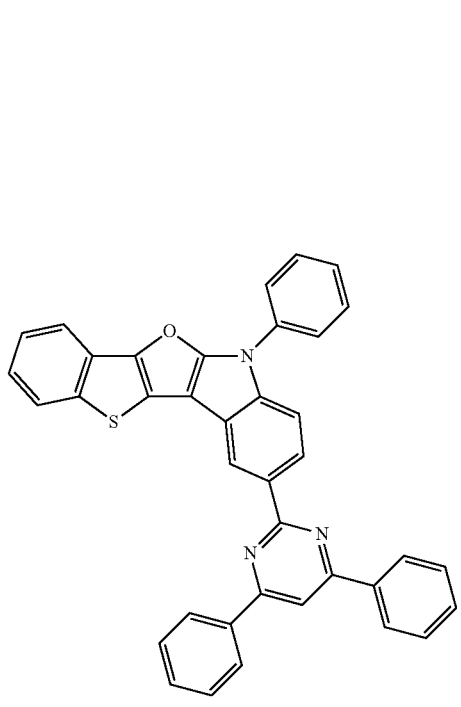

162
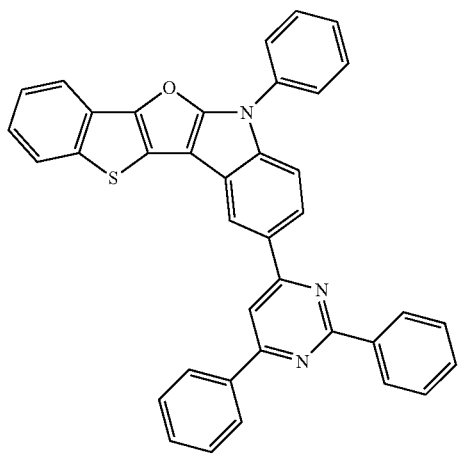
163
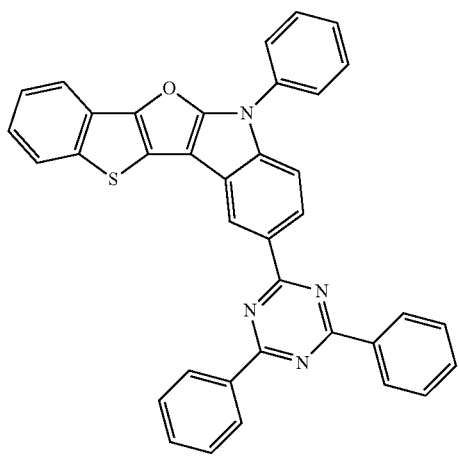
164
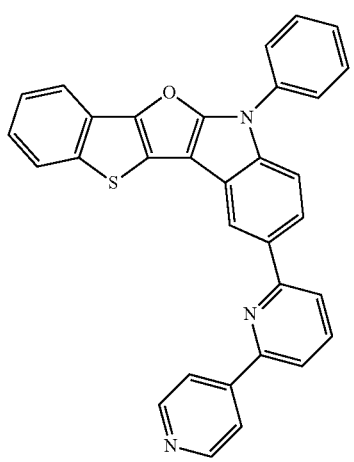
165
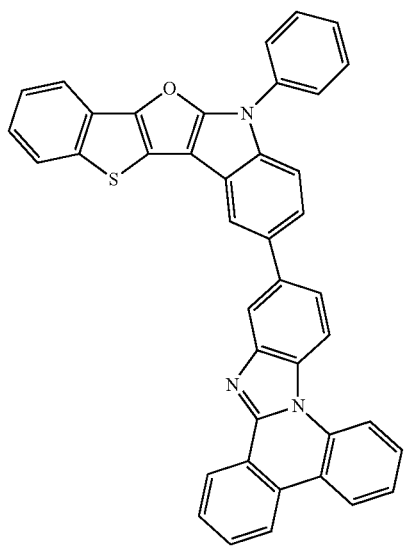
166
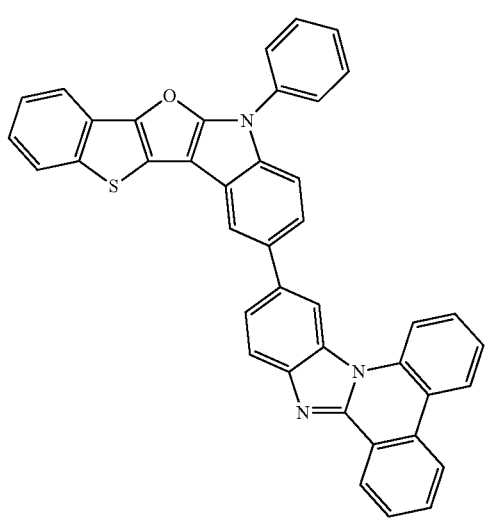
167
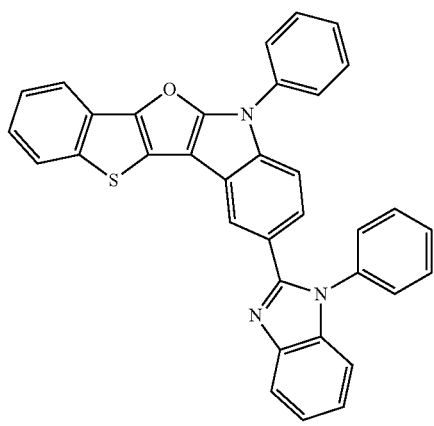

168
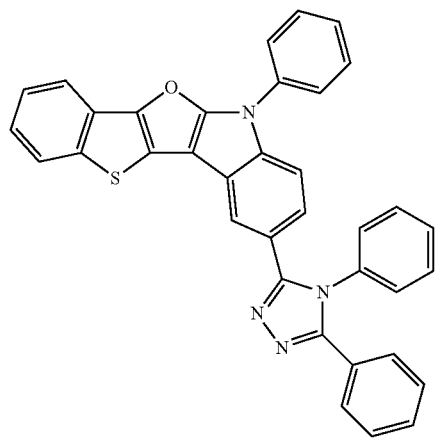
169
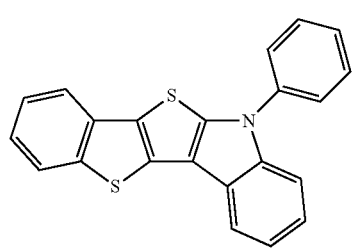
170
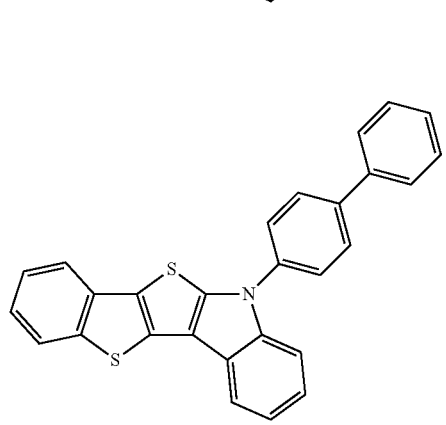
171
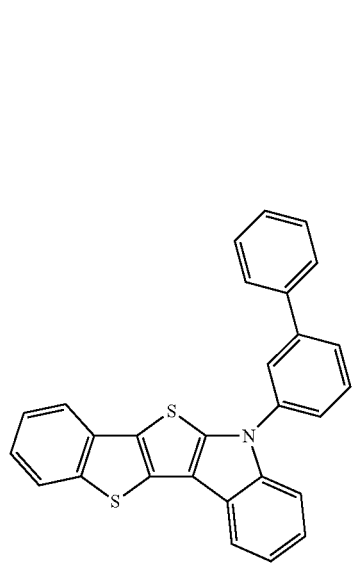
172
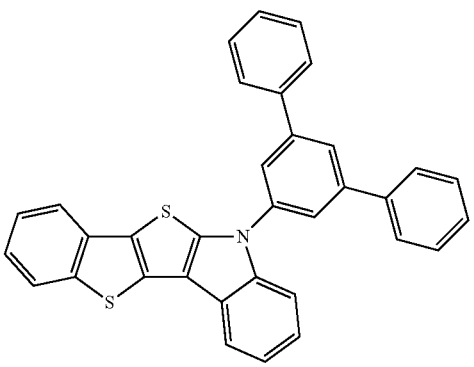
173
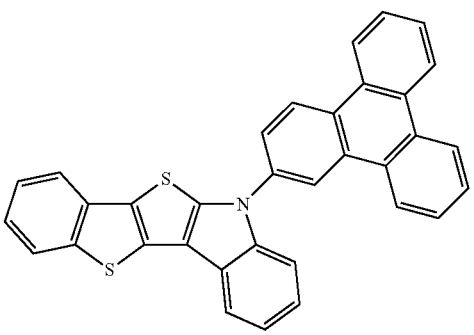
174
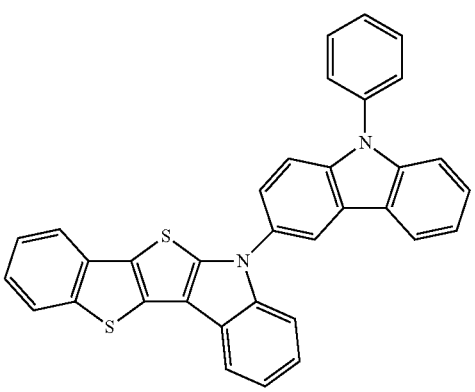
175
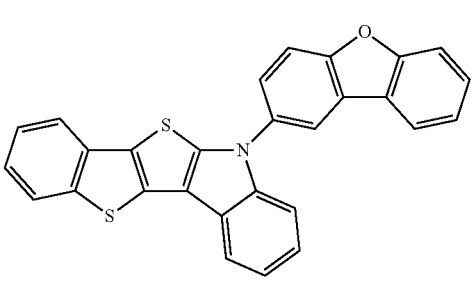
176
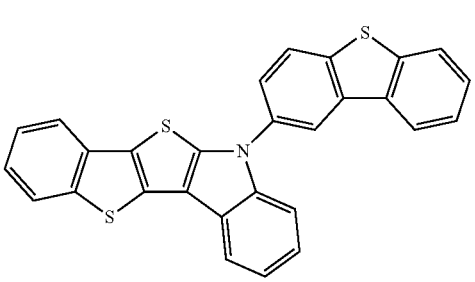

177
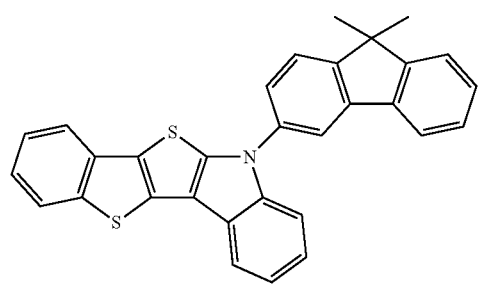
178
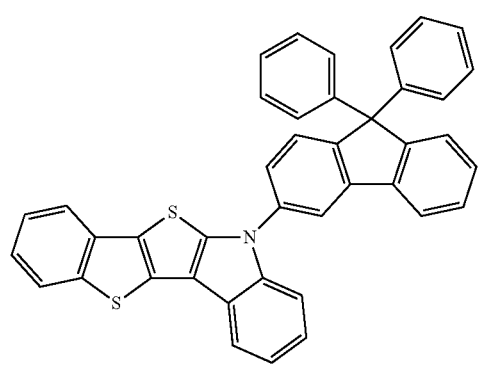
179
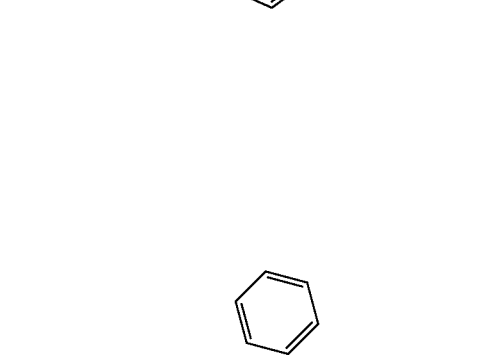
180
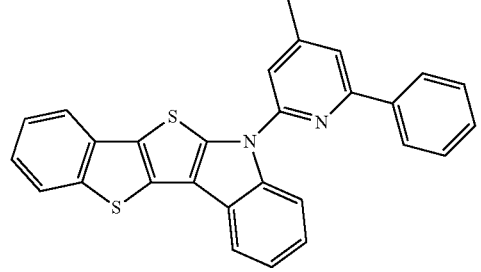
181
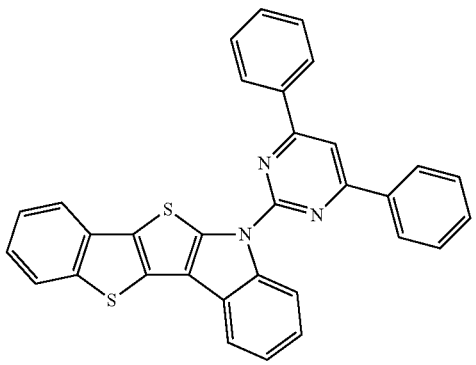
182
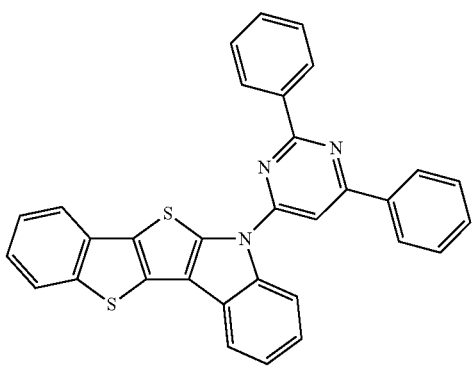
183
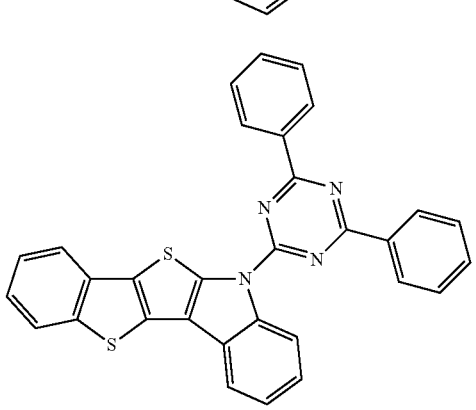
184
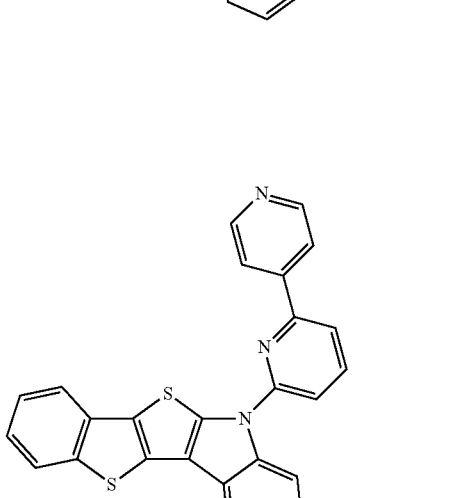

185
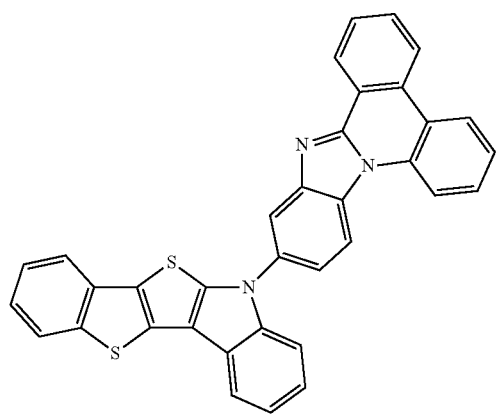
186
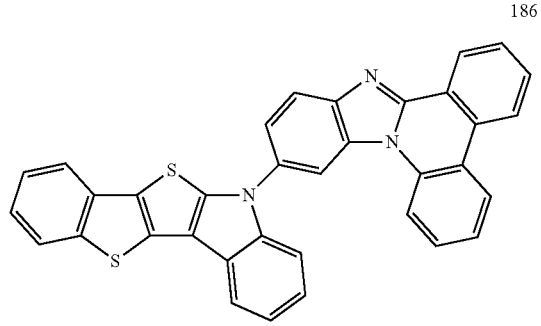
187
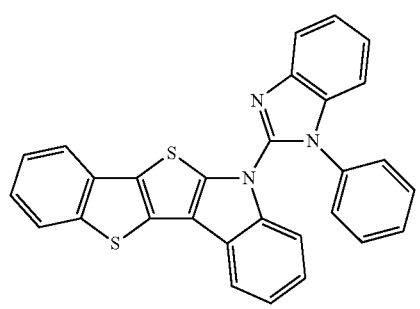
188
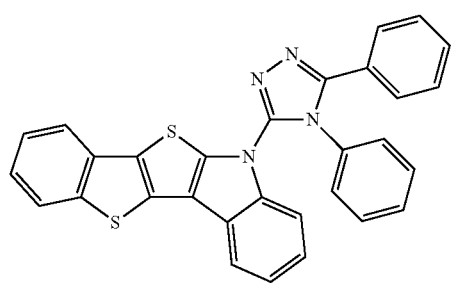
189
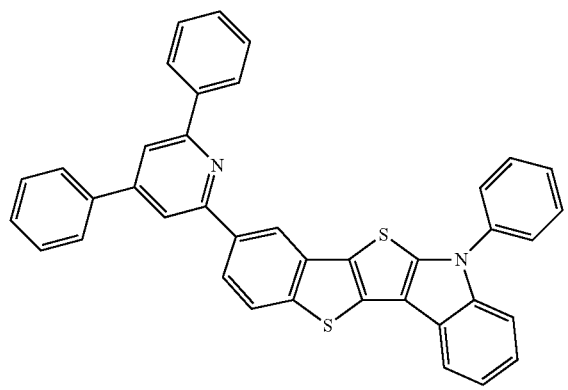
190
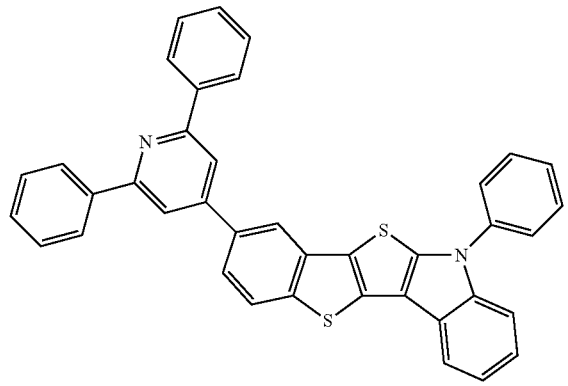
191
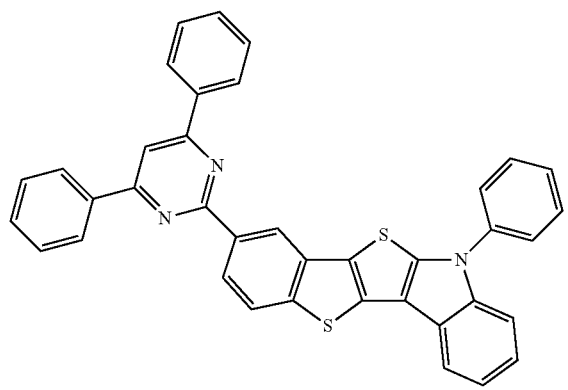
192
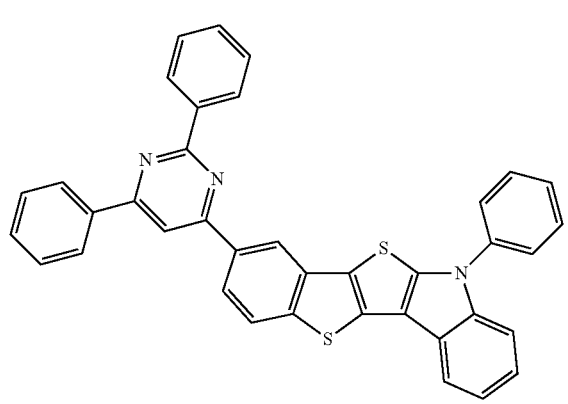

193
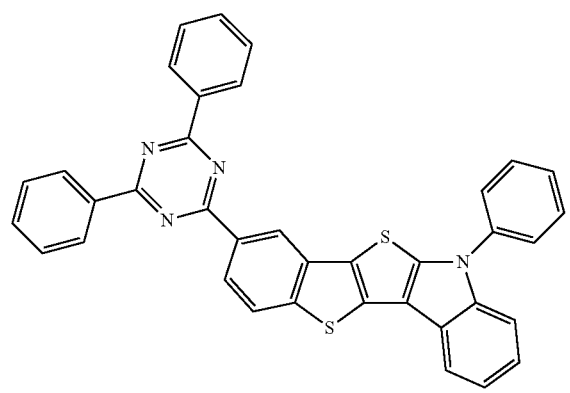
194
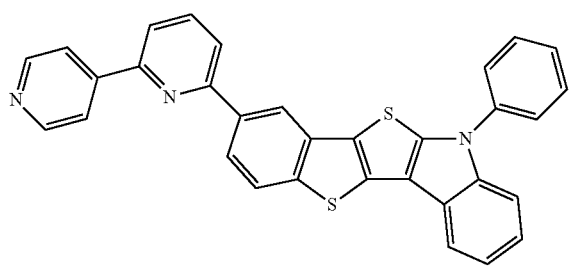
195
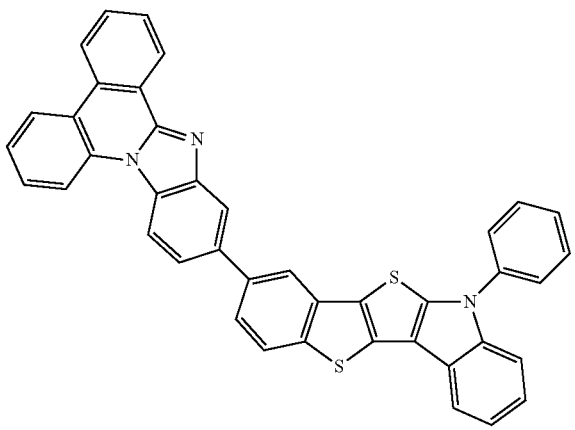
196
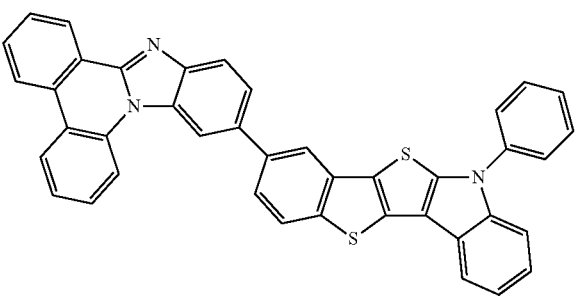
197
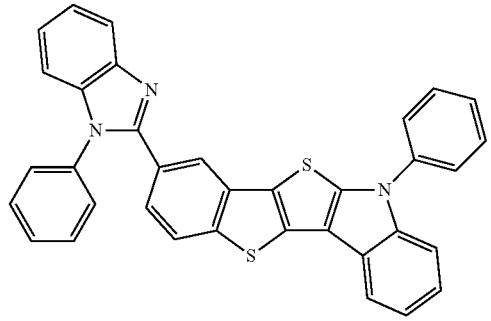
198
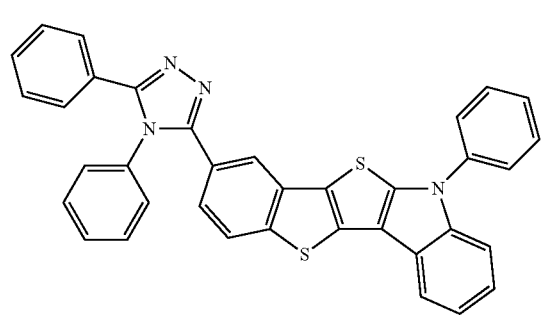
199
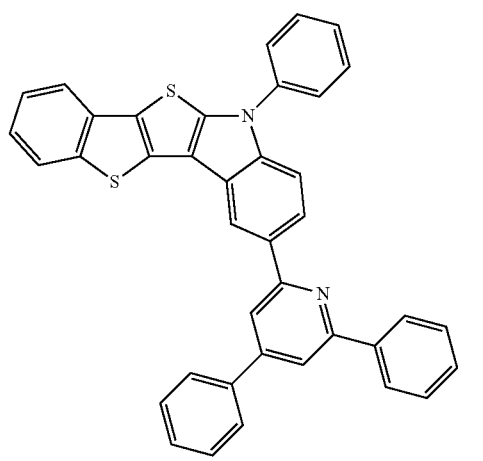
200
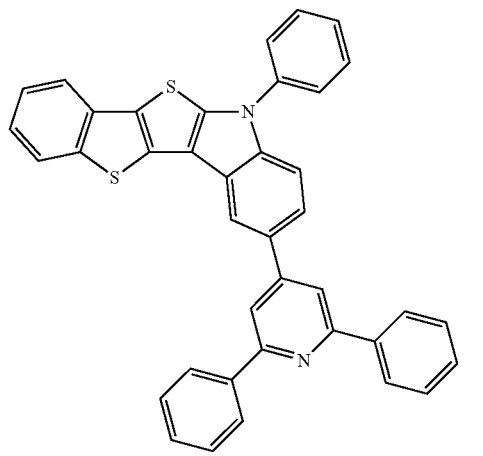

299
-continued
201
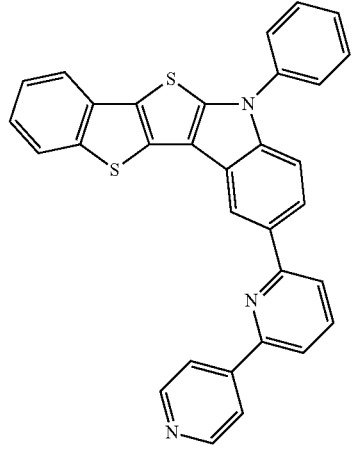
202
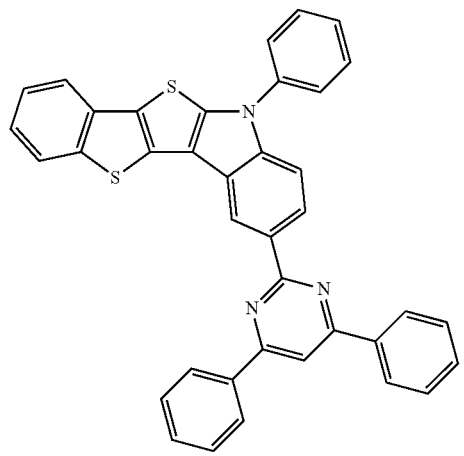
203
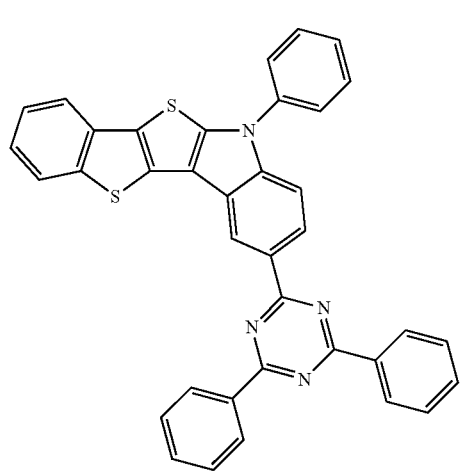
300
-continued
204
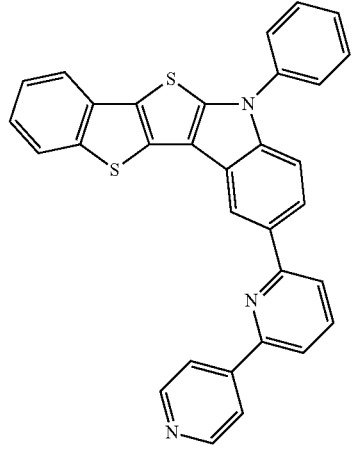
205
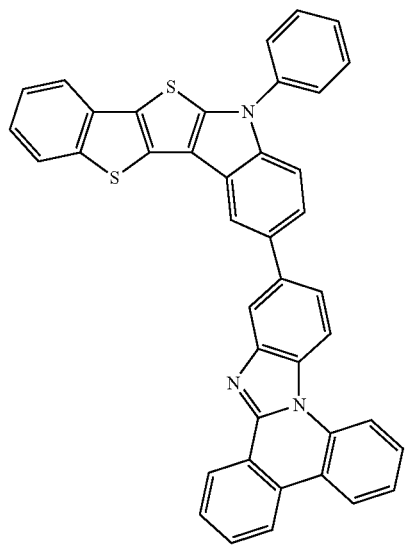
206
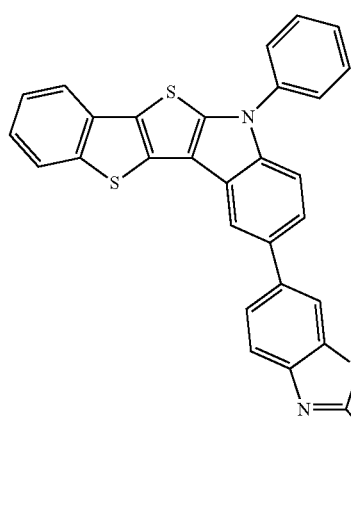

301
-continued

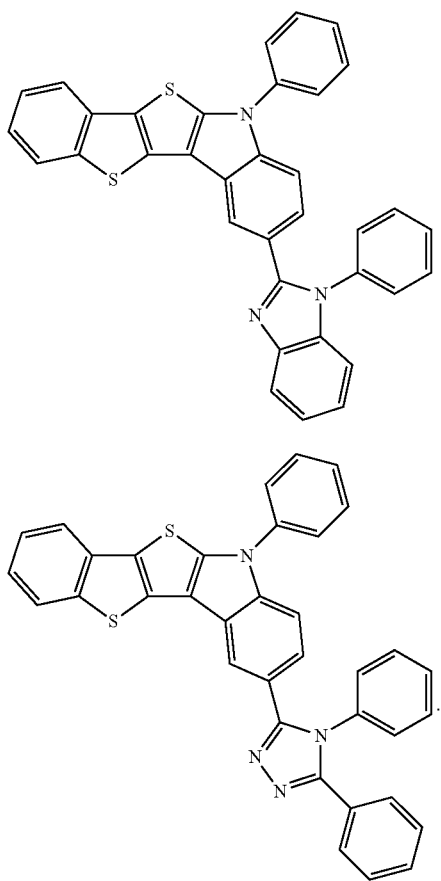

207

208

302

21. An organic light-emitting device comprising:
    a first electrode;
    a second electrode; and
    an organic layer disposed between the first electrode and the second electrode,
    wherein the organic layer comprises an emission layer and at least one of the condensed cyclic compound of claim 1.

22. The organic light-emitting device of claim 21, wherein
    the first electrode is an anode,
    the second electrode is a cathode, and
    the organic layer comprises
    i) a hole transport region that is disposed between the first electrode and the emission layer and comprises at least one of a hole injection layer, a hole transport layer, and an electron blocking layer, and
    ii) an electron transport region that is disposed between the emission layer and the second electrode and comprises at least one layer selected from a hole blocking layer, an electron transport layer, and an electron injection layer.

23. The organic light-emitting device of claim 21, wherein the emission layer comprises the condensed cyclic compound.

24. The organic light-emitting device of claim 23, wherein the emission layer further comprises a dopant, and the condensed cyclic compound,
    wherein the condensed cyclic compound is a host.

* * * * *